US011236152B2

(12) United States Patent
Kwong et al.

(10) Patent No.: US 11,236,152 B2
(45) Date of Patent: Feb. 1, 2022

(54) NEUTRALIZING ANTIBODIES TO HIV-1 GP41 AND THEIR USE

(71) Applicants: The United States of America, as represented by the Secretary, Department of Health and Human Services, Bethesda, MD (US); The Trustees of Columbia University in the City of New York, New York, NY (US)

(72) Inventors: Peter Kwong, Washington, DC (US); Young Do Kwon, Kensington, MD (US); Ivelin Georgiev, Nashville, TN (US); Gilad Ofek, Gaithersburg, MD (US); Baoshan Zhang, Bethesda, MD (US); Krisha McKee, Columbia, MD (US); John Mascola, Rockville, MD (US); Mark Connors, Bethesda, MD (US); Gwo-Yu Chuang, Rockville, MD (US); Sijy O'Dell, Silver Spring, MD (US); Robert Bailer, Adamstown, MD (US); Mark Louder, Mt. Airy, MD (US); Mangaiarkarasi Asokan, Rockville, MD (US); Richard Schwartz, Bethesda, MD (US); Jonathan Cooper, Arlington, VA (US); Kevin Carlton, Gaithersburg, MD (US); Michael Bender, Washington, DC (US); Amarendra Pegu, Potomac, MD (US); Lawrence Shapiro, New York, NY (US); Tatyana Gindin, New York, NY (US); Lisa Kueltzo, Gaithersburg, MD (US)

(73) Assignees: The United States of America, as represented by the Sectetary, Department of Health and Human Services, Bethesda, MD (US); The Trustees of Columbia University in the City of New York, New York, NY (US)

(*) Notice: Subject to any disclaimer, the term of this patent is extended or adjusted under 35 U.S.C. 154(b) by 500 days.

(21) Appl. No.: 15/772,443

(22) PCT Filed: Nov. 3, 2016

(86) PCT No.: PCT/US2016/060390
§ 371 (c)(1),
(2) Date: Apr. 30, 2018

(87) PCT Pub. No.: WO2017/079479
PCT Pub. Date: May 11, 2017

(65) Prior Publication Data
US 2019/0077849 A1 Mar. 14, 2019

Related U.S. Application Data

(60) Provisional application No. 62/250,360, filed on Nov. 3, 2015.

(51) Int. Cl.
C07K 16/10 (2006.01)
A61P 31/18 (2006.01)

(52) U.S. Cl.
CPC .......... C07K 16/1063 (2013.01); A61P 31/18 (2018.01); C07K 2317/21 (2013.01); C07K 2317/31 (2013.01); C07K 2317/33 (2013.01); C07K 2317/52 (2013.01); C07K 2317/565 (2013.01); C07K 2317/567 (2013.01); C07K 2317/76 (2013.01); C07K 2317/92 (2013.01); C07K 2317/94 (2013.01)

(58) Field of Classification Search
None
See application file for complete search history.

(56) References Cited

U.S. PATENT DOCUMENTS

| 7,378,276 B2 | 5/2008 | Ettinger et al. |
| 2011/0064760 A1 | 3/2011 | Cho et al. |
| 2019/0054182 A1* | 2/2019 | Yang .................... C07K 16/468 |

FOREIGN PATENT DOCUMENTS

| CN | 104087545 A | 10/2014 |
| WO | WO 2005/111079 | 11/2005 |
| WO | WO 2006/117586 | 11/2006 |
| WO | WO 2010/089402 | 8/2010 |
| WO | WO 2011/038290 | 3/2011 |
| WO | WO 2011/046623 | 4/2011 |
| WO | WO 2013/070776 | 5/2013 |
| WO | WO 2013/070776 A1 * | 5/2013 |

(Continued)

OTHER PUBLICATIONS

Chatellier, J., et al., 1996, Functional mapping of conserved residues located atteh VL and VH domain interface of a Fab, J. Mol. Biol. 264:1-6.*

(Continued)

Primary Examiner — Jeffrey S Parkin
(74) Attorney, Agent, or Firm — Klarquist Sparkman, LLP

(57) ABSTRACT

Neutralizing antibodies that specifically bind to HIV-1 Env and antigen binding fragments of these antibodies are disclosed. Nucleic acids encoding these antibodies, vectors and host cells are also provided. Methods for detecting HIV-1 using these antibodies are disclosed. In addition, the use of these antibodies, antigen binding fragment, nucleic acids and vectors to prevent and/or treat an HIV-1 infection is disclosed.

22 Claims, 40 Drawing Sheets

Specification includes a Sequence Listing.

(56) References Cited

FOREIGN PATENT DOCUMENTS

| WO | WO 2013/163427 | 10/2013 |
|---|---|---|
| WO | WO 2014/040025 A2 | 3/2014 |
| WO | WO 2014/084859 A1 | 6/2014 |

OTHER PUBLICATIONS

Kala, M., et al., 2002, Phage displayed antibodies to heat stable alkaline phosphatase: framework region as a determinant of specificity, J. Biochem. 132:535-541.*

Tempest, P. R., et al., 1995, Identification of framework residues required to restore antigen binding during reshaping of a monoclonal antibody against teh glycoprotein GB of human cytomegalovirus, Int. J. Biol. Macromol. 17(1):37-42.*

Huang, J., et al., Nov. 2012, Broad and potent neutralization of HIV-1 by a gp41-specific human antibody, Nature 491:406-414.*

Alam, et al. "Role of HIV membrane in neutralization by two broadly neutralizing antibodies." *Proceedings of the National Academy of Sciences*, 106.48 (2009): 20234-20239.

Bigott-Hennkens et al. "In vitro receptor binding assays: general methods and considerations," *The Quarterly Journal of Nuclear Medicine and Molecular Imaging*, vol. 52, No. 3 (Sep. 1, 2008): 245-253.

Bonsignori, et al. "Analysis of a clonal lineage of HIV-1 envelope V2/V3 conformational epitope-specific broadly neutralizing antibodies and their inferred unmutated common ancestors." *Journal of Virology*, 85.19 (2011): 9998-10009.

Burton, et al. "Efficient neutralization of primary isolates of HIV-1 by a recombinant human monoclonal antibody." *Science*, 266.5187 (1994): 1024-1027.

Cardoso, et al. "Broadly neutralizing anti-HIV antibody 4E10 recognizes a helical conformation of a highly conserved fusion-associated motif in gp41." *Immunity*, 22.2 (2005): 163-173.

Cardoso, et al. "Structural basis of enhanced binding of extended and helically constrained peptide epitopes of the broadly neutralizing HIV-1 antibody 4E10." *Journal of Molecular Biology*, 365.5 (2007): 1533-1544.

Chakrabarti, et al. "Direct antibody access to the HIV-1 membrane-proximal external region positively correlates with neutralization sensitivity." *Journal of Virology*, 85.16 (2011): 8217-8226.

Doria-Rose, et al. "Breadth of human immunodeficiency virus-specific neutralizing activity in sera: clustering analysis and association with clinical variables." *Journal of Virology*, 84.3 (2010): 1631-1636.

Duebel, et al. "Handbook of Therapeutic Antibodies, Chapter 6." *Handbook of Therapeutic Antibodies*, Wiley-VCH, Weinheim (Jan. 1, 2007): 119-144.

Examination Report issued by the European Patent Office dated May 3, 2016, in corresponding EPC Patent Application No. 12847241. 2, filed Jun. 10, 2014 (6 pages).

Extended European Search Report mailed by the European Patent Office dated Feb. 24, 2015 in European Patent Application No. 12847241.2 (11 pages).

Frey, et al. "A fusion-intermediate state of HIV-1 gp41 targeted by broadly neutralizing antibodies." *Proceedings of the National Academy of Sciences*, 105.10 (2008): 3739-3744.

Georgiev et al. "Antibodies VRC01 and 10E8 neutralize HIV-1 with high breadth and potency even with Ig-framework regions substantially reverted to germline," *J. Immunol.* 192(2014): 1100-6.

Gray, et al. "Antibody specificities associated with neutralization breadth in plasma from human immunodeficiency virus type 1 subtype C-infected blood donors." *Journal of Virology*, 83.17 (2009): 8925-8937.

Gray, et al. "Broad neutralization of human immunodeficiency virus type 1 mediated by plasma antibodies against the gp41 membrane proximal external region." *Journal of Virology*, 83.21 (2009): 11265-11274.

Gray, et al. "Neutralizing antibody responses in acute human immunodeficiency virus type 1 subtype C infection." *Journal of Virology*, 81.12 (2007): 6187-6196.

Haynes, et al. "B-cell-lineage immunogen design in vaccine development with HIV-1 as a case study." *Nature Biotechnology*, 30.5 (2012): 423-433.

Haynes, et al. "Cardiolipin polyspecific autoreactivity in two broadly neutralizing HIV-1 antibodies." *Science*, 308.5730 (2005): 1906-1908.

Huang, et al. "Broad and potent HIV-1 neutralization by a human antibody that binds the gp41-gp120 interface," *Nature*, 515, (2014): 1-17.

Huang, et al. "Broad and potent neutralization of HIV-1 by a gp41-specific human antibody." *Nature*, 491, (2012): 406-412.

International Search Report issued by the Australian Patent Office dated Jan. 10, 2013, in Application PCT/US2012/063958 (5 pages).

Julien, et al. "Structural details of HIV-1 recognition by the broadly neutralizing monoclonal antibody 2F5: epitope conformation, antigen-recognition loop mobility, and anion-binding site." *Journal of Molecular Biology*, 384.2 (2008): 377-392.

Kershaw, et al. "Immunization against endogenous retroviral tumor-associated antigens." *Cancer Research*, 61.21, (2001): 7920-7924.

Konforte, et al. "IL-21: an executor of B cell fate." *The Journal of Immunology*, 182.4, (2009): 1781-1787.

Kwon, et al. "Enhancing the solubility of HIV-1-neutralizing Antibody 10E8." *AIDS Research and Human Retroviruses* 30, No. S1 (2014): A150-A150.

Kwon, et al. "Optimization of the solubility of HIV-1-neutralizing antibody 10E8 through somatic variation and structure-based design." *Journal of Virology* 90, No. 13 (2016): 5899-5914.

Kwon, et al. "Surface-Matrix Screening Identifies Semi-specific Interactions that Improve Potency of a Near Pan-reactive HIV-1-Neutralizing Antibody." *Cell Reports* 22, No. 7 (2018): 1798-1809.

Li, et al. "Human immunodeficiency virus type 1 env clones from acute and early subtype B infections for standardized assessments of vaccine-elicited neutralizing antibodies." *Journal of Virology*, 79.16 (2005): 10108-10125.

Liu, et al. "Potent and broad anti-HIV-1 activity exhibited bv a glycosyl-phosphatidylinositol-anchored peptide derived from the CDR H3 of broadly neutralizing antibody PG16." *Journal of Virology*, 85.17, (2011): 8467-8476.

Migueles, et al. "Lytic Granule Loading of CD8<sup>+</sup> T Cells Is Required for HIV-Infected Cell Elimination Associated with Immune Control." *Immunity*, 29.6 (2008): 1009-1021.

Montero, et al. "The membrane-proximal external region of the human immunodeficiency virus type 1 envelope: dominant site of antibody neutralization and target for vaccine design." *Microbiology and Molecular Biology Reviews* 72.1 (2008): 54-84.

Morris, et al. "Isolation of a human anti-HIV gp41 membrane proximal region neutralizing antibody by antigen-specific single B cell sorting." *PloS One*, 6.9 (2011): e23532.

Muster, et al. "A conserved neutralizing epitope on gp41 of human immunodeficiency virus type 1." *Journal of Virology*, 67.11 (1993): 6642-6647.

Nelson, et al. "An affinity-enhanced neutralizing antibody against the membrane-proximal external region of human immunodeficiency virus type 1 gp41 recognizes an epitope between those of 2F5 and 4E10." *Journal of Virology*, 81.8, (2007): 4033-4043.

Ofek, et al. "Elicitation of structure-specific antibodies by epitope scaffolds." *Proceedings of the National Academy of Sciences*, 107.42 (2010): 17880-17887.

Ofek, et al. "Structure and mechanistic analysis of the anti-human immunodeficiency virus type 1 antibody 2F5 in complex with its gp41 epitope." *Journal of Virology*, 78.19 (2004): 10724-10737/.

Ohno, et al. "Antigen-binding specificities of antibodies are primarily determined by seven residues of VH." *Proceedings of the National Academy of Sciences* 82, No. 9 (1985): 2945-2949.

Pegu et al. "Neutralizing antibodies to HIV-1 envelope protect more effectively in vivo than those to the CD4 receptor." *Science Translational Medicine* 6.243 (2014): 243ra88-243ra88.

(56) References Cited

OTHER PUBLICATIONS

Pejchal, et al. "A conformational switch in human immunodeficiency virus gp41 revealed by the structures of overlapping epitopes recognized by neutralizing antibodies." *Journal of Virology*, 83.17, (2009): 8451-8462.
Rathinakumar, et al. "Binding of anti-membrane-proximal gp41 monoclonal antibodies to CD4-liganded and-unliganded human immunodeficiency virus type 1 and simian immunodeficiency virus virions." *Journal of Virology*, 86.3 (2012): 1820-1831.
Rudikoff et al. "Single amino acid substitution altering antigen-binding specificity." *Proceedings of the National Academy of Sciences* 79, No. 6 (1982): 1979-1983.
Schaefer, et al. "Immunoglobulin domain crossover as a generic approach for the production of bispecific IgG antibodies." *Proceedings of the National Academy of Sciences* 108, No. 27 (2011): 11187-11192.
Scheid, et al. "A method for identification of HIV gp140 binding memory B cells in human blood." *Journal of Immunological Methods*, 343.2, (2009): 65-67.
Scheid, et al. "Broad diversity of neutralizing antibodies isolated from memory B cells in HIV-infected individuals." *Nature*, 458. 7238, (2009): 636-640.
Scheid, et al. "Sequence and structural convergence of broad and potent HIV antibodies that mimic CD4 binding." *Science*, 333.6049 (2011): 1633-1637.
Song, et al. "Broadly neutralizing anti-HIV-1 antibodies disrupt a hinge-related function of gp41 at the membrane interface." *Proceedings of the National Academy of Sciences*, 106.22, pp. 9057-9062 (2009): 9057-9062.
Story, et al. "Profiling antibody responses by multi parametric analysis of primary B cells." *Proceedings of the National Academy of Sciences*, 105.46 (2008): 17902-17907.
Tiller, et al. "Efficient generation of monoclonal antibodies from single human B cells by single cell RT-PCR and expression vector cloning." *Journal of Immunological Methods*, 329.1 (2008): 112-124.
Tomaras, et al. "Polyclonal B cell responses to conserved neutralization epitopes in a subset of HIV-1-infected individuals." *Journal of Virology*, 85.21 (2011): 11502-11519.
Walker, et al. "A limited number of antibody specificities mediate broad and potent serum neutralization in selected HIV-1 infected individuals."*PLoS Ppathogens*, 6.8 (2010): e1001028.
Walker, et al. "Broad and potent neutralizing antibodies from an African donor reveal a new HIV-1 vaccine target." *Science*, 326. 5950, (2009): 285-289.
Walker, et al. "Broad neutralization coverage of HIV by multiple highly potent antibodies." *Nature*, 477.7365 (2011): 466-470.
Walker, et al. "Rational antibody-based HIV-1 vaccine design: current approaches and future directions." *Current opinion in immunology*, 22.3 (2010): 358-366.
Ward, et al. "Targeting FcRn for the modulation of antibody dynamics." *Molecular Immunology* 67, No. 2 (2015): 131-141.
Written Opinion issued by the Australian Patent Office dated Jan. 10, 2013, in Application PCT/US2012/063958 (5 pages).
Wu, et al. "Focused evolution of HIV-1 neutralizing antibodies revealed by structures and deep sequencing." *Science*, 333.6049 (2011): 1593-1602.
Wu, et al. "Rational design of envelope identifies broadly neutralizing human monoclonal antibodies to HIV-1." *Science*, 329.5993 (2010): 856-861.
Wu et al. "Selection pressure on HIV-1 envelope by broadly neutralizing antibodies to the conserved CD4-binding site." *Journal of Virology*, 86.10 (2012): 5844-5856.
Zhou et al. "Transplanting Supersites of HIV-1 Vulnerability." *PloS One* 9.1 (2014): e99881.
Zhu, et al. "Mining the antibodyome for HIV-1-neutralizing antibodies with nextgeneration sequencing and phylogenetic pairing of heavy/light chains." *Proceedings of the National Academy of Sciences* 110 (2013): 6470-6475.
Zhu, et al. "Somatic populations of PGT135-137 HIV-1-neutralizing antibodies identified by 454 pyrosequencing and bioinformatics." *Frontiers in Microbiology*, 3 (2012).
Zwick, et al. "Anti-human immunodeficiency virus type 1 (HIV-1) antibodies 2F5 and 4E10 require surprisingly few crucial residues in the membrane-proximal external region of glycoprotein gp41 to neutralize HIV-1." *Journal of Virology*, 19.2 (2005): 1252-1261.
Zwick, et al. "Broadly neutralizing antibodies targeted to the membrane-proximal external region of human immunodeficiency virus type 1 glycoprotein gp41." *Journal of Virology*, 75.22 (2001): 10892-10905.

\* cited by examiner

FIG. 1A

V_H Kabat numbering, IMGT CDRs

```
                  1         10        20        30              40        50  52abc
                  -         -         -         -               -         -   |||
                                                                                |||
10E8 WT           EVQLVESGGGLVKPGGSLRLSCSAS GFDFDNAW MTWVRQPPGKGLEWVGR ITGPGEGWSV
HC6-S74Y          EVRLAESGGGLVKPGGSLRLSCSAS GFDFDNAW MTWVRQPPGKGLEWVGR ITGPGEGWSV
HC6-S74Y-511      EVRLAESGGGLVKPGGSLRLSCSAS GFDFDNAW MTWVRQPPGKGLEWVGR ITGPGEGWSV
H6                EVRLVESGGGLVKPGGSLRLSCSAS GFNFDDAW MTWVRQPPGKGLEWVGR ISGPGEGWSV
H6-511            EVRLVESGGGLVKPGGSLRLSCSAS GFNFDDAW MTWVRQPPGKGLEWVGR ISGPGEGWSV
H6-511-4mut       EVRLVESGGGLVKPGGSLRLSCSAS GFDFDNAW MTWVRQPPGKGLEWVGR ITGPGEGWSV
IMGT              -------FR1--------------- ---CDR1- -----FR2--------- ---CDR2-

60        70        8082abc         90                     100abcdefghijkl       110
                  -         -         ||||            -                      ||||||||||||||        -
                                                                                                    -
10E8 WT           DYAAPVEGRFTISRLNSINFLYLEMNNLRMEDSGLYFC ARTGKYYDFWSGYPPGEEYFQD WGRGTLVTVSS
HC6-S74Y          DYAAPVEGRFTISRLNYINFLYLEMNNLRMEDSGLYFC ARTGKYYDFWSGYPPGEEYFQD WGRGTLVIVSS
HC6-S74Y-511      DYAAPVEGRFTISRDNYKNTLYLEMNNLRTEDSGLYFC ARTGKYYDFWSGYPPGEEYFQD WGRGTLVIVSS
H6                DYAESVKGRFTISRLNSINFLYLEMNNVRTEDTGYYFC ARTGKHYDFWSGYPPGEEYFQD WGRGTLVIVSS
H6-511            DYAESVKGRFTISRDNTKNTLYLEMNNVRTEDTGYYFC ARTGKHYDFWSGYPPGEEYFQD WGQGTLVIVSS
H6-511-4mut       DYAESVKGRFTISRDNTKNTLYLEMNNVRTEDTGYYFC ARTGKYYDFWSGYPPGEEYFQD WGQGTLVIVSS
IMGT              ------------FR3---------------------- --------CDR3---------- ----FR4----
```

FIG. 1C

V_H Kabat numbering, kabat CDRs

```
                    1           10          20          30                    40                   5052abc      60
                    |           |           |           |                     |                    ||||         |
10E8 WT             EVQLVESGGGLVKPGGSLRLSCSASGFDFD   NAWMT   WVRQPPGKGLEWVG    RITGPGEGWSVDYAAPVEG
HC6-S74Y            EVRLAESGGGLVKPGGSLRLSCSASGFDFD   NAWMT   WVRQPPGKGLEWVG    RITGPGEGWSVDYAAPVEG
HC6-S74Y-511        EVRLAESGGGLVKPGGSLRLSCSASGFDFD   NAWMT   WVRQPPGKGLEWVG    RITGPGEGWSVDYAAPVEG
H6                  EVRLVESGGGLVKPGGSLRLSCSASGFNFD   DAWMT   WVRQPPGKGLEWVG    RISGPGEGWSVDYAESVKG
H6-511              EVRLVESGGGLVKPGGSLRLSCSASGFNFD   DAWMT   WVRQPPGKGLEWVG    RISGPGEGWSVDYAESVKG
H6-511-4mut         EVRLVESGGGLVKPGGSLRLSCSASGFDFD   NAWMT   WVRQPPGKGLEWVG    RITGPGEGWSVDYAESVKG
kabat               -------FR1-------------------   -CDR1-  ----FR2-------    ---CDR2----------

70          8082abc     90                 100abcdefghijkl              110
                    |           ||||        |                  ||||||||||||||                |
10E8 WT             RFTISRLNSINFLYLEMNNLRMEDSGLYFCAR   TGKYYDFWSGYPPGEEYFQD    WGRGTLVTVSS
HC6-S74Y            RFTISRLNYINFLYLEMNNLRMEDSGLYFCAR   TGKYYDFWSGYPPGEEYFQD    WGRGTLVTVSS
HC6-S74Y-511        RFTISRDNYKNTLYLEMNNLRTEDSGLYFCAR   TGKYYDFWSGYPPGEEYFQD    WGRGTLVIVSS
H6                  RFTISRLNSINFLYLEMNNLRTEDSGLYFCAR   TGKHYDFWSGYPPGEEYFQD    WGQGTLVIVSS
H6-511              RFTISRDNTKNTLYLEMNNVRTEDTGYYFCAR   TGKHYDFWSGYPPGEEYFQD    WGQGTLVIVSS
H6-511-4mut         RFTISRDNTKNTLYLEMNNVRTEDTGYYFCAR   TGKYYDFWSGYPPGEEYFQD    WGQGTLVIVSS
kabat               -----------FR3-----------------   -------CDR3---------    ---FR4---
```

FIG. 1E

V_H Kabat numbering, IMGT CDRs

```
                      1           10          20          30          40          50  52abc
                      |           |           |           |           |           |   ||||
10E8 WT               EVQLVESGGGLVKPGGSLRLSCSAS  GFDFDNAW  MTWVRQPPGKGLEWVGR  ITGPGEGWSV
10E8v4                EVRLVESGGGLVKPGGSLRLSCSAS  GFDFDNAW  MTWVRQPPGKGLEWVGR  ITGPGEGWSV
10E8v4 S100cF         EVRLVESGGGLVKPGGSLRLSCSAS  GFDFDNAW  MTWVRQPPGKGLEWVGR  ITGPGEGWSV
10E8v4 V5R S100cF     EVRLRESGGGLVKPGGSLRLSCSAS  GFDFDNAW  MTWVRQPPGKGLEWVGR  ITGPGEGWSV
IMGT                  --------FR1-------------   --CDR1--  -------FR2-------  ---CDR2---

60          70      8082abc        90                      100abcdefghijkl        110
                      |           |       ||||           |                       |||||||||||||||        |
10E8 WT               DYAAPVEGRFTISRLNSINFLYLEMNNLRMEDSGLYFC  ARTGKYDFWSGYPPGEEYFQD  WGRGTLVTVSS
10E8v4                DYAESVKGRFTISRDNTKNTLYLEMNNVRTEDTGYYFC  ARTGKYDFWSGYPPGEEYFQD  WGQGTLVIVSS
10E8v4 S100cF         DYAESVKGRFTISRDNTKNTLYLEMNNVRTEDTGYYFC  ARTGKYDFWFGYPPGEEYFQD  WGQGTLVIVSS
10E8v4 V5R S100cF     DYAESVKGRFTISRDNTKNTLYLEMNNVRTEDTGYYFC  ARTGKYDFWFGYPPGEEYFQD  WGQGTLVIVSS
IMGT                  --------------FR3-------------------   --------CDR3--------   ---FR4---
```

| virus | HC6-S74Y-511 + rL3 | HC6-S74Y + rL3 | 10E8 WT |
|---|---|---|---|
| Q23.17.SG3 | 3.900 | 1.390 | 5.020 |
| UG037.8.SG3 | 0.359 | 0.187 | 1.030 |
| AC10.29.SG3 | 0.224 | 0.217 | 0.699 |
| JRFL.JB.SG3 | 2.020 | 0.713 | 2.070 |
| DU151.02.SG3 | 1.260 | 1.180 | 3.100 |
| ZM53.12.SG3 | 6.600 | 4.710 | 12.000 |
| ZM106.9.SG3 | 50.000 | 50.000 | 50.000 |
| TV1.29.SG3 | 0.401 | 0.450 | 1.190 |
| Median IC80 | 1.640 | 0.947 | 2.585 |
| Geometric Mean | 1.790 | 1.224 | 3.368 |

| clade | virus | 1<br>10E8_H6_511<br>/L3<br>YDK | 7<br>10E8_H6_511<br>_H98Y_N28D<br>_D31N_S52T/<br>L3<br>YDK | 8<br>10E8_H6_520<br>_H98Y_N28D<br>_D31N_S52T/<br>L3<br>YDK | 10E8<br>10E8wt<br>YDK |
|---|---|---|---|---|---|
| A | KER2008.12.SG3 | >50 | >50 | >50 | >25 |
| ACD | 6095.V1.C10.SG3 | | | | |
| AE | TH966.8.SG3 | | | | |
| B | 6101.10.SG3 | | | | |
| B | PVO.04.SG3 | 1.72 | 0.943 | 0.287 | 1.90 |
| B | YU2.DG.SG3 | 3.20 | 2.04 | 1.11 | 2.80 |
| C | CNE31.SG3 | 1.99 | 1.68 | 0.584 | 1.73 |
| C | ZM106.9.SG3 | >50 | >50 | >50 | >25 |
| C | ZM215.8.SG3 | | | | |
| | Geometric Mean | 0.125 | 0.072 | 0.041 | 0.140 |

1. H6-511 $V_H$ + rL3 $V_L$
7. H6-511-N28D-D31N-S52T-H98Y $V_H$ + rL3 $V_L$
8. H6-520-N28D-D31N-S52T-H98Y $V_H$ +rL3 $V_L$

Turbidity at 1X PBS

Turbidity at 1X PBS (by dialysis)

All light chains paired with 10E8 $V_H$
Light Chain Variants (conc. 0.3 mg/ml)

1. H6-511-4mut $V_H$ + rL3 $V_L$
2. H6-511-4mut $V_H$ + rL3-6mut $V_L$

| clade | virus | 10E8_H6_511/L3 | 1 | 2 | 10E8wt |
|---|---|---|---|---|---|
| A | KER2008.12.SG3 | >50 | >50 | >50 | >25 |
| ACD | 6095.V1.C10.SG3 | | | | |
| AE | TH966.8.SG3 | | | | |
| B | 6101.10.SG3 | | | | |
| B | PVO.04.SG3 | 1.72 | 0.943 | 1.10 | 1.90 |
| B | YU2.DG.SG3 | 3.20 | 2.04 | 2.03 | 2.80 |
| C | CNE31.SG3 | 1.99 | 1.68 | 1.08 | 1.73 |
| C | ZM106.9.SG3 | >50 | >50 | >50 | >25 |
| C | ZM215.8.SG3 | | | | |
| | Geometric Mean | 0.125 | 0.072 | 0.073 | 0.140 |

IC80 (μg/ml)

| | | | | |
|---|---|---|---|---|
| >50 | >50 | >50 | >25 |
| | | | |
| 0.172 | 0.118 | 0.151 | 0.253 |
| 0.648 | 0.109 | 0.151 | 0.217 |
| 7.67 | 5.49 | 6.42 | 9.57 |
| 14.7 | 9.99 | 10.7 | 16.3 |
| 2.24 | 3.19 | 3.07 | 5.33 |
| >50 | >50 | >50 | >25 |
| 0.194 | 0.142 | 0.114 | 0.304 |
| 0.706 | 0.440 | 0.504 | 0.814 |

1. H6-511-4mut $V_H$ + rL3 $V_L$
2. H6-511-4mut $V_H$ + rL3-6mut $V_L$

Volume after centrifugation

Protein oncentration
after centrifugation (OD)

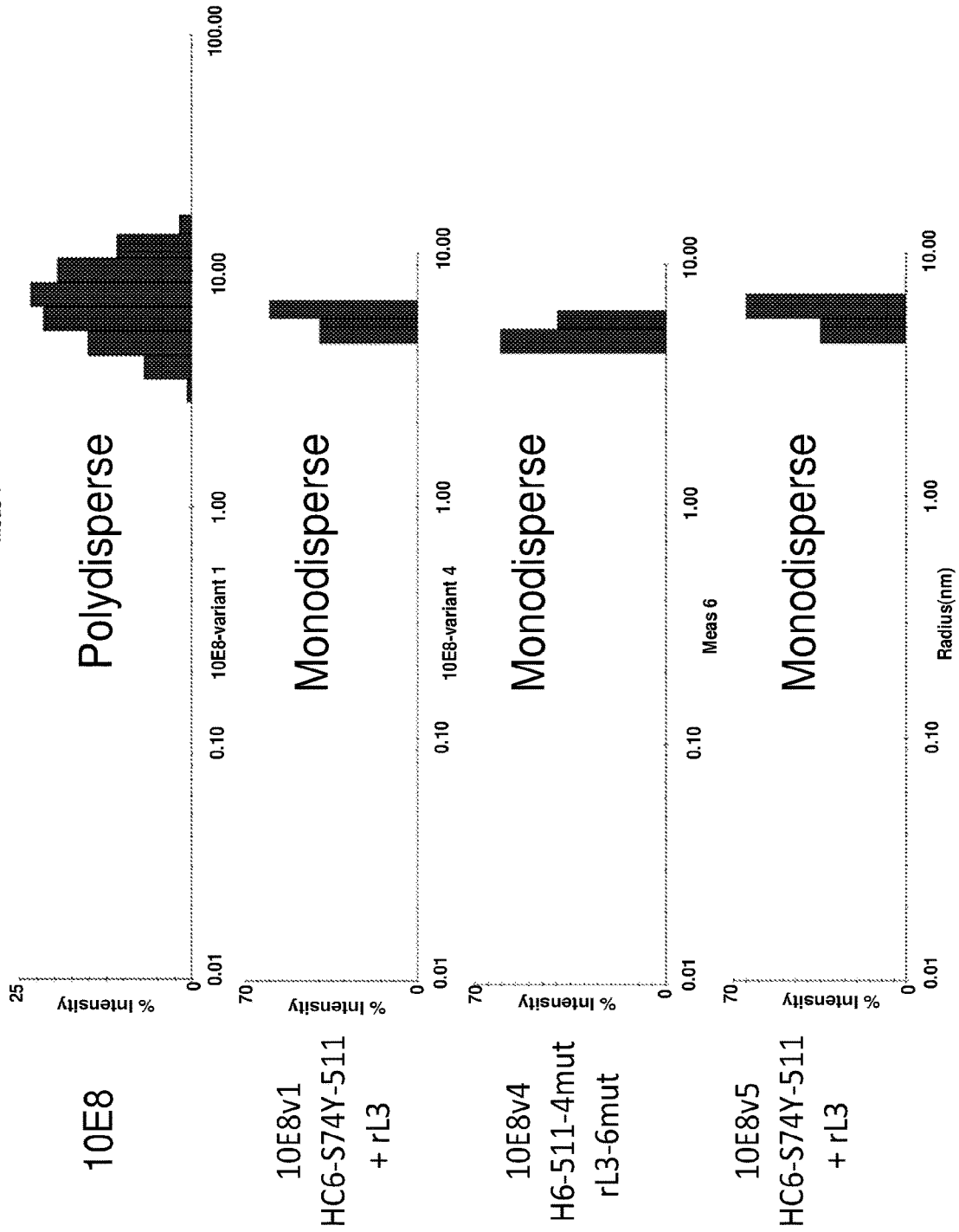

FIG. 16A

| Virus ID | Clade | 10E8 Var1 | 10E8 Var4 | 10E8 Var5 | 10E8 | Virus ID | Clade | 10E8 Var1 | 10E8 Var4 | 10E8 Var5 | 10E8 |
|---|---|---|---|---|---|---|---|---|---|---|---|
| 0260.v5.c36 | A | 9.170 | 11.500 | 10.400 | 9.870 | M02138 | AE | | | | |
| 0330.v4.c3 | A | 1.510 | 2.090 | 1.740 | 1.120 | R1166.c1 | AE | 0.415 | 0.431 | 0.534 | 0.488 |
| 0439.v5.c1 | A | 0.982 | 1.490 | 1.490 | 1.230 | R2184.c4 | AE | 0.662 | 0.594 | 0.518 | 0.576 |
| 3365.v2.c20 | A | 1.310 | 1.240 | 1.280 | 1.600 | R3265.c6 | AE | 1.540 | 1.990 | 1.480 | 1.580 |
| 3415.v1.c1 | A | 3.520 | 4.400 | 4.240 | 4.690 | TH023.6 | AE | | | | |
| 3718.v3.c11 | A | 1.130 | 1.840 | 1.680 | 0.838 | TH966.8 | AE | 0.034 | 0.046 | 0.051 | 0.039 |
| 398-F1_F6_20 | A | 1.080 | 1.470 | 0.857 | 0.704 | TH976.17 | AE | 0.582 | 0.473 | 0.359 | 0.392 |
| BB201.B42 | A | 0.680 | 0.849 | 1.010 | 0.613 | 235-47 | AG | 0.119 | 0.121 | 0.112 | 0.244 |
| BB539.2B13 | A | | | | | 242-14 | AG | 0.460 | 0.431 | 0.431 | 0.568 |
| BG505.W6M.C2 | A | 0.469 | 0.555 | 0.803 | 0.689 | 263-8 | AG | 0.103 | 0.104 | 0.192 | 0.229 |
| BI369.9A | A | 0.315 | 0.393 | 0.414 | 0.356 | 269-12 | AG | 0.025 | 0.095 | 0.142 | 0.124 |
| BS208.B1 | A | 0.252 | 0.324 | 0.332 | 0.319 | 271-11 | AG | 0.686 | 0.882 | 0.836 | 0.891 |
| KER2008.12 | A | 100 | 100 | 100 | 100 | 928-28 | AG | 0.013 | 0.018 | 0.021 | 0.079 |
| KER2018.11 | A | 1.600 | 2.320 | 2.250 | 1.890 | DJ263.8 | AG | 0.0008 | 0.002 | 0.003 | 0.009 |
| KNH1209.18 | A | 0.315 | 0.468 | 0.325 | 0.406 | T250-4 | AG | 0.745 | 0.823 | 0.804 | 1.070 |
| MB201.A1 | A | 0.346 | 0.492 | 0.374 | 0.411 | T251-18 | AG | 0.426 | 0.336 | 0.307 | 0.666 |
| MB539.2B7 | A | 28.700 | 30.300 | 21.500 | 100.000 | T253-11 | AG | 0.960 | 1.160 | 0.986 | 1.210 |
| MI369.A5 | A | 0.835 | 1.170 | 0.904 | 0.671 | T255-34 | AG | 0.149 | 0.183 | 0.202 | 0.228 |
| MS208.A1 | A | 0.546 | 0.889 | 0.392 | 0.187 | T257-31 | AG | 0.435 | 0.304 | 0.368 | 0.336 |
| Q23.17 | A | 0.931 | 1.180 | 0.667 | 0.461 | T266-60 | AG | 100 | 100 | 100 | 100 |
| Q259.17 | A | 4.100 | 3.370 | 5.060 | 4.760 | T278-50 | AG | 0.303 | 0.293 | 0.253 | 0.357 |
| Q769.d22 | A | 1.390 | 1.590 | 1.720 | 1.910 | T280-5 | AG | | | | |
| Q769.h5 | A | 2.530 | 2.840 | 3.000 | 2.890 | T33-7 | AG | 0.897 | 1.010 | 1.240 | 0.818 |
| Q842.d12 | A | 2.320 | 1.990 | 2.600 | 2.820 | 3988.25 | B | 0.029 | 0.050 | 0.080 | 0.070 |
| QH209.14M.A2 | A | 1.080 | 0.867 | 0.887 | 1.300 | 5768.04 | B | 1.860 | 2.190 | 2.540 | 1.630 |
| RW020.2 | A | 1.020 | 1.020 | 0.883 | 0.902 | 6101.10 | B | 0.001 | 0.002 | 0.002 | 0.001 |
| UG037.8 | A | 0.035 | 0.080 | 0.058 | 0.048 | 6535.3 | B | 0.026 | 0.046 | 0.078 | 0.190 |
| 246-F3.C10.2 | AC | 0.072 | 0.088 | 0.128 | 0.210 | 7165.18 | B | 0.232 | 0.258 | 0.421 | 0.659 |
| 3301.V1.C24 | AC | 3.100 | 3.310 | 3.210 | 2.970 | 45_01dG5 | B | 0.198 | 0.182 | 0.276 | 0.106 |
| 3589.V1.C4 | AC | 3.370 | 5.150 | 4.860 | 5.770 | 89.6.DG | B | 0.264 | 0.126 | 0.378 | 0.318 |
| 6540.v4.c1 | AC | 2.510 | 2.320 | 2.870 | 2.240 | AC10.29 | B | 0.016 | 0.046 | 0.050 | 0.102 |
| 6545.V4.C1 | AC | 1.930 | 1.740 | 3.200 | 2.540 | ADA.DG | B | 0.010 | 0.023 | 0.036 | 0.055 |
| 0815.V3.C3 | ACD | 1.080 | 1.040 | 0.788 | 0.491 | Bal.01 | B | 0.412 | 0.531 | 0.661 | 0.421 |
| 6095.V1.C10 | ACD | 0.0003 | 0.0003 | 0.0003 | 0.0005 | BaL.26 | B | 0.506 | 0.524 | 0.811 | 0.518 |
| 3468.V1.C12 | AD | 0.318 | 0.307 | 0.291 | 0.381 | BG1168.01 | B | 0.142 | 0.305 | 0.233 | 0.396 |
| Q168.a2 | AD | 0.709 | 0.964 | 0.466 | 0.463 | BL01.DG | B | 0.427 | 0.505 | 0.521 | 0.362 |
| Q461.e2 | AD | 2.080 | 2.270 | 2.140 | 2.290 | BR07.DG | B | 0.064 | 0.099 | 0.162 | 0.118 |
| 620345.c1 | AE | 0.620 | 0.462 | 0.761 | 0.989 | BX08.16 | B | 0.089 | 0.108 | 0.184 | 0.213 |
| BJOX009000.02.4 | AE | 0.196 | 0.229 | 0.286 | 0.251 | CAAN.A2 | B | 2.350 | 2.330 | 3.570 | 1.450 |
| BJOX010000.06.2 | AE | 0.014 | 0.049 | 0.055 | 0.060 | CNE10 | B | 0.012 | 0.005 | 0.019 | 0.014 |
| BJOX025000.01.1 | AE | 0.095 | 0.234 | 0.209 | 0.228 | CNE12 | B | 0.119 | 0.130 | 0.240 | 0.301 |
| BJOX028000.10.3 | AE | 0.021 | 0.125 | 0.110 | 0.167 | CNE14 | B | 0.437 | 0.309 | 0.508 | 0.151 |
| C1080.c3 | AE | 0.030 | 0.038 | 0.112 | 0.108 | CNE4 | B | 0.062 | 0.057 | 0.121 | 0.059 |
| C2101.c1 | AE | 1.160 | 1.120 | 1.300 | 1.200 | CNE57 | B | 0.065 | 0.065 | 0.068 | 0.059 |
| C3347.c11 | AE | 0.002 | 0.005 | 0.002 | 0.019 | HO86.8 | B | 0.373 | 0.275 | 0.368 | 0.326 |
| C4118.09 | AE | 0.319 | 0.268 | 0.384 | 0.421 | HT593.1 | B | 0.029 | 0.031 | 0.038 | 0.049 |
| CM244.ec1 | AE | 0.714 | 0.890 | 0.432 | 0.365 | HXB2.DG | B | 0.0003 | .0003 | .0003 | 0.003 |
| CNE3 | AE | 0.924 | 0.528 | 1.280 | 1.370 | JRCSF.JB | B | 0.636 | 0.632 | 0.876 | 0.429 |
| CNE5 | AE | 0.792 | 0.678 | 0.900 | 1.170 | JRFL.JB | B | 0.219 | 0.313 | 0.318 | 0.174 |
| CNE55 | AE | 0.026 | 0.027 | 0.026 | 0.038 | MN.3 | B | .0003 | .0003 | .0003 | .0003 |
| CNE56 | AE | 0.022 | 0.029 | 0.026 | 0.060 | PVO.04 | B | 1.670 | 2.650 | 1.540 | 1.600 |
| CNE59 | AE | 0.0003 | .00071 | 0.0003 | 0.001 | QH0515.01 | B | 1.890 | 2.450 | 2.650 | 2.250 |
| CNE8 | AE | 0.051 | 0.096 | 0.090 | 0.140 | | | | | | |

FIG. 16B

| Virus ID | Clade | 10E8 Var1 | 10E8 Var4 | 10E8 Var5 | 10E8 | Virus ID | Clade | 10E8 Var1 | 10E8 Var4 | 10E8 Var5 | 10E8 |
|---|---|---|---|---|---|---|---|---|---|---|---|
| QH0692.42 | B | 0.474 | 0.492 | 0.348 | 0.531 | CAP45.G3 | C | 0.531 | 0.787 | 0.694 | 0.722 |
| REJO.67 | B | 0.419 | 0.451 | 0.425 | 0.302 | Ce1176.A3 | C | 0.226 | 0.311 | 0.341 | 0.252 |
| RHPA.7 | B | 0.925 | 0.981 | 0.968 | 1.010 | CE703010217.B6 | C | 0.049 | 0.137 | 0.113 | 0.096 |
| SC422.8 | B | 0.356 | 0.343 | 0.363 | 0.343 | CNE30 | C | 0.370 | 0.354 | 0.327 | 0.456 |
| SF162.LS | B | 0.639 | 0.701 | 0.673 | 0.245 | CNE31 | C | 0.805 | 0.785 | 1.220 | 1.320 |
| SS1196.01 | B | 0.165 | 0.119 | 0.173 | 0.244 | CNE53 | C | 0.108 | 0.130 | 0.091 | 0.213 |
| THRO.18 | B | 0.074 | 0.108 | 0.105 | 0.092 | CNE58 | C | 0.119 | 0.193 | 0.240 | 0.229 |
| TRJO.58 | B | 2.980 | 3.130 | 2.390 | 1.130 | DU123.06 | C | 0.053 | 0.046 | 0.062 | 0.132 |
| TRO.11 | B | 0.059 | 0.072 | 0.048 | 0.028 | DU151.02 | C | 0.481 | 0.321 | 0.499 | 0.461 |
| WITO.33 | B | 0.051 | 0.045 | 0.042 | 0.031 | DU156.12 | C | 0.004 | 0.003 | 0.008 | 0.023 |
| X2278.C2.B1 | B | 0.605 | 0.611 | 0.671 | 0.442 | DU172.17 | C | 0.018 | 0.011 | 0.030 | 0.057 |
| YU2.DG | B | 2.070 | 1.990 | 2.200 | 1.170 | DU422.01 | C | 0.247 | 0.202 | 0.337 | 0.224 |
| BJOX002000.03.2 | BC | 0.147 | 0.254 | 0.502 | 0.384 | MW965.26 | C | 0.000 | 0.000 | 0.000 | 0.001 |
| CH038.12 | BC | 0.230 | 0.265 | 0.275 | 0.271 | SO18.18 | C | 1.080 | 0.675 | 1.150 | 1.600 |
| CH070.1 | BC | 5.500 | 5.730 | 7.840 | 6.650 | TV1.29 | C | 0.408 | 0.421 | 0.310 | 0.248 |
| CH117.4 | BC | 0.225 | 0.222 | 0.303 | 0.270 | TZA125.17 | C | 0.250 | 0.218 | 0.154 | 0.217 |
| CH119.10 | BC | 0.664 | 0.344 | 0.667 | 0.591 | TZBD.02 | C | 2.010 | 1.960 | 1.720 | 1.410 |
| CH181.12 | BC | 0.683 | 0.602 | 1.000 | 0.754 | ZA012.29 | C | 1.290 | 1.660 | 1.670 | 1.470 |
| CNE15 | BC | 0.503 | 0.568 | 0.742 | 0.844 | ZM106.9 | C | 100 | 100 | 100 | 100 |
| CNE19 | BC | 0.146 | 0.155 | 0.154 | 0.251 | ZM109.4 | C | 0.063 | 0.118 | 0.096 | 0.161 |
| CNE20 | BC | 0.066 | 0.102 | 0.132 | 0.131 | ZM135.10a | C | 0.020 | 0.040 | 0.051 | 0.033 |
| CNE21 | BC | 0.509 | 0.354 | 0.499 | 0.979 | ZM176.66 | C | 0.386 | 0.590 | 0.661 | 0.267 |
| CNE40 | BC | 0.000 | 0.001 | 0.001 | 0.001 | ZM197.7 | C | 0.015 | 0.022 | 0.040 | 0.055 |
| CNE7 | BC | 0.072 | 0.093 | 0.093 | 0.130 | ZM214.15 | C | 2.040 | 2.140 | 2.920 | 2.220 |
| 286.36 | C | 0.529 | 0.746 | 0.853 | 1.190 | ZM215.8 | C | 0.008 | 0.026 | 0.024 | 0.044 |
| 288.38 | C | 0.385 | 0.491 | 0.462 | 0.435 | ZM233.6 | C | 0.122 | 0.214 | 0.194 | 0.270 |
| 0013095-2.11 | C | 0.002 | 0.002 | 0.002 | 0.009 | ZM249.1 | C | 0.704 | 0.682 | 0.752 | 0.830 |
| 001428-2.42 | C | 2.240 | 0.726 | 1.890 | 1.710 | ZM53.12 | C | 2.300 | 2.160 | 3.080 | 2.620 |
| 0077_V1.C16 | C | 1.410 | 1.310 | 2.600 | 1.860 | ZM55.28a | C | 2.750 | 2.560 | 2.980 | 2.340 |
| 00836-2.5 | C | 0.538 | 0.445 | 0.452 | 0.666 | 3326.V4.C3 | CD | 1.180 | 1.260 | 0.664 | 1.400 |
| 0921.V2.C14 | C | 1.160 | 1.680 | 1.130 | 0.908 | 3337.V2.C6 | CD | 0.883 | 1.400 | 0.825 | 1.090 |
| 16055-2.3 | C | 1.040 | 1.480 | 1.280 | 1.100 | 3817.v2.c59 | CD | 0.543 | 1.210 | 0.679 | 0.229 |
| 16845-2.22 | C | 0.007 | 0.010 | 0.010 | 0.020 | 191821.E6.1 | D | | | | |
| 16936-2.21 | C | 0.205 | 0.353 | 0.259 | 0.264 | 231965.c1 | D | 8.010 | 8.660 | 9.400 | 11.000 |
| 25710-2.43 | C | 0.011 | 0.025 | 0.053 | 0.064 | 247-23 | D | 0.245 | 0.441 | 0.403 | 0.344 |
| 25711-2.4 | C | 0.652 | 0.595 | 0.669 | 0.516 | 3016.v5.c45 | D | 0.610 | 0.604 | 0.580 | 0.710 |
| 25925-2.22 | C | 0.234 | 0.461 | 0.456 | 0.402 | 57128.vrc15 | D | 0.123 | 0.067 | 0.195 | 0.212 |
| 26191-2.48 | C | 1.550 | 0.969 | 1.260 | 1.830 | 6405.v4.c34 | D | 0.781 | 0.617 | 1.080 | 0.461 |
| 3168.V4.C10 | C | 2.020 | 2.940 | 1.920 | 2.830 | A03349M1.vrc4a | D | 0.169 | 0.332 | 0.288 | 0.270 |
| 3637.V5.C3 | C | 1.530 | 2.480 | 2.120 | 2.120 | A07412M1.vrc12 | D | 0.094 | 0.119 | 0.145 | 0.140 |
| 3873.V1.C24 | C | 3.380 | 3.300 | 4.700 | 5.510 | NKU3006.ec1 | D | 0.726 | 1.020 | 0.616 | 0.673 |
| 6322.V4.C1 | C | 0.372 | 0.691 | 0.706 | 0.923 | UG021.16 | D | | | | |
| 6471.V1.C16 | C | 4.650 | 5.370 | 6.740 | 4.980 | UG024.2 | D | | | | |
| 6631.V3.C10 | C | 1.360 | 1.440 | 2.300 | 0.934 | P0402.c2.11 | G | 0.032 | 0.055 | 0.081 | 0.057 |
| 6644.V2.C33 | C | 0.008 | 0.011 | 0.029 | 0.013 | P1981.C5.3 | G | 0.004 | 0.010 | 0.005 | 0.024 |
| 6785.V5.C14 | C | 0.756 | 1.100 | 0.924 | 0.701 | X1193.c1 | G | 0.222 | 0.201 | 0.354 | 0.341 |
| 6838.V1.C35 | C | 0.168 | 0.153 | 0.354 | 0.292 | X1254.c3 | G | 2.070 | 2.370 | 2.940 | 3.670 |
| 96ZM651.02 | C | 0.004 | 0.009 | 0.010 | 0.033 | X1632.S2.B10 | G | 0.289 | 0.285 | 0.415 | 0.387 |
| BR025.9 | C | 0.235 | 0.498 | 0.398 | 0.307 | X2088.c9 | G | 100 | 100 | 100 | 100 |
| CAP210.E8 | C | 0.346 | 0.439 | 0.321 | 0.474 | X2131.C1.B5 | G | 0.003 | 0.010 | 0.015 | 0.039 |
| CAP244.D3 | C | 0.239 | 0.334 | 0.307 | 0.369 | SIVmac251.30.SG3 | NA | >50 | >50 | >50 | >50 |
| CAP256.206.C9 | C | 0.657 | 0.913 | 0.804 | 0.713 | SVA.MLV | NA | >50 | >50 | >50 | >50 |

FIG. 16C

|  | 10E8 Var1 | 10E8 Var4 | 10E8 Var5 | 10E8 |
|---|---|---|---|---|
| # Viruses | 200 | 200 | 200 | 200 |
| Total Virus Neutralized | | | | |
| IC50 <50ug/ml | 196 | 196 | 196 | 195 |
| IC50 <10ug/ml | 195 | 194 | 194 | 194 |
| IC50 <1.0ug/ml | 148 | 143 | 146 | 145 |
| IC50 <0.1ug/ml | 53 | 46 | 42 | 38 |
| IC50 <0.01ug/ml | 17 | 13 | 12 | 9 |
| % Virus Neutralized | | | | |
| IC50 <50ug/ml | 98 | 98 | 98 | 98 |
| IC50 <10ug/ml | 98 | 97 | 97 | 97 |
| IC50 <1.0ug/ml | 74 | 72 | 73 | 73 |
| IC50 <0.1ug/ml | 27 | 23 | 21 | 19 |
| IC50 <0.01ug/ml | 9 | 7 | 6 | 5 |
| Median IC50 | 0.397 | 0.435 | 0.418 | 0.392 |
| Geometric Mean | 0.228 | 0.276 | 0.307 | 0.315 |

FIG. 16D

| Virus ID | Clade | 10E8 Var1 | 10E8 Var4 | 10E8 Var5 | 10E8 | Virus ID | Clade | 10E8 Var1 | 10E8 Var4 | 10E8 Var5 | 10E8 |
|---|---|---|---|---|---|---|---|---|---|---|---|
| 0260.v5.c36 | A | 14.100 | 30.200 | 26.700 | 21.700 | M02138 | AE | | | | |
| 0330.v4.c3 | A | 4.150 | 6.580 | 4.720 | 3.640 | R1166.c1 | AE | 2.000 | 2.600 | 1.870 | 2.020 |
| 0439.v5.c1 | A | 3.420 | 5.210 | 4.170 | 3.950 | R2184.c4 | AE | 2.190 | 2.700 | 2.050 | 2.200 |
| 3365.v2.c20 | A | 4.150 | 4.980 | 3.940 | 4.560 | R3265.c6 | AE | 8.400 | 9.750 | 8.610 | 9.280 |
| 3415.v1.c1 | A | 9.390 | 11.700 | 14.000 | 11.500 | TH023.6 | AE | | | | |
| 3718.v3.c11 | A | 4.360 | 6.970 | 6.840 | 4.420 | TH966.8 | AE | 0.392 | 0.440 | 0.339 | 0.291 |
| 398-F1_F6_20 | A | 5.440 | 10.600 | 7.230 | 6.170 | TH976.17 | AE | 2.390 | 2.340 | 1.850 | 1.750 |
| BB201.B42 | A | 3.490 | 4.240 | 3.620 | 1.960 | 235-47 | AG | 0.664 | 1.110 | 0.596 | 0.786 |
| BB539.2B13 | A | | | | | 242-14 | AG | 1.870 | 2.170 | 2.060 | 3.170 |
| BG505.W6M.C2 | A | 1.940 | 2.690 | 2.390 | 2.140 | 263-8 | AG | 0.864 | 0.974 | 0.909 | 0.991 |
| BI369.9A | A | 1.340 | 2.000 | 1.570 | 1.290 | 269-12 | AG | 0.305 | 0.793 | 0.479 | 0.475 |
| BS208.B1 | A | 2.130 | 3.380 | 2.170 | 3.270 | 271-11 | AG | 3.890 | 4.820 | 3.830 | 4.340 |
| KER2008.12 | A | 100 | 100 | 100 | 100 | 928-28 | AG | 0.243 | 0.639 | 0.276 | 0.365 |
| KER2018.11 | A | 5.670 | 8.460 | 6.460 | 7.160 | DJ263.8 | AG | 0.050 | 0.054 | 0.070 | 0.100 |
| KNH1209.18 | A | 2.030 | 2.700 | 1.900 | 2.390 | T250-4 | AG | 2.720 | 3.090 | 3.460 | 3.450 |
| MB201.A1 | A | 1.800 | 2.270 | 1.730 | 1.360 | T251-18 | AG | 2.230 | 2.860 | 2.180 | 2.550 |
| MB539.2B7 | A | 100 | 100 | 100 | 100 | T253-11 | AG | 3.100 | 4.590 | 4.120 | 4.050 |
| MI369.A5 | A | 2.360 | 3.630 | 2.770 | 1.770 | T255-34 | AG | 1.220 | 1.810 | 1.470 | 1.140 |
| MS208.A1 | A | 1.940 | 3.890 | 1.530 | 1.140 | T257-31 | AG | 1.740 | 2.150 | 1.840 | 1.580 |
| Q23.17 | A | 2.660 | 4.280 | 3.050 | 1.600 | T266-60 | AG | 100 | 100 | 100 | 100 |
| Q259.17 | A | 9.750 | 11.600 | 11.600 | 12.000 | T278-50 | AG | 1.640 | 1.970 | 1.600 | 2.100 |
| Q769.d22 | A | 3.570 | 5.220 | 3.990 | 4.470 | T280-5 | AG | | | | |
| Q769.h5 | A | 6.020 | 9.460 | 8.650 | 7.440 | T33-7 | AG | 3.440 | 2.730 | 4.410 | 2.830 |
| Q842.d12 | A | 5.530 | 7.200 | 7.020 | 7.580 | 3988.25 | B | 0.376 | 0.607 | 0.409 | 0.293 |
| QH209.14M.A2 | A | 3.880 | 4.940 | 3.590 | 4.090 | 5768.04 | B | 5.870 | 9.010 | 8.640 | 5.260 |
| RW020.2 | A | 2.810 | 3.820 | 3.820 | 2.920 | 6101.10 | B | 0.020 | 0.025 | 0.019 | 0.005 |
| UG037.8 | A | 0.497 | 0.677 | 0.356 | 0.353 | 6535.3 | B | 0.567 | 1.150 | 1.120 | 1.280 |
| 246-F3.C10.2 | AC | 1.200 | 1.780 | 1.130 | 1.490 | 7165.18 | B | 1.540 | 2.230 | 2.290 | 2.710 |
| 3301.V1.C24 | AC | 8.590 | 11.200 | 9.950 | 9.500 | 45_01dG5 | B | 1.360 | 1.310 | 1.590 | 0.703 |
| 3589.V1.C4 | AC | 7.560 | 13.300 | 10.900 | 11.700 | 89.6.DG | B | 1.320 | 1.340 | 1.500 | 1.480 |
| 6540.v4.c1 | AC | 8.050 | 9.240 | 9.630 | 7.010 | AC10.29 | B | 0.372 | 0.577 | 0.511 | 0.512 |
| 6545.V4.C1 | AC | 7.570 | 7.590 | 8.650 | 7.500 | ADA.DG | B | 0.229 | 0.342 | 0.363 | 0.358 |
| 0815.V3.C3 | ACD | 3.310 | 3.970 | 2.870 | 1.810 | Bal.01 | B | 2.310 | 3.410 | 2.850 | 1.910 |
| 6095.V1.C10 | ACD | 0.0007 | 0.001 | 0.001 | 0.004 | BaL.26 | B | 2.880 | 3.180 | 3.890 | 2.390 |
| 3468.V1.C12 | AD | 1.610 | 2.390 | 1.650 | 2.040 | BG1168.01 | B | 0.806 | 1.590 | 1.040 | 1.480 |
| Q168.a2 | AD | 2.590 | 4.620 | 2.930 | 2.880 | BL01.DG | B | 2.900 | 3.230 | 2.600 | 1.570 |
| Q461.e2 | AD | 4.750 | 5.750 | 4.880 | 4.680 | BR07.DG | B | 0.539 | 0.781 | 0.891 | 0.445 |
| 620345.c1 | AE | 3.610 | 4.180 | 3.540 | 3.730 | BX08.16 | B | 1.050 | 1.660 | 1.310 | 1.300 |
| BJOX009000.02.4 | AE | 1.580 | 2.240 | 1.670 | 1.470 | CAAN.A2 | B | 8.050 | 12.000 | 10.900 | 5.700 |
| BJOX010000.06.2 | AE | 0.325 | 0.524 | 0.572 | 0.476 | CNE10 | B | 0.335 | 0.304 | 0.331 | 0.169 |
| BJOX025000.01.1 | AE | 1.540 | 2.200 | 1.630 | 1.540 | CNE12 | B | 0.789 | 0.939 | 1.040 | 1.090 |
| BJOX028000.10.3 | AE | 0.433 | 1.140 | 0.864 | 0.876 | CNE14 | B | 2.030 | 1.910 | 2.560 | 0.649 |
| C1080.c3 | AE | 0.447 | 0.582 | 0.831 | 0.613 | CNE4 | B | 0.824 | 0.918 | 1.170 | 0.437 |
| C2101.c1 | AE | 4.010 | 5.260 | 4.970 | 4.120 | CNE57 | B | 0.510 | 0.743 | 0.538 | 0.317 |
| C3347.c11 | AE | 0.019 | 0.053 | 0.050 | 0.089 | HO86.8 | B | 2.640 | 2.210 | 2.810 | 1.520 |
| C4118.09 | AE | 2.760 | 3.360 | 2.900 | 2.300 | HT593.1 | B | 0.404 | 0.497 | 0.421 | 0.285 |
| CM244.ec1 | AE | 3.100 | 3.870 | 2.930 | 1.460 | HXB2.DG | B | 0.001 | 0.004 | 0.003 | 0.015 |
| CNE3 | AE | 3.530 | 2.920 | 4.640 | 4.010 | JRCSF.JB | B | 3.080 | 3.750 | 3.710 | 1.890 |
| CNE5 | AE | 2.330 | 4.130 | 3.590 | 2.520 | JRFL.JB | B | 1.330 | 1.530 | 1.410 | 0.768 |
| CNE55 | AE | 0.566 | 0.594 | 0.558 | 0.605 | MN.3 | B | 0.0007 | 0.001 | 0.0009 | 0.001 |
| CNE56 | AE | 0.236 | 0.489 | 0.205 | 0.314 | PVO.04 | B | 7.080 | 10.100 | 7.470 | 6.430 |
| CNE59 | AE | 0.002 | 0.004 | 0.003 | 0.010 | QH0515.01 | B | 5.100 | 8.390 | 7.070 | 5.540 |

FIG. 16E

| Virus ID | Clade | 10E8 Var1 | 10E8 Var4 | 10E8 Var5 | 10E8 | Virus ID | Clade | 10E8 Var1 | 10E8 Var4 | 10E8 Var5 | 10E8 |
|---|---|---|---|---|---|---|---|---|---|---|---|
| QH0692.42 | B | 2.750 | 4.090 | 2.850 | 2.350 | CAP45.G3 | C | 3.250 | 3.720 | 2.770 | 3.410 |
| REJO.67 | B | 2.020 | 2.440 | 1.990 | 1.180 | Ce1176.A3 | C | 1.180 | 1.720 | 1.420 | 1.150 |
| RHPA.7 | B | 5.660 | 8.010 | 5.520 | 5.100 | CE703010217.B6 | C | 0.862 | 1.190 | 0.888 | 0.679 |
| SC422.8 | B | 1.310 | 1.570 | 1.600 | 1.150 | CNE30 | C | 2.190 | 1.960 | 2.080 | 2.290 |
| SF162.LS | B | 2.790 | 3.880 | 2.960 | 1.060 | CNE31 | C | 2.630 | 3.120 | 3.160 | 3.570 |
| SS1196.01 | B | 1.230 | 1.250 | 1.050 | 1.250 | CNE53 | C | 0.747 | 0.910 | 0.755 | 1.010 |
| THRO.18 | B | 0.684 | 0.774 | 0.587 | 0.587 | CNE58 | C | 0.997 | 1.800 | 1.220 | 1.090 |
| TRJO.58 | B | 7.740 | 9.560 | 8.350 | 4.180 | DU123.06 | C | 0.421 | 0.497 | 0.474 | 0.423 |
| TRO.11 | B | 0.625 | 0.717 | 0.358 | 0.286 | DU151.02 | C | 1.830 | 1.760 | 1.970 | 1.710 |
| WITO.33 | B | 0.519 | 0.445 | 0.395 | 0.305 | DU156.12 | C | 0.059 | 0.053 | 0.102 | 0.120 |
| X2278.C2.B1 | B | 3.610 | 3.360 | 3.480 | 2.240 | DU172.17 | C | 0.220 | 0.203 | 0.281 | 0.238 |
| YU2.DG | B | 8.260 | 10.400 | 10.100 | 5.460 | DU422.01 | C | 1.260 | 1.430 | 1.430 | 0.812 |
| BJOX002000.03.2 | BC | 1.000 | 1.880 | 1.800 | 1.560 | MW965.26 | C | 0.001 | 0.002 | 0.002 | 0.007 |
| CH038.12 | BC | 1.900 | 2.170 | 1.770 | 1.410 | SO18.18 | C | 3.390 | 3.890 | 3.970 | 4.480 |
| CH070.1 | BC | 15.90 | 19.80 | 14.70 | 13.50 | TV1.29 | C | 1.150 | 1.320 | 0.826 | 0.719 |
| CH117.4 | BC | 1.150 | 0.791 | 1.260 | 0.859 | TZA125.17 | C | 1.700 | 1.770 | 1.360 | 1.190 |
| CH119.10 | BC | 2.710 | 2.490 | 3.320 | 2.360 | TZBD.02 | C | 4.450 | 6.410 | 5.300 | 4.310 |
| CH181.12 | BC | 2.560 | 3.710 | 3.300 | 2.790 | ZA012.29 | C | 3.870 | 5.270 | 4.770 | 4.120 |
| CNE15 | BC | 2.580 | 3.120 | 2.940 | 2.970 | ZM106.9 | C | 100 | 100 | 100 | 100 |
| CNE19 | BC | 1.190 | 1.100 | 1.060 | 1.110 | ZM109.4 | C | 1.090 | 1.420 | 1.150 | 1.070 |
| CNE20 | BC | 0.765 | 0.768 | 0.955 | 0.732 | ZM135.10a | C | 0.356 | 0.575 | 0.535 | 0.408 |
| CNE21 | BC | 3.150 | 2.740 | 3.390 | 3.250 | ZM176.66 | C | 2.300 | 3.230 | 2.700 | 1.730 |
| CNE40 | BC | .0007 | 0.011 | 0.008 | 0.009 | ZM197.7 | C | 0.190 | 0.365 | 0.293 | 0.369 |
| CNE7 | BC | 0.577 | 0.786 | 0.645 | 0.603 | ZM214.15 | C | 5.370 | 8.230 | 7.960 | 5.980 |
| 286.36 | C | 3.540 | 4.630 | 4.810 | 5.000 | ZM215.8 | C | 0.106 | 0.247 | 0.249 | 0.230 |
| 288.38 | C | 2.470 | 3.940 | 2.340 | 3.080 | ZM233.6 | C | 0.708 | 0.974 | 0.873 | 0.737 |
| 0013095-2.11 | C | 0.025 | 0.015 | 0.046 | 0.077 | ZM249.1 | C | 2.150 | 2.940 | 2.740 | 2.270 |
| 001428-2.42 | C | 6.200 | 5.860 | 6.960 | 6.280 | ZM53.12 | C | 5.750 | 7.730 | 7.840 | 6.720 |
| 0077_V1.C16 | C | 6.740 | 8.460 | 8.670 | 7.110 | ZM55.28a | C | 6.560 | 8.330 | 7.730 | 6.780 |
| 00836-2.5 | C | 1.520 | 1.910 | 2.020 | 1.770 | 3326.V4.C3 | CD | 4.200 | 5.560 | 3.250 | 4.290 |
| 0921.V2.C14 | C | 3.530 | 5.010 | 3.860 | 3.030 | 3337.V2.C6 | CD | 4.100 | 6.510 | 3.680 | 4.870 |
| 16055-2.3 | C | 3.560 | 5.270 | 4.060 | 3.310 | 3817.v2.c59 | CD | 2.170 | 4.480 | 2.650 | 1.430 |
| 16845-2.22 | C | 0.085 | 0.161 | 0.200 | 0.172 | 191821.E6.1 | D | | | | |
| 16936-2.21 | C | 1.290 | 2.000 | 1.480 | 1.310 | 231965.c1 | D | 17.500 | 24.30 | 18.70 | 20.400 |
| 25710-2.43 | C | 0.104 | 0.297 | 0.301 | 0.304 | 247-23 | D | 1.060 | 2.010 | 1.260 | 1.290 |
| 25711-2.4 | C | 1.880 | 2.000 | 2.280 | 1.690 | 3016.v5.c45 | D | 2.240 | 2.530 | 2.830 | 2.170 |
| 25925-2.22 | C | 1.470 | 2.510 | 1.900 | 1.530 | 57128.vrc15 | D | 1.450 | 1.750 | 1.420 | 1.500 |
| 26191-2.48 | C | 4.500 | 4.700 | 5.550 | 4.900 | 6405.v4.c34 | D | 4.170 | 5.330 | 5.160 | 1.800 |
| 3168.V4.C10 | C | 5.050 | 10.500 | 7.230 | 8.180 | A03349M1.vrc4a | D | 0.727 | 1.380 | 1.040 | 0.663 |
| 3637.V5.C3 | C | 4.990 | 7.650 | 5.600 | 6.680 | A07412M1.vrc12 | D | 0.989 | 1.090 | 1.110 | 0.873 |
| 3873.V1.C24 | C | 10.800 | 12.800 | 14.300 | 15.700 | NKU3006.ec1 | D | 2.870 | 3.890 | 2.370 | 2.460 |
| 6322.V4.C1 | C | 2.670 | 4.270 | 3.050 | 3.680 | UG021.16 | D | | | | |
| 6471.V1.C16 | C | 13.30 | 14.60 | 16.30 | 14.90 | UG024.2 | D | | | | |
| 6631.V3.C10 | C | 4.610 | 5.660 | 7.090 | 3.360 | P0402.c2.11 | G | 0.525 | 0.645 | 0.291 | 0.460 |
| 6644.V2.C33 | C | 0.142 | 0.229 | 0.277 | 0.124 | P1981.C5.3 | G | 0.066 | 0.152 | 0.072 | 0.124 |
| 6785.V5.C14 | C | 2.990 | 4.230 | 3.840 | 2.420 | X1193.c1 | G | 0.952 | 1.210 | 1.500 | 1.150 |
| 6838.V1.C35 | C | 1.010 | 1.460 | 1.340 | 1.010 | X1254.c3 | G | 7.200 | 8.500 | 8.500 | 15.700 |
| 96ZM651.02 | C | 0.070 | 0.130 | 0.300 | 0.177 | X1632.S2.B10 | G | 1.720 | 2.230 | 1.880 | 1.760 |
| BR025.9 | C | 1.330 | 2.390 | 1.570 | 1.110 | X2088.c9 | G | 100 | 100 | 100 | 100 |
| CAP210.E8 | C | 1.920 | 2.950 | 2.040 | 2.010 | X2131.C1.B5 | G | 0.071 | 0.170 | 0.139 | 0.175 |
| CAP244.D3 | C | 1.390 | 2.370 | 1.710 | 1.480 | SIVmac251.30.SG3 | NA | >50 | >50 | >50 | >50 |
| CAP256.206.C9 | C | 3.190 | 4.480 | 3.940 | 2.970 | SVA.MLV | NA | >50 | >50 | >50 | >50 |

|  | 10E8 Var1 | 10E8 Var4 | 10E8 Var5 | 10E8 |
|---|---|---|---|---|
| # Viruses | 200 | 200 | 200 | 200 |
| Total Virus Neutralized | | | | |
| IC80 <50ug/ml | 195 | 195 | 195 | 195 |
| IC80 <10ug/ml | 190 | 181 | 185 | 186 |
| IC80 <1.0ug/ml | 57 | 49 | 51 | 57 |
| IC80 <0.1ug/ml | 15 | 11 | 11 | 9 |
| IC80 <0.01ug/ml | 6 | 5 | 6 | 5 |
| % Virus Neutralized | | | | |
| IC80 <50ug/ml | 98 | 98 | 98 | 98 |
| IC80 <10ug/ml | 95 | 91 | 93 | 93 |
| IC80 <1.0ug/ml | 29 | 25 | 26 | 29 |
| IC80 <0.1ug/ml | 8 | 6 | 6 | 5 |
| IC80 <0.01ug/ml | 3 | 3 | 3 | 3 |
| Median IC80 | 1.940 | 2.390 | 2.040 | 1.710 |
| Geometric Mean | 1.271 | 1.753 | 1.532 | 1.370 |

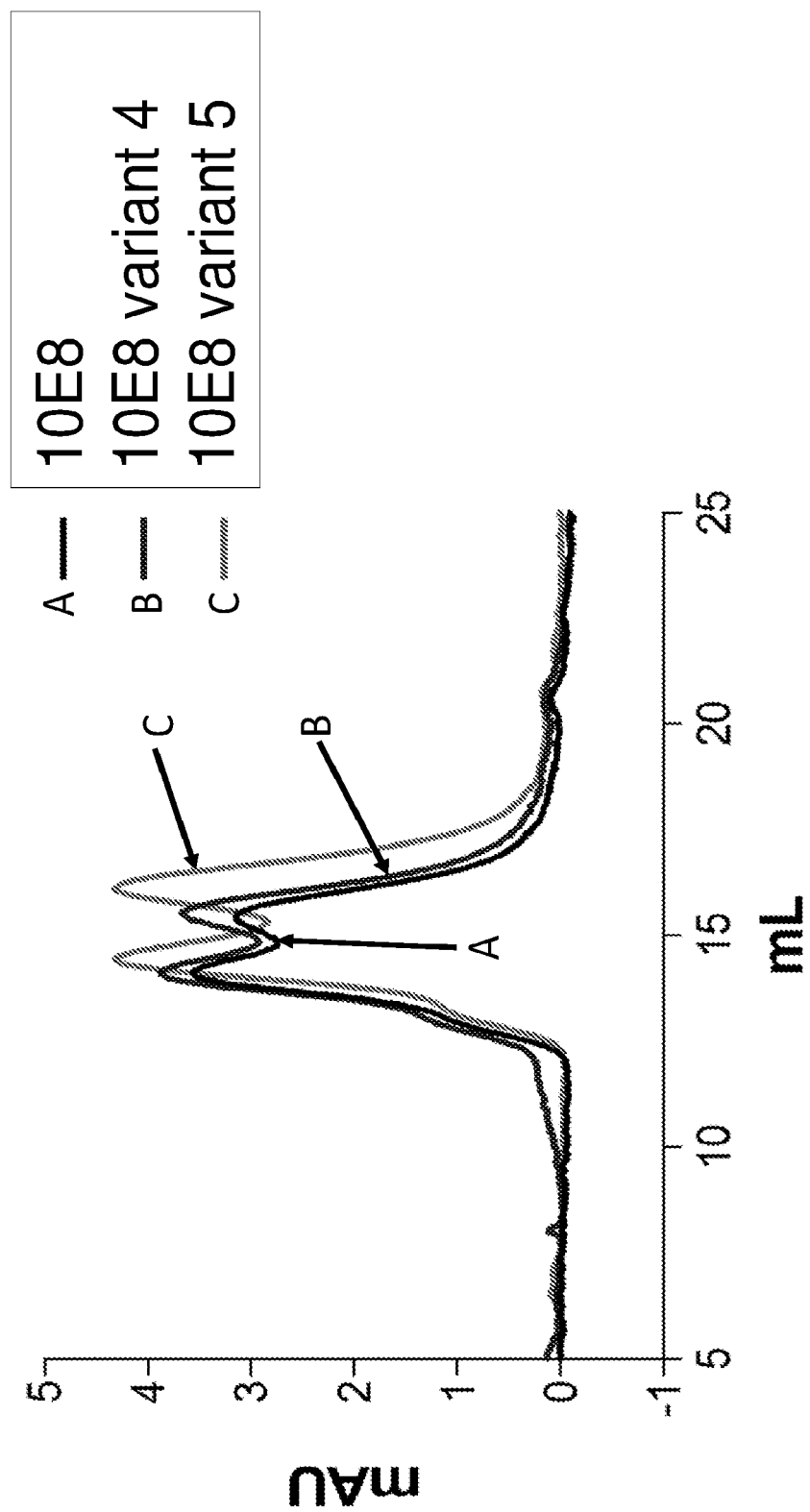

Turbidity of 10E8v4 with Y32A, F, I, L, M, P, V, or W

| IC50 | VRC01 | 3BNC117 | VRC07-523 | PGT121 | 10-1074 | PGDM 1400 | CAP256-VRC26.25 | 10E8 | 10E8v4 100cW |
|---|---|---|---|---|---|---|---|---|---|
| # Viruses | 208 | 208 | 208 | 208 | 208 | 208 | 208 | 208 | 208 |
| % VS Neutralized | | | | | | | | | |
| IC50 <50ug/ml | 90 | 86 | 96 | 63 | 66 | 80 | 58 | 98 | 98 |
| IC50 <10ug/ml | 89 | 83 | 96 | 60 | 64 | 79 | 57 | 97 | 98 |
| IC50 <1.0ug/ml | 73 | 79 | 91 | 52 | 61 | 75 | 55 | 73 | 98 |
| IC50 <0.1ug/ml | 23 | 50 | 62 | 45 | 49 | 64 | 50 | 20 | 91 |
| IC50 <0.01ug/ml | 0 | 7 | 12 | 28 | 20 | 41 | 39 | 5 | 68 |
| *For Sensitive Viruses Only:* | | | | | | | | | |
| Median IC50 | 0.314 | 0.070 | 0.055 | 0.013 | 0.021 | 0.009 | 0.003 | 0.392 | 0.0006 |
| Geometric Mean | 0.306 | 0.089 | 0.053 | 0.024 | 0.033 | 0.017 | 0.003 | 0.299 | 0.003 |
| *For All Viruses:* | | | | | | | | | |
| Median IC50 | 0.358 | 0.098 | 0.063 | 0.579 | 0.127 | 0.025 | 0.096 | 0.404 | 0.0006 |
| Geometric Mean | 0.533 | 0.246 | 0.074 | 0.521 | 0.507 | 0.099 | 0.233 | 0.344 | 0.004 |

| IC80 | VRC01 | 3BNC117 | VRC07-523 | PGT121 | 10-1074 | PGDM 1400 | CAP256-VRC26.25 | 10E8 | 10E8v4 100cW |
|---|---|---|---|---|---|---|---|---|---|
| # Viruses | 208 | 208 | 208 | 208 | 208 | 208 | 208 | 208 | 208 |
| % VS Neutralized | | | | | | | | | |
| IC80 <50ug/ml | 88 | 80 | 96 | 54 | 63 | 73 | 48 | 98 | 98 |
| IC80 <10ug/ml | 85 | 77 | 94 | 52 | 60 | 72 | 47 | 93 | 98 |
| IC80 <1.0ug/ml | 49 | 64 | 84 | 47 | 50 | 64 | 44 | 29 | 96 |
| IC80 <0.1ug/ml | 5 | 14 | 36 | 35 | 33 | 48 | 34 | 5 | 60 |
| IC80 <0.01ug/ml | 0 | 0 | 3 | 13 | 2 | 12 | 18 | 2 | 25 |
| *For Sensitive Viruses Only:* | | | | | | | | | |
| Median IC80 | 0.819 | 0.296 | 0.177 | 0.054 | 0.092 | 0.037 | 0.025 | 1.69 | 0.054 |
| Geometric Mean | 0.847 | 0.327 | 0.182 | 0.057 | 0.159 | 0.063 | 0.025 | 1.34 | 0.031 |
| *For All Viruses:* | | | | | | | | | |
| Median IC80 | 1.03 | 0.458 | 0.198 | 2.82 | 0.843 | 0.160 | 1.00 | 1.74 | 0.058 |
| Geometric Mean | 1.54 | 1.01 | 0.240 | 1.73 | 1.78 | 0.472 | 1.87 | 1.49 | 0.038 |

| clade | IC50 virus | 10E8-1053 | 10E8-1054 | 10E8-1055 | 10E8-1056 | 10E8-1057 | 10E8-1058 | 10E8-1059 | 10E8-1060 | 10E8-1061 |
|---|---|---|---|---|---|---|---|---|---|---|
| A | KER2008.12.SG3 | 2.4600 | 0.8380 | 3.4700 | 0.7980 | 0.7690 | 0.7020 | 50.0000 | 50.0000 | 50.0000 |
| A | RW020.2.SG3 | 0.0530 | 0.0580 | 0.1440 | 0.0500 | 0.1200 | 0.0460 | 0.0350 | 0.0390 | 0.0230 |
| ACD | 6095.V1.C10 | 0.0006 | 0.0006 | 0.0003 | 0.0006 | 0.0003 | 0.0003 | 0.0006 | 0.0006 | 0.0006 |
| AE | CM244.ec1.SG3 | 0.0080 | 0.0020 | 0.0240 | 0.0050 | 0.0140 | 0.0120 | 0.0180 | 0.0100 | 0.0100 |
| AE | TH966.8 | 0.0006 | 0.0006 | 0.0020 | 0.0006 | 0.0030 | 0.0003 | 0.0006 | 0.0006 | 0.0006 |
| B | 6101.1 | 0.0006 | 0.0006 | 0.0020 | 0.0006 | 0.0020 | 0.0006 | 0.0006 | 0.0006 | 0.0006 |
| B | CAAN.A2.SG3 | 0.2250 | 0.2170 | 0.3430 | 0.1390 | 0.1880 | 0.0870 | 0.2430 | 0.1360 | 0.1010 |
| B | PVO.04.SG3 | 0.1660 | 0.1540 | 0.3220 | 0.1460 | 0.4990 | 0.1560 | 0.0700 | 0.1190 | 0.0570 |
| B | YU2.DG.SG3 | 0.0860 | 0.1080 | 0.1350 | 0.0750 | 0.1930 | 0.0580 | 0.0370 | 0.0540 | 0.0130 |
| C | CNE31.SG3 | 0.0340 | 0.0300 | 0.0790 | 0.0490 | 0.0780 | 0.0370 | 0.0350 | 0.0360 | 0.0170 |
| C | ZM106.9.SG3 | 50.0000 | 12.3000 | 25.0000 | 50.0000 | 25.0000 | 9.1400 | 50.0000 | 50.0000 | 50.0000 |
| C | ZM215.8 | 0.0006 | 0.0006 | 0.0050 | 0.0006 | 0.0060 | 0.0020 | 0.0006 | 0.0006 | 0.0006 |
| C | ZM55.28a.SG3 | 0.1000 | 0.0880 | 0.1150 | 0.0850 | 0.1600 | 0.0550 | 0.0650 | 0.0510 | 0.0350 |
| | Median IC50 | 0.053 | 0.058 | 0.115 | 0.050 | 0.120 | 0.046 | 0.035 | 0.039 | 0.017 |
| | Geometric Mean | 0.034 | 0.025 | 0.063 | 0.029 | 0.058 | 0.023 | 0.038 | 0.036 | 0.027 |
| | Fold Improvement over 10E8v4 V5R S100cF | 1.8 | 2.4 | 1.0 | 2.1 | 1.1 | 2.6 | 1.6 | 1.7 | 2.3 |

| clade | IC50 virus | 10E8-1062 | 10E8-1063 | 10E8-1064 | 10E8-1022 | 10e8 |
|---|---|---|---|---|---|---|
| A | KER2008.12.SG3 | 1.3400 | 1.0400 | 1.5800 | 42.0000 | 50.0000 |
| A | RW020.2.SG3 | 0.0340 | 0.0430 | 0.0320 | 0.0850 | 1.3500 |
| ACD | 6095.V1.C10 | 0.0006 | 0.0003 | 0.0006 | 0.0006 | 0.0006 |
| AE | CM244.ec1.SG3 | 0.0080 | 0.0180 | 0.0120 | 0.0480 | 0.2160 |
| AE | TH966.8 | 0.0006 | 0.0003 | 0.0006 | 0.0006 | 0.0400 |
| B | 6101.1 | 0.0006 | 0.0030 | 0.0006 | 0.0006 | 0.0030 |
| B | CAAN.A2.SG3 | 0.0930 | 0.1520 | 0.2070 | 0.1890 | 2.8700 |
| B | PVO.04.SG3 | 0.1580 | 0.2010 | 0.0800 | 0.2550 | 2.5400 |
| B | YU2.DG.SG3 | 0.0840 | 0.1340 | 0.0470 | 0.0900 | 1.1200 |
| C | CNE31.SG3 | 0.0300 | 0.0440 | 0.0200 | 0.0620 | 1.1800 |
| C | ZM106.9.SG3 | 42.3000 | 25.0000 | 19.9000 | 50.0000 | 50.0000 |
| C | ZM215.8 | 0.0006 | 0.0020 | 0.0007 | 0.0020 | 0.0630 |
| C | ZM55.28a.SG3 | 0.0500 | 0.0760 | 0.0420 | 0.1580 | 2.4400 |
| | Median IC50 | 0.034 | 0.044 | 0.032 | 0.085 | 1.180 |
| | Geometric Mean | 0.027 | 0.036 | 0.025 | 0.061 | 0.483 |
| | Fold Improvement | 2.3 | 1.7 | 2.5 | 1.0 | |

FIG. 23B

| clade | IC80 virus | 10E8-1053 | 10E8-1054 | 10E8-1055 | 10E8-1056 | 10E8-1057 | 10E8-1058 | 10E8-1059 | 10E8-1060 | 10E8-1061 |
|---|---|---|---|---|---|---|---|---|---|---|
| A | KER2008.12.SG3 | 50.0000 | 12.4000 | 25.0000 | 7.9200 | 5.5000 | 6.2700 | 50.0000 | 50.0000 | 50.0000 |
| A | RW020.2.SG3 | 0.2310 | 0.2380 | 0.4830 | 0.2370 | 0.3780 | 0.1570 | 0.1570 | 0.1620 | 0.1040 |
| ACD | 6095.V1.C10 | 0.0006 | 0.0006 | 0.0003 | 0.0006 | 0.0003 | 0.0003 | 0.0006 | 0.0006 | 0.0006 |
| AE | CM244.ec1.SG3 | 0.1360 | 0.1050 | 0.1890 | 0.0770 | 0.1210 | 0.0660 | 0.1180 | 0.0770 | 0.0640 |
| AE | TH966.8 | 0.0080 | 0.0110 | 0.0240 | 0.0120 | 0.0250 | 0.0100 | 0.0006 | 0.0030 | 0.0006 |
| B | 6101.1 | 0.0050 | 0.0110 | 0.0200 | 0.0140 | 0.0230 | 0.0070 | 0.0080 | 0.0110 | 0.0070 |
| B | CAAN.A2.SG3 | 0.7410 | 0.7970 | 1.1000 | 0.6120 | 0.6790 | 0.4210 | 1.3100 | 0.7040 | 0.6440 |
| B | PVO.04.SG3 | 0.8430 | 0.9000 | 1.2400 | 0.7100 | 1.4100 | 0.7850 | 0.5680 | 0.6730 | 0.2870 |
| B | YU2.DG.SG3 | 0.6240 | 0.6450 | 0.8160 | 0.5340 | 0.9670 | 0.4820 | 0.4700 | 0.5390 | 0.2140 |
| C | CNE31.SG3 | 0.1630 | 0.1520 | 0.3010 | 0.1740 | 0.2600 | 0.1280 | 0.1550 | 0.1380 | 0.0760 |
| C | ZM106.9.SG3 | 50.0000 | 50.0000 | 25.0000 | 50.0000 | 25.0000 | 25.0000 | 50.0000 | 50.0000 | 50.0000 |
| C | ZM215.8 | 0.0120 | 0.0210 | 0.0280 | 0.0170 | 0.0320 | 0.0190 | 0.0110 | 0.0140 | 0.0070 |
| C | ZM55.28a.SG3 | 0.3500 | 0.3310 | 0.4390 | 0.3250 | 0.5190 | 0.2680 | 0.3090 | 0.2560 | 0.1630 |
| | Median IC80 | 0.231 | 0.238 | 0.439 | 0.237 | 0.378 | 0.157 | 0.157 | 0.162 | 0.104 |
| | Geometric Mean | 0.193 | 0.194 | 0.266 | 0.177 | 0.227 | 0.132 | 0.153 | 0.167 | 0.103 |
| | Fold improvement | 1.5 | 1.5 | 1.1 | 1.6 | 1.2 | 2.2 | 1.9 | 1.7 | 2.8 |

| clade | IC80 virus | 10E8-1062 | 10E8-1063 | 10E8-1064 | 10E8-1022 | 10e8 |
|---|---|---|---|---|---|---|
| A | KER2008.12.SG3 | 30.7000 | 7.7600 | 14.4000 | 50.0000 | 50.0000 |
| A | RW020.2.SG3 | 0.1600 | 0.1830 | 0.1360 | 0.3910 | 4.5700 |
| ACD | 6095.V1.C10 | 0.0006 | 0.0003 | 0.0006 | 0.0006 | 0.0050 |
| AE | CM244.ec1.SG3 | 0.0930 | 0.0970 | 0.0640 | 0.3150 | 1.8400 |
| AE | TH966.8 | 0.0080 | 0.0100 | 0.0050 | 0.0090 | 0.1580 |
| B | 6101.1 | 0.0130 | 0.0270 | 0.0090 | 0.0140 | 0.0630 |
| B | CAAN.A2.SG3 | 0.6320 | 0.5810 | 0.7450 | 0.9630 | 9.5400 |
| B | PVO.04.SG3 | 0.7430 | 0.7440 | 0.4830 | 1.1200 | 11.6000 |
| B | YU2.DG.SG3 | 0.6380 | 0.7390 | 0.4000 | 0.8650 | 8.0100 |
| C | CNE31.SG3 | 0.1240 | 0.1720 | 0.1040 | 0.3080 | 4.7000 |
| C | ZM106.9.SG3 | 50.0000 | 25.0000 | 50.0000 | 50.0000 | 50.0000 |
| C | ZM215.8 | 0.0110 | 0.0120 | 0.0060 | 0.0170 | 0.5800 |
| C | ZM55.28a.SG3 | 0.2670 | 0.2960 | 0.2030 | 0.6630 | 7.3300 |
| | Median IC80 | 0.160 | 0.183 | 0.136 | 0.391 | 4.700 |
| | Geometric Mean | 0.176 | 0.162 | 0.130 | 0.283 | 2.130 |
| | Fold improvement | 1.6 | 1.7 | 2.2 | 1 | |

| clade | virus | 10E8-1065 | 10E8-1068 | 10E8-1069 | 10E8-1070 | 10E8-1072 | 10E8-1073 | 10E8-1074 | 10E8-1075 | 10E8-1076 |
|---|---|---|---|---|---|---|---|---|---|---|
| A | KER2008.12.SG3 | 1.5500 | 2.9900 | 3.6200 | 3.6900 | 5.8600 | 0.9370 | 4.6400 | 5.7700 | 1.9000 |
| A | RW020.2.SG3 | 0.0550 | 0.0970 | 0.0580 | 0.1490 | 0.0850 | 0.0520 | 0.0660 | 0.0700 | 0.0900 |
| ACD | 6095.V1.C10 | 0.0004 | 0.0006 | 0.0003 | 0.0006 | <0.0003 | 0.0004 | 0.0003 | 0.0004 | 0.0005 |
| AE | CM244.ec1.SG3 | 0.0260 | 0.0290 | 0.0240 | 0.0520 | 0.0330 | 0.0320 | 0.0350 | 0.0410 | 0.0540 |
| AE | TH966.8 | 0.0050 | 0.0080 | 0.0050 | 0.0110 | 0.0060 | 0.0050 | 0.0060 | 0.0060 | 0.0080 |
| B | 6101.1 | <0.0003 | 0.0020 | 0.0010 | 0.0040 | 0.0010 | 0.0010 | 0.0020 | 0.0020 | 0.0020 |
| B | CAAN.A2.SG3 | 0.0940 | 0.1220 | 0.1030 | 0.1470 | 0.1410 | 0.0610 | 0.1260 | 0.1010 | 0.1020 |
| B | PVO.04.SG3 | 0.0890 | 0.1350 | 0.0700 | 0.2570 | 0.0880 | 0.1290 | 0.1730 | 0.1440 | 0.2260 |
| B | YU2.DG.SG3 | 0.0690 | 0.0790 | 0.0350 | 0.1080 | 0.0400 | 0.0340 | 0.0430 | 0.0510 | 0.0720 |
| C | CNE31.SG3 | 0.0490 | 0.0750 | 0.0360 | 0.0750 | 0.0520 | 0.0330 | 0.0410 | 0.0370 | 0.0530 |
| C | ZM106.9.SG3 | >25 | >25 | >20 | 18.9000 | >25 | 16.2000 | 18.1000 | >25 | 13.2000 |
| C | ZM215.8 | 0.0060 | 0.0060 | 0.0030 | 0.0070 | 0.0050 | 0.0050 | 0.0040 | 0.0050 | 0.0060 |
| C | ZM55.28a.SG3 | 0.0890 | 0.1070 | 0.0670 | 0.1330 | 0.1150 | 0.0680 | 0.0910 | 0.0840 | 0.1410 |
| | Median IC50 | 0.055 | 0.077 | 0.036 | 0.108 | 0.052 | 0.034 | 0.043 | 0.046 | 0.072 |
| | Geometric Mean | 0.034 | 0.036 | 0.022 | 0.078 | 0.045 | 0.036 | 0.049 | 0.031 | 0.057 |

IC50

| clade | virus | 10E8-1077 | 10E8-1078 | 10E8-1079 | 10E8-1080 | 10E8-1081 | 10E8-1082 | 10E8-1083 | 10E8-1084 | 10E8-1086 |
|---|---|---|---|---|---|---|---|---|---|---|
| A | KER2008.12.SG3 | 4.0300 | 3.8500 | 2.4000 | >25 | >25 | >25 | >25 | >25 | 6.5600 |
| A | RW020.2.SG3 | 0.1000 | 0.1010 | 0.0800 | 0.1080 | 0.0420 | 0.0880 | 0.4050 | 0.0850 | 0.0630 |
| ACD | 6095.V1.C10 | 0.0004 | 0.0005 | 0.0004 | 0.0006 | <0.0003 | 0.0004 | 0.0030 | <0.0003 | <0.0003 |
| AE | CM244.ec1.SG3 | 0.0450 | 0.0690 | 0.0530 | 0.0430 | 0.0350 | 0.0360 | 0.2640 | 0.0880 | 0.0500 |
| AE | TH966.8 | 0.0110 | 0.0080 | 0.0070 | 0.0060 | 0.0020 | 0.0050 | 0.0280 | 0.0040 | 0.0030 |
| B | 6101.1 | 0.0020 | 0.0020 | 0.0010 | 0.0030 | 0.0020 | 0.0050 | 0.1280 | <0.0003 | <0.0003 |
| B | CAAN.A2.SG3 | 0.1100 | 0.1540 | 0.1480 | 0.1550 | 0.1310 | 0.2240 | 0.6820 | 0.1830 | 0.0940 |
| B | PVO.04.SG3 | 0.2170 | 0.2160 | 0.2250 | 0.1540 | 0.0490 | 0.1310 | 1.3300 | 0.1060 | 0.0800 |
| B | YU2.DG.SG3 | 0.0640 | 0.0490 | 0.0480 | 0.0830 | 0.0140 | 0.0700 | 0.2450 | 0.0600 | 0.0390 |
| C | CNE31.SG3 | 0.0510 | 0.0510 | 0.0500 | 0.0540 | 0.0190 | 0.0360 | 0.2640 | 0.0500 | 0.0390 |
| C | ZM106.9.SG3 | >25 | >25 | >25 | >25 | >25 | >25 | >25 | >25 | >25 |
| C | ZM215.8 | 0.0070 | 0.0040 | 0.0050 | 0.0050 | 0.0020 | 0.0040 | 0.0330 | 0.0050 | 0.0040 |
| C | ZM55.28a.SG3 | 0.1280 | 0.1270 | 0.1230 | 0.1010 | 0.0340 | 0.0880 | 0.3640 | 0.0890 | 0.0780 |
| | Median IC50 | 0.058 | 0.060 | 0.052 | 0.054 | 0.027 | 0.036 | 0.264 | 0.085 | 0.057 |
| | Geometric Mean | 0.039 | 0.038 | 0.033 | 0.025 | 0.015 | 0.023 | 0.149 | 0.045 | 0.054 |

| clade | virus | 10E8-1087 | 10E8-1088 | 10E8-1089 | 10E8-1090 | 10E8-1091 | 10E8-1092 | 10E8-1093 | 10E8-1094 | 10E8-1095 |
|---|---|---|---|---|---|---|---|---|---|---|
| A | KER2008.12.SG3 | 11.1000 | 12.1000 | 12.0000 | 4.7500 | >25 | >25 | >25 | >25 | >25 |
| A | RW020.2.SG3 | 0.0710 | 0.0680 | 0.0390 | 0.0550 | 0.0560 | 0.0520 | 0.0480 | 0.0550 | 0.0680 |
| ACD | 6095.V1.C10 | <0.0003 | <0.0003 | <0.0003 | 0.0005 | 0.0004 | <0.0003 | <0.0003 | <0.0003 | <0.0003 |
| AE | CM244.ec1.SG3 | 0.0600 | 0.0300 | 0.0400 | 0.0380 | 0.0450 | 0.1240 | 0.0320 | 0.0480 | 0.0410 |
| AE | TH966.8 | 0.0060 | 0.0050 | 0.0040 | 0.0070 | 0.0050 | 0.0110 | 0.0030 | 0.0040 | 0.0040 |
| B | 6101.1 | <0.0003 | 0.0005 | 0.0010 | 0.0020 | 0.0040 | 0.0030 | 0.0020 | 0.0020 | 0.0030 |
| B | CAAN.A2.SG3 | 0.1300 | 0.1320 | 0.0890 | 0.1100 | 0.1760 | 0.0700 | 0.1450 | 0.1010 | 0.1600 |
| B | PVO.04.SG3 | 0.0660 | 0.0620 | 0.0860 | 0.1250 | 0.0810 | 0.0880 | 0.0620 | 0.0350 | 0.0460 |
| B | YU2.DG.SG3 | 0.0490 | 0.0430 | 0.0330 | 0.0500 | 0.0360 | 0.0340 | 0.0240 | 0.0320 | 0.0470 |
| C | CNE31.SG3 | 0.0450 | 0.0390 | 0.0300 | 0.0540 | 0.0430 | 0.0240 | 0.0360 | 0.0330 | 0.0460 |
| C | ZM106.9.SG3 | >25 | >25 | >25 | >25 | >25 | >25 | >25 | >25 | >25 |
| C | ZM215.8 | 0.0050 | 0.0040 | 0.0030 | 0.0050 | 0.0050 | 0.0020 | 0.0030 | 0.0040 | 0.0040 |
| C | ZM55.28a.SG3 | 0.0960 | 0.0880 | 0.0620 | 0.0960 | 0.0760 | 0.0420 | 0.0730 | 0.0590 | 0.0470 |
|  | Median IC50 | 0.063 | 0.043 | 0.039 | 0.052 | 0.043 | 0.038 | 0.034 | 0.034 | 0.046 |
|  | Geometric Mean | 0.069 | 0.039 | 0.035 | 0.032 | 0.020 | 0.025 | 0.021 | 0.021 | 0.025 |

IC50

| clade | virus | 10E8-1022 | 10E8-1022 | 10E8-1022 | 10E8v4 | 10E8v4 S100cF |
|---|---|---|---|---|---|---|
| A | KER2008.12.SG3 | >25 | >25 | >25 | >50 | >50 |
| A | RW020.2.SG3 | 0.1220 | 0.1290 | 0.0860 | 0.8650 | 0.0290 |
| ACD | 6095.V1.C10 | 0.0004 | 0.0004 | <0.0003 | 0.0006 | 0.0000 |
| AE | CM244.ec1.SG3 | 0.0530 | 0.0670 | 0.0360 | 0.7250 | 0.0460 |
| AE | TH966.8 | 0.0100 | 0.0110 | 0.0060 | 0.0350 | 0.0010 |
| B | 6101.1 | 0.0030 | 0.0030 | 0.0020 | 0.0010 | 0.0000 |
| B | CAAN.A2.SG3 | 0.2250 | 0.2330 | 0.1560 | 2.2700 | 0.1450 |
| B | PVO.04.SG3 | 0.0990 | 0.1100 | 0.0510 | 2.5800 | 0.1000 |
| B | YU2.DG.SG3 | 0.0940 | 0.0880 | 0.0570 | 2.0900 | 0.0810 |
| C | CNE31.SG3 | 0.0880 | 0.0800 | 0.0850 | 1.1400 | 0.0500 |
| C | ZM106.9.SG3 | >25 | >25 | >25 | >50 | >50 |
| C | ZM215.8 | 0.0060 | 0.0070 | 0.0050 | 0.0260 | 0.0080 |
| C | ZM55.28a.SG3 | 0.1800 | 0.1850 | 0.1430 | 2.0600 | 0.1400 |
|  | Median IC50 | 0.088 | 0.080 | 0.054 | 0.865 | 0.046 |
|  | Geometric Mean | 0.030 | 0.031 | 0.032 | 0.187 | 0.009 |

| clade | virus | 10E8-1065 | 10E8-1068 | 10E8-1069 | 10E8-1070 | 10E8-1072 | 10E8-1073 | 10E8-1074 | 10E8-1075 | 10E8-1076 |
|---|---|---|---|---|---|---|---|---|---|---|
| A | KER2008.12.SG3 | >25 | >25 | >20 | >25 | >25 | 9.9700 | >25 | >25 | >25 |
| A | RW020.2.SG3 | 0.2340 | 0.4330 | 0.3310 | 0.5020 | 0.3570 | 0.2200 | 0.2820 | 0.2810 | 0.3450 |
| ACD | 6095.V1.C10 | 0.0020 | 0.0020 | 0.0010 | 0.0020 | 0.0010 | 0.0010 | 0.0010 | 0.0010 | 0.0020 |
| AE | CM244.ec1.SG3 | 0.1470 | 0.1770 | 0.1480 | 0.2700 | 0.2610 | 0.1790 | 0.2150 | 0.1790 | 0.3620 |
| AE | TH966.8 | 0.0290 | 0.0260 | 0.0190 | 0.0410 | 0.0250 | 0.0200 | 0.0230 | 0.0270 | 0.0410 |
| B | 6101.1 | 0.0070 | 0.0150 | 0.0080 | 0.0230 | 0.0070 | 0.0060 | 0.0070 | 0.0080 | 0.0090 |
| B | CAAN.A2.SG3 | 0.4770 | 0.6400 | 0.5510 | 0.7560 | 0.6390 | 0.3960 | 0.6770 | 0.5700 | 0.6570 |
| B | PVO.04.SG3 | 0.6240 | 0.7220 | 0.4330 | 1.3100 | 0.4480 | 0.8300 | 0.9600 | 0.8210 | 1.0500 |
| B | YU2.DG.SG3 | 0.3770 | 0.5750 | 0.3180 | 0.7780 | 0.2950 | 0.3020 | 0.3520 | 0.3890 | 0.5060 |
| C | CNE31.SG3 | 0.1540 | 0.2280 | 0.1380 | 0.2630 | 0.1640 | 0.1260 | 0.1430 | 0.1440 | 0.1850 |
| C | ZM106.9.SG3 | >25 | >25 | >20 | >25 | >25 | >25 | >25 | >25 | >25 |
| C | ZM215.8 | 0.0190 | 0.0190 | 0.0130 | 0.0270 | 0.0170 | 0.0170 | 0.0150 | 0.0170 | 0.0220 |
| C | ZM55.28a.SG3 | 0.3360 | 0.3970 | 0.2690 | 0.4800 | 0.4320 | 0.3040 | 0.3710 | 0.3410 | 0.4810 |
| | Median IC80 | 0.154 | 0.228 | 0.148 | 0.270 | 0.261 | 0.200 | 0.215 | 0.179 | 0.345 |
| | Geometric Mean | 0.084 | 0.110 | 0.072 | 0.147 | 0.085 | 0.110 | 0.085 | 0.085 | 0.118 |

IC80

| clade | virus | 10E8-1077 | 10E8-1078 | 10E8-1079 | 10E8-1080 | 10E8-1081 | 10E8-1082 | 10E8-1083 | 10E8-1084 | 10E8-1086 |
|---|---|---|---|---|---|---|---|---|---|---|
| A | KER2008.12.SG3 | >25 | >25 | >25 | >25 | >25 | >25 | >25 | >25 | >25 |
| A | RW020.2.SG3 | 0.3700 | 0.3850 | 0.3280 | 0.3640 | 0.1540 | 0.3450 | 1.4400 | 0.2750 | 0.2280 |
| ACD | 6095.V1.C10 | 0.0020 | 0.0020 | 0.0010 | 0.0020 | 0.0009 | 0.0020 | 0.0120 | 0.0010 | 0.0010 |
| AE | CM244.ec1.SG3 | 0.3040 | 0.3000 | 0.2580 | 0.1810 | 0.1240 | 0.1660 | 1.0100 | 0.3170 | 0.1850 |
| AE | TH966.8 | 0.0430 | 0.0350 | 0.0300 | 0.0240 | 0.0110 | 0.0250 | 0.1370 | 0.0180 | 0.0200 |
| B | 6101.1 | 0.0090 | 0.0080 | 0.0060 | 0.0220 | 0.0090 | 0.0280 | 0.6640 | 0.0130 | 0.0070 |
| B | CAAN.A2.SG3 | 0.5550 | 0.8030 | 0.8010 | 0.8760 | 0.5070 | 0.8840 | 3.2400 | 1.2400 | 0.5870 |
| B | PVO.04.SG3 | 0.9600 | 0.9840 | 0.9260 | 0.6340 | 0.2840 | 0.4990 | 4.9600 | 0.5010 | 0.4670 |
| B | YU2.DG.SG3 | 0.3910 | 0.4050 | 0.3900 | 0.5350 | 0.1230 | 0.5450 | 1.3400 | 0.4200 | 0.2750 |
| C | CNE31.SG3 | 0.1770 | 0.1750 | 0.1580 | 0.1990 | 0.0720 | 0.1740 | 0.7930 | 0.1630 | 0.1200 |
| C | ZM106.9.SG3 | >25 | >25 | >25 | >25 | >25 | >25 | >25 | >25 | >25 |
| C | ZM215.8 | 0.0240 | 0.0140 | 0.0130 | 0.0160 | 0.0080 | 0.0150 | 0.1190 | 0.0210 | 0.0170 |
| C | ZM55.28a.SG3 | 0.4660 | 0.4460 | 0.4120 | 0.3550 | 0.1250 | 0.4160 | 1.3200 | 0.3760 | 0.3310 |
| | Median IC80 | 0.304 | 0.300 | 0.258 | 0.199 | 0.123 | 0.174 | 1.010 | 0.275 | 0.185 |
| | Geometric Mean | 0.112 | 0.108 | 0.091 | 0.108 | 0.046 | 0.107 | 0.609 | 0.097 | 0.073 |

FIG. 23F

| clade | virus | IC80 10E8-1087 | 10E8-1088 | 10E8-1089 | 10E8-1090 | 10E8-1091 | 10E8-1092 | 10E8-1093 | 10E8-1094 | 10E8-1095 |
|---|---|---|---|---|---|---|---|---|---|---|
| A | KER2008.12.SG3 | >25 | >25 | >25 | >25 | >25 | >25 | >25 | >25 | >25 |
| A | RW020.2.SG3 | 0.2460 | 0.2760 | 0.1430 | 0.2220 | 0.2080 | 0.1890 | 0.1480 | 0.1840 | 0.2210 |
| ACD | 6095.V1.C10 | 0.0010 | 0.0010 | 0.0010 | 0.0020 | 0.0010 | 0.0010 | 0.0008 | 0.0007 | 0.0010 |
| AE | CM244.ec1.SG3 | 0.2520 | 0.1660 | 0.1730 | 0.1670 | 0.1670 | 0.5440 | 0.1190 | 0.1580 | 0.1320 |
| AE | TH966.8 | 0.0250 | 0.0220 | 0.0210 | 0.0310 | 0.0230 | 0.0450 | 0.0150 | 0.0140 | 0.0170 |
| B | 6101.1 | 0.0070 | 0.0070 | 0.0060 | 0.0080 | 0.0160 | 0.0130 | 0.0090 | 0.0130 | 0.0120 |
| B | CAAN.A2.SG3 | 0.6300 | 0.5980 | 0.3410 | 0.4690 | 0.6640 | 0.3900 | 0.7160 | 0.5530 | 0.6690 |
| B | PVO.04.SG3 | 0.4360 | 0.4940 | 0.4050 | 0.5710 | 0.4040 | 0.4230 | 0.2680 | 0.1730 | 0.2390 |
| B | YU2.DG.SG3 | 0.2820 | 0.2960 | 0.1700 | 0.2560 | 0.2130 | 0.1810 | 0.1370 | 0.1750 | 0.2100 |
| C | CNE31.SG3 | 0.1520 | 0.1350 | 0.0920 | 0.1300 | 0.1210 | 0.0720 | 0.1040 | 0.1060 | 0.1310 |
| C | ZM106.9.SG3 | >25 | >25 | >25 | >25 | >25 | >25 | >25 | >25 | >25 |
| C | ZM215.8 | 0.0200 | 0.0150 | 0.0120 | 0.0190 | 0.0200 | 0.0100 | 0.0120 | 0.0090 | 0.0120 |
| C | ZM55.28a.SG3 | 0.3250 | 0.3640 | 0.1940 | 0.2870 | 0.2530 | 0.1280 | 0.1950 | 0.1790 | 0.1840 |
| | Median IC80 | 0.246 | 0.166 | 0.143 | 0.167 | 0.167 | 0.128 | 0.119 | 0.158 | 0.132 |
| | Geometric Mean | 0.080 | 0.076 | 0.056 | 0.080 | 0.075 | 0.069 | 0.054 | 0.054 | 0.063 |

| clade | virus | IC80 10E8-1022 | 10E8-1022 | 10E8-1022 | 10E8v4 | 10E8v4 S100cF |
|---|---|---|---|---|---|---|
| A | KER2008.12.SG3 | >25 | >25 | >25 | >50 | >50 |
| A | RW020.2.SG3 | 0.4450 | 0.4370 | 0.3370 | 3.3100 | 0.2870 |
| ACD | 6095.V1.C10 | 0.0020 | 0.0020 | 0.0010 | 0.0010 | 0.0000 |
| AE | CM244.ec1.SG3 | 0.2340 | 0.2640 | 0.1710 | 2.7700 | 0.3180 |
| AE | TH966.8 | 0.0520 | 0.0480 | 0.0340 | 0.1920 | 0.0580 |
| B | 6101.1 | 0.0180 | 0.0160 | 0.0100 | 0.0560 | 0.0090 |
| B | CAAN.A2.SG3 | 1.0200 | 1.0800 | 0.8090 | 9.4600 | 0.9760 |
| B | PVO.04.SG3 | 0.5630 | 0.6290 | 0.3580 | 9.8600 | 0.6960 |
| B | YU2.DG.SG3 | 0.4300 | 0.4700 | 0.2980 | 9.2200 | 1.0100 |
| C | CNE31.SG3 | 0.2700 | 0.2290 | 0.1800 | 3.4700 | 0.2390 |
| C | ZM106.9.SG3 | >25 | >25 | >25 | >50 | >50 |
| C | ZM215.8 | 0.0240 | 0.0270 | 0.0170 | 0.2670 | 0.0510 |
| C | ZM55.28a.SG3 | 0.5110 | 0.5870 | 0.4410 | 7.8600 | 0.5160 |
| | Median IC80 | 0.270 | 0.264 | 0.180 | 3.310 | 0.287 |
| | Geometric Mean | 0.129 | 0.132 | 0.087 | 0.957 | 0.092 |

```
                        SEQUENCE LISTING

<160> NUMBER OF SEQ ID NOS: 86

<210> SEQ ID NO 1
<211> LENGTH: 131
<212> TYPE: PRT
<213> ORGANISM: Artificial Sequence
<220> FEATURE:
<223> OTHER INFORMATION: Variant Antibody Sequence

<400> SEQUENCE: 1

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asn Ser Ile Asn Phe
65                  70                  75                  80

Leu Tyr Leu Glu Met Asn Asn Leu Arg Met Glu Asp Ser Gly Leu Tyr
                85                  90                  95
```

```
Phe Cys Ala Arg Thr Gly Lys Tyr Tyr Asp Phe Trp Ser Gly Tyr Pro
              100                 105                 110

Pro Gly Glu Glu Tyr Phe Gln Asp Trp Gly Arg Gly Thr Leu Val Thr
        115                 120                 125

Val Ser Ser
    130

<210> SEQ ID NO 2
<211> LENGTH: 109
<212> TYPE: PRT
<213> ORGANISM: Artificial Sequence
<220> FEATURE:
<223> OTHER INFORMATION: Variant Antibody Sequence

<400> SEQUENCE: 2

Ser Tyr Glu Leu Thr Gln Glu Thr Gly Val Ser Val Ala Leu Gly Arg
1               5                   10                  15

Thr Val Thr Ile Thr Cys Arg Gly Asp Ser Leu Arg Ser His Tyr Ala
            20                  25                  30

Ser Trp Tyr Gln Lys Lys Pro Gly Gln Ala Pro Ile Leu Leu Phe Tyr
        35                  40                  45

Gly Lys Asn Asn Arg Pro Ser Gly Val Pro Asp Arg Phe Ser Gly Ser
    50                  55                  60

Ala Ser Gly Asn Arg Ala Ser Leu Thr Ile Ser Gly Ala Gln Ala Glu
65                  70                  75                  80

Asp Asp Ala Glu Tyr Tyr Cys Ser Ser Arg Asp Lys Ser Gly Ser Arg
                85                  90                  95

Leu Ser Val Phe Gly Gly Gly Thr Lys Leu Thr Val Leu
            100                 105

<210> SEQ ID NO 3
<211> LENGTH: 131
<212> TYPE: PRT
<213> ORGANISM: Artificial Sequence
<220> FEATURE:
<223> OTHER INFORMATION: Variant Antibody Sequence

<400> SEQUENCE: 3

Glu Val Arg Leu Ala Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Asp Asn Tyr Lys Asn Thr
65                  70                  75                  80

Leu Tyr Leu Glu Met Asn Asn Leu Arg Thr Glu Asp Ser Gly Leu Tyr
                85                  90                  95

Phe Cys Ala Arg Thr Gly Lys Tyr Tyr Asp Phe Trp Ser Gly Tyr Pro
              100                 105                 110

Pro Gly Glu Glu Tyr Phe Gln Asp Trp Gly Arg Gly Thr Leu Val Ile
        115                 120                 125

Val Ser Ser
    130
```

```
<210> SEQ ID NO 4
<211> LENGTH: 109
<212> TYPE: PRT
<213> ORGANISM: Artificial Sequence
<220> FEATURE:
<223> OTHER INFORMATION: Variant Antibody Sequence

<400> SEQUENCE: 4

Ser Tyr Glu Leu Thr Gln Asp Thr Gly Val Ser Val Ala Leu Gly Arg
1               5                   10                  15

Thr Val Thr Ile Thr Cys Arg Gly Asp Ser Leu Arg Ser His Tyr Ala
            20                  25                  30

Ser Trp Tyr Gln Lys Lys Pro Gly Gln Ala Pro Val Leu Leu Phe Tyr
        35                  40                  45

Gly Lys Asn Asn Arg Pro Ser Gly Ile Pro Asp Arg Phe Ser Gly Ser
    50                  55                  60

Ala Ser Gly Asn Arg Ala Ser Leu Thr Ile Thr Gly Ala Gln Ala Glu
65                  70                  75                  80

Asp Glu Ala Asp Tyr Tyr Cys Ser Ser Arg Asp Lys Ser Gly Ser Arg
                85                  90                  95

Leu Ser Val Phe Gly Gly Gly Thr Lys Leu Thr Val Leu
            100                 105

<210> SEQ ID NO 5
<211> LENGTH: 131
<212> TYPE: PRT
<213> ORGANISM: Artificial Sequence
<220> FEATURE:
<223> OTHER INFORMATION: Variant Antibody Sequence

<400> SEQUENCE: 5

Glu Val Arg Leu Val Glu Ser Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Glu
    50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Gln Gly Thr Leu Val Ile
        115                 120                 125

Val Ser Ser
    130

<210> SEQ ID NO 6
<211> LENGTH: 109
<212> TYPE: PRT
<213> ORGANISM: Artificial Sequence
<220> FEATURE:
<223> OTHER INFORMATION: Variant Antibody Sequence

<400> SEQUENCE: 6

Ala Ser Glu Leu Thr Gln Asp Pro Ala Val Ser Val Ala Leu Lys Gln
1               5                   10                  15
```

-continued

```
Thr Val Thr Ile Thr Cys Arg Gly Asp Ser Leu Arg Ser His Tyr Ala
             20                  25                  30

Ser Trp Tyr Gln Lys Lys Pro Gly Gln Ala Pro Val Leu Leu Phe Tyr
         35                  40                  45

Gly Lys Asn Asn Arg Pro Ser Gly Ile Pro Asp Arg Phe Ser Gly Ser
 50                  55                  60

Ala Ser Gly Asn Arg Ala Ser Leu Thr Ile Thr Gly Ala Gln Ala Glu
 65                  70                  75                  80

Asp Glu Ala Asp Tyr Tyr Cys Ser Ser Arg Asp Lys Ser Gly Ser Arg
                 85                  90                  95

Leu Ser Val Phe Gly Gly Gly Thr Lys Leu Thr Val Leu
            100                 105

<210> SEQ ID NO 7
<211> LENGTH: 8
<212> TYPE: PRT
<213> ORGANISM: Artificial Sequence
<220> FEATURE:
<223> OTHER INFORMATION: Variant Antibody Sequence

<400> SEQUENCE: 7

Gly Phe Asp Phe Asp Asn Ala Trp
1               5

<210> SEQ ID NO 8
<211> LENGTH: 10
<212> TYPE: PRT
<213> ORGANISM: Artificial Sequence
<220> FEATURE:
<223> OTHER INFORMATION: Variant Antibody Sequence

<400> SEQUENCE: 8

Ile Thr Gly Pro Gly Glu Gly Trp Ser Val
1               5                   10

<210> SEQ ID NO 9
<211> LENGTH: 22
<212> TYPE: PRT
<213> ORGANISM: Artificial Sequence
<220> FEATURE:
<223> OTHER INFORMATION: Variant Antibody Sequence

<400> SEQUENCE: 9

Ala Arg Thr Gly Lys Tyr Tyr Asp Phe Trp Ser Gly Tyr Pro Pro Gly
1               5                   10                  15

Glu Glu Tyr Phe Gln Asp
            20

<210> SEQ ID NO 10
<211> LENGTH: 6
<212> TYPE: PRT
<213> ORGANISM: Artificial Sequence
<220> FEATURE:
<223> OTHER INFORMATION: Variant Antibody Sequence

<400> SEQUENCE: 10

Ser Leu Arg Ser His Tyr
1               5

<210> SEQ ID NO 11
<211> LENGTH: 3
<212> TYPE: PRT
<213> ORGANISM: Artificial Sequence
```

```
<220> FEATURE:
<223> OTHER INFORMATION: Variant Antibody Sequence

<400> SEQUENCE: 11

Gly Lys Asn
1

<210> SEQ ID NO 12
<211> LENGTH: 12
<212> TYPE: PRT
<213> ORGANISM: Artificial Sequence
<220> FEATURE:
<223> OTHER INFORMATION: Variant Antibody Sequence

<400> SEQUENCE: 12

Ser Ser Arg Asp Lys Ser Gly Ser Arg Leu Ser Val
1               5                   10

<210> SEQ ID NO 13
<211> LENGTH: 131
<212> TYPE: PRT
<213> ORGANISM: Artificial Sequence
<220> FEATURE:
<223> OTHER INFORMATION: Variant Antibody Sequence

<400> SEQUENCE: 13

Glu Val Arg Leu Ala Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
                20                  25                  30

Trp Met Thr Trp Val Arg Gln Pro Pro Gly Lys Gly Leu Glu Trp Val
            35                  40                  45

Gly Arg Ile Thr Gly Pro Gly Glu Gly Trp Ser Val Asp Tyr Ala Ala
        50                  55                  60

Pro Val Glu Gly Arg Phe Thr Ile Ser Arg Leu Asn Tyr Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Ile
        115                 120                 125

Val Ser Ser
        130

<210> SEQ ID NO 14
<211> LENGTH: 131
<212> TYPE: PRT
<213> ORGANISM: Artificial Sequence
<220> FEATURE:
<223> OTHER INFORMATION: Variant Antibody Sequence

<400> SEQUENCE: 14

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asn Phe Asp Asp Ala
                20                  25                  30

Trp Met Thr Trp Val Arg Gln Pro Pro Gly Lys Gly Leu Glu Trp Val
            35                  40                  45

Gly Arg Ile Ser Gly Pro Gly Glu Gly Trp Ser Val Asp Tyr Ala Glu
        50                  55                  60
```

```
Ser Val Lys Gly Arg Phe Thr Ile Ser Arg Leu Asn Ser Ile Asn Phe
 65                  70                  75                  80

Leu Tyr Leu Glu Met Asn Asn Val Arg Thr Glu Asp Thr Gly Tyr Tyr
                 85                  90                  95

Phe Cys Ala Arg Thr Gly Lys His Tyr Asp Phe Trp Ser Gly Tyr Pro
            100                 105                 110

Pro Gly Glu Glu Tyr Phe Gln Asp Trp Gly Gln Gly Thr Leu Val Ile
        115                 120                 125

Val Ser Ser
    130

<210> SEQ ID NO 15
<211> LENGTH: 131
<212> TYPE: PRT
<213> ORGANISM: Artificial Sequence
<220> FEATURE:
<223> OTHER INFORMATION: Variant Antibody Sequence

<400> SEQUENCE: 15

Glu Val Arg Leu Val Glu Ser Gly Gly Gly Leu Val Lys Pro Gly Gly
 1               5                  10                  15

Ser Leu Arg Leu Ser Cys Ser Ala Ser Gly Phe Asn Phe Asp Asp Ala
                20                  25                  30

Trp Met Thr Trp Val Arg Gln Pro Pro Gly Lys Gly Leu Glu Trp Val
            35                  40                  45

Gly Arg Ile Ser Gly Pro Gly Glu Gly Trp Ser Val Asp Tyr Ala Glu
        50                  55                  60

Ser Val Lys Gly Arg Phe Thr Ile Ser Arg Asp Asn Thr Lys Asn Thr
 65                  70                  75                  80

Leu Tyr Leu Glu Met Asn Asn Val Arg Thr Glu Asp Thr Gly Tyr Tyr
                 85                  90                  95

Phe Cys Ala Arg Thr Gly Lys His Tyr Asp Phe Trp Ser Gly Tyr Pro
            100                 105                 110

Pro Gly Glu Glu Tyr Phe Gln Asp Trp Gly Gln Gly Thr Leu Val Ile
        115                 120                 125

Val Ser Ser
    130

<210> SEQ ID NO 16
<211> LENGTH: 131
<212> TYPE: PRT
<213> ORGANISM: Artificial Sequence
<220> FEATURE:
<223> OTHER INFORMATION: Variant Antibody Sequence

<400> SEQUENCE: 16

Glu Val Arg Leu Val Glu Ser Gly Gly Arg Leu Val Arg Pro Gly Gly
 1               5                  10                  15

Ser Leu Arg Leu Ser Cys Ser Ala Ser Gly Phe Asn Phe Asp Asn Ala
                20                  25                  30

Trp Met Thr Trp Val Arg Gln Pro Pro Gly Lys Gly Leu Glu Trp Val
            35                  40                  45

Gly Arg Ile Thr Gly Pro Gly Glu Gly Trp Ser Val Asp Tyr Ala Ala
        50                  55                  60

Ser Val Lys Gly Arg Phe Thr Ile Ser Arg Met Asn Ser Ile Asn Phe
 65                  70                  75                  80

Phe Tyr Leu Glu Met Asn Asn Leu Lys Ile Glu Asp Thr Gly Leu Tyr
```

```
                    85                  90                  95

Phe Cys Ala Arg Thr Gly Lys His Tyr Ala Phe Trp Gly Gly Tyr Pro
                100                 105                 110

Pro Gly Glu Glu Tyr Leu Glu Asp Trp Gly Gln Gly Thr Leu Val Ile
            115                 120                 125

Val Ser Ser
        130

<210> SEQ ID NO 17
<211> LENGTH: 131
<212> TYPE: PRT
<213> ORGANISM: Artificial Sequence
<220> FEATURE:
<223> OTHER INFORMATION: Variant Antibody Sequence

<400> SEQUENCE: 17

Glu Val Arg Leu Val Glu Ser Gly Gly Arg Leu Val Arg Pro Gly Gly
1               5                   10                  15

Ser Leu Arg Leu Ser Cys Ser Ala Ser Gly Phe Asn Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Ser Val Lys Gly Arg Phe Thr Ile Ser Arg Asp Asn Tyr Lys Asn Thr
65                  70                  75                  80

Phe Tyr Leu Glu Met Asn Asn Leu Lys Thr Glu Asp Thr Gly Leu Tyr
                85                  90                  95

Phe Cys Ala Arg Thr Gly Lys His Tyr Ala Phe Trp Gly Gly Tyr Pro
                100                 105                 110

Pro Gly Glu Glu Tyr Leu Glu Asp Trp Gly Gln Gly Thr Leu Val Ile
            115                 120                 125

Val Ser Ser
        130

<210> SEQ ID NO 18
<211> LENGTH: 109
<212> TYPE: PRT
<213> ORGANISM: Artificial Sequence
<220> FEATURE:
<223> OTHER INFORMATION: Variant Antibody Sequence

<400> SEQUENCE: 18

Ala Ser Glu Leu Thr Gln Asp Pro Ala Val Ser Val Ala Leu Lys Gln
1               5                   10                  15

Thr Val Thr Ile Thr Cys Arg Gly Asp Ser Leu Arg Ser His Tyr Val
            20                  25                  30

Ser Trp Tyr Gln Lys Lys Pro Gly Gln Ala Pro Val Leu Val Phe Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Ala Gly Ala Gln Ala Glu
65                  70                  75                  80

Asp Asp Ala Asp Tyr Tyr Cys Ser Ser Arg Asp Lys Ser Gly Ser Arg
                85                  90                  95

Leu Ser Val Phe Gly Gly Gly Thr Lys Leu Thr Val Leu
                100                 105
```

<210> SEQ ID NO 19
<211> LENGTH: 109
<212> TYPE: PRT
<213> ORGANISM: Artificial Sequence
<220> FEATURE:
<223> OTHER INFORMATION: Variant Antibody Sequence

<400> SEQUENCE: 19

```
Ala Ser Glu Leu Thr Gln Asp Pro Thr Val Ser Val Ala Leu Gly Gln
1               5                   10                  15

Thr Val Thr Ile Thr Cys Arg Gly Asp Ser Leu Arg Asn Tyr Tyr Thr
            20                  25                  30

Ser Trp Tyr Gln Gln Lys Pro Gly Gln Ala Pro Val Leu Leu Ile Tyr
        35                  40                  45

Pro Lys His Asn Arg Pro Pro Gly Ile Ser Asp Arg Phe Ser Ala Ser
    50                  55                  60

Ser Ser Gly Asn Thr Ala Ser Leu Thr Ile Thr Gly Ala Gln Thr Glu
65                  70                  75                  80

Asp Glu Gly Asp Tyr Tyr Cys Ser Ser Arg Asp Lys Ser Gly Ser Arg
                85                  90                  95

Leu Val Thr Phe Gly Arg Gly Thr Lys Leu Thr Val Val
            100                 105
```

<210> SEQ ID NO 20
<211> LENGTH: 1443
<212> TYPE: DNA
<213> ORGANISM: Artificial Sequence
<220> FEATURE:
<223> OTHER INFORMATION: Variant Antibody Sequence

<400> SEQUENCE: 20

| | | | | | |
|---|---|---|---|---|---|
| atgggatggt | catgtatcat | ccttttcta | gtagcaactg | caaccggtgt | acattctgaa | 60 |
| gtgcggctgg | ctgagagcgg | cggggggctg | gtcaaacctg | gcgggtcact | gcggctgtcc | 120 |
| tgttctgcct | ccggcttcga | ttttgataac | gcatggatga | catgggtgcg | acagccacct | 180 |
| ggaaaggggc | tggagtgggt | cggcagaatc | actggacctg | gcgaagggtg | gtctgtggac | 240 |
| tacgcagctc | cagtcgaggg | acgattcacc | attagtagag | ataactacaa | gaatacactg | 300 |
| tatctggaga | tgaacaatct | gaggactgaa | gacagcggcc | tgtatttctg | cgcccgcacc | 360 |
| gggaaatact | atgattttg | gtctgggtac | ccacccggag | aggaatattt | tcaggactgg | 420 |
| ggacggggca | ccctggtgat | cgtcagctcc | gcgtcgacca | agggcccatc | ggtcttcccc | 480 |
| ctggcaccct | cctccaagag | cacctctggg | ggcacagcgg | ccctgggctg | cctggtcaag | 540 |
| gactacttcc | ccgaaccggt | gacggtgtcg | tggaactcag | gcgccctgac | cagcggcgtg | 600 |
| cacaccttcc | cggctgtcct | acagtcctca | ggactctact | ccctcagcag | cgtggtgacc | 660 |
| gtgccctcca | gcagcttggg | cacccagacc | tacatctgca | acgtgaatca | caagcccagc | 720 |
| aacaccaagg | tggacaagaa | agttgagccc | aaatcttgtg | acaaaactca | cacatgccca | 780 |
| ccgtgcccag | cacctgaact | cctgggggga | ccgtcagtct | tcctcttccc | cccaaaaccc | 840 |
| aaggacaccc | tcatgatctc | ccggacccct | gaggtcacat | gcgtggtggt | ggacgtgagc | 900 |
| cacgaagacc | ctgaggtcaa | gttcaactgg | tacgtggacg | gcgtggaggt | gcataatgcc | 960 |
| aagacaaagc | cgcgggagga | gcagtacaac | agcacgtacc | gtgtggtcag | cgtcctcacc | 1020 |
| gtcctgcacc | aggactggct | gaatggcaag | gagtacaagt | gcaaggtctc | caacaaagcc | 1080 |
| ctcccagccc | ccatcgagaa | aaccatctcc | aaagccaaag | ggcagccccg | agaaccacag | 1140 |

| gtgtacaccc tgcccccatc ccgggatgag ctgaccaaga accaggtcag cctgacctgc | 1200 |
| ctggtcaaag gcttctatcc cagcgacatc gccgtggagt gggagagcaa tgggcagccg | 1260 |
| gagaacaact acaagaccac gcctcccgtg ctggactccg acggctcctt cttcctctac | 1320 |
| agcaagctca ccgtggacaa gagcaggtgg cagcagggga acgtcttctc atgctccgtg | 1380 |
| atgcatgagg ctctgcacaa ccactacacg cagaagagcc tctccctgtc tccgggtaaa | 1440 |
| tga | 1443 |

<210> SEQ ID NO 21
<211> LENGTH: 1440
<212> TYPE: DNA
<213> ORGANISM: Artificial Sequence
<220> FEATURE:
<223> OTHER INFORMATION: Variant Antibody Sequence

<400> SEQUENCE: 21

| atgggatggt catgtatcat ccttttttcta gtagcaactg caaccggtgt acattctgag | 60 |
| gttagactgg tggagtcagg agggggggctt gtgaagcccg gtgggtctct ccgcctgagc | 120 |
| tgttctgcct ccggctttga tttcgataac gcctggatga cctgggtcag gcagcctcca | 180 |
| ggtaagggac tggagtgggt gggaagaatc acaggtccag gcgagggctg gtccgtggac | 240 |
| tacgcggaat ctgttaaagg cggtttaca atctcaaggg acaataccaa gaataccttg | 300 |
| tatttggaga tgaacaacgt gagaactgaa gacaccggat attacttctg tgccagaaca | 360 |
| ggcaaatact acgacttctg gtccggctat cccctggcg aggaatattt tcaagactgg | 420 |
| ggtcagggaa cccttgttat cgtgtcctcc gcgtcgacca agggcccatc ggtcttcccc | 480 |
| ctggcaccct cctccaagag cacctctggg ggcacagcgg ccctgggctg cctggtcaag | 540 |
| gactacttcc ccgaaccggt gacggtgtcg tggaactcag gcgccctgac cagcggcgtg | 600 |
| cacaccttcc cggctgtcct acagtcctca ggactctact ccctcagcag cgtggtgacc | 660 |
| gtgccctcca gcagcttggg cacccagacc tacatctgca acgtgaatca caagcccagc | 720 |
| aacaccaagg tggacaagaa agttgagccc aaatcttgtg acaaaactca cacatgccca | 780 |
| ccgtgcccag cacctgaact cctgggggga ccgtcagtct tcctcttccc cccaaaaccc | 840 |
| aaggacaccc tcatgatctc ccggacccct gaggtcacat gcgtggtggt ggacgtgagc | 900 |
| cacgaagacc ctgaggtcaa gttcaactgg tacgtggacg gcgtggaggt gcataatgcc | 960 |
| aagacaaagc cgcgggagga gcagtacaac agcacgtacc gtgtggtcag cgtcctcacc | 1020 |
| gtcctgcacc aggactggct gaatggcaag gagtacaagt gcaaggtctc caacaaagcc | 1080 |
| ctcccagccc ccatcgagaa aaccatctcc aaagccaaag ggcagccccg agaaccacag | 1140 |
| gtgtacaccc tgcccccatc ccgggatgag ctgaccaaga accaggtcag cctgacctgc | 1200 |
| ctggtcaaag gcttctatcc cagcgacatc gccgtggagt gggagagcaa tgggcagccg | 1260 |
| gagaacaact acaagaccac gcctcccgtg ctggactccg acggctcctt cttcctctac | 1320 |
| agcaagctca ccgtggacaa gagcaggtgg cagcagggga acgtcttctc atgctccgtg | 1380 |
| atgcatgagg ctctgcacaa ccactacacg cagaagagcc tctccctgtc tccgggtaaa | 1440 |

<210> SEQ ID NO 22
<211> LENGTH: 461
<212> TYPE: PRT
<213> ORGANISM: Artificial Sequence
<220> FEATURE:
<223> OTHER INFORMATION: Variant Antibody Sequence

<400> SEQUENCE: 22

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Gly Lys Gly Leu Glu Trp Val
        35                  40                  45

Gly Arg Ile Thr Gly Pro Gly Glu Gly Trp Ser Val Asp Tyr Ala Glu
        50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Gln Gly Thr Leu Val Ile
            115                 120                 125

Val Ser Ser Ala Ser Thr Lys Gly Pro Ser Val Phe Pro Leu Ala Pro
130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
                180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
        210                 215                 220

Val Asp Lys Lys Val Glu Pro Lys Ser Cys Asp Lys Thr His Thr Cys
225                 230                 235                 240

Pro Pro Cys Pro Ala Pro Glu Leu Leu Gly Gly Pro Ser Val Phe Leu
            245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
            290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
            355                 360                 365

Arg Asp Glu Leu Thr Lys Asn Gln Val Ser Leu Thr Cys Leu Val Lys
        370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

```
Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
        450                 455                 460

<210> SEQ ID NO 23
<211> LENGTH: 461
<212> TYPE: PRT
<213> ORGANISM: Artificial Sequence
<220> FEATURE:
<223> OTHER INFORMATION: Variant Antibody Sequence

<400> SEQUENCE: 23

Glu Val Arg Leu Ala Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
                20                  25                  30

Trp Met Thr Trp Val Arg Gln Pro Pro Gly Lys Gly Leu Glu Trp Val
            35                  40                  45

Gly Arg Ile Thr Gly Pro Gly Glu Gly Trp Ser Val Asp Tyr Ala Ala
        50                  55                  60

Pro Val Glu Gly Arg Phe Thr Ile Ser Arg Asp Asn Tyr Lys Asn Thr
65                  70                  75                  80

Leu Tyr Leu Glu Met Asn Asn Leu Arg Thr Glu Asp Ser Gly Leu Tyr
                85                  90                  95

Phe Cys Ala Arg Thr Gly Lys Tyr Tyr Asp Phe Trp Ser Gly Tyr Pro
                100                 105                 110

Pro Gly Glu Glu Tyr Phe Gln Asp Trp Gly Arg Gly Thr Leu Val Ile
            115                 120                 125

Val Ser Ser Ala Ser Thr Lys Gly Pro Ser Val Phe Pro Leu Ala Pro
        130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320
```

Thr Val Leu His Gln Asp Trp Leu Asn Gly Lys Glu Tyr Lys Cys Lys
            325                 330                 335

Val Ser Asn Lys Ala Leu Pro Ala Pro Ile Glu Lys Thr Ile Ser Lys
        340                 345                 350

Ala Lys Gly Gln Pro Arg Glu Pro Gln Val Tyr Thr Leu Pro Pro Ser
    355                 360                 365

Arg Asp Glu Leu Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 24
<211> LENGTH: 648
<212> TYPE: PRT
<213> ORGANISM: Artificial Sequence
<220> FEATURE:
<223> OTHER INFORMATION: Variant Antibody Sequence

<400> SEQUENCE: 24

Thr Cys Ala Thr Ala Cys Gly Ala Ala Cys Thr Gly Ala Cys Thr Cys
1               5                   10                  15

Ala Gly Gly Ala Cys Ala Cys Thr Gly Gly Cys Gly Thr Cys Thr Cys
            20                  25                  30

Thr Gly Thr Gly Gly Cys Ala Cys Thr Gly Gly Gly Ala Gly Gly Gly
        35                  40                  45

Ala Cys Thr Gly Thr Gly Ala Cys Thr Ala Thr Ala Cys Thr Thr
50                  55                  60

Gly Cys Cys Gly Ala Gly Gly Cys Gly Ala Cys Thr Cys Ala Cys Thr
65                  70                  75                  80

Gly Cys Gly Gly Ala Gly Cys Ala Cys Thr Ala Cys Gly Cys Thr
        85                  90                  95

Thr Cys Cys Thr Gly Gly Thr Ala Thr Cys Ala Gly Ala Ala Gly Ala
            100                 105                 110

Ala Ala Cys Cys Cys Gly Gly Cys Ala Gly Gly Cys Ala Cys Cys
        115                 120                 125

Thr Gly Thr Gly Cys Thr Gly Cys Thr Gly Thr Cys Thr Ala Cys
    130                 135                 140

Gly Gly Ala Ala Ala Gly Ala Ala Cys Ala Ala Thr Ala Gly Gly Cys
145                 150                 155                 160

Cys Ala Thr Cys Thr Gly Gly Cys Ala Thr Cys Cys Cys Gly Ala
        165                 170                 175

Cys Cys Gly Cys Thr Thr Thr Cys Thr Gly Gly Cys Ala Gly Thr
            180                 185                 190

Gly Cys Ala Thr Cys Ala Gly Gly Ala Ala Cys Cys Gly Ala Gly
        195                 200                 205

Cys Cys Ala Gly Thr Cys Thr Gly Ala Cys Cys Ala Thr Thr Ala Cys
    210                 215                 220

-continued

```
Cys Gly Gly Cys Gly Cys Cys Cys Ala Gly Gly Cys Thr Gly Ala Gly
225                 230                 235                 240
Gly Ala Cys Gly Ala Ala Gly Cys Cys Gly Ala Thr Thr Ala Cys Thr
                245                 250                 255
Ala Thr Thr Gly Cys Ala Gly Cys Thr Cys Cys Gly Gly Gly Ala
            260                 265                 270
Thr Ala Ala Gly Ala Gly Cys Gly Gly Cys Thr Cys Ala Gly Ala
            275                 280                 285
Cys Thr Gly Ala Gly Cys Gly Thr Gly Thr Thr Cys Gly Gly Ala Gly
290                 295                 300
Gly Ala Gly Gly Ala Ala Cys Thr Ala Ala Cys Thr Gly Ala Cys
305                 310                 315                 320
Cys Gly Thr Cys Cys Thr Cys Ala Gly Thr Cys Ala Gly Cys Cys Cys
                325                 330                 335
Ala Ala Gly Gly Cys Thr Gly Cys Cys Cys Cys Thr Cys Gly Gly
                340                 345                 350
Thr Cys Ala Cys Thr Cys Thr Gly Thr Thr Cys Cys Gly Cys Cys
            355                 360                 365
Cys Thr Cys Gly Ala Gly Thr Gly Ala Gly Gly Ala Gly Cys Thr Thr
            370                 375                 380
Cys Ala Ala Gly Cys Cys Ala Ala Cys Ala Ala Gly Gly Cys Cys Ala
385                 390                 395                 400
Cys Ala Cys Thr Gly Gly Thr Gly Thr Gly Thr Cys Thr Cys Ala Thr
                405                 410                 415
Ala Ala Gly Thr Gly Ala Cys Thr Thr Cys Thr Ala Cys Cys Cys Gly
            420                 425                 430
Gly Gly Ala Gly Cys Cys Gly Thr Gly Ala Cys Ala Gly Thr Gly Gly
            435                 440                 445
Cys Cys Thr Gly Gly Ala Ala Gly Gly Cys Ala Gly Ala Thr Ala Gly
            450                 455                 460
Cys Ala Gly Cys Cys Cys Gly Thr Cys Ala Ala Gly Gly Cys Gly
465                 470                 475                 480
Gly Gly Ala Gly Thr Gly Gly Ala Gly Cys Cys Ala Cys Cys Ala
                485                 490                 495
Cys Ala Cys Cys Cys Thr Cys Ala Ala Cys Ala Ala Ala Gly
            500                 505                 510
Cys Ala Ala Cys Ala Ala Cys Ala Gly Thr Ala Cys Gly Cys Gly
            515                 520                 525
Gly Cys Cys Ala Gly Cys Ala Gly Cys Thr Ala Cys Cys Thr Gly Ala
530                 535                 540
Gly Cys Cys Thr Gly Ala Cys Gly Cys Cys Thr Gly Ala Gly Cys Ala
545                 550                 555                 560
Gly Thr Gly Gly Ala Ala Gly Thr Cys Cys Ala Cys Ala Gly Ala
                565                 570                 575
Ala Gly Cys Thr Ala Cys Ala Gly Cys Thr Gly Cys Ala Gly Gly
            580                 585                 590
Thr Cys Ala Cys Gly Cys Ala Thr Gly Ala Ala Gly Gly Gly Ala Gly
            595                 600                 605
Cys Ala Cys Cys Gly Thr Gly Ala Cys Ala Ala Gly Ala Gly Cys Ala
            610                 615                 620
Gly Thr Gly Gly Cys Cys Cys Thr Ala Cys Ala Gly Ala Ala Thr
625                 630                 635                 640

Gly Thr Thr Cys Ala Thr Ala Gly
```

645

<210> SEQ ID NO 25
<211> LENGTH: 678
<212> TYPE: PRT
<213> ORGANISM: Artificial Sequence
<220> FEATURE:
<223> OTHER INFORMATION: Variant Antibody Sequence

<400> SEQUENCE: 25

Ala Cys Cys Ala Cys Cys Ala Thr Gly Gly Gly Ala Thr Gly Gly Thr
1 5 10 15

Cys Ala Thr Gly Thr Ala Thr Cys Ala Thr Cys Cys Thr Thr Thr Thr
20 25 30

Thr Cys Thr Ala Gly Thr Ala Gly Cys Ala Ala Cys Thr Gly Cys Ala
35 40 45

Ala Cys Cys Gly Gly Thr Thr Cys Thr Gly Thr Gly Ala Cys Cys Gly
50 55 60

Cys Ala Thr Cys Cys Gly Ala Ala Cys Thr Gly Ala Cys Thr Cys Ala
65 70 75 80

Gly Gly Ala Cys Cys Cys Thr Gly Cys Cys Gly Thr Cys Thr Cys Thr
85 90 95

Gly Thr Gly Gly Cys Ala Cys Thr Gly Ala Ala Gly Cys Ala Gly Ala
100 105 110

Cys Thr Gly Thr Gly Ala Cys Thr Ala Thr Thr Ala Cys Thr Thr Gly
115 120 125

Cys Cys Gly Ala Gly Gly Cys Gly Ala Cys Thr Cys Ala Cys Thr Gly
130 135 140

Cys Gly Gly Ala Gly Cys Cys Ala Cys Thr Ala Cys Gly Cys Thr Thr
145 150 155 160

Cys Cys Thr Gly Gly Thr Ala Thr Cys Ala Gly Ala Ala Gly Ala Ala
165 170 175

Ala Cys Cys Cys Gly Gly Cys Cys Ala Gly Gly Cys Ala Cys Cys Thr
180 185 190

Gly Thr Gly Cys Thr Gly Cys Thr Gly Thr Thr Cys Thr Ala Cys Gly
195 200 205

Gly Ala Ala Ala Gly Ala Ala Cys Ala Ala Thr Ala Gly Gly Cys Cys
210 215 220

Ala Thr Cys Thr Gly Gly Cys Ala Thr Cys Cys Cys Cys Gly Ala Cys
225 230 235 240

Cys Gly Cys Thr Thr Thr Thr Cys Thr Gly Gly Cys Ala Gly Thr Gly
245 250 255

Cys Ala Thr Cys Ala Gly Gly Gly Ala Ala Cys Cys Gly Ala Gly Cys
260 265 270

Cys Ala Gly Thr Cys Thr Gly Ala Cys Cys Ala Thr Thr Ala Cys Cys
275 280 285

Gly Gly Cys Gly Cys Cys Cys Ala Gly Gly Cys Thr Gly Ala Gly Gly
290 295 300

Ala Cys Gly Ala Ala Gly Cys Cys Gly Ala Thr Thr Ala Cys Thr Ala
305 310 315 320

Thr Thr Gly Cys Ala Gly Cys Thr Cys Cys Cys Gly Gly Gly Ala Thr
325 330 335

Ala Ala Gly Ala Gly Cys Gly Gly Cys Thr Cys Cys Ala Gly Ala Cys
340 345 350

Thr Gly Ala Gly Cys Gly Thr Gly Thr Thr Cys Gly Gly Ala Gly Gly

Ala Gly Gly Ala Ala Cys Thr Ala Ala Cys Thr Gly Ala Cys Cys
                370                 375                 380

Gly Thr Cys Cys Thr Cys Ala

-continued

```
Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
               100                 105                 110

Asp Gln Ser Leu Lys Pro Cys Val Lys Leu Thr Pro Leu Cys Val Ser
           115                 120                 125

Leu Lys Cys Thr Asp Leu Lys Asn Asp Thr Asn Thr Asn Ser Ser Ser
130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
               165                 170                 175

Tyr Lys Leu Asp Ile Ile Pro Ile Asp Asn Asp Thr Thr Ser Tyr Lys
           180                 185                 190

Leu Thr Ser Cys Asn Thr Ser Val Ile Thr Gln Ala Cys Pro Lys Val
       195                 200                 205

Ser Phe Glu Pro Ile Pro Ile His Tyr Cys Ala Pro Ala Gly Phe Ala
   210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
               245                 250                 255

Thr Gln Leu Leu Leu Asn Gly Ser Leu Ala Glu Glu Val Val Ile
           260                 265                 270

Arg Ser Val Asn Phe Thr Asp Asn Ala Lys Thr Ile Ile Val Gln Leu
       275                 280                 285

Asn Thr Ser Val Glu Ile Asn Cys Thr Arg Pro Asn Asn Asn Thr Arg
   290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
               325                 330                 335

Lys Trp Asn Asn Thr Leu Lys Gln Ile Ala Ser Lys Leu Arg Glu Gln
           340                 345                 350

Phe Gly Asn Asn Lys Thr Ile Ile Phe Lys Gln Ser Ser Gly Gly Asp
       355                 360                 365

Pro Glu Ile Val Thr His Ser Phe Asn Cys Gly Gly Glu Phe Phe Tyr
   370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
               405                 410                 415

Pro Cys Arg Ile Lys Gln Ile Ile Asn Met Trp Gln Lys Val Gly Lys
           420                 425                 430

Ala Met Tyr Ala Pro Pro Ile Ser Gly Gln Ile Arg Cys Ser Ser Asn
       435                 440                 445

Ile Thr Gly Leu Leu Leu Thr Arg Asp Gly Gly Asn Ser Asn Asn Glu
   450                 455                 460

Ser Glu Ile Phe Arg Pro Gly Gly Gly Asp Met Arg Asp Asn Trp Arg
```

```
            465                 470                 475                 480
        Ser Glu Leu Tyr Lys Tyr Lys Val Val Lys Ile Glu Pro Leu Gly Val
                        485                 490                 495

Ala Pro Thr Lys Ala Lys Arg Val Val Gln Arg Glu Lys Arg Ala
                        500                 505                 510

Val Gly Ile Gly Ala Leu Phe Leu Gly Phe Leu Gly Ala Ala Gly Ser
                        515                 520                 525

Thr Met Gly Ala Ala Ser Met Thr Leu Thr Val Gln Ala Arg Gln Leu
                        530                 535                 540

Leu Ser Gly Ile Val Gln Gln Gln Asn Asn Leu Leu Arg Ala Ile Glu
        545                 550                 555                 560

Ala Gln Gln His Leu Leu Gln Leu Thr Val Trp Gly Ile Lys Gln Leu
                        565                 570                 575

Gln Ala Arg Ile Leu Ala Val Glu Arg Tyr Leu Lys Asp Gln Gln Leu
                        580                 585                 590

Leu Gly Ile Trp Gly Cys Ser Gly Lys Leu Ile Cys Thr Thr Ala Val
                        595                 600                 605

Pro Trp Asn Ala Ser Trp Ser Asn Lys Ser Leu Glu Gln Ile Trp Asn
                        610                 615                 620

His Thr Thr Trp Met Glu Trp Asp Arg Glu Ile Asn Asn Tyr Thr Ser
        625                 630                 635                 640

Leu Ile His Ser Leu Ile Glu Glu Ser Gln Asn Gln Gln Glu Lys Asn
                        645                 650                 655

Glu Gln Glu Leu Leu Glu Leu Asp Lys Trp Ala Ser Leu Trp Asn Trp
                        660                 665                 670

Phe Asn Ile Thr Asn Trp Leu Trp Tyr Ile Lys Leu Phe Ile Met Ile
                        675                 680                 685

Val Gly Gly Leu Val Gly Leu Arg Ile Val Phe Ala Val Leu Ser Ile
                        690                 695                 700

Val Asn Arg Val Arg Gln Gly Tyr Ser Pro Leu Ser Phe Gln Thr His
        705                 710                 715                 720

Leu Pro Thr Pro Arg Gly Pro Asp Arg Pro Glu Gly Ile Glu Glu Glu
                        725                 730                 735

Gly Gly Glu Arg Asp Arg Asp Arg Ser Ile Arg Leu Val Asn Gly Ser
                        740                 745                 750

Leu Ala Leu Ile Trp Asp Asp Leu Arg Ser Leu Cys Leu Phe Ser Tyr
                        755                 760                 765

His Arg Leu Arg Asp Leu Leu Leu Ile Val Thr Arg Ile Val Glu Leu
                        770                 775                 780

Leu Gly Arg Arg Gly Trp Glu Ala Leu Lys Tyr Trp Trp Asn Leu Leu
        785                 790                 795                 800

Gln Tyr Trp Ser Gln Glu Leu Lys Asn Ser Ala Val Ser Leu Leu Asn
                        805                 810                 815

Ala Thr Ala Ile Ala Val Ala Glu Gly Thr Asp Arg Val Ile Glu Val
                        820                 825                 830

Val Gln Gly Ala Cys Arg Ala Ile Arg His Ile Pro Arg Arg Ile Arg
                        835                 840                 845

Gln Gly Leu Glu Arg Ile Leu Leu
            850                 855

<210> SEQ ID NO 27
<211> LENGTH: 121
<212> TYPE: PRT
<213> ORGANISM: Artificial Sequence
```

```
<220> FEATURE:
<223> OTHER INFORMATION: Variant Antibody Sequence

<400> SEQUENCE: 27

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120

<210> SEQ ID NO 28
<211> LENGTH: 103
<212> TYPE: PRT
<213> ORGANISM: Artificial Sequence
<220> FEATURE:
<223> OTHER INFORMATION: Variant Antibody Sequence

<400> SEQUENCE: 28

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys
            100

<210> SEQ ID NO 29
<211> LENGTH: 125
<212> TYPE: PRT
<213> ORGANISM: Artificial Sequence
<220> FEATURE:
<223> OTHER INFORMATION: Variant Antibody Sequence

<400> SEQUENCE: 29

Gln Val Arg Leu Ser Gln Ser Gly Gly Gln Met Lys Lys Pro Gly Asp
1               5                   10                  15

Ser Met Arg Ile Ser Cys Arg Ala Ser Gly Tyr Glu Phe Ile Asn Cys
            20                  25                  30

Pro Ile Asn Trp Ile Arg Leu Ala Pro Gly Lys Arg Pro Glu Trp Met
        35                  40                  45
```

```
Gly Trp Met Lys Pro Arg Gly Gly Ala Val Ser Tyr Ala Arg Gln Leu
        50                  55                  60

Gln Gly Arg Val Thr Met Thr Arg Asp Met Tyr Ser Glu Thr Ala Phe
 65                  70                  75                  80

Leu Glu Leu Arg Ser Leu Thr Ser Asp Asp Thr Ala Val Tyr Phe Cys
                85                  90                  95

Thr Arg Gly Lys Tyr Cys Thr Ala Arg Asp Tyr Tyr Asn Trp Asp Phe
             100                 105                 110

Glu His Trp Gly Gln Gly Thr Pro Val Thr Val Ser Ser
             115                 120                 125

<210> SEQ ID NO 30
<211> LENGTH: 125
<212> TYPE: PRT
<213> ORGANISM: Artificial Sequence
<220> FEATURE:
<223> OTHER INFORMATION: Variant Antibody Sequence

<400> SEQUENCE: 30

Gln Val Arg Leu Ser Gln Ser Gly Gly Gln Met Lys Lys Pro Gly Asp
 1               5                  10                  15

Ser Met Arg Ile Ser Cys Arg Ala Ser Gly Tyr Glu Phe Ile Asn Cys
                20                  25                  30

Pro Ile Asn Trp Ile Arg Leu Ala Pro Gly Lys Arg Pro Glu Trp Met
             35                  40                  45

Gly Trp Met Lys Pro Arg His Gly Ala Val Ser Tyr Ala Arg Gln Leu
         50                  55                  60

Gln Gly Arg Val Thr Met Thr Arg Asp Met Tyr Ser Glu Thr Ala Phe
 65                  70                  75                  80

Leu Glu Leu Arg Ser Leu Thr Ser Asp Asp Thr Ala Val Tyr Phe Cys
                85                  90                  95

Thr Arg Gly Lys Tyr Cys Thr Ala Arg Asp Tyr Tyr Asn Trp Asp Phe
             100                 105                 110

Glu His Trp Gly Gln Gly Thr Pro Val Thr Val Ser Ser
             115                 120                 125

<210> SEQ ID NO 31
<211> LENGTH: 101
<212> TYPE: PRT
<213> ORGANISM: Artificial Sequence
<220> FEATURE:
<223> OTHER INFORMATION: Variant Antibody Sequence

<400> SEQUENCE: 31

Ser Leu Thr Gln Ser Pro Gly Thr Leu Ser Leu Ser Pro Gly Glu Thr
 1               5                  10                  15

Ala Ile Ile Ser Cys Arg Thr Ser Gln Tyr Gly Ser Leu Ala Trp Tyr
                20                  25                  30

Gln Gln Arg Pro Gly Gln Ala Pro Arg Leu Val Ile Tyr Ser Gly Ser
             35                  40                  45

Thr Arg Ala Ala Gly Ile Pro Asp Arg Phe Ser Gly Ser Arg Trp Gly
         50                  55                  60

Pro Asp Tyr Asn Leu Thr Ile Ser Asn Leu Glu Ser Gly Asp Phe Gly
 65                  70                  75                  80

Val Tyr Tyr Cys Gln Gln Tyr Glu Phe Phe Gly Gln Gly Thr Lys Val
                85                  90                  95

Gln Val Asp Ile Lys
             100
```

<210> SEQ ID NO 32
<211> LENGTH: 125
<212> TYPE: PRT
<213> ORGANISM: Artificial Sequence
<220> FEATURE:
<223> OTHER INFORMATION: Variant Antibody Sequence

<400> SEQUENCE: 32

Gln Val Arg Leu Ser Gln Ser Gly Gly Gln Met Lys Lys Pro Gly Asp
1               5                   10                  15

Ser Met Arg Ile Ser Cys Arg Ala Ser Gly Tyr Glu Phe Ile Asn Cys
            20                  25                  30

Pro Ile Asn Trp Val Arg Leu Ala Pro Gly Lys Arg Pro Glu Trp Met
        35                  40                  45

Gly Trp Met Lys Pro Arg His Gly Ala Val Ser Tyr Ala Arg Gln Leu
    50                  55                  60

Gln Gly Arg Val Thr Met Thr Arg Asp Met Tyr Ser Glu Thr Ala Phe
65                  70                  75                  80

Leu Glu Leu Arg Ser Leu Thr Ser Asp Thr Ala Val Tyr Phe Cys
                85                  90                  95

Ala Arg Gly Lys Tyr Cys Thr Ala Arg Asp Tyr Tyr Asn Trp Asp Phe
            100                 105                 110

Glu His Trp Gly Gln Gly Thr Pro Val Thr Val Ser Ser
        115                 120                 125

<210> SEQ ID NO 33
<211> LENGTH: 101
<212> TYPE: PRT
<213> ORGANISM: Artificial Sequence
<220> FEATURE:
<223> OTHER INFORMATION: Variant Antibody Sequence

<400> SEQUENCE: 33

Ser Leu Thr Gln Ser Pro Gly Thr Leu Ser Leu Ser Pro Gly Glu Thr
1               5                   10                  15

Ala Ile Ile Ser Cys Arg Thr Ser Gln Tyr Gly Ser Leu Ala Trp Tyr
            20                  25                  30

Gln Gln Arg Pro Gly Gln Ala Pro Arg Leu Val Ile Tyr Ser Gly Ser
        35                  40                  45

Thr Arg Ala Ala Gly Ile Pro Asp Arg Phe Ser Gly Ser Arg Trp Gly
    50                  55                  60

Pro Asp Tyr Asn Leu Thr Ile Ser Asn Leu Glu Ser Gly Asp Phe Gly
65                  70                  75                  80

Val Tyr Tyr Cys Gln Gln Tyr Glu Phe Phe Gly Gln Gly Thr Lys Val
                85                  90                  95

Gln Val Asp Ile Lys
            100

<210> SEQ ID NO 34
<211> LENGTH: 28
<212> TYPE: PRT
<213> ORGANISM: Human immunodeficiency virus type 1

<400> SEQUENCE: 34

Asn Glu Gln Glu Leu Leu Glu Leu Asp Lys Trp Ala Ser Leu Trp Asn
1               5                   10                  15

Trp Phe Asp Ile Thr Asn Trp Leu Trp Tyr Ile Arg
            20                  25

<210> SEQ ID NO 35
<211> LENGTH: 131
<212> TYPE: PRT
<213> ORGANISM: Artificial Sequence
<220> FEATURE:
<223> OTHER INFORMATION: Variant Antibody Sequence

<400> SEQUENCE: 35

```
Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Glu
    50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Trp Gly Tyr Pro
            100                 105                 110

Pro Gly Glu Glu Tyr Phe Gln Asp Trp Gly Gln Gly Thr Leu Val Ile
        115                 120                 125

Val Ser Ser
    130
```

<210> SEQ ID NO 36
<211> LENGTH: 131
<212> TYPE: PRT
<213> ORGANISM: Artificial Sequence
<220> FEATURE:
<223> OTHER INFORMATION: Variant Antibody Sequence

<400> SEQUENCE: 36

```
Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Glu
    50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Ser Gly Cys Pro
            100                 105                 110

Pro Gly Glu Glu Tyr Phe Gln Asp Trp Gly Gln Gly Thr Leu Val Ile
        115                 120                 125

Val Ser Ser
    130
```

<210> SEQ ID NO 37
<211> LENGTH: 131
<212> TYPE: PRT

<213> ORGANISM: Artificial Sequence
<220> FEATURE:
<223> OTHER INFORMATION: Variant Antibody Sequence

<400> SEQUENCE: 37

```
Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Glu
    50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Trp Gly Cys Pro
            100                 105                 110

Pro Gly Glu Glu Tyr Phe Gln Asp Trp Gly Gln Gly Thr Leu Val Ile
        115                 120                 125

Val Ser Ser
    130
```

<210> SEQ ID NO 38
<211> LENGTH: 131
<212> TYPE: PRT
<213> ORGANISM: Artificial Sequence
<220> FEATURE:
<223> OTHER INFORMATION: Variant Antibody Sequence

<400> SEQUENCE: 38

```
Glu Val Arg Leu Ala Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Asp Asn Tyr Lys Asn Thr
65                  70                  75                  80

Leu Tyr Leu Glu Met Asn Asn Leu Arg Thr Glu Asp Ser Gly Leu Tyr
                85                  90                  95

Phe Cys Ala Arg Thr Gly Lys Tyr Tyr Asp Phe Trp Trp Gly Tyr Pro
            100                 105                 110

Pro Gly Glu Glu Tyr Phe Gln Asp Trp Gly Arg Gly Thr Leu Val Ile
        115                 120                 125

Val Ser Ser
    130
```

<210> SEQ ID NO 39
<211> LENGTH: 131
<212> TYPE: PRT
<213> ORGANISM: Artificial Sequence
<220> FEATURE:
<223> OTHER INFORMATION: Variant Antibody Sequence

<400> SEQUENCE: 39

Glu Val Arg Leu Ala Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
                35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Asp Asn Tyr Lys Asn Thr
65                  70                  75                  80

Leu Tyr Leu Glu Met Asn Asn Leu Arg Thr Glu Asp Ser Gly Leu Tyr
                85                  90                  95

Phe Cys Ala Arg Thr Gly Lys Tyr Tyr Asp Phe Trp Ser Gly Cys Pro
                100                 105                 110

Pro Gly Glu Glu Tyr Phe Gln Asp Trp Gly Arg Gly Thr Leu Val Ile
            115                 120                 125

Val Ser Ser
    130

<210> SEQ ID NO 40
<211> LENGTH: 131
<212> TYPE: PRT
<213> ORGANISM: Artificial Sequence
<220> FEATURE:
<223> OTHER INFORMATION: Variant Antibody Sequence

<400> SEQUENCE: 40

Glu Val Arg Leu Ala Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
                35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Asp Asn Tyr Lys Asn Thr
65                  70                  75                  80

Leu Tyr Leu Glu Met Asn Asn Leu Arg Thr Glu Asp Ser Gly Leu Tyr
                85                  90                  95

Phe Cys Ala Arg Thr Gly Lys Tyr Tyr Asp Phe Trp Trp Gly Cys Pro
                100                 105                 110

Pro Gly Glu Glu Tyr Phe Gln Asp Trp Gly Arg Gly Thr Leu Val Ile
            115                 120                 125

Val Ser Ser
    130

<210> SEQ ID NO 41
<211> LENGTH: 109
<212> TYPE: PRT
<213> ORGANISM: Artificial Sequence
<220> FEATURE:
<223> OTHER INFORMATION: Variant Antibody Sequence

<400> SEQUENCE: 41

Ala Ser Glu Leu Thr Gln Asp Pro Ala Val Ser Val Ala Leu Lys Gln
1               5                   10                  15

Thr Val Thr Ile Thr Cys Arg Gly Asp Ser Leu Arg Cys His Tyr Ala

```
                20                  25                  30

Ser Trp Tyr Gln Lys Lys Pro Gly Gln Ala Pro Val Leu Leu Phe Tyr
            35                  40                  45

Gly Lys Asn Asn Arg Pro Ser Gly Ile Pro Asp Arg Phe Ser Gly Ser
        50                  55                  60

Ala Ser Gly Asn Arg Ala Ser Leu Thr Ile Thr Gly Ala Gln Ala Glu
 65                  70                  75                  80

Asp Glu Ala Asp Tyr Tyr Cys Ser Ser Arg Asp Lys Ser Gly Ser Arg
                85                  90                  95

Leu Ser Val Phe Gly Gly Gly Thr Lys Leu Thr Val Leu
            100                 105

<210> SEQ ID NO 42
<211> LENGTH: 109
<212> TYPE: PRT
<213> ORGANISM: Artificial Sequence
<220> FEATURE:
<223> OTHER INFORMATION: Variant Antibody Sequence

<400> SEQUENCE: 42

Ala Ser Glu Leu Thr Gln Asp Pro Ala Val Ser Val Ala Leu Lys Gln
 1               5                  10                  15

Thr Val Thr Ile Thr Cys Arg Gly Asp Ser Leu Arg Ser His Trp Ala
                20                  25                  30

Ser Trp Tyr Gln Lys Lys Pro Gly Gln Ala Pro Val Leu Leu Phe Tyr
            35                  40                  45

Gly Lys Asn Asn Arg Pro Ser Gly Ile Pro Asp Arg Phe Ser Gly Ser
        50                  55                  60

Ala Ser Gly Asn Arg Ala Ser Leu Thr Ile Thr Gly Ala Gln Ala Glu
 65                  70                  75                  80

Asp Glu Ala Asp Tyr Tyr Cys Ser Ser Arg Asp Lys Ser Gly Ser Arg
                85                  90                  95

Leu Ser Val Phe Gly Gly Gly Thr Lys Leu Thr Val Leu
            100                 105

<210> SEQ ID NO 43
<211> LENGTH: 109
<212> TYPE: PRT
<213> ORGANISM: Artificial Sequence
<220> FEATURE:
<223> OTHER INFORMATION: Variant Antibody Sequence

<400> SEQUENCE: 43

Ala Ser Glu Leu Thr Gln Asp Pro Ala Val Ser Val Ala Leu Lys Gln
 1               5                  10                  15

Thr Val Thr Ile Thr Cys Arg Gly Asp Ser Leu Arg Ser His Phe Ala
                20                  25                  30

Ser Trp Tyr Gln Lys Lys Pro Gly Gln Ala Pro Val Leu Leu Phe Tyr
            35                  40                  45

Gly Lys Asn Asn Arg Pro Ser Gly Ile Pro Asp Arg Phe Ser Gly Ser
        50                  55                  60

Ala Ser Gly Asn Arg Ala Ser Leu Thr Ile Thr Gly Ala Gln Ala Glu
 65                  70                  75                  80

Asp Glu Ala Asp Tyr Tyr Cys Ser Ser Arg Asp Lys Ser Gly Ser Arg
                85                  90                  95

Leu Ser Val Phe Gly Gly Gly Thr Lys Leu Thr Val Leu
            100                 105
```

<210> SEQ ID NO 44
<211> LENGTH: 393
<212> TYPE: DNA
<213> ORGANISM: Artificial Sequence
<220> FEATURE:
<223> OTHER INFORMATION: Variant Antibody Sequence

<400> SEQUENCE: 44

```
gaagtgcggc tggctgagag cggcgggggg ctggtcaaac ctggcgggtc actgcggctg     60
tcctgttctg cctccggctt cgattttgat aacgcatgga tgacatgggt gcgacagcca    120
cctggaaagg gctggagtg gtcggcaga atcactggac ctggcgaagg gtggtctgtg     180
gactacgcag ctccagtcga gggacgattc accattagta gagataacta caagaataca    240
ctgtatctgg agatgaacaa tctgaggact gaagacagcg gcctgtattt ctgcgcccgc    300
accgggaaat actatgattt tggtctgggt acccacccg gagaggaata ttttcaggac     360
tggggacggg gcaccctggt gatcgtcagc tcc                                 393
```

<210> SEQ ID NO 45
<211> LENGTH: 393
<212> TYPE: DNA
<213> ORGANISM: Artificial Sequence
<220> FEATURE:
<223> OTHER INFORMATION: Variant Antibody Sequence

<400> SEQUENCE: 45

```
gaggttagac tggtggagtc aggagggggg cttgtgaagc ccggtgggtc tctccgcctg     60
agctgttctg cctccggctt tgatttcgat aacgcctgga tgacctgggt caggcagcct   120
ccaggtaagg gactggagtg gtgggaaga atcacaggtc caggcgaggg ctggtccgtg    180
gactacgcgg aatctgttaa agggcggttt acaatctcaa gggacaatac caagaatacc    240
ttgtatttgg agatgaacaa cgtgagaact gaagacaccg gatattactt ctgtgccaga    300
acaggcaaat actacgactt ctggtccggc tatcccctg gcgaggaata ttttcaagac    360
tggggtcagg gaacccttgt tatcgtgtcc tcc                                 393
```

<210> SEQ ID NO 46
<211> LENGTH: 327
<212> TYPE: DNA
<213> ORGANISM: Artificial Sequence
<220> FEATURE:
<223> OTHER INFORMATION: Variant Antibody Sequence

<400> SEQUENCE: 46

```
tcatacgaac tgactcagga cactggcgtc tctgtggcac tggggaggac tgtgactatt     60
acttgccgag cgactcact gcggagccac tacgcttcct ggtatcagaa gaaacccggc   120
caggcacctg tgctgctgtt ctacggaaag aacaataggc catctggcat ccccgaccgc    180
ttttctggca gtgcatcagg gaaccgagcc agtctgacca ttaccggcgc ccaggctgag    240
gacgaagccg attactattg cagctcccgg gataagagcg gctccagact gagcgtgttc    300
ggaggaggaa ctaaactgac cgtcctc                                        327
```

<210> SEQ ID NO 47
<211> LENGTH: 390
<212> TYPE: DNA
<213> ORGANISM: Artificial Sequence
<220> FEATURE:
<223> OTHER INFORMATION: Variant Antibody Sequence

<400> SEQUENCE: 47

| | |
|---|---:|
| accaccatgg gatggtcatg tatcatcctt tttctagtag caactgcaac cggttctgtg | 60 |
| accgcatccg aactgactca ggaccctgcc gtctctgtgg cactgaagca gactgtgact | 120 |
| attacttgcc gaggcgactc actgcggagc cactacgctt cctggtatca gaagaaaccc | 180 |
| ggccaggcac ctgtgctgct gttctacgga agaacaata ggccatctgg catccccgac | 240 |
| cgcttttctg gcagtgcatc agggaaccga gccagtctga ccattaccgg cgcccaggct | 300 |
| gaggacgaag ccgattacta ttgcagctcc cgggataaga gcggctccag actgagcgtg | 360 |
| ttcggaggag gaactaaaact gaccgtcctc | 390 |

<210> SEQ ID NO 48
<211> LENGTH: 5856
<212> TYPE: DNA
<213> ORGANISM: Artificial Sequence
<220> FEATURE:
<223> OTHER INFORMATION: Variant Antibody Sequence

<400> SEQUENCE: 48

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acaaacttta cggtaaatgg | 420 |
| cccgcctggc tgaccgccca acgacccccg cccattgacg tcaataatga cgtatgttcc | 480 |
| catagtaacg ccaatagga ctttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctcca tcggctcgca tctctccttc acgcgcccgc | 1020 |
| cgccctacct gaggccgcca tccacgccgg ttgagtcgcg ttctgccgcc tcccgcctgt | 1080 |
| ggtgcctcct gaactgcgtc cgccgtctag gtaagtttaa agctcaggtc gagaccgggc | 1140 |
| ctttgtccgg cgctcccttg gagcctacct agactcagcc ggctctccac gctttgcctg | 1200 |
| accctgcttg ctcaactcta gttaacggtg gagggcagtg tagtctgagc agtactcgtt | 1260 |
| gctgccgcgc gcgccaccag acataatagc tgacagacta acagactgtt cctttccatg | 1320 |
| ggtcttttct gcagtcaccg tcgtcgacac gtgtgatcag atatcgcggc cgctctagac | 1380 |
| caccatggga tggtcatgta tcatcctttt tctagtagca actgcaaccg gtgtacattc | 1440 |
| tgaagtgcgg ctggctgaga gcggcggggg gctggtcaaa cctggcgggt cactgcggct | 1500 |
| gtcctgttct gcctccggct tcgatttga taacgcatgg atgacatggg tgcgacagcc | 1560 |
| acctggaaag gggctggagt gggtcggcag aatcactgga cctggcgaag gtggtctgt | 1620 |

```
ggactacgca gctccagtcg agggacgatt caccattagt agagataact acaagaatac   1680
actgtatctg gagatgaaca atctgaggac tgaagacagc ggcctgtatt tctgcgcccg   1740
caccgggaaa tactatgatt tttggtctgg gtacccaccc ggagaggaat attttcagga   1800
ctggggacgg ggcaccctgg tgatcgtcag ctccgcgtcg accaagggcc catcggtctt   1860 cccccctggca ccctcctcca agagcacctc tgggggcaca gcggccctgg gctgcctggt   1920
caaggactac ttccccgaac cggtgacggt gtcgtggaac tcaggcgccc tgaccagcgg   1980
cgtgcacacc ttcccggctg tcctacagtc ctcaggactc tactccctca gcagcgtggt   2040
gaccgtgccc tccagcagct gggcaccca gacctacatc tgcaacgtga atcacaagcc   2100
cagcaacacc aaggtggaca gaaagttga gcccaaatct tgtgacaaaa ctcacacatg   2160
cccaccgtgc ccagcacctg aactcctggg gggaccgtca gtcttcctct tccccccaaa   2220
acccaaggac accctcatga tctcccggac ccctgaggtc acatgcgtgg tggtggacgt   2280
gagccacgaa gaccctgagg tcaagttcaa ctggtacgtg gacggcgtgg aggtgcataa   2340
tgccaagaca aagccgcggg aggagcagta caacagcacg taccgtgtgg tcagcgtcct   2400
caccgtcctg caccaggact ggctgaatgg caaggagtac aagtgcaagg tctccaacaa   2460 agcccttccca gcccccatcg agaaaaccat ctccaaagcc aaagggcagc ccgagaacc   2520 acaggtgtac accctgcccc catcccggga tgagctgacc aagaaccagg tcagcctgac   2580
ctgcctggtc aaaggcttct atcccagcga catcgccgtg gagtgggaga gcaatgggca   2640
gccggagaac aactacaaga ccacgcctcc cgtgctggac tccgacggct ccttcttcct   2700
ctacagcaag ctcaccgtgg acaagagcag gtggcagcag gggaacgtct tctcatgctc   2760
cgtgatgcat gaggctctgc acaaccacta cacgcagaag agcctctccc tgtctccggg   2820
taaatgatga ggatccagat ctgctgtgcc ttctagttgc cagccatctg ttgtttgccc   2880 ctccccccgtg ccttccttga ccctggaagg tgccactccc actgtccttt cctaataaaa   2940
tgaggaaatt gcatcgcatt gtctgagtag gtgtcattct attctggggg gtggggtggg   3000
gcaggacagc aagggggagg attgggaaga caatagcagg catgctgggg atgcggtggg   3060
ctctatgggt acccaggtgc tgaagaattg acccggttcc tcctgggcca gaaagaagca   3120
ggcacatccc cttctctgtg acacaccctg tccacgcccc tggttcttag ttccagcccc   3180
actcatagga cactcatagc tcaggagggc tccgccttca atcccacccg ctaaagtact   3240
tggagcggtc tctccctccc tcatcagccc accaaaccaa acctagcctc caagagtggg   3300
aagaaattaa agcaagatag gctattaagt gcagagggag agaaaatgcc tccaacatgt   3360
gaggaagtaa tgagagaaat catagaattt taaggccatg atttaaggcc atcatggcct   3420
taatcttccg cttcctcgct cactgactcg ctgcgctcgg tcgttcggct gcggcgagcg   3480
gtatcagctc actcaaaggc ggtaatacgg ttatccacag aatcagggga taacgcagga   3540
aagaacatgt gagcaaaagg ccagcaaaag gccaggaacc gtaaaaaggc cgcgttgctg   3600
gcgtttttcc ataggctccg ccccctgac gagcatcaca aaaatcgacg ctcaagtcag   3660
aggtggcgaa acccgacagg actataaaga taccaggcgt ttccccctgg aagctccctc   3720
gtgcgctctc ctgttccgac cctgccgctt accggatacc tgtccgcctt tctcccttcg   3780
ggaagcgtgg cgctttctca tagctcacgc tgtaggtatc tcagttcggt gtaggtcgtt   3840
cgctccaagc tgggctgtgt gcacgaaccc ccgttcagc ccgaccgctg cgccttatcc   3900
ggtaactatc gtcttgagtc caacccggta agacacgact tatcgccact ggcagcagcc   3960
actggtaaca ggattagcag agcgaggtat gtaggcggtg ctacagagtt cttgaagtgg   4020
```

```
tggcctaact acggctacac tagaagaaca gtatttggta tctgcgctct gctgaagcca    4080
gttaccttcg gaaaaagagt tggtagctct tgatccggca acaaaccac cgctggtagc     4140 ggtggttttt tgtttgcaa gcagcagatt acgcgcagaa aaaaggatc tcaagaagat      4200 cctttgatct tttctacggg gtctgacgct cagtggaacg aaaactcacg ttaagggatt    4260
ttggtcatga gattatcaaa aaggatcttc acctagatcc ttttaaatta aaaatgaagt    4320
tttaaatcaa tctaaagtat atatgagtaa acttggtctg acagttacca atgcttaatc    4380
agtgaggcac ctatctcagc gatctgtcta tttcgttcat ccatagttgc ctgactcggg    4440 ggggggggggc gctgaggtct gcctcgtgaa gaaggtgttg ctgactcata ccaggcctga   4500
atcgccccat catccagcca gaaagtgagg gagccacggt tgatgagagc tttgttgtag    4560
gtggaccagt tggtgatttt gaactttttgc tttgccacgg aacggtctgc gttgtcggga   4620
agatgcgtga tctgatcctt caactcagca aaagttcgat ttattcaaca aagccgccgt    4680
cccgtcaagt cagcgtaatg ctctgccagt gttacaacca attaaccaat tctgattaga    4740
aaaactcatc gagcatcaaa tgaaactgca atttattcat atcaggatta tcaataccat    4800 attttttgaaa aagccgtttc tgtaatgaag gagaaaactc accgaggcag ttccatagga   4860
tggcaagatc ctggtatcgg tctgcgattc cgactcgtcc aacatcaata caacctatta   4920
atttcccctc gtcaaaaata aggttatcaa gtgagaaatc accatgagtg acgactgaat   4980
ccggtgagaa tggcaaaagc ttatgcattt cttttccagac ttgttcaaca ggccagccat   5040
tacgctcgtc atcaaaatca ctcgcatcaa ccaaaccgtt attcattcgt gattgcgcct    5100
gagcgagacg aaatacgcga tcgctgttaa aaggacaatt acaaacagga atcgaatgca    5160
accggcgcag gaacactgcc agcgcatcaa caatattttc acctgaatca ggatattctt    5220
ctaatacctg gaatgctgtt ttcccgggga tcgcagtggt gagtaaccat gcatcatcag    5280
gagtacggat aaaatgcttg atggtcggaa gaggcataaa ttccgtcagc cagtttagtc    5340
tgaccatctc atctgtaaca tcattggcaa cgctacctt gccatgtttc agaaacaact    5400
ctggcgcatc gggcttccca tacaatcgat agattgtcgc acctgattgc ccgacattat    5460
cgcgagccca tttataccca tataaatcag catccatgtt ggaatttaat cgcggcctcg    5520
agcaagacgt ttcccgttga atatggctca taacacccct tgtattactg tttatgtaag    5580
cagacagttt tattgttcat gatgatatat ttttatcttg tgcaatgtaa catcagagat    5640
tttgagacac aacgtggctt tcccccccccc cccattattg aagcatttat cagggttatt    5700
gtctcatgag cggatacata tttgaatgta tttagaaaaa taaacaaata ggggttccgc    5760
gcacatttcc ccgaaaagtg ccacctgacg tctaagaaac cattattatc atgacattaa    5820
cctataaaaa taggcgtatc acgaggccct ttcgtc                              5856
```

<210> SEQ ID NO 49
<211> LENGTH: 5856
<212> TYPE: DNA
<213> ORGANISM: Artificial Sequence
<220> FEATURE:
<223> OTHER INFORMATION: Variant Antibody Sequence

<400> SEQUENCE: 49

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
```

```
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca cgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140 cttttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
caccatggga tggtcatgta tcatcctttt tctagtagca actgcaaccg gtgtacattc   1440
tgaggttaga ctggtggagt caggaggggg gcttgtgaag cccggtgggt ctctccgcct   1500
gagctgttct gcctccggct ttgatttcga taacgcctgg atgacctggg tcaggcagcc   1560
tccaggtaag ggactggagt gggtgggaag aatcacaggt ccaggcgagg gctggtccgt   1620
ggactacgcg gaatctgtta aagggcggtt tacaatctca agggacaata ccaagaatac   1680
cttgtatttg gagatgaaca acgtgagaac tgaagacacc ggatattact tctgtgccag   1740
aacaggcaaa tactacgact tctggtccgg ctatccccct ggcgaggaat attttcaaga   1800
ctggggtcag ggaacccttg ttatcgtgtc ctccgcgtcg accaagggcc catcggtctt   1860
ccccctggca ccctcctcca agagcacctc tgggggcaca gcggccctgg gctgcctggt   1920
caaggactac ttccccgaac cggtgacggt gtcgtggaac tcaggcgccc tgaccagcgg   1980
cgtgcacacc ttcccggctg tcctacagtc ctcaggactc tactccctca gcagcgtggt   2040
gaccgtgccc tccagcagct gggcaccca gacctacatc tgcaacgtga atcacaagcc   2100
cagcaacacc aaggtggaca gaaagttga gcccaaatct tgtgacaaaa ctcacacatg   2160
cccaccgtgc ccagcacctg aactcctggg gggaccgtca gtcttcctct tccccccaaa   2220
acccaaggac accctcatga tctcccggac ccctgaggtc acatgcgtgg tggtggacgt   2280
gagccacgaa gaccctgagg tcaagttcaa ctggtacgtg gacggcgtgg aggtgcataa   2340
tgccaagaca aagccgcggg aggagcagta caacagcacg taccgtgtgg tcagcgtcct   2400
caccgtcctg caccaggact ggctgaatgg caaggagtac aagtgcaagg tctccaacaa   2460
agccctccca gcccccatcg agaaaaccat ctccaaagcc aaagggcagc cccgagaacc   2520
acaggtgtac accctgcccc catcccggga tgagctgacc aagaaccagg tcagcctgac   2580
```

```
ctgcctggtc aaaggcttct atcccagcga catcgccgtg gagtgggaga gcaatgggca    2640
gccggagaac aactacaaga ccacgcctcc cgtgctggac tccgacggct ccttcttcct    2700
ctacagcaag ctcaccgtgg acaagagcag gtggcagcag gggaacgtct tctcatgctc    2760
cgtgatgcat gaggctctgc acaaccacta cacgcagaag agcctctccc tgtctccggg    2820
taaatgatga ggatccagat ctgctgtgcc ttctagttgc cagccatctg ttgtttgccc    2880
ctcccccgtg ccttccttga ccctggaagg tgccactccc actgtccttt cctaataaaa    2940
tgaggaaatt gcatcgcatt gtctgagtag gtgtcattct attctggggg gtggggtggg    3000
gcaggacagc aaggggggagg attgggaaga caatagcagg catgctgggg atgcggtggg    3060
ctctatgggt acccaggtgc tgaagaattg acccggttcc tcctgggcca gaaagaagca    3120
ggcacatccc cttctctgtg acacaccctg tccacgcccc tggttcttag ttccagcccc    3180
actcatagga cactcatagc tcaggagggc tccgccttca atcccacccg ctaaagtact    3240
tggagcggtc tctccctccc tcatcagccc accaaaccaa acctagcctc caagagtggg    3300
aagaaattaa agcaagatag gctattaagt gcagagggag agaaaatgcc tccaacatgt    3360
gaggaagtaa tgagagaaat catagaattt taaggccatg atttaaggcc atcatggcct    3420
taatcttccg cttcctcgct cactgactcg ctgcgctcgg tcgttcggct gcggcgagcg    3480
gtatcagctc actcaaaggc ggtaatacgg ttatccacag aatcagggga taacgcagga    3540
aagaacatgt gagcaaaagg ccagcaaaag gccaggaacc gtaaaaaggc cgcgttgctg    3600
gcgtttttcc ataggctccg ccccctgac gagcatcaca aaaatcgacg ctcaagtcag    3660
aggtggcgaa acccgacagg actataaaga taccaggcgt ttccccctgg aagctccctc    3720
gtgcgctctc ctgttccgac cctgccgctt accggatacc tgtccgcctt tctcccttcg    3780
ggaagcgtgg cgctttctca tagctcacgc tgtaggtatc tcagttcggt gtaggtcgtt    3840
cgctccaagc tgggctgtgt gcacgaaccc cccgttcagc ccgaccgctg cgccttatcc    3900
ggtaactatc gtcttgagtc caacccggta agacacgact tatcgccact ggcagcagcc    3960
actggtaaca ggattagcag agcgaggtat gtaggcggtg ctacagagtt cttgaagtgg    4020
tggcctaact acggctacac tagaagaaca gtatttggta tctgcgctct gctgaagcca    4080
gttaccttcg gaaaaagagt tggtagctct tgatccggca aacaaaccac cgctggtagc    4140
ggtggttttt ttgtttgcaa gcagcagatt acgcgcagaa aaaaggatc tcaagaagat    4200 cctttgatct tttctacggg gtctgacgct cagtggaacg aaaactcacg ttaagggatt    4260
ttggtcatga gattatcaaa aaggatcttc acctagatcc ttttaaatta aaaatgaagt    4320
tttaaatcaa tctaaagtat atatgagtaa acttggtctg acagttacca atgcttaatc    4380
agtgaggcac ctatctcagc gatctgtcta tttcgttcat ccatagttgc ctgactcggg    4440
gggggggggc gctgaggtct gcctcgtgaa gaaggtgttg ctgactcata ccaggcctga    4500
atcgccccat catccagcca gaaagtgagg gagccacggt tgatgagagc tttgttgtag    4560
gtggaccagt tggtgatttt gaactttgc tttgccacgg aacggtctgc gttgtcggga    4620
agatgcgtga tctgatcctt caactcagca aaagttcgat ttattcaaca aagccgccgt    4680
cccgtcaagt cagcgtaatg ctctgccagt gttacaacca attaaccaat tctgattaga    4740
aaaactcatc gagcatcaaa tgaaactgca atttattcat atcaggatta tcaataccat    4800 attttttgaaa aagccgtttc tgtaatgaag gagaaaactc accgaggcag ttccatagga    4860
tggcaagatc ctggtatcgg tctgcgattc cgactcgtcc aacatcaata caacctatta    4920
```

| | |
|---|---|
| atttcccctc gtcaaaaata aggttatcaa gtgagaaatc accatgagtg acgactgaat | 4980 |
| ccggtgagaa tggcaaaagc ttatgcattt cttccagac ttgttcaaca ggccagccat | 5040 |
| tacgctcgtc atcaaaatca ctcgcatcaa ccaaaccgtt attcattcgt gattgcgcct | 5100 |
| gagcgagacg aaatacgcga tcgctgttaa aaggacaatt acaaacagga atcgaatgca | 5160 |
| accggcgcag gaacactgcc agcgcatcaa caatattttc acctgaatca ggatattctt | 5220 |
| ctaatacctg gaatgctgtt ttcccgggga tcgcagtggt gagtaaccat gcatcatcag | 5280 |
| gagtacggat aaaatgcttg atggtcggaa gaggcataaa ttccgtcagc cagtttagtc | 5340 |
| tgaccatctc atctgtaaca tcattggcaa cgctacctt gccatgtttc agaaacaact | 5400 |
| ctggcgcatc gggcttccca tacaatcgat agattgtcgc acctgattgc ccgacattat | 5460 |
| cgcgagccca tttataccca tataaatcag catccatgtt ggaatttaat cgcggcctcg | 5520 |
| agcaagacgt ttcccgttga atatggctca taacacccct tgtattactg tttatgtaag | 5580 |
| cagacagttt tattgttcat gatgatatat ttttatcttg tgcaatgtaa catcagagat | 5640 |
| tttgagacac aacgtggctt tcccccccccc cccattattg aagcatttat cagggttatt | 5700 |
| gtctcatgag cggatacata tttgaatgta tttagaaaaa taaacaaata ggggttccgc | 5760 |
| gcacatttcc ccgaaaagtg ccacctgacg tctaagaaac cattattatc atgacattaa | 5820 |
| cctataaaaa taggcgtatc acgaggccct ttcgtc | 5856 |

<210> SEQ ID NO 50
<211> LENGTH: 5119
<212> TYPE: DNA
<213> ORGANISM: Artificial Sequence
<220> FEATURE:
<223> OTHER INFORMATION: Variant Antibody Sequence

<400> SEQUENCE: 50

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaatagggga cttttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt tgacctcca | 960 |
| tagaagacac cgggaccgat ccagcctcca tcggctcgca tctctccttc acgcgcccgc | 1020 |
| cgccctacct gaggccgcca tccacgccgg ttgagtcgcg ttctgccgcc tcccgcctgt | 1080 |
| ggtgcctcct gaactgcgtc cgccgtctag gtaagtttaa agctcaggtc gagaccgggc | 1140 |

```
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcag atatcgcggc cgctctagac    1380
caccatggga tggtcatgta tcatcctttt tctagtagca actgcaaccg gttctgtgac    1440
ctcatacgaa ctgactcagg acactggcgt tctctgtggca ctggggagga ctgtgactat    1500
tacttgccga ggcgactcac tgcggagcca ctacgcttcc tggtatcaga agaaacccgg    1560
ccaggcacct gtgctgctgt tctacggaaa gaacaatagg ccatctggca tccccgaccg    1620
cttttctggc agtgcatcag ggaaccgagc cagtctgacc attaccggcg cccaggctga    1680
ggacgaagcc gattactatt gcagctcccg ggataagagc ggctccagac tgagcgtgtt    1740
cggaggagga actaaactga ccgtcctcag tcagcccaag gctgcccct cggtcactct    1800 gttcccgccc tcgagtgagg agcttcaagc caacaaggcc acactggtgt gtctcataag    1860
tgacttctac ccgggagccg tgacagtggc ctggaaggca gatagcagcc ccgtcaaggc    1920
gggagtggag accaccacac cctccaaaca aagcaacaac aagtacgcgg ccagcagcta    1980
cctgagcctg acgcctgagc agtggaagtc ccacagaagc tacagctgcc aggtcacgca    2040
tgaagggagc accgtggaga agacagtggc ccctacagaa tgttcataga agctgatcca    2100
gatctgctgt gccttctagt tgccagccat ctgttgtttg cccctccccc gtgccttcct    2160
tgaccctgga aggtgccact cccactgtcc tttcctaata aaatgaggaa attgcatcgc    2220
attgtctgag taggtgtcat tctattctgg ggggtggggt ggggcaggac agcaaggggg    2280
aggattggga agacaatagc aggcatgctg gggatgcggt gggctctatg ggtacccagg    2340
tgctgaagaa ttgacccggt tcctcctggg ccagaaagaa gcaggcacat cccctttctct    2400 gtgacacacc ctgtccacgc ccctggttct tagttccagc cccactcata ggacactcat    2460
agctcaggag ggctccgcct tcaatcccac ccgctaaagt acttggagcg gtctctccct    2520
ccctcatcag cccaccaaac caaacctagc ctccaagagt gggaagaaat taaagcaaga    2580
taggctatta agtgcagagg gagagaaaat gcctccaaca tgtgaggaag taatgagaga    2640
aatcatagaa ttttaaggcc atgatttaag gccatcatgg ccttaatctt ccgcttcctc    2700
gctcactgac tcgctgcgct cggtcgttcg gctgcggcga gcggtatcag ctcactcaaa    2760
ggcggtaata cggttatcca cagaatcagg ggataacgca ggaaagaaca tgtgagcaaa    2820
aggccagcaa aaggccagga accgtaaaaa ggccgcgttg ctggcgtttt tccataggct    2880
ccgcccccct gacgagcatc acaaaaatcg acgctcaagt cagaggtggc gaaacccgac    2940
aggactataa agataccagg cgtttccccc tggaagctcc ctcgtgcgct ctcctgttcc    3000
gaccctgccg cttaccggat acctgtccgc cttttctccct tcgggaagcg tggcgctttc    3060
tcatagctca cgctgtaggt atctcagttc ggtgtaggtc gttcgctcca agctgggctg    3120
tgtgcacgaa ccccccgttc agcccgaccg ctgcgcctta ccggtaact atcgtcttga    3180 gtccaacccg gtaagacacg acttatcgcc actggcagca gccactggta acaggattag    3240
cagagcgagg tatgtaggcg gtgctacaga gttcttgaag tggtggccta actacggcta    3300
cactagaaga acagtatttg gtatctgcgc tctgctgaag ccagttacct tcggaaaaag    3360
agttggtagc tcttgatccg gcaaacaaac caccgctggt agcggtggtt ttttgtttg    3420 caagcagcag attacgcgca gaaaaaaagg atctcaagaa gatcctttga tcttttctac    3480
```

```
ggggtctgac gctcagtgga acgaaaactc acgttaaggg attttggtca tgagattatc    3540
aaaaaggatc ttcacctaga tccttttaaa ttaaaaatga agttttaaat caatctaaag    3600
tatatatgag taaacttggt ctgacagtta ccaatgctta atcagtgagg cacctatctc    3660
agcgatctgt ctatttcgtt catccatagt tgcctgactc ggggggggggg ggcgctgagg    3720 tctgcctcgt gaagaaggtg ttgctgactc ataccaggcc tgaatcgccc catcatccag    3780
ccagaaagtg agggagccac ggttgatgag agctttgttg taggtggacc agttggtgat    3840
tttgaacttt tgctttgcca cggaacggtc tgcgttgtcg ggaagatgcg tgatctgatc    3900
cttcaactca gcaaaagttc gatttattca acaaagccgc cgtcccgtca agtcagcgta    3960
atgctctgcc agtgttacaa ccaattaacc aattctgatt agaaaaactc atcgagcatc    4020
aaatgaaact gcaatttatt catatcagga ttatcaatac catattttg aaaaagccgt     4080 ttctgtaatg aaggagaaaa ctcaccgagg cagttccata ggatggcaag atcctggtat    4140
cggtctgcga ttccgactcg tccaacatca atacaaccta ttaatttccc ctcgtcaaaa    4200
ataaggttat caagtgagaa atcaccatga gtgacgactg aatccggtga atgggcaaa    4260 agcttatgca tttctttcca gacttgttca acaggccagc cattacgctc gtcatcaaaa    4320
tcactcgcat caaccaaacc gttattcatt cgtgattgcg cctgagcgag acgaaatacg    4380
cgatcgctgt taaaaggaca attacaaaca ggaatcgaat gcaaccggcg caggaacact    4440
gccagcgcat caacaatatt ttcacctgaa tcaggatatt cttctaatac ctggaatgct    4500
gttttcccgg ggatcgcagt ggtgagtaac catgcatcat caggagtacg ataaaatgc    4560 ttgatggtcg gaagaggcat aaattccgtc agccagttta gtctgaccat ctcatctgta    4620
acatcattgg caacgctacc tttgccatgt ttcagaaaca actctggcgc atcgggcttc    4680
ccatacaatc gatagattgt cgcacctgat tgcccgacat tatcgcgagc ccatttatac    4740
ccatataaat cagcatccat gttggaattt aatcgcggcc tcgagcaaga cgtttcccgt    4800
tgaatatggc tcataacacc ccttgtatta ctgtttatgt aagcagacag ttttattgtt    4860
catgatgata tatttttatc ttgtgcaatg taacatcaga gattttgaga cacaacgtgg    4920
ctttcccccc cccccccatta ttgaagcatt tatcagggtt attgtctcat gagcggatac    4980
atatttgaat gtatttagaa aaataaacaa atagggggttc cgcgcacatt tccccgaaaa    5040
gtgccacctg acgtctaaga aaccattatt atcatgacat taacctataa aaataggcgt    5100
atcacgaggc cctttcgtc                                                  5119
```

<210> SEQ ID NO 51
<211> LENGTH: 5119
<212> TYPE: DNA
<213> ORGANISM: Artificial Sequence
<220> FEATURE:
<223> OTHER INFORMATION: Variant Antibody Sequence

<400> SEQUENCE: 51

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
```

```
cccgcctggc tgaccgccca acgaccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgccccta ttgacgtcaa     600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt tgacctcca    960
tagaagacac cggaccgat ccagcctcca tcggctcgca tctctccttc acgcgcccgc    1020
cgccctacct gaggccgcca tccacgccgg ttgagtcgcg ttctgccgcc tcccgcctgt    1080
ggtgcctcct gaactgcgtc cgccgtctag gtaagtttaa agctcaggtc gagaccgggc    1140
cttttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcag atatcgcggc cgctctagac    1380
caccatggga tggtcatgta tcatcctttt tctagtagca actgcaaccg gttctgtgac    1440
cgcatccgaa ctgactcagg accctgccgt ctctgtggca ctgaagcaga ctgtgactat    1500
tacttgccga ggcgactcac tgcggagcca ctacgcttcc tggtatcaga agaaacccgg    1560
ccaggcacct gtgctgctgt tctacggaaa gaacaatagg ccatctggca tccccgaccg    1620
cttttctggc agtgcatcag ggaaccgagc cagtctgacc attaccggcg cccaggctga    1680
ggacgaagcc gattactatt gcagctcccg ggataagagc ggctccagac tgagcgtgtt    1740
cggaggagga actaaactga ccgtcctcag tcagcccaag gctgcccct cggtcactct     1800
gttcccgccc tcgagtgagg agcttcaagc caacaaggcc acactggtgt gtctcataag    1860
tgacttctac ccgggagccg tgacagtggc ctggaaggca gatagcagcc ccgtcaaggc    1920
gggagtggag accaccacac cctccaaaca aagcaacaac aagtacgcgg ccagcagcta    1980
cctgagcctg acgcctgagc agtggaagtc ccacagaagc tacagctgcc aggtcacgca    2040
tgaagggagc accgtggaga agacagtggc ccctacagaa tgttcataga agctgatcca    2100
gatctgctgt gccttctagt tgccagccat ctgttgtttg cccctcccc gtgccttcct     2160
tgaccctgga aggtgccact cccactgtcc tttcctaata aaatgaggaa attgcatcgc    2220
attgtctgag taggtgtcat tctattctgg ggggtgggt gggcaggac agcaagggg      2280
aggattggga agacaatagc aggcatgctg gggatgcggt gggctctatg gtacccagg    2340
tgctgaagaa ttgacccggt tcctcctggg ccagaaagaa gcaggcacat cccttctct    2400
gtgacacacc ctgtccacgc ccctggttct tagttccagc cccactcata ggacactcat    2460
agctcaggag ggctccgcct tcaatccac ccgctaaagt acttggagcg gtctctccct    2520
ccctcatcag cccaccaaac caaacctagc ctccaagagt gggaagaaat taaagcaaga    2580
taggctatta agtgcagagg gagagaaaat gcctccaaca tgtgaggaag taatgagaga    2640
aatcatagaa ttttaaggcc atgatttaag gccatcatgg ccttaatctt ccgcttcctc    2700
gctcactgac tcgctgcgct cggtcgttcg gctgcggcga gcggtatcag ctcactcaaa    2760
```

-continued

```
ggcggtaata cggttatcca cagaatcagg ggataacgca ggaaagaaca tgtgagcaaa   2820
aggccagcaa aaggccagga accgtaaaaa ggccgcgttg ctggcgtttt tccataggct   2880
ccgcccccct gacgagcatc acaaaaatcg acgctcaagt cagaggtggc gaaacccgac   2940
aggactataa agataccagg cgtttccccc tggaagctcc ctcgtgcgct ctcctgttcc   3000
gaccctgccg cttaccggat acctgtccgc ctttctccct tcgggaagcg tggcgctttc   3060
tcatagctca cgctgtaggt atctcagttc ggtgtaggtc gttcgctcca agctgggctg   3120
tgtgcacgaa ccccccgttc agcccgaccg ctgcgcctta tccggtaact atcgtcttga   3180
gtccaacccg gtaagacacg acttatcgcc actggcagca gccactggta acaggattag   3240
cagagcgagg tatgtaggcg gtgctacaga gttcttgaag tggtggccta actacggcta   3300
cactagaaga acagtatttg gtatctgcgc tctgctgaag ccagttacct tcggaaaaag   3360
agttggtagc tcttgatccg gcaaacaaac caccgctggt agcggtggtt tttttgtttg   3420
caagcagcag attacgcgca gaaaaaaagg atctcaagaa gatcctttga tcttttctac   3480
ggggtctgac gctcagtgga acgaaaactc acgttaaggg attttggtca tgagattatc   3540
aaaaaggatc ttcacctaga tccttttaaa ttaaaaatga agttttaaat caatctaaag   3600
tatatatgag taaacttggt ctgacagtta ccaatgctta atcagtgagg cacctatctc   3660
agcgatctgt ctatttcgtt catccatagt tgcctgactc cccccccccg ggcgctgagg   3720
tctgcctcgt gaagaaggtg ttgctgactc ataccaggcc tgaatcgccc catcatccag   3780
ccagaaagtg agggagccac ggttgatgag agctttgttg taggtggacc agttggtgat   3840
tttgaacttt tgctttgcca cggaacggtc tgcgttgtcg ggaagatgcg tgatctgatc   3900
cttcaactca gcaaaagttc gatttattca acaaagccgc cgtcccgtca agtcagcgta   3960
atgctctgcc agtgttacaa ccaattaacc aattctgatt agaaaaactc atcgagcatc   4020
aaatgaaact gcaatttatt catatcagga ttatcaatac catattttg aaaaagccgt   4080 ttctgtaatg aaggagaaaa ctcaccgagg cagttccata ggatggcaag atcctggtat   4140
cggtctgcga ttccgactcg tccaacatca atacaaccta ttaatttccc ctcgtcaaaa   4200
ataaggttat caagtgagaa atcaccatga gtgacgactg aatccggtga gaatggcaaa   4260
agcttatgca tttctttcca gacttgttca acaggccagc cattacgctc gtcatcaaaa   4320
tcactcgcat caaccaaacc gttattcatt cgtgattgcg cctgagcgag acgaaatacg   4380
cgatcgctgt taaaaggaca attacaaaca ggaatcgaat gcaaccggcg caggaacact   4440
gccagcgcat caacaatatt ttcacctgaa tcaggatatt cttctaatac ctggaatgct   4500
gttttcccgg ggatcgcagt ggtgagtaac catgcatcat caggagtacg gataaaatgc   4560
ttgatggtcg gaagaggcat aaattccgtc agccagttta gtctgaccat ctcatctgta   4620
acatcattgg caacgctacc tttgccatgt ttcagaaaca actctggcgc atcgggcttc   4680
ccatacaatc gatagattgt cgcacctgat tgcccgacat atcgcgagc ccatttatac   4740 ccatataaat cagcatccat gttggaattt aatcgcggcc tcgagcaaga cgtttcccgt   4800
tgaatatggc tcataacacc ccttgtatta ctgtttatgt aagcagacag ttttattgtt   4860
catgatgata tatttttatc ttgtgcaatg taacatcaga gattttgaga cacaacgtgg   4920
ctttcccccc cccccccatta ttgaagcatt tatcagggtt attgtctcat gagcggatac   4980
atatttgaat gtatttagaa aaataaacaa ataggggttc cgcgcacatt tccccgaaaa   5040
gtgccacctg acgtctaaga aaccattatt atcatgacat taacctataa aaataggcgt   5100
atcacgaggc cctttcgtc                                                5119
```

```
<210> SEQ ID NO 52
<211> LENGTH: 22
<212> TYPE: PRT
<213> ORGANISM: Artificial Sequence
<220> FEATURE:
<223> OTHER INFORMATION: Variant Antibody Sequence

<400> SEQUENCE: 52

Ala Arg Thr Gly Lys Tyr Tyr Asp Phe Trp Trp Gly Tyr Pro Pro Gly
1               5                   10                  15
Glu Glu Tyr Phe Gln Asp
            20

<210> SEQ ID NO 53
<211> LENGTH: 22
<212> TYPE: PRT
<213> ORGANISM: Artificial Sequence
<220> FEATURE:
<223> OTHER INFORMATION: Variant Antibody Sequence

<400> SEQUENCE: 53

Ala Arg Thr Gly Lys Tyr Tyr Asp Phe Trp Ser Gly Cys Pro Pro Gly
1               5                   10                  15
Glu Glu Tyr Phe Gln Asp
            20

<210> SEQ ID NO 54
<211> LENGTH: 22
<212> TYPE: PRT
<213> ORGANISM: Artificial Sequence
<220> FEATURE:
<223> OTHER INFORMATION: Variant Antibody Sequence

<400> SEQUENCE: 54

Ala Arg Thr Gly Lys Tyr Tyr Asp Phe Trp Trp Gly Cys Pro Pro Gly
1               5                   10                  15
Glu Glu Tyr Phe Gln Asp
            20

<210> SEQ ID NO 55
<211> LENGTH: 6
<212> TYPE: PRT
<213> ORGANISM: Artificial Sequence
<220> FEATURE:
<223> OTHER INFORMATION: Variant Antibody Sequence

<400> SEQUENCE: 55

Ser Leu Arg Cys His Tyr
1               5

<210> SEQ ID NO 56
<211> LENGTH: 6
<212> TYPE: PRT
<213> ORGANISM: Artificial Sequence
<220> FEATURE:
<223> OTHER INFORMATION: Variant Antibody Sequence

<400> SEQUENCE: 56

Ser Leu Arg Ser His Trp
1               5

<210> SEQ ID NO 57
<211> LENGTH: 6
<212> TYPE: PRT
```

<213> ORGANISM: Artificial Sequence
<220> FEATURE:
<223> OTHER INFORMATION: Variant Antibody Sequence

<400> SEQUENCE: 57

Ser Leu Arg Ser His Phe
1               5

<210> SEQ ID NO 58
<211> LENGTH: 109
<212> TYPE: PRT
<213> ORGANISM: Artificial Sequence
<220> FEATURE:
<223> OTHER INFORMATION: Variant Antibody Sequence

<400> SEQUENCE: 58

Ala Ser Glu Leu Thr Gln Asp Pro Ala Val Ser Val Ala Leu Lys Gln
1               5                   10                  15

Thr Val Thr Ile Thr Cys Arg Gly Asp Ser Leu Arg Cys His Trp Ala
            20                  25                  30

Ser Trp Tyr Gln Lys Pro Gly Gln Ala Pro Val Leu Leu Phe Tyr
        35                  40                  45

Gly Lys Asn Asn Arg Pro Ser Gly Ile Pro Asp Arg Phe Ser Gly Ser
50                  55                  60

Ala Ser Gly Asn Arg Ala Ser Leu Thr Ile Thr Gly Ala Gln Ala Glu
65                  70                  75                  80

Asp Glu Ala Asp Tyr Tyr Cys Ser Ser Arg Asp Lys Ser Gly Ser Arg
                85                  90                  95

Leu Ser Val Phe Gly Gly Gly Thr Lys Leu Thr Val Leu
            100                 105

<210> SEQ ID NO 59
<211> LENGTH: 109
<212> TYPE: PRT
<213> ORGANISM: Artificial Sequence
<220> FEATURE:
<223> OTHER INFORMATION: Variant Antibody Sequence

<400> SEQUENCE: 59

Ala Ser Glu Leu Thr Gln Asp Pro Ala Val Ser Val Ala Leu Lys Gln
1               5                   10                  15

Thr Val Thr Ile Thr Cys Arg Gly Asp Ser Leu Arg Cys His Phe Ala
            20                  25                  30

Ser Trp Tyr Gln Lys Pro Gly Gln Ala Pro Val Leu Leu Phe Tyr
        35                  40                  45

Gly Lys Asn Asn Arg Pro Ser Gly Ile Pro Asp Arg Phe Ser Gly Ser
50                  55                  60

Ala Ser Gly Asn Arg Ala Ser Leu Thr Ile Thr Gly Ala Gln Ala Glu
65                  70                  75                  80

Asp Glu Ala Asp Tyr Tyr Cys Ser Ser Arg Asp Lys Ser Gly Ser Arg
                85                  90                  95

Leu Ser Val Phe Gly Gly Gly Thr Lys Leu Thr Val Leu
            100                 105

<210> SEQ ID NO 60
<211> LENGTH: 5856
<212> TYPE: DNA
<213> ORGANISM: Artificial Sequence
<220> FEATURE:
<223> OTHER INFORMATION: Variant Antibody Sequence

```
<400> SEQUENCE: 60
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca cgacccccg cccattgacg tcaataatga cgtatgttcc     480
catagtaacg ccaatagggA ctttccattg acgtcaatgg gtggagtatt tacggtaaac     540
tgcccacttg gcagtacatc aagtgtatca tatgccaagt acgccccta ttgacgtcaa     600 tgacggtaaa tggcccgcct ggcattatgc ccagtacatg accttatggg actttcctac     660
ttggcagtac atctacgtat tagtcatcgc tattaccatg tgatgcggt tttggcagta     720 catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctcca tcggctcgca tctctccttc acgcgcccgc    1020
cgccctacct gaggccgcca tcacgccgg ttgagtcgcg ttctgccgcc tcccgcctgt    1080
ggtgcctcct gaactgcgtc cgccgtctag gtaagtttaa agctcaggtc gagaccgggc    1140
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcag atatcgcggc cgctctagac    1380
caccatggga tggtcatgta tcatcctttt tctagtagca actgcaaccg gtgtacattc    1440
tgaggttaga ctggtggagt caggaggggg gcttgtgaag cccggtgggt ctctccgcct    1500
gagctgttct gcctccggct ttgatttcga taacgcctgg atgacctggg tcaggcagcc    1560
tccaggtaag ggactggagt gggtgggaag aatcacaggt ccaggcgagg gctggtccgt    1620
ggactacgcg gaatctgtta aagggcggtt acaatctca agggacaata ccaagaatac    1680
cttgtatttg gagatgaaca acgtgagaac tgaagacacc ggatattact tctgtgccag    1740
aacaggcaaa tactacgact tctggtccgg ctgcccccct ggcgaggaat attttcaaga    1800
ctggggtcag ggaacccttg ttatcgtgtc ctccgcgtcg accaagggcc catcggtctt    1860 cccctggca ccctcctcca agagcacctc tgggggcaca gcggccctgg gctgcctggt    1920
caaggactac ttccccgaac cggtgacggt gtcgtggaac tcaggcgccc tgaccagcgg    1980
cgtgcacacc ttcccggctg tcctacagtc ctcaggactc tactccctca gcagcgtggt    2040
gaccgtgccc tccagcagct tgggcaccca gacctcatc tgcaacgtga atcacaagcc    2100
cagcaacacc aaggtggaca agaaagttga gcccaaatct tgtgacaaaa ctcacacatg    2160
cccaccgtgc ccagcacctg aactcctggg gggaccgtca gtcttcctct tccccccaaa    2220
acccaaggac accctcatga tctcccggac ccctgaggtc acatgcgtgg tggtggacgt    2280
gagccacgaa gaccctgagg tcaagttcaa ctggtacgtg gacggcgtgg aggtgcataa    2340
```

```
tgccaagaca aagccgcggg aggagcagta caacagcacg taccgtgtgg tcagcgtcct    2400
caccgtcctg caccaggact ggctgaatgg caaggagtac aagtgcaagg tctccaacaa    2460
agccctccca gcccccatcg agaaaaccat ctccaaagcc aagggcagc cccgagaacc     2520 acaggtgtac accctgcccc catcccggga tgagctgacc aagaaccagg tcagcctgac    2580
ctgcctggtc aaaggcttct atcccagcga catcgccgtg gagtgggaga gcaatgggca    2640
gccggagaac aactacaaga ccacgcctcc cgtgctggac tccgacggct ccttcttcct    2700
ctacagcaag ctcaccgtgg acaagagcag gtggcagcag gggaacgtct tctcatgctc    2760
cgtgatgcat gaggctctgc acaaccacta cacgcagaag agcctctccc tgtctccggg    2820
taaatgatga ggatccagat ctgctgtgcc ttctagttgc cagccatctg ttgtttgccc    2880
ctcccccgtg ccttccttga ccctggaagg tgccactccc actgtccttt cctaataaaa    2940
tgaggaaatt gcatcgcatt gtctgagtag gtgtcattct attctggggg gtggggtggg    3000
gcaggacagc aaggggagg attgggaaga caatagcagg catgctgggg atgcggtggg    3060
ctctatgggt acccaggtgc tgaagaattg acccggttcc tcctgggcca gaaagaagca    3120
ggcacatccc cttctctgtg acacaccctg tccacgcccc tggttcttag ttccagcccc    3180
actcatagga cactcatagc tcaggagggc tccgccttca atcccacccg ctaaagtact    3240
tggagcggtc tctccctccc tcatcagccc accaaaccaa acctagcctc caagagtggg    3300
aagaaattaa agcaagatag gctattaagt gcagagggag agaaaatgcc tccaacatgt    3360
gaggaagtaa tgagagaaat catagaattt taaggccatg atttaaggcc atcatggcct    3420
taatcttccg cttcctcgct cactgactcg ctgcgctcgg tcgttcggct gcggcgagcg    3480
gtatcagctc actcaaaggc ggtaatacgg ttatccacag aatcagggga taacgcagga    3540
aagaacatgt gagcaaaagg ccagcaaaag gccaggaacc gtaaaaaggc cgcgttgctg    3600 gcgttttttcc ataggctccg ccccctgac gagcatcaca aaaatcgacg ctcaagtcag    3660
aggtggcgaa acccgacagg actataaaga taccaggcgt ttccccctgg aagctccctc    3720
gtgcgctctc ctgttccgac cctgccgctt accggatacc tgtccgcctt tctcccttcg    3780
ggaagcgtgg cgctttctca tagctcacgc tgtaggtatc tcagttcggt gtaggtcgtt    3840
cgctccaagc tgggctgtgt gcacgaaccc cccgttcagc ccgaccgctg cgccttatcc    3900
ggtaactatc gtcttgagtc aacccggta agacacgact tatcgccact ggcagcagcc    3960
actggtaaca ggattagcag agcgaggtat gtaggcggtg ctacagagtt cttgaagtgg    4020
tggcctaact acggctacac tagaagaaca gtatttggta tctgcgctct gctgaagcca    4080
gttaccttcg gaaaaagagt ggtagctctt gatccggca aacaaaccac cgctggtagc    4140
ggtggttttt tgtttgcaa gcagcagatt acgcgcagaa aaaaggatc tcaagaagat    4200 cctttgatct tttctacggg gtctgacgct cagtggaacg aaaactcacg ttaagggatt    4260
ttggtcatga gattatcaaa aaggatcttc acctagatcc ttttaaatta aaaatgaagt    4320
tttaaatcaa tctaaagtat atatgagtaa acttggtctg acagttacca atgcttaatc    4380
agtgaggcac ctatctcagc gatctgtcta tttcgttcat ccatagttgc ctgactcggg    4440 ggggggggc gctgaggtct gcctcgtgaa gaaggtgttg ctgactcata ccaggcctga    4500
atcgccccat catccagcca gaaagtgagg gagccacggt tgatgagagc tttgttgtag    4560
gtggaccagt tggtgatttt gaacttttgc tttgccacgg aacggtctgc gttgtcggga    4620
agatgcgtga tctgatcctt caactcagca aaagttcgat ttattcaaca aagccgccgt    4680
```

```
cccgtcaagt cagcgtaatg ctctgccagt gttacaacca attaaccaat tctgattaga      4740
aaaactcatc gagcatcaaa tgaaactgca atttattcat atcaggatta tcaataccat      4800 attttttgaaa aagccgtttc tgtaatgaag gagaaaactc accgaggcag ttccatagga     4860
tggcaagatc ctggtatcgg tctgcgattc cgactcgtcc aacatcaata caacctatta     4920
atttcccctc gtcaaaaata aggttatcaa gtgagaaatc accatgagtg acgactgaat     4980
ccggtgagaa tggcaaaagc ttatgcattt cttccagac ttgttcaaca ggccagccat      5040
tacgctcgtc atcaaaatca ctcgcatcaa ccaaaccgtt attcattcgt gattgcgcct     5100
gagcgagacg aaatacgcga tcgctgttaa aggacaatt acaaacagga atcgaatgca      5160
accggcgcag gaacactgcc agcgcatcaa caatattttc acctgaatca ggatattctt     5220
ctaatacctg gaatgctgtt ttcccgggga tcgcagtggt gagtaaccat gcatcatcag     5280
gagtacggat aaaatgcttg atggtcggaa gaggcataaa ttccgtcagc cagtttagtc     5340
tgaccatctc atctgtaaca tcattggcaa cgctacctt gccatgtttc agaaacaact      5400
ctggcgcatc gggcttccca tacaatcgat agattgtcgc acctgattgc ccgacattat     5460
cgcgagccca tttataccca tataaatcag catccatgtt ggaatttaat cgcggcctcg     5520
agcaagacgt ttcccgttga atatggctca taacacccct tgtattactg tttatgtaag     5580
cagacagttt tattgttcat gatgatatat ttttatcttg tgcaatgtaa catcagagat     5640
tttgagacac aacgtggctt tccccccccc cccattattg aagcatttat cagggttatt     5700
gtctcatgag cggatacata tttgaatgta tttagaaaaa taaacaaata ggggttccgc     5760
gcacatttcc ccgaaaagtg ccacctgacg tctaagaaac cattattatc atgacattaa     5820
cctataaaaa taggcgtatc acgaggccct ttcgtc                               5856
```

<210> SEQ ID NO 61
<211> LENGTH: 5119
<212> TYPE: DNA
<213> ORGANISM: Artificial Sequence
<220> FEATURE:
<223> OTHER INFORMATION: Variant Antibody Sequence

<400> SEQUENCE: 61

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcagattgg      240
ctattggcca ttgcatacgt tgtatccata tcataatatg tacatttata ttggctcatg      300
tccaacatta ccgccatgtt gacattgatt attgactagt tattaatagt aatcaattac      360
ggggtcatta gttcatagcc catatatgga gttccgcgtt acataactta cggtaaatgg      420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgccccta ttgacgtcaa      600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
```

```
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
caccatggga tggtcatgta tcatcctttt tctagtagca actgcaaccg gttctgtgac   1440
cgcatccgaa ctgactcagg accctgccgt ctctgtggca ctgaagcaga ctgtgactat   1500
tacttgccga ggcgactcac tgcggtgcca ctacgcttcc tggtatcaga agaaacccgg   1560
ccaggcacct gtgctgctgt tctacggaaa gaacaatagg ccatctggca tccccgaccg   1620
cttttctggc agtgcatcag ggaaccgagc cagtctgacc attaccggcg cccaggctga   1680
ggacgaagcc gattactatt gcagctcccg ggataagagc ggctccagac tgagcgtgtt   1740
cggaggagga actaaactga ccgtcctcag tcagcccaag gctgcccccct cggtcactct   1800
gttcccgccc tcgagtgagg agcttcaagc caacaaggcc acactggtgt gtctcataag   1860
tgacttctac ccgggagccg tgacagtggc ctggaaggca gatagcagcc ccgtcaaggc   1920
gggagtggag accaccacac cctccaaaca aagcaacaac aagtacgcgg ccagcagcta   1980
cctgagcctg acgcctgagc agtggaagtc ccacagaagc tacagctgcc aggtcacgca   2040
tgaagggagc accgtggaga agacagtggc ccctacagaa tgttcataga agctgatcca   2100
gatctgctgt gccttctagt tgccagccat ctgttgtttg cccctccccc gtgccttcct   2160
tgaccctgga aggtgccact cccactgtcc tttcctaata aaatgaggaa attgcatcgc   2220
attgtctgag taggtgtcat tctattctgg ggggtggggt ggggcaggac agcaagggg   2280
aggattggga agacaatagc aggcatgctg gggatgcggt gggctctatg gtacccagg   2340
tgctgaagaa ttgacccggt tcctcctggg ccagaaagaa gcaggcacat ccccttctct   2400
gtgacacacc ctgtccacgc ccctggttct tagttccagc cccactcata ggacactcat   2460
agctcaggag ggctccgcct tcaatcccac ccgctaaagt acttggagcg gtctctccct   2520
ccctcatcag cccaccaaac caaacctagc ctccaagagt gggaagaaat taaagcaaga   2580
taggctatta agtgcagagg gagagaaaat gcctccaaca tgtgaggaag taatgagaga   2640
aatcatagaa ttttaaggcc atgatttaag gccatcatgg ccttaatctt ccgcttcctc   2700
gctcactgac tcgctgcgct cggtcgttcg gctgcggcga gcggtatcag ctcactcaaa   2760
ggcggtaata cggttatcca cagaatcagg ggataacgca ggaaagaaca tgtgagcaaa   2820
aggccagcaa aaggccagga accgtaaaaa ggccgcgttg ctggcgtttt tccataggct   2880
ccgcccccct gacgagcatc acaaaaatcg acgctcaagt cagaggtggc gaaacccgac   2940
aggactataa agataccagg cgtttccccc tggaagctcc ctcgtgcgct ctcctgttcc   3000
gaccctgccg cttaccggat acctgtccgc ctttctccct tcgggaagcg tggcgctttc   3060
tcatagctca cgctgtaggt atctcagttc ggtgtaggtc gttcgctcca agctgggctg   3120
tgtgcacgaa ccccccgttc agcccgaccg ctgcgcctta tccggtaact atcgtcttga   3180
gtccaacccg gtaagacacg acttatcgcc actggcagca gccactggta acaggattag   3240
```

```
cagagcgagg tatgtaggcg gtgctacaga gttcttgaag tggtggccta actacggcta   3300
cactagaaga acagtatttg gtatctgcgc tctgctgaag ccagttacct tcggaaaaag   3360
agttggtagc tcttgatccg gcaaacaaac caccgctggt agcggtggtt ttttttgtttg  3420 caagcagcag attacgcgca gaaaaaaagg atctcaagaa gatcctttga tcttttctac   3480
ggggtctgac gctcagtgga acgaaaactc acgttaaggg attttggtca tgagattatc   3540
aaaaaggatc ttcacctaga tccttttaaa ttaaaaatga agttttaaat caatctaaag   3600
tatatatgag taaacttggt ctgacagtta ccaatgctta atcagtgagg cacctatctc   3660
agcgatctgt ctatttcgtt catccatagt tgcctgactc ggggggggggg ggcgctgagg  3720 tctgcctcgt gaagaaggtg ttgctgactc ataccaggcc tgaatcgccc catcatccag   3780
ccagaaagtg agggagccac ggttgatgag agctttgttg taggtggacc agttggtgat   3840
tttgaacttt tgctttgcca cggaacggtc tgcgttgtcg ggaagatgcg tgatctgatc   3900
cttcaactca gcaaaagttc gatttattca acaaagccgc cgtcccgtca agtcagcgta   3960
atgctctgcc agtgttacaa ccaattaacc aattctgatt agaaaaactc atcgagcatc   4020
aaatgaaact gcaatttatt catatcagga ttatcaatac catattttg aaaaagccgt    4080 ttctgtaatg aaggagaaaa ctcaccgagg cagttccata ggatggcaag atcctggtat   4140
cggtctgcga ttccgactcg tccaacatca atacaaccta ttaatttccc ctcgtcaaaa   4200
ataaggttat caagtgagaa atcaccatga gtgacgactg aatccggtga atgcaa       4260 agcttatgca tttctttcca gacttgttca acaggccagc cattacgctc gtcatcaaaa   4320
tcactcgcat caaccaaacc gttattcatt cgtgattgcg cctgagcgag acgaaatacg   4380
cgatcgctgt taaaaggaca attacaaaca ggaatcgaat gcaaccggcg caggaacact   4440
gccagcgcat caacaatatt ttcacctgaa tcaggatatt cttctaatac ctggaatgct   4500
gttttcccgg ggatcgcagt ggtgagtaac catgcatcat caggagtacg gataaaatgc   4560
ttgatggtcg gaagaggcat aaattccgtc agccagttta gtctgaccat ctcatctgta   4620
acatcattgg caacgctacc tttgccatgt ttcagaaaca actctggcgc atcgggcttc   4680
ccatacaatc gatagattgt cgcacctgat tgcccgacat tatcgcgagc ccatttatac   4740
ccatataaat cagcatccat gttggaattt aatcgcggcc tcgagcaaga cgtttcccgt   4800
tgaatatggc tcataacacc ccttgtatta ctgtttatgt aagcagacag ttttattgtt   4860
catgatgata tatttttatc ttgtgcaatg taacatcaga gattttgaga cacaacgtgg   4920
ctttcccccc ccccccatta ttgaagcatt tatcagggtt attgtctcat gagcggatac   4980
atatttgaat gtatttagaa aaataaacaa ataggggttc cgcgcacatt tccccgaaaa   5040
gtgccacctg acgtctaaga accattatt atcatgacat taacctataa aataggcgt    5100 atcacgaggc cctttcgtc                                                 5119
```

<210> SEQ ID NO 62
<211> LENGTH: 5856
<212> TYPE: DNA
<213> ORGANISM: Artificial Sequence
<220> FEATURE:
<223> OTHER INFORMATION: Variant Antibody Sequence

<400> SEQUENCE: 62

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
```

-continued

```
accatatgcg gtgtgaaata ccgcacagat gcgtaaggag aaaataccgc atcagattgg      240
ctattggcca ttgcatacgt tgtatccata tcataatatg tacatttata ttggctcatg      300
tccaacatta ccgccatgtt gacattgatt attgactagt tattaatagt aatcaattac      360
ggggtcatta gttcatagcc catatatgga gttccgcgtt acataactta cggtaaatgg      420
cccgcctggc tgaccgccca acgacccccg cccattgacg tcaataatga cgtatgttcc      480
catagtaacg ccaataggga ctttccattg acgtcaatgg gtggagtatt tacggtaaac      540
tgcccacttg gcagtacatc aagtgtatca tatgccaagt acgcccccta ttgacgtcaa      600
tgacggtaaa tggcccgcct ggcattatgc ccagtacatg accttatggg actttcctac      660
ttggcagtac atctacgtat tagtcatcgc tattaccatg gtgatgcggt tttggcagta      720
catcaatggg cgtggatagc ggtttgactc acggggattt ccaagtctcc accccattga      780
cgtcaatggg agtttgtttt ggcaccaaaa tcaacgggac tttccaaaat gtcgtaacaa      840
ctccgcccca ttgacgcaaa tgggcggtag gcgtgtacgg tgggaggtct atataagcag      900
agctcgttta gtgaaccgtc agatcgcctg gagacgccat ccacgctgtt tgacctcca      960 tagaagacac cgggaccgat ccagcctcca tcggctcgca tctctccttc acgcgcccgc     1020
cgccctacct gaggccgcca tccacgccgg ttgagtcgcg ttctgccgcc tcccgcctgt     1080
ggtgcctcct gaactgcgtc cgccgtctag gtaagtttaa agctcaggtc gagaccgggc     1140
ctttgtccgg cgctcccttg gagcctacct agactcagcc ggctctccac gctttgcctg     1200
accctgcttg ctcaactcta gttaacggtg gagggcagtg tagtctgagc agtactcgtt     1260
gctgccgcgc gcgccaccag acataatagc tgacagacta acagactgtt cctttccatg     1320
ggtcttttct gcagtcaccg tcgtcgacac gtgtgatcag atatcgcggc cgctctagac     1380
caccatgggc tggtcctgta ttatcctgtt cctggtcgca actgctactg gcgtccattc     1440
agaagtgagg ctggtcgaga gcggcggcgg cctggtgaag ccaggaggaa gcctgcgact     1500
gagctgctcc gcctctggct tcgactttga taacgcttgg atgacatggg tgcgacagcc     1560
ccctggaaaa ggcctggagt gggtcggaag aatcaccggc cccggagagg gatggagtgt     1620
ggactacgca gaatcagtca agggccggtt caccattagc cgggataaca ccaaaaatac     1680
actgtatctg gagatgaaca atgtcaggac tgaagacacc gggtactatt tctgtgcccg     1740
caccggaaag tactatgatt tttggtgggg ctacccaccc ggagaagaat actttcagga     1800
ctggggacag ggaacactgg tcatcgtcag cagcgcctcg accaagggcc catcggtctt     1860 cccccctggca ccctcctcca agagcacctc tgggggcaca gcggccctgg gctgcctggt     1920
caaggactac ttccccgaac cggtgacggt gtcgtggaac tcaggcgccc tgaccagcgg     1980
cgtgcacacc ttcccggctg tcctacagtc ctcaggactc tactccctca gcagcgtggt     2040
gaccgtgccc tccagcagct tgggcaccca gacctacatc tgcaacgtga atcacaagcc     2100
cagcaacacc aaggtggaca gaaagttga gcccaaatct tgtgacaaaa ctcacacatg     2160
cccaccgtgc ccagcacctg aactcctggg gggaccgtca gtcttcctct tccccccaaa     2220
acccaaggac accctcatga tctcccggac ccctgaggtc acatgcgtgg tggtggacgt     2280
gagccacgaa gaccctgagg tcaagttcaa ctggtacgtg gacggcgtgg aggtgcataa     2340
tgccaagaca aagccgcggg aggagcagta caacagcacg taccgtgtgg tcagcgtcct     2400
caccgtcctg caccaggact ggctgaatgg caaggagtac aagtgcaagg tctccaacaa     2460
agccctccca gcccccatcg agaaaaccat ctccaaagcc aaagggcagc cccgagaacc     2520
```

```
acaggtgtac accctgcccc catcccggga tgagctgacc aagaaccagg tcagcctgac    2580
ctgcctggtc aaaggcttct atcccagcga catcgccgtg gagtgggaga gcaatgggca    2640
gccggagaac aactacaaga ccacgcctcc cgtgctggac tccgacggct ccttcttcct    2700
ctacagcaag ctcaccgtgg acaagagcag gtggcagcag gggaacgtct tctcatgctc    2760
cgtgatgcat gaggctctgc acaaccacta cacgcagaag agcctctccc tgtctccggg    2820
taaatgatga ggatccagat ctgctgtgcc ttctagttgc cagccatctg ttgtttgccc    2880
ctcccccgtg ccttccttga ccctggaagg tgccactccc actgtccttt cctaataaaa    2940
tgaggaaatt gcatcgcatt gtctgagtag gtgtcattct attctggggg gtggggtggg    3000
gcaggacagc aagggggagg attgggaaga caatagcagg catgctgggg atgcggtggg    3060
ctctatgggt acccaggtgc tgaagaattg acccggttcc tcctgggcca gaaagaagca    3120
ggcacatccc cttctctgtg acacaccctg tccacgcccc tggttcttag ttccagcccc    3180
actcatagga cactcatagc tcaggagggc tccgccttca atcccacccg ctaaagtact    3240
tggagcggtc tctccctccc tcatcagccc accaaaccaa acctagcctc caagagtggg    3300
aagaaattaa agcaagatag gctattaagt gcagagggag agaaaatgcc tccaacatgt    3360
gaggaagtaa tgagagaaat catagaattt taaggccatg atttaaggcc atcatggcct    3420
taatcttccg cttcctcgct cactgactcg ctgcgctcgg tcgttcggct gcggcgagcg    3480
gtatcagctc actcaaaggc ggtaatacgg ttatccacag aatcagggga taacgcagga    3540
aagaacatgt gagcaaaagg ccagcaaaag gccaggaacc gtaaaaaggc cgcgttgctg    3600
gcgtttttcc ataggctccg ccccctgac gagcatcaca aaaatcgacg ctcaagtcag    3660
aggtggcgaa acccgacagg actataaaga taccaggcgt ttccccctgg aagctccctc    3720
gtgcgctctc ctgttccgac cctgccgctt accggatacc tgtccgcctt tctcccttcg    3780
ggaagcgtgg cgctttctca tagctcacgc tgtaggtatc tcagttcggt gtaggtcgtt    3840
cgctccaagc tgggctgtgt gcacgaaccc cccgttcagc ccgaccgctg cgccttatcc    3900
ggtaactatc gtcttgagtc aacccggta agacacgact tatcgccact ggcagcagcc    3960
actggtaaca ggattagcag agcgaggtat gtaggcggtg ctacagagtt cttgaagtgg    4020
tggcctaact acggctacac tagaagaaca gtatttggta tctgcgctct gctgaagcca    4080
gttaccttcg gaaaaagagt tggtagctct tgatccggca acaaaccac cgctggtagc    4140 ggtggttttt ttgtttgcaa gcagcagatt acgcgcagaa aaaaggatc tcaagaagat    4200 cctttgatct tttctacggg gtctgacgct cagtggaacg aaaactcacg ttaagggatt    4260
ttggtcatga gattatcaaa aaggatcttc acctagatcc ttttaaatta aaatgaagt    4320 tttaaatcaa tctaaagtat atatgagtaa acttggtctg acagttacca atgcttaatc    4380
agtgaggcac ctatctcagc gatctgtcta tttcgttcat ccatagttgc ctgactcggg    4440 ggggggggggc gctgaggtct gcctcgtgaa gaaggtgttg ctgactcata ccaggcctga    4500
atcgccccat catccagcca gaaagtgagg gagccacggt tgatgagagc tttgttgtag    4560
gtggaccagt tggtgatttt gaacttttgc tttgccacgg aacggtctgc gttgtcggga    4620
agatgcgtga tctgatcctt caactcagca aaagttcgat ttattcaaca agccgccgt    4680 cccgtcaagt cagcgtaatg ctctgccagt gttacaacca attaaccaat tctgattaga    4740
aaaactcatc gagcatcaaa tgaaactgca atttattcat atcaggatta tcaataccat    4800
atttttgaaa aagccgtttc tgtaatgaag gagaaaactc accgaggcag ttccatagga    4860
tggcaagatc ctggtatcgg tctgcgattc cgactcgtcc aacatcaata caacctatta    4920
```

| | |
|---|---|
| atttccctc gtcaaaaata aggttatcaa gtgagaaatc accatgagtg acgactgaat | 4980 |
| ccggtgagaa tggcaaaagc ttatgcattt ctttccagac ttgttcaaca ggccagccat | 5040 |
| tacgctcgtc atcaaaatca ctcgcatcaa ccaaaccgtt attcattcgt gattgcgcct | 5100 |
| gagcgagacg aaatacgcga tcgctgttaa aaggacaatt acaaacagga atcgaatgca | 5160 |
| accggcgcag gaacactgcc agcgcatcaa caatattttc acctgaatca ggatattctt | 5220 |
| ctaatacctg gaatgctgtt ttcccgggga tcgcagtggt gagtaaccat gcatcatcag | 5280 |
| gagtacggat aaaatgcttg atggtcggaa gaggcataaa ttccgtcagc cagtttagtc | 5340 |
| tgaccatctc atctgtaaca tcattggcaa cgctaccttt gccatgtttc agaaacaact | 5400 |
| ctggcgcatc gggcttccca tacaatcgat agattgtcgc acctgattgc ccgacattat | 5460 |
| cgcgagccca tttatacccca tataaatcag catccatgtt ggaatttaat cgcggcctcg | 5520 |
| agcaagacgt ttcccgttga atatggctca taacacccct tgtattactg tttatgtaag | 5580 |
| cagacagttt tattgttcat gatgatatat ttttatcttg tgcaatgtaa catcagagat | 5640 |
| tttgagacac aacgtggctt tccccccccc cccattattg aagcatttat cagggttatt | 5700 |
| gtctcatgag cggatacata tttgaatgta tttagaaaaa taaacaaata ggggttccgc | 5760 |
| gcacatttcc ccgaaaagtg ccacctgacg tctaagaaac cattattatc atgacattaa | 5820 |
| cctataaaaa taggcgtatc acgaggccct ttcgtc | 5856 |

<210> SEQ ID NO 63
<211> LENGTH: 5856
<212> TYPE: DNA
<213> ORGANISM: Artificial Sequence
<220> FEATURE:
<223> OTHER INFORMATION: Variant Antibody Sequence

<400> SEQUENCE: 63

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca cgacccccg cccattgacg tcaataatga cgtatgttcc | 480 |
| catagtaacg ccaatagggga ctttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctcca tcggctcgca tctctccttc acgcgcccgc | 1020 |
| cgccctacct gaggccgcca tccacgccgg ttgagtcgcg ttctgccgcc tcccgcctgt | 1080 |

```
ggtgcctcct gaactgcgtc cgccgtctag gtaagtttaa agctcaggtc gagaccgggc    1140
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcag atatcgcggc cgctctagac    1380
caccatggga tggtcatgta tcatcctttt tctagtagca actgcaaccg gtgtacattc    1440
tgaggttaga ctggtggagt caggaggggg gcttgtgaag cccgtgggt ctctccgcct     1500 gagctgttct gcctccggct ttgatttcga taacgcctgg atgacctggg tcaggcagcc    1560
tccaggtaag ggactggagt gggtgggaag aatcacaggt ccaggcgagg gctggtccgt    1620
ggactacgcg gaatctgtta aagggcggtt tacaatctca agggacaata ccaagaatac    1680
cttgtatttg gagatgaaca acgtgagaac tgaagacacc ggatattact tctgtgccag    1740
aacaggcaaa tactacgact tctggtgggg ctgccccccct ggcgaggaat attttcaaga    1800
ctggggtcag ggaacccttg ttatcgtgtc ctccgcgtcg accaagggcc catcggtctt    1860
ccccctggca ccctcctcca agagcacctc tgggggcaca gcggccctgg gctgcctggt    1920
caaggactac ttccccgaac cggtgacggt gtcgtggaac tcaggcgccc tgaccagcgg    1980
cgtgcacacc ttcccggctg tcctacagtc ctcaggactc tactccctca gcagcgtggt    2040
gaccgtgccc tccagcagct tgggcaccca gacctacatc tgcaacgtga atcacaagcc    2100
cagcaacacc aaggtggaca agaaagttga gcccaaatct tgtgacaaaa ctcacacatg    2160
cccaccgtgc ccagcacctg aactcctggg gggaccgtca gtcttcctct tccccccaaa    2220
acccaaggac accctcatga tctcccggac ccctgaggtc acatgcgtgg tggtggacgt    2280
gagccacgaa gaccctgagg tcaagttcaa ctggtacgtg gacggcgtgg aggtgcataa    2340
tgccaagaca aagccgcggg aggagcagta caacagcacg taccgtgtgg tcagcgtcct    2400
caccgtcctg caccaggact ggctgaatgg caaggagtac aagtgcaagg tctccaacaa    2460
agccctccca gcccccatcg agaaaaccat ctccaaagcc aaagggcagc ccgagaacc     2520 acaggtgtac accctgcccc catcccggga tgagctgacc aagaaccagg tcagcctgac    2580
ctgcctggtc aaaggcttct atcccagcga catcgccgtg gagtgggaga gcaatgggca    2640
gccggagaac aactacaaga ccacgcctcc cgtgctggac tccgacggct ccttcttcct    2700
ctacagcaag ctcaccgtgg acaagagcag gtggcagcag gggaacgtct tctcatgctc    2760
cgtgatgcat gaggctctgc acaaccacta cacgcagaag agcctctccc tgtctccggg    2820
taaatgatga ggatccagat ctgctgtgcc ttctagttgc cagccatctg ttgtttgccc    2880 ctccccgtg ccttccttga ccctggaagg tgccactccc actgtccttt cctaataaaa    2940
tgaggaaatt gcatcgcatt gtctgagtag gtgtcattct attctggggg gtggggtggg    3000
gcaggacagc aagggggagg attgggaaga caatagcagg catgctgggg atgcggtggg    3060
ctctatgggt acccaggtgc tgaagaattg acccggttcc tcctgggcca gaaagaagca    3120
ggcacatccc cttctctgtg acacaccctg tccacgcccc tggttcttag ttccagcccc    3180
actcatagga cactcatagc tcaggagggc tccgccttca atcccacccg ctaaagtact    3240
tggagcggtc tctccctccc tcatcagccc accaaaccaa acctagcctc caagagtggg    3300
aagaaattaa agcaagatag gctattaagt gcagagggag agaaaatgcc tccaacatgt    3360
gaggaagtaa tgagagaaat catagaattt taaggccatg atttaaggcc atcatggcct    3420
taatcttccg cttcctcgct cactgactcg ctgcgctcgg tcgttcggct gcggcgagcg    3480
```

```
gtatcagctc actcaaaggc ggtaatacgg ttatccacag aatcagggga taacgcagga    3540
aagaacatgt gagcaaaagg ccagcaaaag gccaggaacc gtaaaaaggc cgcgttgctg    3600 gcgttttcc  ataggctccg ccccctgac  gagcatcaca aaaatcgacg ctcaagtcag    3660
aggtggcgaa acccgacagg actataaaga taccaggcgt ttccccctgg aagctccctc    3720
gtgcgctctc ctgttccgac cctgccgctt accggatacc tgtccgcctt tctcccttcg    3780
ggaagcgtgg cgctttctca tagctcacgc tgtaggtatc tcagttcggt gtaggtcgtt    3840
cgctccaagc tgggctgtgt gcacgaaccc cccgttcagc ccgaccgctg cgccttatcc    3900
ggtaactatc gtcttgagtc aacccggta  agacacgact tatcgccact ggcagcagcc    3960
actggtaaca ggattagcag agcgaggtat gtaggcggtg ctacagagtt cttgaagtgg    4020
tggcctaact acggctacac tagaagaaca gtatttggta tctgcgctct gctgaagcca    4080
gttaccttcg aaaaagagt  tggtagctct tgatccggca acaaaccac  cgctggtagc    4140 ggtggttttt tgtttgcaa  gcagcagatt acgcgcagaa aaaaggatc  tcaagaagat    4200 cctttgatct tttctacggg gtctgacgct cagtggaacg aaaactcacg ttaagggatt    4260
ttggtcatga gattatcaaa aaggatcttc acctagatcc ttttaaatta aaaatgaagt    4320
tttaaatcaa tctaaagtat atatgagtaa acttggtctg acagttacca atgcttaatc    4380
agtgaggcac ctatctcagc gatctgtcta tttcgttcat ccatagttgc ctgactcggg    4440 ggggggggc  gctgaggtct gcctcgtgaa gaaggtgttg ctgactcata ccaggcctga    4500
atcgccccat catccagcca gaaagtgagg gagccacggt tgatgagagc tttgttgtag    4560
gtggaccagt tggtgatttt gaacttttgc tttgccacgg aacggtctgc gttgtcggga    4620
agatgcgtga tctgatcctt caactcagca aaagttcgat ttattcaaca aagccgccgt    4680
cccgtcaagt cagcgtaatg ctctgccagt gttacaacca attaaccaat tctgattaga    4740
aaaactcatc gagcatcaaa tgaaactgca atttattcat atcaggatta tcaataccat    4800
atttttgaaa aagccgtttc tgtaatgaag gagaaaactc accgaggcag ttccatagga    4860
tggcaagatc ctggtatcgg tctgcgattc cgactcgtcc aacatcaata caacctatta    4920
atttcccctc gtcaaaaata aggttatcaa gtgagaaatc accatgagtg acgactgaat    4980
ccggtgagaa tggcaaaagc ttatgcattt cttttccagac ttgttcaaca ggccagccat    5040
tacgctcgtc atcaaaatca ctcgcatcaa ccaaaccgtt attcattcgt gattgcgcct    5100
gagcgagacg aaatacgcga tcgctgttaa aaggacaatt acaaacagga atcgaatgca    5160
accggcgcag gaacactgcc agcgcatcaa caatatttc  acctgaatca ggatattctt    5220
ctaatacctg gaatgctgtt ttcccgggga tcgcagtggt gagtaaccat gcatcatcag    5280
gagtacggat aaaatgcttg atggtcgaa  gaggcataaa ttccgtcagc cagtttagtc    5340
tgaccatctc atctgtaaca tcattggcaa cgctacctt  gccatgtttc agaaacaact    5400
ctggcgcatc gggcttccca tacaatcgat agattgtcgc acctgattgc ccgacattat    5460
cgcgagccca tttatacca  tataaatcag catccatgtt ggaatttaat cgcggcctcg    5520
agcaagacgt ttcccgttga atatggctca taacacccct tgtattactg tttatgtaag    5580
cagacagttt tattgttcat gatgatatat ttttatcttg tgcaatgtaa catcagagat    5640
tttgagacac aacgtggctt tccccccccc cccattattg aagcatttat cagggttatt    5700
gtctcatgag cggatacata tttgaatgta tttagaaaaa taaacaaata ggggttccgc    5760
gcacatttcc ccgaaaagtg ccacctgacg tctaagaaac cattattatc atgacattaa    5820
```

```
cctataaaaa taggcgtatc acgaggccct ttcgtc                              5856
```

```
<210> SEQ ID NO 64
<211> LENGTH: 450
<212> TYPE: DNA
<213> ORGANISM: Artificial Sequence
<220> FEATURE:
<223> OTHER INFORMATION: Variant Antibody Sequence

<400> SEQUENCE: 64
atgggctggt cctgtattat cctgttcctg gtcgcaactg ctactggcgt ccattcagaa     60
gtgaggctgg tcgagagcgg cggcggcctg gtgaagccag gaggaagcct gcgactgagc    120
tgctccgcct ctggcttcga ctttgataac gcttggatga catgggtgcg acagcccct    180 ggaaaaggcc tggagtgggt cggaagaatc accggcccg gagagggatg gagtgtggac     240
tacgcagaat cagtcaaggg ccggttcacc attagccggg ataacaccaa aaatacactg    300
tatctggaga tgaacaatgt caggactgaa gacaccgggt actatttctg tgcccgcacc    360
ggaaagtact atgattttg gtggggctac ccacccggag aagaatactt tcaggactgg    420
ggacagggaa cactggtcat cgtcagcagc                                    450
```

```
<210> SEQ ID NO 65
<211> LENGTH: 450
<212> TYPE: DNA
<213> ORGANISM: Artificial Sequence
<220> FEATURE:
<223> OTHER INFORMATION: Variant Antibody Sequence

<400> SEQUENCE: 65
atgggatggt catgtatcat ccttttcta gtagcaactg caaccggtgt acattctgag     60
gttagactgg tggagtcagg agggggcctt gtgaagcccg gtgggtctct ccgcctgagc    120
tgttctgcct ccggctttga tttcgataac gcctggatga cctgggtcag gcagcctcca    180
ggtaagggac tggagtgggt gggaagaatc acaggtccag gcgagggctg gtccgtggac    240
tacgcggaat ctgttaaagg gcggtttaca atctcaaggg acaataccaa gaataccttg    300
tatttggaga tgaacaacgt gagaactgaa gacaccggat attacttctg tgccagaaca    360
ggcaaatact acgacttctg gtccggctgc ccccctggcg aggaatattt tcaagactgg    420
ggtcagggaa cccttgttat cgtgtcctcc                                    450
```

```
<210> SEQ ID NO 66
<211> LENGTH: 450
<212> TYPE: DNA
<213> ORGANISM: Artificial Sequence
<220> FEATURE:
<223> OTHER INFORMATION: Variant Antibody Sequence

<400> SEQUENCE: 66
atgggatggt catgtatcat ccttttcta gtagcaactg caaccggtgt acattctgag     60
gttagactgg tggagtcagg agggggcctt gtgaagcccg gtgggtctct ccgcctgagc    120
tgttctgcct ccggctttga tttcgataac gcctggatga cctgggtcag gcagcctcca    180
ggtaagggac tggagtgggt gggaagaatc acaggtccag gcgagggctg gtccgtggac    240
tacgcggaat ctgttaaagg gcggtttaca atctcaaggg acaataccaa gaataccttg    300
tatttggaga tgaacaacgt gagaactgaa gacaccggat attacttctg tgccagaaca    360
ggcaaatact acgacttctg gtggggctgc ccccctggcg aggaatattt tcaagactgg    420
ggtcagggaa cccttgttat cgtgtcctcc                                    450
```

<210> SEQ ID NO 67
<211> LENGTH: 393
<212> TYPE: DNA
<213> ORGANISM: Artificial Sequence
<220> FEATURE:
<223> OTHER INFORMATION: Variant Antibody Sequence

<400> SEQUENCE: 67

```
gaagtgcggc tggctgagag cggcgggggg ctggtcaaac ctggcgggtc actgcggctg      60
tcctgttctg cctccggctt cgattttgat aacgcatgga tgacatgggt gcgacagcca     120
cctggaaagg ggctggagtg ggtcggcaga atcactggac ctggcgaagg gtggtctgtg     180
gactacgcag ctccagtcga gggacgattc accattagta gagataacta caagaataca     240
ctgtatctgg agatgaacaa tctgaggact gaagacagcg gcctgtattt ctgcgcccgc     300
accgggaaat actatgattt ttggtggggg tacccacccg gagaggaata ttttcaggac     360
tggggacggg gcaccctggt gatcgtcagc tcc                                  393
```

<210> SEQ ID NO 68
<211> LENGTH: 393
<212> TYPE: DNA
<213> ORGANISM: Artificial Sequence
<220> FEATURE:
<223> OTHER INFORMATION: Variant Antibody Sequence

<400> SEQUENCE: 68

```
gaagtgcggc tggctgagag cggcgggggg ctggtcaaac ctggcgggtc actgcggctg      60
tcctgttctg cctccggctt cgattttgat aacgcatgga tgacatgggt gcgacagcca     120
cctggaaagg ggctggagtg ggtcggcaga atcactggac ctggcgaagg gtggtctgtg     180
gactacgcag ctccagtcga gggacgattc accattagta gagataacta caagaataca     240
ctgtatctgg agatgaacaa tctgaggact gaagacagcg gcctgtattt ctgcgcccgc     300
accgggaaat actatgattt ttggtctggg tgcccacccg gagaggaata ttttcaggac     360
tggggacggg gcaccctggt gatcgtcagc tcc                                  393
```

<210> SEQ ID NO 69
<211> LENGTH: 393
<212> TYPE: DNA
<213> ORGANISM: Artificial Sequence
<220> FEATURE:
<223> OTHER INFORMATION: Variant Antibody Sequence

<400> SEQUENCE: 69

```
gaagtgcggc tggctgagag cggcgggggg ctggtcaaac ctggcgggtc actgcggctg      60
tcctgttctg cctccggctt cgattttgat aacgcatgga tgacatgggt gcgacagcca     120
cctggaaagg ggctggagtg ggtcggcaga atcactggac ctggcgaagg gtggtctgtg     180
gactacgcag ctccagtcga gggacgattc accattagta gagataacta caagaataca     240
ctgtatctgg agatgaacaa tctgaggact gaagacagcg gcctgtattt ctgcgcccgc     300
accgggaaat actatgattt ttggtggggg tgcccacccg gagaggaata ttttcaggac     360
tggggacggg gcaccctggt gatcgtcagc tcc                                  393
```

<210> SEQ ID NO 70
<211> LENGTH: 384
<212> TYPE: DNA
<213> ORGANISM: Artificial Sequence
<220> FEATURE:

<223> OTHER INFORMATION: Variant Antibody Sequence

<400> SEQUENCE: 70

```
atgggatggt catgtatcat cctttttcta gtagcaactg caaccggttc tgtgaccgca    60
tccgaactga ctcaggaccc tgccgtctct gtggcactga agcagactgt gactattact   120
tgccgaggcg actcactgcg gtgccactac gcttcctggt atcagaagaa acccggccag   180
gcacctgtgc tgctgttcta cggaaagaac aataggccat ctggcatccc cgaccgcttt   240
tctggcagtg catcagggaa ccgagccagt ctgaccatta ccggcgccca ggctgaggac   300
gaagccgatt actattgcag ctcccgggat aagagcggct ccagactgag cgtgttcgga   360
ggaggaacta aactgaccgt cctc                                          384
```

<210> SEQ ID NO 71
<211> LENGTH: 384
<212> TYPE: DNA
<213> ORGANISM: Artificial Sequence
<220> FEATURE:
<223> OTHER INFORMATION: Variant Antibody Sequence

<400> SEQUENCE: 71

```
atgggatggt catgtatcat cctttttcta gtagcaactg caaccggttc tgtgaccgca    60
tccgaactga ctcaggaccc tgccgtctct gtggcactga agcagactgt gactattact   120
tgccgaggcg actcactgcg gagccactgg gcttcctggt atcagaagaa acccggccag   180
gcacctgtgc tgctgttcta cggaaagaac aataggccat ctggcatccc cgaccgcttt   240
tctggcagtg catcagggaa ccgagccagt ctgaccatta ccggcgccca ggctgaggac   300
gaagccgatt actattgcag ctcccgggat aagagcggct ccagactgag cgtgttcgga   360
ggaggaacta aactgaccgt cctc                                          384
```

<210> SEQ ID NO 72
<211> LENGTH: 384
<212> TYPE: DNA
<213> ORGANISM: Artificial Sequence
<220> FEATURE:
<223> OTHER INFORMATION: Variant Antibody Sequence

<400> SEQUENCE: 72

```
atgggatggt catgtatcat cctttttcta gtagcaactg caaccggttc tgtgaccgca    60
tccgaactga ctcaggaccc tgccgtctct gtggcactga agcagactgt gactattact   120
tgccgaggcg actcactgcg gagccacttt gcttcctggt atcagaagaa acccggccag   180
gcacctgtgc tgctgttcta cggaaagaac aataggccat ctggcatccc cgaccgcttt   240
tctggcagtg catcagggaa ccgagccagt ctgaccatta ccggcgccca ggctgaggac   300
gaagccgatt actattgcag ctcccgggat aagagcggct ccagactgag cgtgttcgga   360
ggaggaacta aactgaccgt cctc                                          384
```

<210> SEQ ID NO 73
<211> LENGTH: 384
<212> TYPE: DNA
<213> ORGANISM: Artificial Sequence
<220> FEATURE:
<223> OTHER INFORMATION: Variant Antibody Sequence

<400> SEQUENCE: 73

```
atgggatggt catgtatcat cctttttcta gtagcaactg caaccggttc tgtgaccgca    60
tccgaactga ctcaggaccc tgccgtctct gtggcactga agcagactgt gactattact   120
```

```
tgccgaggcg actcactgcg gagccactgg gcttcctggt atcagaagaa acccggccag    180
gcacctgtgc tgctgttcta cggaaagaac aataggccat ctggcatccc cgaccgcttt    240
tctggcagtg catcagggaa ccgagccagt ctgaccatta ccggcgccca ggctgaggac    300
gaagccgatt actattgcag ctcccgggat aagagcggct ccagactgag cgtgttcgga    360
ggaggaacta aactgaccgt cctc                                           384
```

<210> SEQ ID NO 74
<211> LENGTH: 384
<212> TYPE: DNA
<213> ORGANISM: Artificial Sequence
<220> FEATURE:
<223> OTHER INFORMATION: Variant Antibody Sequence

<400> SEQUENCE: 74

```
atgggatggt catgtatcat ccttttttcta gtagcaactg caaccggttc tgtgaccgca    60
tccgaactga ctcaggaccc tgccgtctct gtggcactga agcagactgt gactattact    120
tgccgaggcg actcactgcg gagccacttt gcttcctggt atcagaagaa acccggccag    180
gcacctgtgc tgctgttcta cggaaagaac aataggccat ctggcatccc cgaccgcttt    240
tctggcagtg catcagggaa ccgagccagt ctgaccatta ccggcgccca ggctgaggac    300
gaagccgatt actattgcag ctcccgggat aagagcggct ccagactgag cgtgttcgga    360
ggaggaacta aactgaccgt cctc                                           384
```

<210> SEQ ID NO 75
<211> LENGTH: 131
<212> TYPE: PRT
<213> ORGANISM: Artificial Sequence
<220> FEATURE:
<223> OTHER INFORMATION: Variant Antibody Sequence

<400> SEQUENCE: 75

Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Glu
    50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Phe Gly Tyr Pro
            100                 105                 110

Pro Gly Glu Glu Tyr Phe Gln Asp Trp Gly Gln Gly Thr Leu Val Ile
        115                 120                 125

Val Ser Ser
    130

<210> SEQ ID NO 76
<211> LENGTH: 131
<212> TYPE: PRT
<213> ORGANISM: Artificial Sequence
<220> FEATURE:
<223> OTHER INFORMATION: Variant Antibody Sequence

<400> SEQUENCE: 76

Glu Val Arg Leu Arg Glu Ser Gly Gly Leu Val Lys Pro Gly Gly
1               5                   10                  15

Ser Leu Arg Leu Ser Cys Ser Ala Ser Gly Phe Asp Phe Asp Asn Ala
                20                  25                  30

Trp Met Thr Trp Val Arg Gln Pro Pro Gly Lys Gly Leu Glu Trp Val
                35                  40                  45

Gly Arg Ile Thr Gly Pro Gly Glu Gly Trp Ser Val Asp Tyr Ala Glu
        50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Phe Gly Tyr Pro
                100                 105                 110

Pro Gly Glu Glu Tyr Phe Gln Asp Trp Gly Gln Gly Thr Leu Val Ile
            115                 120                 125

Val Ser Ser
    130

<210> SEQ ID NO 77
<211> LENGTH: 22
<212> TYPE: PRT
<213> ORGANISM: Artificial Sequence
<220> FEATURE:
<223> OTHER INFORMATION: Variant Antibody Sequence

<400> SEQUENCE: 77

Ala Arg Thr Gly Lys Tyr Tyr Asp Phe Trp Phe Gly Tyr Pro Pro Gly
1               5                   10                  15

Glu Glu Tyr Phe Gln Asp
            20

<210> SEQ ID NO 78
<211> LENGTH: 393
<212> TYPE: DNA
<213> ORGANISM: Artificial Sequence
<220> FEATURE:
<223> OTHER INFORMATION: Variant Antibody Sequence

<400> SEQUENCE: 78
gaggttagac tggtggagtc aggagggggg cttgtgaagc ccgtggggtc tctccgcctg        60
agctgttctg cctccggctt tgatttcgat aacgcctgga tgacctgggt caggcagcct       120
ccaggtaagg gactggagtg ggtgggaaga atcacaggtc caggcgaggg ctggtccgtg       180
gactacgcgg aatctgttaa agggcggttt acaatctcaa gggacaatac caagaatacc       240
ttgtatttgg agatgaacaa cgtgagaact gaagacaccg gatattactt ctgtgccaga       300
acaggcaaat actacgactt ctggttcggc tatccccctg gcgaggaata ttttcaagac       360
tggggtcagg gaacccttgt tatcgtgtcc tcc                                    393

<210> SEQ ID NO 79
<211> LENGTH: 393
<212> TYPE: DNA
<213> ORGANISM: Artificial Sequence
<220> FEATURE:
<223> OTHER INFORMATION: Variant Antibody Sequence

<400> SEQUENCE: 79

```
gaggttagac tgcgggagtc aggaggggg cttgtgaagc ccggtgggtc tctccgcctg    60
agctgttctg cctccggctt tgatttcgat aacgcctgga tgacctgggt caggcagcct   120
ccaggtaagg gactggagtg ggtgggaaga atcacaggtc caggcgaggg ctggtccgtg   180
gactacgcgg aatctgttaa agggcggttt acaatctcaa gggacaatac caagaatacc   240
ttgtatttgg agatgaacaa cgtgagaact gaagacaccg gatattactt ctgtgccaga   300
acaggcaaat actacgactt ctggttcggc tatcccctg cgaggaata ttttcaagac   360 tggggtcagg gaaccttgt tatcgtgtcc tcc                                393
```

<210> SEQ ID NO 80
<211> LENGTH: 5856
<212> TYPE: DNA
<213> ORGANISM: Artificial Sequence
<220> FEATURE:
<223> OTHER INFORMATION: Variant Antibody Sequence

<400> SEQUENCE: 80

```
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg   120 ttggcgggtg tcggggctgg cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acaaacttac ggtaaatgg   420 cccgcctggc tgaccgccca acgacccccg cccattgacg tcaataatga cgtatgttcc   480
catagtaacg ccaatagggra ctttccattg acgtcaatgg gtggagtatt tacggtaaac   540
tgcccacttg gcagtacatc aagtgtatca tatgccaagt acgcccccta ttgacgtcaa   600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt tgacctccaa   960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320 ggtctttttct gcagtcaccg tcgtcgacac gtgtgatcag atatcgcggc cgctctagac  1380
caccatggga tggtcatgta tcatcctttt tctagtagca actgcaaccg gtgtacattc  1440
tgaggttaga ctggtggagt caggagggg gcttgtgaag cccggtgggt ctctccgcct  1500
gagctgttct gcctccggct ttgatttcga taacgcctgg atgacctggg tcaggcagcc  1560
tccaggtaag gactggagt gggtgggaag aatcacaggt ccaggcgagg gctggtccgt  1620
```

-continued

```
ggactacgcg gaatctgtta aagggcggtt tacaatctca aggacaata ccaagaatac  1680
cttgtatttg gagatgaaca acgtgagaac tgaagacacc ggatattact tctgtgccag  1740
aacaggcaaa tactacgact tctggttcgg ctatccccct ggcgaggaat attttcaaga  1800
ctggggtcag ggaacccttg ttatcgtgtc ctccgcgtcg accaagggcc catcggtctt  1860
ccccctggca ccctcctcca agagcacctc tgggggcaca gcggccctgg gctgcctggt  1920
caaggactac ttccccgaac cggtgacggt gtcgtggaac tcaggcgccc tgaccagcgg  1980
cgtgcacacc ttcccggctg tcctacagtc ctcaggactc tactccctca gcagcgtggt  2040
gaccgtgccc tccagcagct tgggcaccca gacctacatc tgcaacgtga atcacaagcc  2100
cagcaacacc aaggtggaca gaaagttga gcccaaatct tgtgacaaaa ctcacacatg  2160
cccaccgtgc ccagcacctg aactcctggg gggaccgtca gtcttcctct tccccccaaa  2220
acccaaggac accctcatga tctcccggac ccctgaggtc acatgcgtgg tggtggacgt  2280
gagccacgaa gaccctgagg tcaagttcaa ctggtacgtg gacggcgtgg aggtgcataa  2340
tgccaagaca aagccgcggg aggagcagta caacagcacg taccgtgtgg tcagcgtcct  2400
caccgtcctg caccaggact ggctgaatgg caaggagtac aagtgcaagg tctccaacaa  2460
agccctccca gcccccatcg agaaaaccat ctccaaagcc aaagggcagc ccgagaacc  2520
acaggtgtac accctgcccc catcccggga tgagctgacc aagaaccagg tcagcctgac  2580
ctgcctggtc aaaggcttct atcccagcga catcgccgtg gagtgggaga gcaatgggca  2640
gccggagaac aactacaaga ccacgcctcc cgtgctggac tccgacggct ccttcttcct  2700
ctacagcaag ctcaccgtgg acaagagcag gtggcagcag gggaacgtct tctcatgctc  2760
cgtgatgcat gaggctctgc acaaccacta cacgcagaag agcctctccc tgtctccggg  2820
taaatgatga ggatccagat ctgctgtgcc ttctagttgc cagccatctg ttgtttgccc  2880
ctcccccgtg ccttccttga ccctggaagg tgccactccc actgtccttt cctaataaaa  2940
tgaggaaatt gcatcgcatt gtctgagtag gtgtcattct attctggggg gtggggtggg  3000
gcaggacagc aagggggagg attgggaaga caatagcagg catgctgggg atgcggtggg  3060
ctctatgggt acccaggtgc tgaagaattg acccggttcc tcctgggcca gaaagaagca  3120
ggcacatccc cttctctgtg acacaccctg tccacgcccc tggttcttag ttccagcccc  3180
actcatagga cactcatagc tcaggagggc tccgccttca atcccacccg ctaaagtact  3240
tggagcggtc tctccctccc tcatcagccc accaaaccaa acctagcctc caagagtggg  3300
aagaaattaa agcaagatag gctattaagt gcagagggag agaaaatgcc tccaacatgt  3360
gaggaagtaa tgagagaaat catagaattt taaggccatg atttaaggcc atcatggcct  3420
taatcttccg cttcctcgct cactgactcg ctgcgctcgg tcgttcggct gcggcgagcg  3480
gtatcagctc actcaaaggc ggtaatacgg ttatccacag aatcagggga taacgcagga  3540
aagaacatgt gagcaaaagg ccagcaaaag gccaggaacc gtaaaaaggc cgcgttgctg  3600
gcgttttttcc ataggctccg ccccccctgac gagcatcaca aaaatcgacg ctcaagtcag  3660
aggtggcgaa acccgacagg actataaaga taccaggcgt ttccccctgg aagctccctc  3720
gtgcgctctc ctgttccgac cctgccgctt accggatacc tgtccgcctt tctcccttcg  3780
ggaagcgtgg cgctttctca tagctcacgc tgtaggtatc tcagttcggt gtaggtcgtt  3840
cgctccaagc tgggctgtgt gcacgaaccc ccgttcagc ccgaccgctg cgccttatcc  3900
ggtaactatc gtcttgagtc caacccggta agacacgact tatcgccact ggcagcagcc  3960
actggtaaca ggattagcag agcgaggtat gtaggcggtg ctacagagtt cttgaagtgg  4020
```

| | |
|---|---|
| tggcctaact acggctacac tagaagaaca gtatttggta tctgcgctct gctgaagcca | 4080 |
| gttaccttcg gaaaaagagt tggtagctct tgatccggca acaaaccac cgctggtagc | 4140 |
| ggtggttttt ttgtttgcaa gcagcagatt acgcgcagaa aaaaggatc tcaagaagat | 4200 |
| cctttgatct tttctacggg gtctgacgct cagtggaacg aaaactcacg ttaagggatt | 4260 |
| ttggtcatga gattatcaaa aaggatcttc acctagatcc ttttaaatta aaaatgaagt | 4320 |
| tttaaatcaa tctaaagtat atatgagtaa acttggtctg acagttacca atgcttaatc | 4380 |
| agtgaggcac ctatctcagc gatctgtcta tttcgttcat ccatagttgc ctgactcggg | 4440 |
| ggggggggggc gctgaggtct gcctcgtgaa gaaggtgttg ctgactcata ccaggcctga | 4500 |
| atcgcccat catccagcca gaaagtgagg gagccacggt tgatgagagc tttgttgtag | 4560 |
| gtggaccagt tggtgatttt gaacttttgc tttgccacgg aacggtctgc gttgtcggga | 4620 |
| agatgcgtga tctgatcctt caactcagca aaagttcgat ttattcaaca aagccgccgt | 4680 |
| cccgtcaagt cagcgtaatg ctctgccagt gttacaacca attaaccaat tctgattaga | 4740 |
| aaaactcatc gagcatcaaa tgaaactgca atttattcat atcaggatta tcaataccat | 4800 |
| attttgaaa aagccgtttc tgtaatgaag gagaaaactc accgaggcag ttccatagga | 4860 |
| tggcaagatc ctggtatcgg tctgcgattc cgactcgtcc aacatcaata caacctatta | 4920 |
| atttcccctc gtcaaaaata aggttatcaa gtgagaaatc accatgagtg acgactgaat | 4980 |
| ccggtgagaa tggcaaaagc ttatgcattt cttttccagac ttgttcaaca ggccagccat | 5040 |
| tacgctcgtc atcaaaatca ctcgcatcaa ccaaaccgtt attcattcgt gattgcgcct | 5100 |
| gagcgagacg aaatacgcga tcgctgttaa aaggacaatt acaaacagga tcgaatgca | 5160 |
| accggcgcag gaacactgcc agcgcatcaa caatatttc acctgaatca ggatattctt | 5220 |
| ctaatacctg gaatgctgtt ttcccgggga tcgcagtggt gagtaaccat gcatcatcag | 5280 |
| gagtacggat aaaatgcttg atggtcggaa gaggcataaa ttccgtcagc cagtttagtc | 5340 |
| tgaccatctc atctgtaaca tcattggcaa cgctaccttt gccatgtttc agaaacaact | 5400 |
| ctggcgcatc gggcttccca tacaatcgat agattgtcgc acctgattgc ccgacattat | 5460 |
| cgcgagccca tttatacca tataaatcag catccatgtt ggaatttaat cgcggcctcg | 5520 |
| agcaagacgt ttcccgttga atatggctca taacaccct tgtattactg tttatgtaag | 5580 |
| cagacagttt tattgttcat gatgatatat ttttatcttg tgcaatgtaa catcagagat | 5640 |
| tttgagacac aacgtggctt tcccccccc cccattattg aagcatttat cagggttatt | 5700 |
| gtctcatgag cggatacata tttgaatgta tttagaaaaa taaacaaata ggggttccgc | 5760 |
| gcacatttcc ccgaaaagtg ccacctgacg tctaagaaac cattattatc atgacattaa | 5820 |
| cctataaaaa taggcgtatc acgaggccct ttcgtc | 5856 |

<210> SEQ ID NO 81
<211> LENGTH: 5856
<212> TYPE: DNA
<213> ORGANISM: Artificial Sequence
<220> FEATURE:
<223> OTHER INFORMATION: Variant Antibody Sequence

<400> SEQUENCE: 81

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcggggctgg cttaactatg cggcatcaga gcagattgta ctgagagtgc | 180 |

```
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca cgaccccccg cccattgacg tcaataatga cgtatgttcc    480
catagtaacg ccaataggga cttttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140 cttttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
caccatggga tggtcatgta tcatcctttt tctagtagca actgcaaccg gtgtacattc   1440
tgaggttaga ctgcgggagt caggaggggg gcttgtgaag cccggtgggt ctctccgcct   1500
gagctgttct gcctccggct ttgatttcga taacgcctgg atgacctggg tcaggcagcc   1560
tccaggtaag ggactggagt gggtgggaag aatcacaggt ccaggcgagg gctggtccgt   1620
ggactacgcg gaatctgtta aagggcggtt tacaatctca agggacaata ccaagaatac   1680
cttgtatttg gagatgaaca acgtgagaac tgaagacacc ggatattact tctgtgccag   1740
aacaggcaaa tactacgact tctggttcgg ctatccccct ggcgaggaat attttcaaga   1800
ctggggtcag ggaacccttg ttatcgtgtc ctccgcgtcg accaagggcc catcggtctt   1860 cccccctggca ccctcctcca agagcacctc tgggggcaca gcggccctgg gctgcctggt   1920
caaggactac ttccccgaac cggtgacggt gtcgtggaac tcaggcgccc tgaccagcgg   1980
cgtgcacacc ttcccggctg tcctacagtc ctcaggactc tactccctca gcagcgtggt   2040
gaccgtgccc tccagcagct tgggcaccca gacctacatc tgcaacgtga atcacaagcc   2100
cagcaacacc aaggtggaca agaaagttga gcccaaatct tgtgacaaaa ctcacacatg   2160
cccaccgtgc ccagcacctg aactcctggg gggaccgtca gtcttcctct tccccccaaa   2220
acccaaggac accctcatga tctcccggac ccctgaggtc acatgcgtgg tggtggacgt   2280
gagccacgaa gaccctgagg tcaagttcaa ctggtacgtg gacggcgtgg aggtgcataa   2340
tgccaagaca aagccgcggg aggagcagta caacagcacg taccgtgtgg tcagcgtcct   2400
caccgtcctg caccaggact ggctgaatgg caaggagtac aagtgcaagg tctccaacaa   2460
agccctccca gcccccatcg agaaaaccat ctccaaagcc aaagggcagc cccgagaacc   2520
acaggtgtac accctgcccc catcccggga tgagctgacc aagaaccagg tcagcctgac   2580
```

```
ctgcctggtc aaaggcttct atcccagcga catcgccgtg gagtgggaga gcaatgggca    2640
gccggagaac aactacaaga ccacgcctcc cgtgctggac tccgacggct ccttcttcct    2700
ctacagcaag ctcaccgtgg acaagagcag gtggcagcag gggaacgtct tctcatgctc    2760
cgtgatgcat gaggctctgc acaaccacta cacgcagaag agcctctccc tgtctccggg    2820
taaatgatga ggatccagat ctgctgtgcc ttctagttgc cagccatctg ttgtttgccc    2880
ctcccccgtg ccttccttga ccctggaagg tgccactccc actgtccttt cctaataaaa    2940
tgaggaaatt gcatcgcatt gtctgagtag gtgtcattct attctggggg gtggggtggg    3000
gcaggacagc aagggggagg attgggaaga caatagcagg catgctgggg atgcggtggg    3060
ctctatgggt acccaggtgc tgaagaattg acccggttcc tcctgggcca gaaagaagca    3120
ggcacatccc cttctctgtg acacaccctg tccacgcccc tggttcttag ttccagcccc    3180
actcatagga cactcatagc tcaggagggc tccgccttca atcccacccg ctaaagtact    3240
tggagcggtc tctccctccc tcatcagccc accaaaccaa acctagcctc caagagtggg    3300
aagaaattaa agcaagatag gctattaagt gcagagggag agaaaatgcc tccaacatgt    3360
gaggaagtaa tgagagaaat catagaattt taaggccatg atttaaggcc atcatggcct    3420
taatcttccg cttcctcgct cactgactcg ctgcgctcgg tcgttcggct gcggcgagcg    3480
gtatcagctc actcaaaggc ggtaatacgg ttatccacag aatcagggga taacgcagga    3540
aagaacatgt gagcaaaagg ccagcaaaag gccaggaacc gtaaaaaggc cgcgttgctg    3600 gcgttttttcc ataggctccg ccccctgac gagcatcaca aaaatcgacg ctcaagtcag    3660
aggtggcgaa acccgacagg actataaaga taccaggcgt ttccccctgg aagctccctc    3720
gtgcgctctc ctgttccgac cctgccgctt accggatacc tgtccgcctt tctcccttcg    3780
ggaagcgtgg cgctttctca tagctcacgc tgtaggtatc tcagttcggt gtaggtcgtt    3840
cgctccaagc tgggctgtgt gcacgaaccc cccgttcagc ccgaccgctg cgccttatcc    3900
ggtaactatc gtcttgagtc caacccggta agacacgact tatcgccact ggcagcagcc    3960
actggtaaca ggattagcag agcgaggtat gtaggcggtg ctacagagtt cttgaagtgg    4020
tggcctaact acggctacac tagaagaaca gtatttggta tctgcgctct gctgaagcca    4080
gttaccttcg gaaaaagagt tggtagctct tgatccggca aacaaaccac cgctggtagc    4140
ggtggttttt ttgtttgcaa gcagcagatt acgcgcagaa aaaaggatc tcaagaagat    4200 cctttgatct tttctacggg gtctgacgct cagtggaacg aaaactcacg ttaagggatt    4260
ttggtcatga gattatcaaa aaggatcttc acctagatcc ttttaaatta aaatgaagt    4320 tttaaatcaa tctaaagtat atatgagtaa acttggtctg acagttacca atgcttaatc    4380
agtgaggcac ctatctcagc gatctgtcta tttcgttcat ccatagttgc ctgactcggg    4440 ggggggggc gctgaggtct gcctcgtgaa gaaggtgttg ctgactcata ccaggcctga    4500
atcgccccat catccagcca gaaagtgagg gagccacggt tgatgagagc tttgttgtag    4560
gtggaccagt tggtgatttt gaacttttgc tttgccacgg aacggtctgc gttgtcggga    4620
agatgcgtga tctgatcctt caactcagca aaagttcgat ttattcaaca aagccgccgt    4680
cccgtcaagt cagcgtaatg ctctgccagt gttacaacca attaaccaat tctgattaga    4740
aaaactcatc gagcatcaaa tgaaactgca atttattcat atcaggatta tcaataccat    4800 attttttgaaa aagccgtttc tgtaatgaag gagaaaactc accgaggcag ttccatagga    4860
tggcaagatc ctggtatcgg tctgcgattc cgactcgtcc aacatcaata caacctatta    4920
```

```
atttcccctc gtcaaaaata aggttatcaa gtgagaaatc accatgagtg acgactgaat   4980
ccggtgagaa tggcaaaagc ttatgcattt cttttccagac ttgttcaaca ggccagccat   5040
tacgctcgtc atcaaaatca ctcgcatcaa ccaaaccgtt attcattcgt gattgcgcct   5100
gagcgagacg aaatacgcga tcgctgttaa aaggacaatt acaaacagga atcgaatgca   5160
accggcgcag gaacactgcc agcgcatcaa caatattttc acctgaatca ggatattctt   5220
ctaatacctg gaatgctgtt ttcccgggga tcgcagtggt gagtaaccat gcatcatcag   5280
gagtacggat aaaatgcttg atggtcggaa gaggcataaa ttccgtcagc cagtttagtc   5340
tgaccatctc atctgtaaca tcattggcaa cgctacctt gccatgtttc agaaacaact   5400
ctggcgcatc gggcttccca tacaatcgat agattgtcgc acctgattgc ccgacattat   5460
cgcgagccca tttataccca tataaatcag catccatgtt ggaatttaat cgcggcctcg   5520
agcaagacgt ttcccgttga atatggctca taacacccct tgtattactg tttatgtaag   5580
cagacagttt tattgttcat gatgatatat ttttatcttg tgcaatgtaa catcagagat   5640
tttgagacac aacgtggctt tcccccccccc cccattattg aagcatttat cagggttatt   5700
gtctcatgag cggatacata tttgaatgta tttagaaaaa taaacaaata ggggttccgc   5760
gcacatttcc ccgaaaagtg ccacctgacg tctaagaaac cattattatc atgacattaa   5820
cctataaaaa taggcgtatc acgaggccct ttcgtc                               5856
```

<210> SEQ ID NO 82
<211> LENGTH: 461
<212> TYPE: PRT
<213> ORGANISM: Artificial Sequence
<220> FEATURE:
<223> OTHER INFORMATION: Variant Antibody Sequence

<400> SEQUENCE: 82

```
Glu Val Arg Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Glu
    50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Phe Gly Tyr Pro
            100                 105                 110

Pro Gly Glu Glu Tyr Phe Gln Asp Trp Gly Gln Gly Thr Leu Val Ile
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
```

```
            195                 200                 205
Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
                340                 345                 350

Ala Lys Gly Gln Pro Arg Glu Pro Gln Val Tyr Thr Leu Pro Pro Ser
            355                 360                 365

Arg Asp Glu Leu Thr Lys Asn Gln Val Ser Leu Thr Cys Leu Val Lys
370                 375                 380

Gly Phe Tyr Pro Ser Asp Ile Ala Val Glu Trp Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
    450                 455                 460

<210> SEQ ID NO 83
<211> LENGTH: 461
<212> TYPE: PRT
<213> ORGANISM: Artificial Sequence
<220> FEATURE:
<223> OTHER INFORMATION: Variant Antibody Sequence

<400> SEQUENCE: 83

Glu Val Arg Leu Arg Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
                20                  25                  30

Trp Met Thr Trp Val Arg Gln Pro Pro Gly Lys Gly Leu Glu Trp Val
            35                  40                  45

Gly Arg Ile Thr Gly Pro Gly Glu Gly Trp Ser Val Asp Tyr Ala Glu
    50                  55                  60

Ser Val Lys Gly Arg Phe Thr Ile Ser Arg Asp Asn Thr Lys Asn Thr
65                  70                  75                  80

Leu Tyr Leu Glu Met Asn Asn Val Arg Thr Glu Asp Thr Gly Tyr Tyr
                85                  90                  95

Phe Cys Ala Arg Thr Gly Lys Tyr Tyr Asp Phe Trp Phe Gly Tyr Pro
```

```
                100             105             110
Pro Gly Glu Glu Tyr Phe Gln Asp Trp Gly Gln Gly Thr Leu Val Ile
        115                 120                 125

Val Ser Ser Ala Ser Thr Lys Gly Pro Ser Val Phe Pro Leu Ala Pro
130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Asp Glu Leu Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 84
<211> LENGTH: 215
<212> TYPE: PRT
<213> ORGANISM: Artificial Sequence
<220> FEATURE:
<223> OTHER INFORMATION: Variant Antibody Sequence

<400> SEQUENCE: 84

Ala Ser Glu Leu Thr Gln Asp Pro Ala Val Ser Val Ala Leu Lys Gln
```

```
                1               5                   10                  15
            Thr Val Thr Ile Thr Cys Arg Gly Asp Ser Leu Arg Ser His Tyr Ala
                            20                  25                  30

Ser Trp Tyr Gln Lys Lys Pro Gly Gln Ala Pro Val Leu Leu Phe Tyr
                            35                  40                  45

Gly Lys Asn Asn Arg Pro Ser Gly Ile Pro Asp Arg Phe Ser Gly Ser
                            50                  55                  60

Ala Ser Gly Asn Arg Ala Ser Leu Thr Ile Thr Gly Ala Gln Ala Glu
            65                  70                  75                  80

Asp Glu Ala Asp Tyr Tyr Cys Ser Ser Arg Asp Lys Ser Gly Ser Arg
                            85                  90                  95

Leu Ser Val Phe Gly Gly Gly Thr Lys Leu Thr Val Leu Ser Gln Pro
                            100                 105                 110

Lys Ala Ala Pro Ser Val Thr Leu Phe Pro Pro Ser Ser Glu Glu Leu
                            115                 120                 125

Gln Ala Asn Lys Ala Thr Leu Val Cys Leu Ile Ser Asp Phe Tyr Pro
                            130                 135                 140

Gly Ala Val Thr Val Ala Trp Lys Ala Asp Ser Ser Pro Val Lys Ala
            145                 150                 155                 160

Gly Val Glu Thr Thr Thr Pro Ser Lys Gln Ser Asn Asn Lys Tyr Ala
                            165                 170                 175

Ala Ser Ser Tyr Leu Ser Leu Thr Pro Glu Gln Trp Lys Ser His Arg
                            180                 185                 190

Ser Tyr Ser Cys Gln Val Thr His Glu Gly Ser Thr Val Glu Lys Thr
                            195                 200                 205

Val Ala Pro Thr Glu Cys Ser
                210                 215

<210> SEQ ID NO 85
<211> LENGTH: 6
<212> TYPE: PRT
<213> ORGANISM: Artificial Sequence
<220> FEATURE:
<223> OTHER INFORMATION: Variant Antibody Sequence

<400> SEQUENCE: 85

Ser Leu Arg Cys His Trp
1               5

<210> SEQ ID NO 86
<211> LENGTH: 6
<212> TYPE: PRT
<213> ORGANISM: Artificial Sequence
<220> FEATURE:
<223> OTHER INFORMATION: Variant Antibody Sequence

<400> SEQUENCE: 86

Ser Leu Arg Cys His Phe
1               5
```

NEUTRALIZING ANTIBODIES TO HIV-1 GP41 AND THEIR USE

CROSS REFERENCE TO RELATED APPLICATIONS

This is the U.S. National Stage of International Application No. PCT/US2016/060390, filed Nov. 3, 2016, which was published in English under PCT Article 21(2), which in turn claims the benefit of U.S. Provisional Application No. 62/250,360, filed Nov. 3, 2015. The provisional application is incorporated by reference herein in its entirety.

FIELD OF THE DISCLOSURE

This relates to antibodies and antigen binding fragments that specifically bind to Human Immunodeficiency Virus type 1 (HIV-1) gp41 and their use, for example, in methods of treating a subject with HIV-1 infection.

BACKGROUND

HIV-1 infection, and the resulting Acquired Immunodeficiency Syndrome (AIDS), remain threats to global public health, despite extensive efforts to develop anti-HIV-1 therapeutic agents. An enveloped virus, HIV-1 hides from humoral recognition behind a wide array of protective mechanisms. The major HIV-1 envelope protein (HIV-1 Env) is a glycoprotein of approximately 160 kD (gp160). During infection, proteases of the host cell cleave gp160 into gp120 and gp41. gp41 is an integral membrane protein, while gp120 protrudes from the mature virus. Together gp120 and gp41 make up the HIV-1 envelope spike, which is a target for neutralizing antibodies. Broadly neutralizing antibodies that bind to HIV-1 Env have been identified, including the 10E8 antibody, which specifically binds to the membrane proximal external region (MPER) of gp41 and can neutralize a high percentage of HIV-1 strains. However, there is a need to develop additional neutralizing antibodies for HIV-1 with varying recognition and neutralization profiles for commercial production.

SUMMARY

Disclosed herein are isolated antibodies and antigen binding fragments that specifically bind to HIV-1 gp41 and neutralize HIV-1. In some embodiments, the isolated antibody or antigen binding fragment comprises heavy and light chain variable regions comprising one or more amino acid substitutions (for example in the complementarity determining regions (CDRs) and/or the framework regions) compared to the 10E8 antibody sequence that impart an improved combination of neutralization, solubility, and auto-reactivity properties relative to the 10E8 antibody.

In some embodiments, the isolated antibody or antigen binding fragment comprises a heavy chain variable region ($V_H$) comprising a heavy chain complementarity determining region (HCDR)1, a HCDR2, and a HCDR3 of the $V_H$ set forth as SEQ ID NO: 75 (10E8v4 S100cF), and a light chain variable region ($V_L$) comprising a light chain complementarity determining region (LCDR)1, a LCDR2, and a LCDR3 of the $V_L$ set forth as SEQ ID NO: 6 (rL3-6mut), wherein the antibody or antigen binding fragment specifically binds to gp41 and neutralizes HIV-1. In some embodiments, the HCDR1, the HCDR2, the HCDR3, the LCDR1, the LCDR2, and the LCDR3 comprise the amino acid sequences set forth as SEQ ID NOs: 7, 8, 77, 10, 11, and 12, respectively (10E8v4 S100cF IMGT CDRs). In some embodiments, the $V_H$ and $V_L$ of the isolated antibody or antigen binding fragment comprise the amino acid sequences set forth as SEQ ID NOs: 75 and 6, respectively (10E8v4 S100cF), or SEQ ID NOs: 76 and 6, respectively (10E8v4 V5R S100cF), wherein the antibody or antigen binding fragment specifically binds to gp41 and neutralizes HIV-1.

In additional embodiments, the isolated antibody comprises a $V_H$ comprising a HCDR1, a HCDR2, and a HCDR3 of the $V_H$ set forth as SEQ ID NO: 5, and a $V_L$ comprising a light chain LCDR1, a LCDR2, and a LCDR3 of the $V_L$ set forth as SEQ ID NO: 6, wherein the $V_H$ comprises arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively, and the $V_L$ comprises alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, and wherein the antibody or antigen binding fragment specifically binds to gp41 and neutralizes HIV-1.

Also disclosed are compositions including the antibodies and antigen binding fragments, nucleic acids encoding the antibodies and antigen binding fragments, expression vectors comprising the nucleic acids, and isolated host cells that comprise the nucleic acids. In some embodiments, the nucleic acid molecule can be a bicistronic expression construct encoding the $V_H$ and $V_L$ of the antibody or antigen binding fragment.

The disclosed antibodies and antigen binding fragments potently neutralize HIV-1 in an accepted in vitro model of HIV-1 infection. Accordingly, a method is disclosed for treating or inhibiting an HIV-1 infection in a subject. The methods include administering a therapeutically effective amount of one or more of the disclosed antibodies, antigen binding fragments, nucleic acid molecules, vectors, or compositions, to the subject, for example to a subject at risk of or having an HIV-1 infection.

The antibodies, antigen binding fragments, nucleic acid molecules, vectors, and compositions disclosed herein can be used for a variety of additional purposes, such as for detecting an HIV-1 infection or diagnosing HIV-1 infection in a subject, or detecting HIV-1 in a sample.

The foregoing and other features and advantages of this disclosure will become more apparent from the following detailed description of several embodiments which proceeds with reference to the accompanying figures.

BRIEF DESCRIPTION OF THE FIGURES

FIGS. 1A-1F are sequence alignments of antibody heavy and light chain variable domains. FIGS. 1A and 1C show kabat numbering and IMGT (FIG. 1A) or kabat (FIG. 1C) CDR positioning of the 10E8 (SEQ ID NO: 1), HC6-S74Y (SEQ ID NO: 13), HC6-S74Y-511 (SEQ ID NO: 3), H6 (SEQ ID NO: 14), H6-511 (SEQ ID NO: 15), and H6-511-4mut (SEQ ID NO: 5) heavy chain variable domains. FIGS. 1B and 1D show kabat numbering and IMGT (FIG. 1B) or kabat (FIG. 1D) CDR positioning of the 10E8 (SEQ ID NO: 2), rL3 (SEQ ID NO: 4), and rL3-6mut (SEQ ID NO: 6) light chain variable domains. FIG. 1E shows kabat numbering and IMGT CDR positioning of the $V_H$ for 10E8 (SEQ ID NO: 1), 10E8v4 (SEQ ID NO: 5), 10E8v4 S100cF (SEQ ID NO: 75), and 10E8v4 V5R S100cF (SEQ ID NO: 76). FIG. 1F shows kabat numbering and IMGT CDR positioning of the $V_L$ for 10E8 (SEQ ID NO: 2) and 10E8v4 (SEQ ID NO: 6), which is also used at the VL for 10E8v4 S100cF and 10E8v4 V5R S100cF.

FIG. 3 is a table illustrating neutralization of a representative panel of HIV-1 pseudoviruses by the 10E8 antibody, and 10E8 variants including the HC6-S74Y $V_H$ and the rL3 $V_L$, or the HC6-S74Y-511 $V_H$ and the rL3 $V_L$. Neutralization was determined using the TZM-b1 cell pseudovirus neutralization assay; $IC_{80}$ values are shown.

FIG. 7 is a table illustrating neutralization of a representative panel of HIV-1 pseudoviruses by the 10E8 antibody, and 10E8 variants including the H6-511 $V_H$ and the rL3 $V_L$, or the H6-511-4mut (H6-511 with N28D, D31N, S52T, and H98Y substitutions) $V_H$ and the L10 $V_L$. Neutralization was determined using the TZM-b1 cell pseudovirus neutralization assay; $IC_{50}$ values are shown.

FIG. 11 is a table illustrating neutralization of a representative panel of HIV-1 pseudoviruses by the 10E8 antibody, and the 10E8 variants including the H6-511 $V_H$ and rL3 $V_L$, the H6-511-4mut $V_H$ and rL3, or the H6-511-4mut $V_H$ and the rL3-6mut $V_L$. Neutralization was determined using the TZM-b1 cell pseudovirus neutralization assay; $IC_{50}$ and $IC_{80}$ values are shown.

FIG. 14 is a set of graphs showing the results of dynamic light scattering assays of solutions containing the 10E8 antibody or a 10E8 variant including the HC6-S74Y-511 $V_H$ and the rL3 $V_L$, the HC6-S74Y-511 $V_H$ and the rL3, or the H6-511-4mut and the rL3-6mut $V_L$. The 10E8 antibody was polydisperse, indicating the presence of protein aggregates. Antibodies including the HC6-S74Y-511 $V_H$ and the rL3 $V_L$, the HC6-S74Y-511 $V_H$ and the rL3, or the H6-511-4mut and the rL3-6mut $V_L$ were monodisperse.

FIGS. 16A-16F are a set of tables illustrating the neutralization of a panel of 200 HIV-1 pseudoviruses by the 10E8 antibody and 10E8 variants including the HC6-S74Y-511 $V_H$ and the rL3 $V_L$ (Var1), the HC6-S74Y-511 $V_H$ and the rL3-6mut $V_L$ (Var5), or the H6-511-4mut and the rL3-6mut $V_L$ (Var4). The $IC_{50}$ (FIGS. 16A-16C) and $IC_{80}$ (FIGS. 16D-16F) values are shown.

FIG. 17 is a graph showing the concentration of the 10E8 antibody or 10E8 variant antibody in primate (macaque) serum over time following a single injection of antibody.

FIGS. 18A-18D are a set of graphs illustrating the size exclusion chromatography of 10E8, 10E8v4, and 10E8v5 (FIG. 18A), size exclusion chromatography of several 10E8v4 variants with amino acid substitutions at $V_L$ kabat position 32 (FIGS. 18B and 18C), and the turbidity of several 10E8v4 variants with amino acid substitutions at $V_L$ kabat position 32 (FIG. 18D).

FIG. 19 shows a set of tables illustrating $IC_{50}$ and $IC_{80}$ values for the neutralization of a panel of HIV-1 viruses by several broadly neutralizing HIV-1 antibodies, including the 10E8v4 S100cW antibody.

FIGS. 23A-23F show a set of tables illustrating neutralization of a representative panel of HIV-1 pseudoviruses by several different 10E8 variant antibodies. The 10E8 variants included those in Table 10 (see Example 5). Neutralization was determined using the TZM-b1 cell pseudovirus neutralization assay; $IC_{50}$ (FIGS. 23A, 23C, and 23D) and $IC_{80}$ (FIGS. 23B, 23E, 23F) values are shown.

SEQUENCES

Figure 1B:
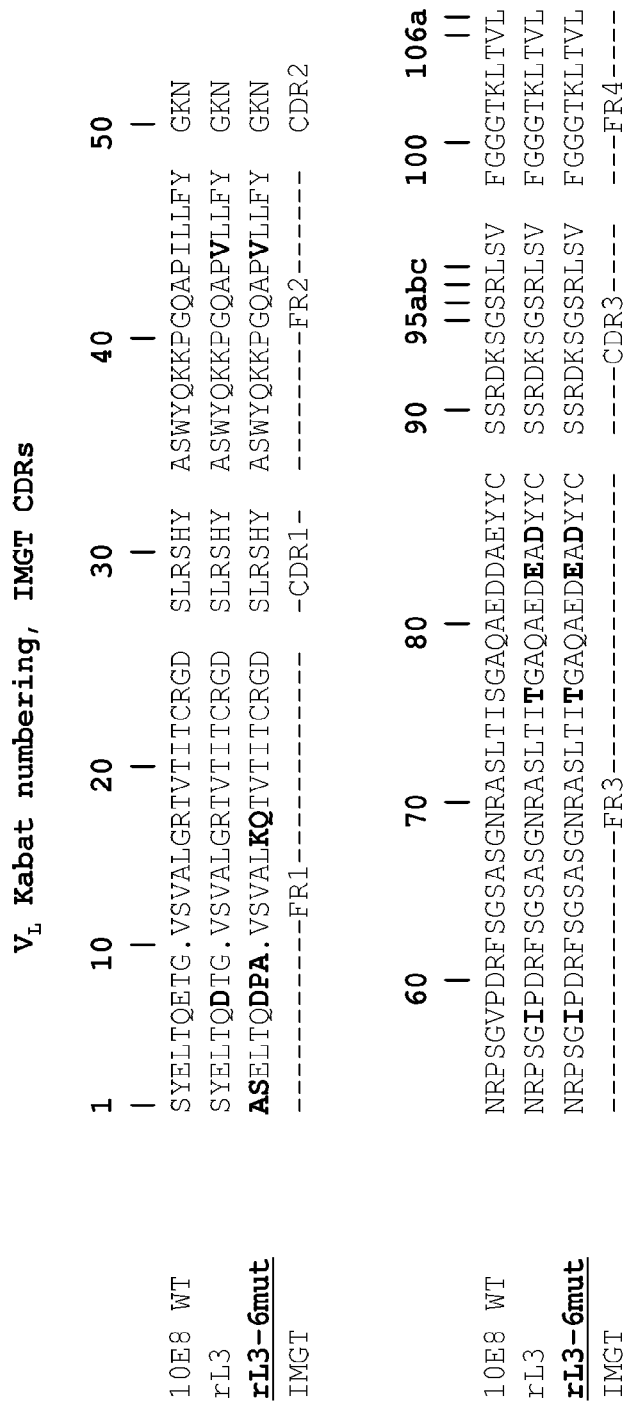

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~165 kb), which was created on Apr. 25, 2018, and which is incorporated by reference herein. In the accompanying sequence listing:

```
SEQ ID NO: 1 is the amino acid sequence of the 10E8 V_H.
EVQLVESGGGLVKPGGSLRLSCSASGFDFDNAWMTWVRQPPGKGLEWVGRITGPGEGWSVDYAAPVEGRFTISRLNSINF

LYLEMNNLRMEDSGLYFCARTGKYYDFWSGYPPGEEYFQDWGRGTLVTVSS

SEQ ID NO: 2 is the amino acid sequence of the 10E8 V_L.
SYELTQETGVSVALGRTVTITCRGDSLRSHYASWYQKKPGQAPILLFYGKNNRPSGVPDRFSGSASGNRASLTISGAQAE

DDAEYYCSSRDKSGSRLSVFGGGTKLTVL

SEQ ID NO: 3 is the amino acid sequence of the HC6-S74Y-511 V_H.
EVRLAESGGGLVKPGGSLRLSCSASGFDFDNAWMTWVRQPPGKGLEWVGRITGPGEGWSVDYAAPVEGRFTISRDNYKNT

LYLEMNNLRTEDSGLYFCARTGKYYDFWSGYPPGEEYFQDWGRGTLVIVSS

SEQ ID NO: 4 is the amino acid sequence of the rL3 V_L.
SYELTQDTGVSVALGRTVTITCRGDSLRSHYASWYQKKPGQAPVLLFYGKNNRPSGIPDRFSGSASGNRASLTITGAQAE

DEADYYCSSRDKSGSRLSVFGGGTKLTVL

SEQ ID NO: 5 is the amino acid sequence of the H6-511-4mut V_H.
EVRLVESGGGLVKPGGSLRLSCSASGFDFDNAWMTWVRQPPGKGLEWVGRITGPGEGWSVDYAESVKGRFTISRDNTKNT

LYLEMNNVRTEDTGYYFCARTGKYYDFWSGYPPGEEYFQDWGQGTLVIVSS

SEQ ID NO: 6 is the amino acid sequence of the rL3-6mut V_L.
ASELTQDPAVSVALKQTVTITCRGDSLRSHYASWYQKKPGQAPVLLFYGKNNRPSGIPDRFSGSASGNRASLTITGAQAE

DEADYYCSSRDKSGSRLSVFGGGTKLTVL

SEQ ID NOs: 7-12 are amino acid sequences of the IMGT CDRs of the 10E8 antibody.

SEQ ID NO: 13 is the amino acid sequence of the HC6-S74Y V_H.
EVRLAESGGGLVKPGGSLRLSCSASGFDFDNAWMTWVRQPPGKGLEWVGRITGPGEGWSVDYAAPVEGRFTISRLNYINF

LYLEMNNLRMEDSGLYFCARTGKYYDFWSGYPPGEEYFQDWGRGTLVIVSS

SEQ ID NO: 14 is the amino acid sequence of the H6 V_H.
EVRLVESGGGLVKPGGSLRLSCSASGFNFDDAWMTWVRQPPGKGLEWVGRISGPGEGWSVDYAESVKGRFTISRLNSINF

LYLEMNNVRTEDTGYYFCARTGKHYDFWSGYPPGEEYFQDWGQGTLVIVSS

SEQ ID NO: 15 is the amino acid sequence of the H6-511 V_H.
EVRLVESGGGLVKPGGSLRLSCSASGFNFDDAWMTWVRQPPGKGLEWVGRISGPGEGWSVDYAESVKGRFTISRDNTKNT

LYLEMNNVRTEDTGYYFCARTGKHYDFWSGYPPGEEYFQDWGQGTLVIVSS

SEQ ID NO: 16 is the amino acid sequence of the H8 V_H.
EVRLVESGGRLVRPGGSLRLSCSASGFNFDNAWMTWVRQPPGKGLEWVGRITGPGEGWSVDYAASVKGRFTISRMNSINF

FYLEMNNLKIEDTGLYFCARTGKHYAFWGGYPPGEEYLEDWGQGTLVIVSS

SEQ ID NO: 17 is the amino acid sequence of the H8-511 V_H.
EVRLVESGGRLVRPGGSLRLSCSASGFNFDNAWMTWVRQPPGKGLEWVGRITGPGEGWSVDYAASVKGRFTISRDNYKNT

FYLEMNNLKTEDTGLYFCARTGKHYAFWGGYPPGEEYLEDWGQGTLVIVSS
```

-continued

SEQ ID NO: 18 is the amino acid sequence of the L10 $V_L$.
ASELTQDPAVSVALKQTVTITCRGDSLRSHYVSWYQKKPGQAPVLVFYGKNNRPSGIPDRFSGSSSGNTASLTIAGAQAE

DDADYYCSSRDKSGSRLSVFGGGTKLTVL

SEQ ID NO: 19 is the amino acid sequence of the L19 $V_L$.
ASELTQDPTVSVALGQTVTITCRGDSLRNYYTSWYQQKPGQAPVLLIYPKHNRPPGISDRFSASSSGNTASLTITGAQTE

DEGDYYCSSRDKSGSRLVTFGRGTKLTVV

SEQ ID NO: 20 is an exemplary nucleic acid sequence encoding the HC6-S74Y-511 $V_H$ linked to an IgG1 constant region.
atgggatggtcatgtatcatccttttttctagtagcaactgcaaccggtgtacattctgaagtgcggctggctgagagcgg cgggggggctggtcaaacctggcgggtcactgcggctgtcctgttctgcctccggcttcgattttgataacgcatggatga catgggtgcgacagccacctggaaaggggctggagtgggtcggcagaatcactggacctggcgaagggtggtctgtggac tacgcagctccagtcgaggacgattcaccattagtagagataactacaagaatacactgtatctggagatgaacaatct gaggactgaagacagcggcctgtatttctgcgcccgcaccggaaatactatgattttggtctgggtacccacccggag aggaatattttcaggactggggacggggcaccctggtgatcgtcagctccgcgtcgaccaagggcccatcggtcttcccc ctggcaccctcctccaagagcacctctgggggcacagcggccctgggctgcctggtcaaggactacttccccgaaccggt gacggtgtcgtggaactcaggcgccctgaccagcggcgtgcacaccttcccggctgtcctacagtcctcaggactctact ccctcagcagcgtggtgaccgtgccctccagcagcttgggcacccagacctacatctgcaacgtgaatcacaagcccagc aacaccaaggtggacaagaaagttgagcccaaatcttgtgacaaaactcacacatgcccaccgtgcccagcacctgaact cctggggggaccgtcagtcttcctcttccccccaaaacccaaggacaccctcatgatctcccggacccctgaggtcacat gcgtggtggtggacgtgagccacgaagaccctgaggtcaagttcaactggtacgtggacggcgtggaggtgcataatgcc aagacaaagccgcgggaggagcagtacaacagcacgtaccgtgtggtcagcgtcctcaccgtcctgcaccaggactggct gaatggcaaggagtacaagtgcaaggtctccaacaaagcccttccagcccccatcgagaaaaccatctccaaagccaaag ggcagccccgagaaccacaggtgtacaccctgcccccatcccgggatgagctgaccaagaaccaggtcagcctgacctgc ctggtcaaaggcttctatcccagcgacatcgccgtggagtgggagagcaatgggcagccggagaacaactacaagaccac gcctcccgtgctggactccgacggctccttcttcctctacagcaagctcaccgtggacaagagcaggtggcagcaggga acgtcttctcatgctccgtgatgcatgaggctctgcacaaccactacacgcagaagagcctctccctgtctccgggtaaa tga SEQ ID NO: 21 is an exemplary nucleic acid sequence encoding the H6-511-4mut $V_H$ linked to an IgG1 constant region.
atgggatggtcatgtatcatccttttttctagtagcaactgcaaccggtgtacattctgaggttagactggtggagtcagg aggggggcttgtgaagcccggtgggtctctccgcctgagctgttctgcctccggctttgatttcgataacgcctggatga cctgggtcaggcagcctccaggtaagggactggagtgggtgggaagaatcacaggtccaggcgagggctggtccgtggac tacgcggaatctgttaaagggcggtttacaatctcaagggacaataccaagaataccttgtatttggagatgaacaacgt gagaactgaagacaccggatattacttctgtgccagaacaggcaaatactacgacttctggtccggctatcccctggcg aggaatattttcaagactgggtcagggaacccttgttatcgtgtcctccgcgtcgaccaagggcccatcggtcttcccc ctggcaccctcctccaagagcacctctgggggcacagcggccctgggctgcctggtcaaggactacttccccgaaccggt gacggtgtcgtggaactcaggcgccctgaccagcggcgtgcacaccttcccggctgtcctacagtcctcaggactctact ccctcagcagcgtggtgaccgtgccctccagcagcttgggcacccagacctacatctgcaacgtgaatcacaagcccagc aacaccaaggtggacaagaaagttgagcccaaatcttgtgacaaaactcacacatgcccaccgtgcccagcacctgaact cctggggggaccgtcagtcttcctcttccccccaaaacccaaggacaccctcatgatctcccggacccctgaggtcacat gcgtggtggtggacgtgagccacgaagaccctgaggtcaagttcaactggtacgtggacggcgtggaggtgcataatgcc aagacaaagccgcgggaggagcagtacaacagcacgtaccgtgtggtcagcgtcctcaccgtcctgcaccaggactggct gaatggcaaggagtacaagtgcaaggtctccaacaaagcccttccagcccccatcgagaaaaccatctccaaagccaaag ggcagccccgagaaccacaggtgtacaccctgcccccatcccgggatgagctgaccaagaaccaggtcagcctgacctgc -continued ctggtcaaaggcttctatcccagcgacatcgccgtggagtgggagagcaatgggcagccggagaacaactacaagaccac gcctcccgtgctggactccgacggctccttcttcctctacagcaagctcaccgtggacaagagcaggtggcagcaggga acgtcttctcatgctccgtgatgcatgaggctctgcacaaccactacacgcagaagagcctctccctgtctccgggtaaa SEQ ID NO: 22 is the amino acid sequence of the H6-511-4mut V$_H$ linked to an IgG1 constant region.
EVRLVESGGGLVKPGGSLRLSCSASGEDFDNAWMTWVRQPPGKGLEWVGRITGPGEGWSVDYAESVKGRFTI

SRDNTKNTLYLEMNNVRTEDTGYYFCARTGKYYDFWSGYPPGEEYFQDWGQGTLVIVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPPVLDSDGSFFLYSKLTVDKSRWQ

QGNVFSCSVMHEALHNHYTQKSLSLSPGK

SEQ ID NO: 23 is the amino acid sequence of the HC6-S74Y-511 V$_H$ linked to an IgG1 constant region.
EVRLAESGGGLVKPGGSLRLSCSASGEDFDNAWMTWVRQPPGKGLEWVGRITGPGEGWSVDYAAPVEGRFTI

SRDNYKNTLYLEMNNLRTEDSGLYFCARTGKYYDFWSGYPPGEEYFQDWGRGTLVIVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPPVLDSDGSFFLYSKLTVDKSRWQ

QGNVFSCSVMHEALHNHYTQKSLSLSPGK

SEQ ID NO: 24 is an exemplary nucleic acid sequence encoding the rL3 V$_L$.
tcatacgaactgactcaggacactggcgtctctgtggcactggggaggactgtgactattacttgccgaggcgactcact gcggagccactacgcttcctggtatcagaagaaacccggccaggcacctgtgctgctgttctacggaaagaacaataggc catctggcatccccgaccgcttttctggcagtgcatcagggaaccgagccagtctgaccattaccggcgcccaggctgag gacgaagccgattactattgcagctcccgggataagagcggctccagactgagcgtgttcggaggaggaactaaactgac cgtcctcagtcagcccaaggctgccccctcggtcactctgttcccgccctcgagtgaggagcttcaagccaacaaggcca cactggtgtgtctcataagtgacttctacccgggagccgtgacagtggcctggaaggcagatagcagccccgtcaaggcg ggagtggagaccaccacacccctccaaacaaagcaacaacaagtacgcggccagcagctacctgagcctgacgcctgagca gtggaagtcccacagaagctacagctgccaggtcacgcatgaagggagcaccgtggagaagacagtggcccctacagaat gttcatag SEQ ID NO: 25 is an exemplary nucleic acid sequence encoding the rL3-6mut V$_L$.
accaccatgggatggtcatgtatcatccttttctagtagcaactgcaaccggttctgtgaccgcatccgaactgactca ggaccctgccgtctctgtggcactgaagcagactgtgactattacttgccgaggcgactcactgcggagccactacgctt cctggtatcagaagaaacccggccaggcacctgtgctgctgttctacggaaagaacaataggccatctggcatccccgac cgcttttctggcagtgcatcagggaaccgagccagtctgaccattaccggcgcccaggctgaggacgaagccgattacta ttgcagctcccgggataagagcggctccagactgagcgtgttcggaggaggaactaaactgaccgtcctcagtcagccca aggctgccccctcggtcactctgttcccgccctcgagtgaggagcttcaagccaacaaggccacactggtgtgtctcata agtgacttctacccgggagccgtgacagtggcctggaaggcagatagcagccccgtcaaggcgggagtggagaccaccac accctccaaacaaagcaacaacaagtacgcggccagcagctacctgagcctgacgcctgancagtggaangtcccacaga agctacagctgccaggtcacgcatgaagggagcaccgt -continued SEQ ID NO: 26 is the amino acid sequence of HIV-1 Env from the HXB2 strain of HIV-1.

SEQ ID NOs: 27-33 are amino acid sequences of the $V_H$ and $V_L$ domains of the VRC01, VRC07, VRC07-523, and VRC07-544 antibodies.

SEQ ID NO: 34 is the amino acid sequence of a MPER peptide.

SEQ ID NO: 35 is the amino acid sequence of the H6-511-4mut-S100cW $V_H$.
EVRLVESGGGLVKPGGSLRLSCSASGFDFDNAWMTWVRQPPGKGLEWVGRITGPGEGWSVDYAESVKGRFTISRDNTKNT

LYLEMNNVRTEDTGYYFCARTGKYYDFWWGYPPGEEYFQDWGQGTLVIVSS

SEQ ID NO: 36 is the amino acid sequence of the H6-511-4mut-DS $V_H$.
EVRLVESGGGLVKPGGSLRLSCSASGFDFDNAWMTWVRQPPGKGLEWVGRITGPGEGWSVDYAESVKGRFTISRDNTKNT

LYLEMNNVRTEDTGYYFCARTGKYYDFWSGCPPGEEYFQDWGQGTLVIVSS

SEQ ID NO: 37 is the amino acid sequence of the H6-511-4mut-S100cW-DS $V_H$.
EVRLVESGGGLVKPGGSLRLSCSASGFDFDNAWMTWVRQPPGKGLEWVGRITGPGEGWSVDYAESVKGRFTISRDNTKNT

LYLEMNNVRTEDTGYYFCARTGKYYDFWWGCPPGEEYFQDWGQGTLVIVSS

SEQ ID NO: 38 is the amino acid sequence of the HC6-S74Y-511-S100cW $V_H$.
EVRLAESGGGLVKPGGSLRLSCSASGFDFDNAWMTWVRQPPGKGLEWVGRITGPGEGWSVDYAAPVEGRFTISRDNYKNT

LYLEMNNLRTEDSGLYFCARTGKYYDFWWGYPPGEEYFQDWGRGTLVIVSS

SEQ ID NO: 39 is the amino acid sequence of the HC6-S74Y-511-DS $V_H$.
EVRLAESGGGLVKPGGSLRLSCSASGFDFDNAWMTWVRQPPGKGLEWVGRITGPGEGWSVDYAAPVEGRFTISRDNYKNT

LYLEMNNLRTEDSGLYFCARTGKYYDFWSGCPPGEEYFQDWGRGTLVIVSS

SEQ ID NO: 40 is the amino acid sequence of the HC6-S74Y-511-S100cW-DS $V_H$.
EVRLAESGGGLVKPGGSLRLSCSASGFDFDNAWMTWVRQPPGKGLEWVGRITGPGEGWSVDYAAPVEGRFTISRDNYKNT

LYLEMNNLRTEDSGLYFCARTGKYYDFWWGCPPGEEYFQDWGRGTLVIVSS

SEQ ID NO: 41 is the amino acid sequence of the rL3-6mut-DS $V_L$.
ASELTQDPAVSVALKQTVTITCRGDSLRCHYASWYQKKPGQAPVLLFYGKNNRPSGIPDRFSGSASGNRASLTITGAQAE

DEADYYCSSRDKSGSRLSVFGGGTKLTVL

SEQ ID NO: 42 is the amino acid sequence of the rL3-6mut-Y32W $V_L$.
ASELTQDPAVSVALKQTVTITCRGDSLRSHWASWYQKKPGQAPVLLFYGKNNRPSGIPDRFSGSASGNRASLTITGAQAE

DEADYYCSSRDKSGSRLSVFGGGTKLTVL

SEQ ID NO: 43 is the amino acid sequence of the rL3-6mut-Y32F $V_L$.
ASELTQDPAVSVALKQTVTITCRGDSLRSHFASWYQKKPGQAPVLLFYGKNNRPSGIPDRFSGSASGNRASLTITGAQAE

DEADYYCSSRDKSGSRLSVFGGGTKLTVL

SEQ ID NO: 44 is an exemplary nucleic acid sequence encoding the HC6-S74Y-511 $V_H$.
gaagtgcggctggctgagagcggcggggggctggtcaaacctggcgggtcactgcggctgtcctgttctgcctccggctt cgatttgataacgcatggatgacatgggtgcgacagccacctggaaaggggctggagtgggtcggcagaatcactggac ctggcgaagggtggtctgtggactacgcagctccagtcgaggacgattcaccattagtagagataactacaagaataca ctgtatctggagatgaacaatctgaggactgaagacagcggcctgtatttctgcgcccgcaccgggaaatactatgattt ttggtctgggtacccacccggagaggaatattttcaggactggggacggggcaccctggtgatcgtcagctcc SEQ ID NO: 45 is an exemplary nucleic acid sequence encoding the H6-511-4mut $V_H$.
gaggttagactggtggagtcaggagggggcttgtgaagcccggtgggtctctccgcctgagctgttctgcctccggctt tgatttcgataacgcctggatgacctgggtcaggcagcctccaggtaagggactggagtgggtgggaagaatcacaggtc caggcgagggctggtccgtggactacgcggaatctgttaaagggcggtttacaatctcaaggacaataccaagaatacc ttgtatttggagatgaacaacgtgagaactgaagacaccggatattacttctgtgccagaacaggcaaatactacgactt ctggtccggctatcccctggcgaggaatattttcaagactggggtcagggaacccttgttatcgtgtcctcc SEQ ID NO: 46 is an exemplary nucleic acid sequence encoding the rL3 VL.
tcatacgaactgactcaggacactggcgtctctgtggcactggggaggactgtgactattacttgccgaggcgactcact gcggagccactacgcttcctggtatcagaagaaaccggccaggcacctgtgctgctgttctacggaaagaacaataggc catctggcatccccgaccgcttttctggcagtgcatcagggaaccgagccagtctgaccattaccggcgcccaggctgag gacgaagccgattactattgcagctcccgggataagagcggctccagactgagcgtgttcggaggaggaactaaactgac cgtcctc SEQ ID NO: 47 is an exemplary nucleic acid sequence encoding the rL3-6mut $V_L$.
accaccatgggatggtcatgtatcatcctttttctagtagcaactgcaaccggttctgtgaccgcatccgaactgactca ggaccctgccgtctctgtggcactgaagcagactgtgactattacttgccgaggcgactcactgcggagccactacgctt cctggtatcagaagaaacccggccaggcacctgtgctgctgttctacggaaagaacaataggccatctggcatccccgac cgcttttctggcagtgcatcagggaaccgagccagtctgaccattaccggcgcccaggctgaggacgaagccgattacta ttgcagctcccgggataagagcggctccagactgagcgtgttcggaggaggaactaaactgaccgtcctc SEQ ID NO: 48 is an exemplary nucleic acid sequence of an expression vector encoding the HC6-S74Y-511 $V_H$.

SEQ ID NO: 49 is an exemplary nucleic acid sequence of an expression vector encoding the H6-511-4mut $V_H$.

SEQ ID NO: 50 is an exemplary nucleic acid sequence of an expression vector encoding the rL3 $V_L$.

SEQ ID NO: 51 is an exemplary nucleic acid sequence of an expression vector encoding the rL3-6mut $V_L$.

SEQ ID NOs: 52-57 are the amino acid sequences of IMGT CDRs.

SEQ ID NO: 58 is the amino acid sequence of the rL3-6mut-DS-Y32W $V_L$.
ASELTQDPAVSVALKQTVTITCRGDSLRCHWASWYQKKPGQAPVLLFYGKNNRPSGIPDRFSGSASGNRASLTITGAQAE

DEADYYCSSRDKSGSRLSVFGGGTKLTVL

SEQ ID NO: 59 is the amino acid sequence of the rL3-6mut-DS-Y32F $V_L$.
ASELTQDPAVSVALKQTVTITCRGDSLRCHFASWYQKKPGQAPVLLFYGKNNRPSGIPDRFSGSASGNRASLTITGAQAE

DEADYYCSSRDKSGSRLSVFGGGTKLTVL

SEQ ID NOs: 60-63 are an exemplary nucleic acid sequence of expression vectors encoding the 10E8v4-DS VH, the 10E8v4-DS (or 10E8v4-100cW-DS) VL, the 10E8v4-100cW $V_H$, or the 10E8v4-100cW-DS VH, respectively.

SEQ ID NO: 64 is an exemplary nucleic acid sequence encoding the H6-511-4mut-S100cW $V_H$ (Seq_35).
atgggctggtcctgtattatcctgttcctggtcgcaactgctactggcgtccattcagaagtgaggctggtcgagagcgg cggcggcctggtgaagccaggaggaagcctgcgactgagctgctccgcctctggcttcgactttgataacgcttggatga catgggtgcgacagcccctggaaaaggcctggagtgggtcggaagaatcaccggccccggagagggatggagtgtggac tacgcagaatcagtcaaggccggttcaccattagccgggataacaccaaaaatacactgtatctggagatgaacaatgt caggactgaagacaccgggtactatttctgtgccgcaccggaaagtactatgatttttggtggggctacccacccggag aagaatactttcaggactggggacagggaacactggtcatcgtcagcagc SEQ ID NO: 65 is an exemplary nucleic acid sequence encoding the H6-511-4mut-DS $V_H$ (Seq_36).
atgggatggtcatgtatcatcctttttctagtagcaactgcaaccggtgtacattctgaggttagactggtggagtcagg aggggggcttgtgaagcccggtgggtctctccgcctgagctgttctgcctccggctttgatttcgataacgcctggatga cctgggtcaggcagcctccaggtaagggactggagtgggtgggaagaatcacaggtccaggcgagggctggtccgtggac tacgcggaatctgttaaagggcggtttacaatctcaagggacaataccaagaataccttgtatttggagatgaacaacgt gagaactgaagacaccggatattacttctgtgccagaacaggcaaatactacgacttctggtccggctgccccctggcg aggaatattttcaagactggggtcagggaacccttgttatcgtgtcctcc SEQ ID NO: 66 is an exemplary nucleic acid sequence encoding the H6-511-4mut-S100cW-DS $V_H$ (Seq_37).
atgggatggtcatgtatcatcctttttctagtagcaactgcaaccggtgtacattctgaggttagactggtggagtcagg aggggggcttgtgaagcccggtgggtctctccgcctgagctgttctgcctccggctttgatttcgataacgcctggatga cctgggtcaggcagcctccaggtaagggactggagtgggtgggaagaatcacaggtccaggcgagggctggtccgtggac tacgcggaatctgttaaagggcggtttacaatctcaagggacaataccaagaataccttgtatttggagatgaacaacgt SEQ ID NO: 67 is an exemplary nucleic acid sequence encoding the HC6-S74Y-511-S100cW V$_H$ (Seq_38).
gaagtgcggctggctgagagcggcgggggggctggtcaaacctggcggtcactgcggctgtcctgttctgcctccggctt cgattttgataacgcatggatgacatgggtgcgacagccacctggaaaggggctggagtgggtcggcagaatcactggac ctggcgaagggtggtctgtggactacgcagctccagtcgagggacgattcaccattagtagagataactacaagaataca ctgtatctggagatgaacaatctgaggactgaagacagcggcctgtatttctgcgcccgcaccgggaaatactatgattt ttggtgggggtacccacccggagaggaatattttcaggactggggacggggcaccctggtgatcgtcagctcc SEQ ID NO: 68 is an exemplary nucleic acid sequence encoding the HC6-S74Y-511-DS V$_H$ (Seq_39).
Gaagtgcggctggctgagagcggcgggggggctggtcaaacctggcggtcactgcggctgtcctgttctgcctccggctt cgattttgataacgcatggatgacatgggtgcgacagccacctggaaaggggctggagtgggtcggcagaatcactggac ctggcgaagggtggtctgtggactacgcagctccagtcgagggacgattcaccattagtagagataactacaagaataca ctgtatctggagatgaacaatctgaggactgaagacagcggcctgtatttctgcgcccgcaccgggaaatactatgattt ttggtctgggtgcccacccggagaggaatattttcaggactggggacggggcaccctggtgatcgtcagctcc SEQ ID NO: 69 is an exemplary nucleic acid sequence of the HC6-S74Y-511-S100cW-DS V$_H$ (Seq_40).
gaagtgcggctggctgagagcggcgggggggctggtcaaacctggcggtcactgcggctgtcctgttctgcctccggctt cgattttgataacgcatggatgacatgggtgcgacagccacctggaaaggggctggagtgggtcggcagaatcactggac ctggcgaagggtggtctgtggactacgcagctccagtcgagggacgattcaccattagtagagataactacaagaataca ctgtatctggagatgaacaatctgaggactgaagacagcggcctgtatttctgcgcccgcaccgggaaatactatgattt ttggtgggggtgcccacccggagaggaatattttcaggactggggacggggcaccctggtgatcgtcagctcc SEQ ID NO: 70 is an exemplary nucleic acid sequence encoding the rL3-6mut-DS V$_L$ (Seq_41).
atgggatggtcatgtatcatcctttttctagtagcaactgcaaccggttctgtgaccgcatccgaactgactcaggaccc tgccgtctctgtggcactgaagcagactgtgactattacttgccgaggcgactcactgcggtgccactacgcttcctggt atcagaagaaacccggccaggcacctgtgctgctgttctacggaaagaacaataggccatctggcatccccgaccgcttt tctggcagtgcatcagggaaccgagccagtctgaccattaccggcgcccaggctgaggacgaagccgattactattgcag ctcccgggataagagcggctccagactgagcgtgttcggaggaggaactaaactgaccgtcctc SEQ ID NO: 71 is an exemplary nucleic acid sequence encoding the rL3-6mut-Y32W V$_L$ (Seq_42).
atgggatggtcatgtatcatcctttttctagtagcaactgcaaccggttctgtgaccgcatccgaactgactcaggaccc tgccgtctctgtggcactgaagcagactgtgactattacttgccgaggcgactcactgcggagccactgggcttcctggt atcagaagaaacccggccaggcacctgtgctgctgttctacggaaagaacaataggccatctggcatccccgaccgcttt tctggcagtgcatcagggaaccgagccagtctgaccattaccggcgcccaggctgaggacgaagccgattactattgcag ctcccgggataagagcggctccagactgagcgtgttcggaggaggaactaaactgaccgtcctc SEQ ID NO: 72 is the amino acid sequence encoding rL3-6mut-Y32F V$_L$ (Seq_43).
atgggatggtcatgtatcatcctttttctagtagcaactgcaaccggttctgtgaccgcatccgaactgactcaggaccc tgccgtctctgtggcactgaagcagactgtgactattacttgccgaggcgactcactgcggagccactttgcttcctggt atcagaagaaacccggccaggcacctgtgctgctgttctacggaaagaacaataggccatctggcatccccgaccgcttt tctggcagtgcatcagggaaccgagccagtctgaccattaccggcgcccaggctgaggacgaagccgattactattgcag ctcccgggataagagcggctccagactgagcgtgttcggaggaggaactaaactgaccgtcctc SEQ ID NO: 73 is an exemplary nucleic acid sequence encoding rL3-6mut-DS-Y32W V$_L$ (Seq_58).
atgggatggtcatgtatcatcctttttctagtagcaactgcaaccggttctgtgaccgcatccgaactgactcaggaccc tgccgtctctgtggcactgaagcagactgtgactattacttgccgaggcgactcactgcggagccactgggcttcctggt atcagaagaaacccggccaggcacctgtgctgctgttctacggaaagaacaataggccatctggcatccccgaccgcttt tctggcagtgcatcagggaaccgagccagtctgaccattaccggcgcccaggctgaggacgaagccgattactattgcag ctcccgggataagagcggctccagactgagcgtgttcggaggaggaactaaactgaccgtcctc SEQ ID NO: 74 is an exemplary nucleic acid sequence encoding rL3-6mut-DS-Y32F $V_L$ (Seq_59).
Atgggatggtcatgtatcatccttttctagtagcaactgcaaccggttctgtgaccgcatccgaactgactcaggaccc tgccgtctctgtggcactgaagcagactgtgactattacttgccgaggcgactcactgcggagccactttgcttcctggt atcagaagaaacccggccaggcacctgtgctgctgttctacggaaagaacaataggccatctggcatccccgaccgcttt tctggcagtgcatcagggaaccgagccagtctgaccattaccggcgcccaggctgaggacgaagccgattactattgcag ctcccgggataagagcggctccagactgagcgtgttcggaggaggaactaaactgaccgtcctc SEQ ID NO: 75 is the amino acid sequence of the H6-511-4mut-S100cF $V_H$.
EVRLVESGGGLVKPGGSLRLSCSASGFDFDNAWMTWVRQPPGKGLEWVGRITGPGEGWSVDYAESVKGRFTISRDNTKNT

LYLEMNNVRTEDTGYYFCARTGKYYDFWFGYPPGEEYFQDWGQGTLVIVSS

SEQ ID NO: 76 is the amino acid sequence of the H6-511-4mut V5R S100cF $V_H$.
EVRLRESGGGLVKPGGSLRLSCSASGFDFDNAWMTWVRQPPGKGLEWVGRITGPGEGWSVDYAESVKGRFTISRDNTKNT

LYLEMNNVRTEDTGYYFCARTGKYYDFWFGYPPGEEYFQDWGQGTLVIVSS

SEQ ID NO: 77 is the amino acid sequence of the HCDR3 of H6-511-4mut-S100cF $V_H$ (IMGT).

SEQ ID NO: 78 is an exemplary nucleic acid sequence encoding H6-511-4mut-S100cF $V_H$ (Seq_75).
gaggttagactggtggagtcaggagggggcttgtgaagcccggtgggtctctccgcctgagctgttctgcctccggctt tgatttcgataacgcctggatgacctgggtcaggcagcctccaggtaagggactggagtgggtgggaagaatcacaggtc caggcgagggctggtccgtggactacgcggaatctgttaaagggcggtttacaatctcaagggacaataccaagaatacc ttgtatttggagatgaacaacgtgagaactgaagacaccggatattacttctgtgccagaacaggcaaatactacgactt ctggttcggctatcccctggcgaggaatatttcaagactggggtcagggaacccttgttatcgtgtcctcc SEQ ID NO: 79 is an exemplary nucleic acid sequence encoding H6-511-4mut V5R S100cF $V_H$ (Seq_76).
gaggttagactgcgggagtcaggagggggcttgtgaagcccggtgggtctctccgcctgagctgttctgcctccggctt tgatttcgataacgcctggatgacctgggtcaggcagcctccaggtaagggactggagtgggtgggaagaatcacaggtc caggcgagggctggtccgtggactacgcggaatctgttaaagggcggtttacaatctcaagggacaataccaagaatacc ttgtatttggagatgaacaacgtgagaactgaagacaccggatattacttctgtgccagaacaggcaaatactacgactt ctggttcggctatcccctggcgaggaatatttcaagactggggtcagggaacccttgttatcgtgtcctcc SEQ ID NOs: 80-81 are nucleic acid sequence of expression vectors encoding the H6-511-4mut-S100cF and H6-511-4mut V5R S100cF $V_H$ regions, respectively.

SEQ ID NO: 82 is the amino acid sequence of the H6-511-4mut-S100cF $V_H$ linked to an IgG1 constant region.
EVRLVESGGGLVKPGGSLRLSCSASGFDFDNAWMTWVRQPPGKGLEWVGRITGPGEGWSVDYAESVKGRFTISRDNTKNT LYLEMNNVRTEDTGYYFCARTGKYYDFWFGYPPGEEYFQDWGQGTLVIVSSASTKGPSVFPLAPSSKSTSGGTAALGCLV

KDYFPEPVTVSWNSGALTSGVHTTPAVLQSSGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNHYTQKSLSLSPGK

SEQ ID NO: 83 is the amino acid sequence of the H6-511-4mut-V5R S100cF $V_H$ linked to an IgG1 constant region.
EVRLRESGGGLVKPGGSLRLSCSASGFDFDNAWMTWVRQPPGKGLEWVGRITGPGEGWSVDYAESVKGRFTISRDNTKNT LYLEMNNVRTEDTGYYFCARTGKYYDFWFGYPPGEEYFQDWGQGTLVIVSSASTKGPSVFPLAPSSKSTSGGTAALGCLV

KDYFPEPVTVSWNSGALTSGVHTFPAVLQSSGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFNWYVDGVEVHNAKTKPREEQYNSTYRVVSVL

-continued

```
TVLHQDWLNGKEYKCKVSNKALPAPIEKTISKAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNHYTQKSLSLSPGK

SEQ ID NO: 84 is the amino acid sequence of the rL3-6mut V_L linked to an Ig lambda
constant region.
ASELTQDPAVSVALKQTVTITCRGDSLRSHYASWYQKKPGQAPVLLFYGKNNRPSGIPDRFSGSASGNRASLTITGAQAE

DEADYYCSSRDKSGSRLSVFGGGTKLTVLSQPKAAPSVTLFPPSSEELQANKATLVCLISDFYPGAVTVAWKADSSPVKA

GVETTTPSKQSNNKYAASSYLSLTPEQWKSHRSYSCQVTHEGSTVEKTVAPTECS
```

DETAILED DESCRIPTION

I. Summary of Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

10E8: A neutralizing antibody that specifically binds to an epitope on the MPER of gp41. The 10E8 antibody and its binding to gp41 have been previously described, see, e.g., Huang et al. *Nature*, 491: 406-412, 2012, which is incorporated by reference herein in its entirety. The amino acid sequences of the heavy and light variable regions of the 10E8 antibody are set forth as SEQ ID NOs: 1 and 2.

Administration: The introduction of a composition into a subject by a chosen route. Administration can be local or systemic. For example, if the chosen route is intravenous, the composition is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of one amino acid in peptide with a different amino acid.

Anti-retroviral agent: An agent that specifically inhibits a retrovirus from replicating or infecting cells. Non-limiting examples of antiretroviral drugs include entry inhibitors (e.g., enfuvirtide), CCR5 receptor antagonists (e.g., aplaviroc, vicriviroc, maraviroc), reverse transcriptase inhibitors (e.g., lamivudine, zidovudine, abacavir, tenofovir, emtricitabine, efavirenz), protease inhibitors (e.g., lopivar, ritonavir, raltegravir, darunavir, atazanavir), maturation inhibitors (e.g., alpha interferon, bevirimat and vivecon).

Anti-retroviral therapy (ART): A therapeutic treatment for HIV-1 infection involving administration of at least one anti-retroviral agents (e.g., one, two, three or four anti-retroviral agents) to an HIV-1 infected individual. One example of an ART regimen includes treatment with a combination of tenofovir, emtricitabine and efavirenz. In some examples, ART includes Highly Active Anti-Retroviral Therapy (HAART). One example of a HAART regimen includes treatment with a combination of tenofovir, emtricitabine and efavirenz.

Antibody: An immunoglobulin, antigen-binding fragment, or derivative thereof, that specifically binds and recognizes an analyte (antigen) such as HIV-1 gp41. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity.

Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2$^{nd}$ Ed., Springer Press, 2010).

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988; Ahmad et al., *Clin. Dev. Immunol.*, 2012, doi:10.1155/2012/980250; Marbry, *IDrugs*, 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used.

In a dsFv the $V_H$ and $V_L$ have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

An antibody may have one or more binding sites. If there is more than one binding site, the binding sites may be identical to one another or may be different. For instance, a naturally occurring immunoglobulin has two identical binding sites, a single-chain antibody or Fab fragment has one binding site, while a bispecific or bifunctional antibody has two different binding sites.

Typically, a naturally occurring immunoglobulin has heavy chains and light chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region (see, e.g., Kindt et al. Kuby Immunology, 6$^{th}$ ed., W. H. Freeman and Co., page 91 (2007).) References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab. In several embodiments, the $V_H$ and $V_L$ combine to specifically bind the antigen. In additional embodiments, only the $V_H$ is required. For example, naturally occurring camelid antibodies consisting of a heavy chain only are functional and stable in the absence of light chain (see, e.g., Hamers-Casterman et al., *Nature*, 363:446-448, 1993; Sheriff et al., *Nat. Struct. Biol.*, 3:733-736, 1996). Any of the disclosed antibodies comprises a heterologous constant region. For example the antibody comprises a constant region that is different from a native constant region, such as a constant region including one or more modifications (such as the "LS" mutations) to increase half-life.

The $V_H$ and $V_L$ contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the $V_H$ of the antibody in which it is found, whereas a $V_L$ CDR1 is the CDR1 from the $V_L$ of the antibody in which it is found. Light chain CDRs are sometimes referred to as LCDR1, LCDR2, and LCDR3. Heavy chain CDRs are sometimes referred to as HCDR1, HCDR2, and HCDR3.

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples monoclonal antibodies are isolated from a subject. Monoclonal antibodies can have conservative amino acid substitutions, which have substantially no effect on antigen binding or other immunoglobulin functions. (See, for example, Harlow & Lane, *Antibodies, A Laboratory Manual*, 2$^{nd}$ ed. Cold Spring Harbor Publications, New York (2013).) In some embodiments, any of the antibodies disclosed herein can be a monoclonal antibody.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, and are typically of different species. In some examples, a chimeric antibody includes one or more CDRs and/or framework regions from one human antibody and CDRs and/or framework regions from another human antibody.

A "fully human antibody" or "human antibody" is an antibody, which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manuel*. 1$^{st}$ Ed. New York: Cold Spring Harbor Laboratory Press, 2004. Print.; Lonberg, *Nat. Biotech.*, 23: 1117-1125, 2005; Lonenberg, *Curr. Opin. Immunol.*, 20:450-459, 2008)

Antibody or antigen binding fragment that neutralizes HIV-1: An antibody or antigen binding fragment that specifically binds to HIV-1 Env (e.g., that binds to gp41) in such a way as to inhibit a biological function associated with HIV-1 Env (such as binding to its target receptor). In several embodiments, an antibody or antigen binding fragment that neutralizes HIV-1 reduces the infectious titer of HIV-1. In some embodiments, an antibody or antigen binding fragment that specifically binds to HIV-1 Env can neutralize two or more (such as 3, 4, 5, 6, 7, 8, 9, 10, or more) strains of HIV-1.

Broadly neutralizing antibodies to HIV-1 are distinct from other antibodies to HIV-1 in that they neutralize a high percentage of the many types of HIV-1 in circulation. Thus, a HIV-1 broadly neutralizing antibody is an antibody that reduces the infectious titer of HIV-1 by binding to and inhibiting the function of related HIV-1 antigens, such as antigens that share at least 85%, 90%, 95%, 96%, 97%, 98% or 99% sequence identity with antigenic surface of the antigen. In some embodiments, broadly neutralizing antibodies to HIV-1 are distinct from other antibodies to HIV-1 in that they neutralize a high percentage (such as at least 80%, at least 85%, at least 90%, or at least 95%) of the many types of HIV-1 in circulation.

Antibody self-reactivity or autoreactivity: A property of an antibody, whereby the antibody reacts with self-epitopes, that is epitopes of proteins and/or lipids that are produced by the subject. An antibody that does not have self-reactivity does not substantially bind to epitopes or lipids present on the membrane of a cell from a subject. Methods of determining if an antibody reacts with self epitopes are known to the person of ordinary skill in the art. In one example, antibody self reactivity is evaluated using HEp-2 cell staining, a cardiolipin binding assay, or an anti-nuclear antigen (ANA) assay. The anti-ANA assay comprises an anti-ANA LUMINEX® assay or an ANA cell-staining assay, for example. In several embodiments, a disclosed antibody is not self-reactive (or autoreactive), or is minimally self-reactive. In one non-limiting example, a disclosed antibody is not substantially more self-reactive that the 10E8 antibody. For example the disclosed antibody or antigen binding fragment can have no more than 10% greater autoreactivity compared to the 10E8 antibody, for example as measured using HEp-2 cell staining, cardiolipin binding, an anti-ANA LUMINEX® assay, or an ANA cell-staining assay. In another non-limiting example, a disclosed antibody noes not have self reactivity above background levels, for example, as measured using an anti-ANA LUMINEX® assay or an ANA cell-staining assay.

Biological sample: A sample obtained from a subject. Biological samples include all clinical samples useful for detection of disease or infection (for example, HIV-1 infection) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having an HIV-1 infection.

Bispecific antibody: A recombinant molecule composed of two different antigen binding domains that consequently binds to two different antigenic epitopes. Bispecific antibodies include chemically or genetically linked molecules of two antigen-binding domains. The antigen binding domains can be linked using a linker. The antigen binding domains can be monoclonal antibodies, antigen-binding fragments (e.g., Fab, scFv), or combinations thereof. A bispecific antibody comprises one or more constant domains, but does not necessarily include a constant region.

Conditions sufficient to form an immune complex: Conditions which allow an antibody or antigen binding fragment to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane, *Antibodies, A Laboratory Manual*, 2$^{nd}$ ed. Cold Spring Harbor Publications, New York (2013), for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Conjugate: A complex of two molecules linked together, for example, linked together by a covalent bond. In one embodiment, an antibody is linked to an effector molecule; for example, an antibody that specifically binds to HIV-1 Env covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative variants: "Conservative" amino acid substitutions are those substitutions that do not substantially affect or decrease a function of a protein, such as the ability of the protein to interact with a target protein. For example, an HIV-specific antibody comprises up to 1, 2, 3, 4, 5, 6, 7, 8, 9, or up to 10 conservative substitutions compared to a reference antibody sequence and retain specific binding activity for HIV-1 antigen, and/or HIV-1 neutralization activity. The term conservative variation also includes the use of a substituted amino acid in place of an unsubstituted parent amino acid.

Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the HIV-specific antibody, such as the ability to specifically bind to gp41. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a negative control, such as sample obtained from a healthy patient not infected with HIV-1. In other embodiments, the control is a positive control, such as a tissue sample obtained from a patient diagnosed with HIV-1 infection. In still other embodiments, the control is a historical control or standard reference value or range of values (such as a previously tested control sample, such as a group of HIV-1 patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Degenerate variant: In the context of the present disclosure, a "degenerate variant" refers to a polynucleotide encoding a protein (for example, an antibody that specifically binds gp41 or variable region thereof) that includes a sequence that is degenerate as a result of the genetic code. There are twenty natural amino acids, most of which are specified by more than one codon. Therefore, all degenerate nucleotide sequences are included as long as the amino acid sequence of the antibody that binds gp41 encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radio labeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}$S or $^{131}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013).

Detecting: To identify the existence, presence, or fact of something. General methods of detecting are known to the skilled artisan and may be supplemented with the protocols and reagents disclosed herein. For example, included herein are methods of detecting a cell that expresses gp41 in a subject.

Effector molecule: A molecule intended to have or produce a desired effect; for example, a desired effect on a cell to which the effector molecule is targeted. Effector molecules comprises, for example, polypeptides and small molecules. In one non-limiting example, the effector molecule is a toxin. The skilled artisan will understand that some effector molecules may have or produce more than one desired effect.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope on gp41.

Expression: Transcription or translation of a nucleic acid sequence. For example, an encoding nucleic acid sequence (such as a gene) can be expressed when its DNA is transcribed into an RNA or RNA fragment, which in some examples is processed to become mRNA. An encoding nucleic acid sequence (such as a gene) may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. Regulation of expression comprises controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked Expression control sequences are operatively linked to a nucleic acid sequence when the expression control sequences control and regulate the transcription and, as appropriate, translation of the nucleic acid sequence. Thus expression control sequences comprises appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences comprises a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Fc region: The polypeptide including the constant region of an antibody excluding the first constant immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not include the tailpiece, and may or may not be bound by the J chain. For IgG, the Fc region includes immunoglobulin domains Cγ2 and Cγ3 and the lower part of the hinge between Cγ1 and Cγ2. Although the boundaries of the Fc region may vary, the human IgG heavy chain Fc region is usually defined to include residues C226 or P230 to its carboxyl-terminus, wherein the numbering is according to the EU index as in Kabat. For IgA, the Fc region includes immunoglobulin domains Cα2 and Cα3 and the lower part of the hinge between Cα1 and Cα2. Any of the disclosed antibodies comprises a heterologous Fc region or heterologous constant domain. For example the antibody comprises a Fc region or constant domain that is different from a native Fc region or constant domain, such as a Fc region or constant domain including one or more modifications (such as the "LS" mutations) to increase half-life.

HIV-1 Envelope protein (Env): The HIV-1 envelope protein is initially synthesized as a precursor protein of 845-870 amino acids in size, designated gp160. Individual gp160 polypeptides form a homotrimer and undergo glycosylation within the Golgi apparatus as well as processing to remove the signal peptide, and cleavage by a cellular protease between approximately positions 511/512 to generate separate gp120 and gp41 polypeptide chains, which remain associated as gp120/gp41 protomers within the homotrimer. The ectodomain (that is, the extracellular portion) of the HIV-1 Env trimer undergoes several structural rearrangements from a prefusion mature (cleaved) closed conformation that evades antibody recognition, through intermediate conformations that bind to receptors CD4 and co-receptor (either CCR5 or CXCR4), to a postfusion conformation.

The numbering used in the disclosed HIV-1 Env proteins and fragments thereof is relative to the HXB2 numbering scheme as set forth in *Numbering Positions in HIV Relative to HXB2CG* Bette Korber et al., Human Retroviruses and AIDS 1998: A Compilation and Analysis of Nucleic Acid and Amino Acid Sequences. Korber et al., Eds. Theoretical Biology and Biophysics Group, Los Alamos National Laboratory, Los Alamos, N. Mex., which is incorporated by reference herein in its entirety.

HIV-1 gp120: A polypeptide that is part of the HIV-1 Env protein. Mature gp120 includes approximately HIV-1 Env residues 31-511, contains most of the external, surface-exposed, domains of the HIV-1 Env trimer, and it is gp120 which binds both to cellular CD4 receptors and to cellular chemokine receptors (such as CCR5). A mature gp120 polypeptide is a heavily N-glycosylated extracellular polypeptide that interacts with the gp41 ectodomain to form an HIV-1 Env protomer that trimerizes to form the HIV-1 Env trimer.

HIV-1 gp41: A polypeptide that is part of the HIV-1 Env protein. Mature gp41 includes approximately HIV-1 Env residues 512-860, and includes cytosolic-, transmembrane-, and ecto-domains. The gp41 ectodomain (including approximately HIV-1 Env residues 512-644) can interact with gp120 to form an HIV-1 Env protomer that trimerizes to form the HIV-1 Env trimer.

Gp41 includes the membrane-proximal external region (MPER), which is immediately N-terminal of the transmembrane region of gp41. The MPER is highly hydrophobic (50% of residues are hydrophobic) and is highly conserved across many HIV-1 clades (Zwick, M. B., et al., *J Virol*, 75 (22): p. 10892-905, 2001). The MPER of HIV-1 gp41 includes the target epitope of the 10E8 monoclonal antibody.

Human Immunodeficiency Virus type 1 (HIV-1): A retrovirus that causes immunosuppression in humans (HIV-1 disease), and leads to a disease complex known as the acquired immunodeficiency syndrome (AIDS). "HIV-1 disease" refers to a well-recognized constellation of signs and symptoms (including the development of opportunistic infections) in persons who are infected by an HIV-1 virus, as determined by antibody or western blot studies. Laboratory findings associated with this disease include a progressive decline in T cells. Related viruses that are used as animal models include simian immunodeficiency virus (SIV) and feline immunodeficiency virus (FIV). Treatment of HIV-1 with HAART has been effective in reducing the viral burden and ameliorating the effects of HIV-1 infection in infected individuals.

HXB2 numbering system: A reference numbering system for HIV-1 protein and nucleic acid sequences, using HIV-1 HXB2 strain sequences as a reference for all other HIV-1 strain sequences. The person of ordinary skill in the art is familiar with the HXB2 numbering system, and this system is set forth in "Numbering Positions in HIV Relative to HXB2CG," Bette Korber et al., Human Retroviruses and AIDS 1998: A Compilation and Analysis of Nucleic Acid and Amino Acid Sequences. Korber B, Kuiken C L, Foley B, Hahn B, McCutchan F, Mellors J W, and Sodroski J, Eds. Theoretical Biology and Biophysics Group, Los Alamos National Laboratory, Los Alamos, N. Mex., which is incorporated by reference herein in its entirety. HXB2 is also known as: HXBc2, for HXB clone 2; HXB2R, in the Los Alamos HIV database, with the R for revised, as it was slightly revised relative to the original HXB2 sequence; and HXB2CG in GENBANK™, for HXB2 complete genome. The numbering used in gp120 and gp41 polypeptides disclosed herein is relative to the HXB2 numbering scheme. For reference, the amino acid sequence of HIV-1 Env of HXB2 is set forth below:

MRVKEKYQHLWRWGWRWGTMLLGMLMICSATEKLWVTVYYGVPVWKEATT

TLFCASDAKAYDTEVHNVWATHACVPTDPNPQEVVLVNVTENFNMWKNDM

VEQMHEDIISLWDQSLKPCVKLTPLCVSLKCTDLKNDTNTNSSSGRMIME

KGEIKNCSFNISTSIRGKVQKEYAFFYKLDIIPIDNDTTSYKLTSCNTSV

ITQACPKVSFEPIPIHYCAPAGFAILKCNNKTFNGTGPCTNVSTVQCTHG

IRPVVSTQLLLNGSLAEEEVVIRSVNFTDNAKTIIVQLNTSVEINCTRPN

-continued

NNTRKRIRIQRGPGRAFVTIGKIGNMRQAHCNISRAKWNNTLKQIASKLR

EQFGNNKTIIFKQSSGGDPEIVTHSFNCGGEFFYCNSTQLFNSTWFNSTW

STEGSNNTEGSDTITLPCRIKQIINMWQKVGKAMYAPPISGQIRCSSNIT

GLLLTRDGGNSNNESEIFRPGGGDMRDNWRSELYKYKVVKIEPLGVAPTK

AKRRVVQREKRAVGIGALFLGFLGAAGSTMGAASMTLTVQARQLLSGIVQ

QQNNLLRAIEAQQHLLQLTVWGIKQLQARILAVERYLKDQQLLGIWGCSG

KLICTTAVPWNASWSNKSLEQIWNHTTWMEWDREINNYTSLIHSLIEESQ

NQQEKNEQELLELDKWASLWNWFNITNWLWYIKLFIMIVGGLVGLRIVFA

VLSIVNRVRQGYSPLSFQTHLPTPRGPDRPEGIEEEGGERDRDRSIRLVN

GSLALIWDDLRSLCLFSYHRLRDLLLIVTRIVELLGRRGWEALKYWWNLL

QYWSQELKNSAVSLLNATAIAVAEGTDRVIEVVQGACRAIRHIPRRIRQG

LERILL (SEQ ID NO: 26; GENBANK ® Accession No.

K03455, incorporated by reference herein as present in the database on May 4, 2015).

IgA: A polypeptide belonging to the class of antibodies that are substantially encoded by a recognized immunoglobulin alpha gene. In humans, this class or isotype comprises $IgA_1$ and $IgA_2$. IgA antibodies can exist as monomers, polymers (referred to as pIgA) of predominantly dimeric form, and secretory IgA. The constant chain of wild-type IgA contains an 18-amino-acid extension at its C-terminus called the tail piece (tp). Polymeric IgA is secreted by plasma cells with a 15-kDa peptide called the J chain linking two monomers of IgA through the conserved cysteine residue in the tail piece.

IgG: A polypeptide belonging to the class or isotype of antibodies that are substantially encoded by a recognized immunoglobulin gamma gene. In humans, this class comprises $IgG_1$, $IgG_2$, $IgG_3$, and $IgG_4$. In mice, this class comprises $IgG_1$, $IgG_{2a}$, $IgG_{2b}$, $IgG_3$.

Immune complex: The binding of antibody or antigen binding fragment (such as a scFv) to a soluble antigen forms an immune complex. The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. A isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Linker: A bi-functional molecule that can be used to link two molecules into one contiguous molecule, for example, to link an effector molecule to an antibody. In some embodiments, the provided conjugates include a linker between the effector molecule or detectable marker and an antibody. In some cases, a linker is a peptide within an antigen binding fragment (such as an Fv fragment) which serves to indirectly bond the $V_H$ and $V_L$. Non-limiting examples of peptide linkers include a $(G_4S)_1$ linker, a $(G_4S)_2$ linker, or a $(G_4S)_3$ linker.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Science*, 22th ed., Pharmaceutical Press, London, UK (2012), describes compositions and formulations suitable for pharmaceutical delivery of the disclosed agents.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers comprises, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, added preservatives (such as on-natural preservatives), and pH buffering agents and the like, for example sodium acetate or sorbitan monolaurate. In particular examples, the pharmaceutically acceptable carrier is sterile and suitable for parenteral administration to a subject for example, by injection. In some embodiments, the active agent and pharmaceutically acceptable carrier are provided in a unit dosage form such as a pill or in a selected quantity in a vial. Unit dosage forms comprises one dosage or multiple dosages (for example, in a vial from which metered dosages of the agents can selectively be dispensed).

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced. A polypeptide has an amino terminal (N-terminal) end and a carboxy-terminal end. In some embodiments, the polypeptide is a disclosed antibody or a fragment thereof.

Polypeptide modifications: polypeptides can be modified by a variety of chemical techniques to produce derivatives having essentially the same activity and conformation as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

Specifically bind: When referring to an antibody or antigen binding fragment, refers to a binding reaction which determines the presence of a target protein, peptide, or polysaccharide in the presence of a heterogeneous population of proteins and other biologics. Thus, under designated conditions, an antibody binds preferentially to a particular target protein, peptide or polysaccharide (such as an antigen present on the surface of a pathogen, for example HIV-1 Env) and does not bind in a significant amount to other proteins or polysaccharides present in the sample or subject. Specific binding can be determined by methods known in the art. With reference to an antibody-antigen complex, specific binding of the antigen and antibody has a $K_D$ of less than about $10^{-7}$ Molar, such as less than about $10^{-8}$ Molar, $10^{-9}$, or even less than about $10^{-10}$ Molar.

$K_D$ refers to the dissociation constant for a given interaction, such as a polypeptide ligand interaction or an antibody antigen interaction. For example, for the bimolecular interaction of an antibody or antigen binding fragment and an antigen it is the concentration of the individual components of the bimolecular interaction divided by the concentration of the complex.

The antibodies disclosed herein specifically bind to a defined target (or multiple targets, in the case of a bispecific antibody). Thus, an antibody that specifically binds to an epitope on gp41 is an antibody that binds substantially to gp41, including cells or tissue expressing gp41, substrate to which the gp41 is attached, or gp41 in a biological specimen. It is, of course, recognized that a certain degree of non-specific interaction may occur between an antibody or conjugate including an antibody (such as an antibody that specifically binds gp41 or conjugate including such antibody) and a non-target (such as a cell that does not express gp41). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, $2^{nd}$ ed., Cold Spring Harbor Publications, New York (2013), for a description of immunoassay formats and conditions that can be used to determine specific immunoreactivity.

Subject: Living multi-cellular vertebrate organisms, a category that includes human and non-human mammals. In an example, a subject is a human. In a particular example, the subject is a newborn infant. In an additional example, a subject is selected that is in need of inhibiting of an HIV-1 infection. For example, the subject is either uninfected and at risk of HIV-1 infection or is infected in need of treatment.

Therapeutically effective amount: The amount of agent, such as a disclosed gp41 specific antibody or antigen binding fragment that is sufficient to prevent, treat (including prophylaxis), reduce and/or ameliorate the symptoms and/or underlying causes of a disorder or disease, for example to prevent, inhibit, and/or treat HIV-1 infection. In some embodiments, a therapeutically effective amount is sufficient to reduce or eliminate a symptom of a disease, such as AIDS. For instance, this can be the amount necessary to inhibit or prevent HIV-1 replication or to measurably alter outward symptoms of the HIV-1 infection. In general, this amount will be sufficient to measurably inhibit HIV-1 replication or infectivity. Ideally, a therapeutically effective amount provides a therapeutic effect without causing a substantial cytotoxic effect in the subject.

In some embodiments, administration of a therapeutically effective amount of a disclosed antibody or antigen binding fragment that binds to gp41 can reduce or inhibit an HIV-1 infection (for example, as measured by infection of cells, or by number or percentage of subjects infected by HIV-1, or by an increase in the survival time of infected subjects) by a desired amount, for example by at least 10%, at least 20%, at least 50%, at least 60%, at least 70%, at least 80%, at least 90%, at least 95%, at least 98%, or even at least 100% (elimination or prevention of detectable HIV-1 infection), as compared to a suitable control.

Several preparations disclosed herein are administered in therapeutically effective amounts. A therapeutically effective amount of an antibody or antigen binding fragment that specifically binds gp41 that is administered to a subject will vary depending upon a number of factors associated with that subject, for example the overall health and/or weight of the subject. A therapeutically effective amount can be determined by varying the dosage and measuring the resulting therapeutic response, such as, for example, a reduction in viral titer. Therapeutically effective amounts also can be determined through various in vitro, in vivo or in situ immunoassays.

A therapeutically effective amount encompasses a fractional dose that contributes in combination with previous or subsequent administrations to attaining a therapeutic response. For example, a therapeutically effective amount of an agent can be administered in a single dose, or in several doses, for example daily, during a course of treatment lasting several days or weeks. However, the therapeutically effective amount can depend on the subject being treated, the severity and type of the condition being treated, and the manner of administration. A unit dosage form of the agent can be packaged in a therapeutic amount, or in multiples of the therapeutic amount, for example, in a vial (e.g., with a pierceable lid) or syringe having sterile components.

Transformed: A transformed cell is a cell into which a nucleic acid molecule has been introduced by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Treating or preventing a disease: Preventing a disease refers to inhibiting the full development of a disease or condition, for example, in a subject who is at risk of or has an HIV-1 infection. Treating a disease refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease for the purpose of reducing the risk of developing pathology.

The term "prevents" does not necessarily mean that an agent completely eliminates the disease or condition, so long as at least one characteristic of the disease or condition is eliminated. Thus, an antibody that inhibits or prevents an infection, can, but does not necessarily completely, eliminate such an infection, so long as the infection is measurably diminished, for example, by at least about 50%, such as by at least about 70%, or about 80%, or even by about 90% the infection in the absence of the agent, or in comparison to a reference agent.

Vector: A vector comprises nucleic acid sequences (for example, mRNA or DNA) that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. In some embodiments, a viral vector is provided that comprises one or more nucleic acid molecules encoding a disclosed antibody or antigen binding fragment that specifically binds to HIV-1 gp41 and neutralizes HIV-1. In some embodiments, the viral vector can be an adeno-associated virus (AAV) vector. A replication deficient viral vector is a vector that requires complementation of one or more regions of the viral genome required for replication due to a deficiency in at least one replication-essential gene function. For example, such that the viral vector does not replicate in typical host cells, especially those in a human patient that could be infected by the viral vector in the course of a therapeutic method.

VRC01-class antibody, heavy chain, or light chain: A class of antibodies that bind to the CD4 binding site on gp120 and can neutralize HIV-1 infection, as well as heavy and light chains thereof. The prototypical member of the VRC01-class of antibodies—VRC01—can neutralize over 90% of circulating HIV-1 isolates with an average 50% inhibitory concentration ($IC_{50}$) of ~0.3 µg/ml. Despite overall sequence differences between VRC01-class antibodies, antibody-gp120 co-crystal structures revealed VRC01-class recognition of gp120 to be consistent across the class. Indeed, three-dimensional structure analysis of HIV-1 gp120 from different HIV-1 clades in complexes with different VRC01-class antibodies from multiple donors show that the VRC01-class antibodies share striking similarity in physical structure, and revealed several antibody features that contribute to gp120 binding and HIV-1 neutralization. The substantial structural and ontogenetic characterization of VRC01-class of antibodies allows recognition of the members of this class by interrogation of antibody sequence.

For example, the $V_H$ of a VRC01-class antibody has a VH1-2 germline origin, wherein the VRC01-class $V_H$ encoding sequence is from 20-35% (such as 25-30%) divergent from the corresponding germline gene sequence. The VRC01-class $V_H$ includes a tryptophan residue at kabat position 50 ($V_H$ $Trp_{50}$), an asparagine residue at kabat position 58 ($V_H$ $Asn_{58}$), and an arginine residue at kabat position 71 ($V_H$ $Arg_{71}$). These residues form specific interactions with amino acids on gp120 that contribute to the VRC01-class specificity and neutralization properties. When a VRC01-class antibody is bound to gp120, $V_H$ $Trp_{50}$ forms a hydrogen bond with gp120 $Asn_{280}$, $V_H$ $Asp_{58}$ forms hydrogen bonds with gp120 $Arg_{456}$ and $Gly_{458}$, $V_H$ $Arg_{71}$ forms salt bridges with gp120 $Asp_{368}$, and $V_H$ Trp100B forms a hydrogen bond with gp120 $Asn_{279}$.

Further, the $V_L$ of a VRC01-class antibody has an IGKV1-33, IGKV3-11, IGKV3-15, IGKV3-20, or IGLV2-14 germline origin, wherein the VRC01-class $V_L$ encoding sequence is from 15-35% (such as 25-30%) divergent from the corresponding germline gene sequence. The VRC01-class $V_L$ includes either a LCDR1 (kabat positioning) with a 2-6 amino acid deletion, or a LCDR1 with glycine residues at kabat positions 28 and 30. The deletion or the presence of the glycine residues provides flexibility that allows the LCDR1 to avoid structural clash with the D loop of gp120 when the antibody is bound to the CD4 binding site. Further, the VRC01-class $V_L$ includes an LCDR3 that is five amino acids in length (according to kabat positioning) and includes a hydrophobic residue (such as leucine or tyrosine) at kabat position 91, deletion of kabat positions 92-95, and a glutamate or glutamine residue at kabat position 96. The hydrophobic residue at position 91 packs against the backbone of gp120 Loop D, and the glutamate or glutamine residue at kabat position 96 interacts with a conserved electropositive region on the base of the gp120 V5 domain.

Non-limiting examples of antibodies that fall within the VRC01-class include the VRC01, VRC03, VRC07, VRC07-523, VRC13, 3BCN117, 12A12, 12A21, VRC-PG04, NIH45-46, VRC23, VRC-CH30, VRC-CH31, and VRC-PG20 antibodies. Description, characterization, and productions of these antibodies, as well as the VRC01-class of antibodies is available and familiar to the person of ordinary skill in the art (see, e.g., Diskin et al., *Science,* 334(6060): 1289-93, 2011; Kwong and Mascola, *Immunity,* 37, 412-425, 2012; Li et al., *J. Virol.,* 85, 8954-8967, 2011; Rudicell et al., *J. Virol.,* 88, 12669-12682, 2012; Scheid et al., *Science,* 333(6049):1633-1637, 2011; West et al., *PNAS,* 109:E2083-2090, 2012; Wu et al., *Science,* 329(5993):856-861, 2010; Wu et al., *Science,* 333(6049):1593-1602, 2011; Zhou et al., *Immunity,* 39:245-258, 2013; Georgiev et al., *Science,* 340:751-756, 2013; Zhu et al., *PNAS,* 110, E4088-E4097, 2013; and WIPO Pub. Nos. WO 2012/158948, WO2011038290, WO2012154312, WO2013142324 and WO2013016468, each of which is incorporated by reference herein in its entirety).

The VRC01, VRC07, VRC07-523 (VRC07H-G54H heavy and VRC01L-E1I2del-V3S light), and VRC07-544 (VRC07H-I37V/G54H/T93A heavy and VRC01-EIdel-V3S light) antibodies are described in U.S. Pat. No. 8,337,036 and 2014/0322163 and Rudicell et al., *J. Virol.,* 88:12669-12682, 2014, each of which is incorporated by reference in its entirety. The $V_H$ and $V_L$ sequences of these antibodies are provided below:

VRC01 $V_H$ (SEQ ID NO: 27)

QVQLVQSGGQMKKPGESMRISCRASGYEFIDCTLNWIRLAPGKRPEWMGW

LKPRGGAVNYARPLQGRVTMTRDVYSDTAFLELRSLTVDDTAVYFCTRGK

NCDYNWDFEHWGRGTPVIVSS

VRC01 $V_L$ (SEQ ID NO: 28)

EIVLTQSPGTLSLSPGETAIISCRTSQYGSLAWYQQRPGQAPRLVIYSGS

TRAAGIPDRFSGSRWGPDYNLTISNLESGDFGVYYCQQYEFFGQGTKVQV

DIK

VRC07 $V_H$ (SEQ ID NO: 29)

QVRLSQSGGQMKKPGDSMRISCRASGYEFINCPINWIRLAPGKRPEWMGW

MKPRGGAVSYARQLQGRVTMTRDMYSETAFLELRSLTSDDTAVYFCTRGK

YCTARDYYNWDFEHWGQGTPVTVSS

VRC07 $V_L$ (SEQ ID NO: 28)

EIVLTQSPGTLSLSPGETAIISCRTSQYGSLAWYQQRPGQAPRLVIYSGS

TRAAGIPDRFSGSRWGPDYNLTISNLESGDFGVYYCQQYEFFGQGTKVQV

DIK

-continued

VRC07-523 V<sub>H</sub>
(SEQ ID NO: 30)
QVRLSQSGGQMKKPGDSMRISCRASGYEFINCPINWIRLAPGKRPEWMGW

MKPRHGAVSYARQLQGRVTMTRDMYSETAFLELRSLTSDDTAVYFCTRGK

YCTARDYYNWDFEHWGQGTPVTVSS

VRC07-523 V<sub>L</sub>
(SEQ ID NO: 31)
SLTQSPGTLSLSPGETAIISCRTSQYGSLAWYQQRPGQAPRLVIYSGSTR

AAGIPDRFSGSRWGPDYNLTISNLESGDFGVYYCQQYEFFGQGTKVQVDI

K

VRC07-544 V<sub>H</sub>
(SEQ ID NO: 32)
QVRLSQSGGQMKKPGDSMRISCRASGYEFINCPINWVRLAPGKRPEWMGW

MKPRHGAVSYARQLQGRVTMTRDMYSETAFLELRSLTSDDTAVYFCARGK

YCTARDYYNWDFEHWGQGTPVTVSS

VRC07-544 V<sub>L</sub>
(SEQ ID NO: 33)
SLTQSPGTLSLSPGETAIISCRTSQYGSLAWYQQRPGQAPRLVIYSGSTR

AAGIPDRFSGSRWGPDYNLTISNLESGDFGVYYCQQYEFFGQGTKVQVDI

K

II. Description of Several Embodiments

Isolated monoclonal antibodies and antigen binding fragments that specifically bind an epitope on gp41 are provided. The antibodies and antigen binding fragments can be fully human. In several embodiments, the antibodies and antigen binding fragments can be used to neutralize HIV-1 infection. Also disclosed herein are compositions including the antibodies and antigen binding fragments and a pharmaceutically acceptable carrier. Nucleic acids encoding the antibodies or antigen binding fragments, expression vectors (such as adeno-associated virus (AAV) viral vectors) including these nucleic acids are also provided.

The antibodies, antigen binding fragments, nucleic acid molecules, expression vectors, and compositions can be used for research, diagnostic and therapeutic purposes. For example, the monoclonal antibodies and antigen binding fragments can be used to diagnose or treat a subject with an HIV-1 infection, or can be administered prophylactically to prevent HIV-1 infection in a subject. In some embodiments, the antibodies can be used to determine HIV-1 titer in a subject.

A. Neutralizing Monoclonal Antibodies and Antigen Binding Fragments

The parent 10E8 antibody neutralizes 98% of a panel of 200 HIV-1 pseudotyped viruses with an $IC_{50}$ of less than 50 µg/ml (see Example 1). However, as disclosed in Example 1, the solubility of the 10E8 antibody may not be optimal for commercial production purposes. Earlier attempts at modifying the 10E8 antibody successfully improved the solubility and potency of the antibody, but caused an increase in auto-reactivity. In some embodiments, disclosed herein are modified 10E8 antibodies and antigen binding fragments having the CDRs of the 10E8 antibody and framework region amino acid substitutions compared to the parent 10E8 antibody sequence that impart an improved combination of neutralization, solubility, and auto-reactivity properties relative to 10E8. In additional embodiments, the modified 10E8 antibodies include amino acid substitutions in the CDRs that impart an improved combination of neutralization, solubility, and auto-reactivity properties relative to 10E8.

The discussion of monoclonal antibodies below refers to monoclonal antibodies that include a $V_H$ and a $V_L$ including CDRs with reference to the IMGT numbering scheme (unless the context indicates otherwise). The person of ordinary skill in the art will understand that various CDR numbering schemes (such as the Kabat, Chothia or IMGT numbering schemes) can be used to determine CDR positions. The amino acid sequence and the CDR positions of the heavy and light chains of the 10E8 antibody, and several variants thereof, according to the IMGT numbering scheme are shown in Table 1.

TABLE 1

IMGT CDR sequences of 10E8 and 10E8 variants.

10E8 $V_H$

| $V_H$ | SEQ ID NO: 1 positions (linear) | CDR protein sequence | HCDR SEQ ID NO |
|---|---|---|---|
| HCDR1 | 26-33 | GEDFDNAW | 7 |
| HCDR2 | 51-60 | ITGPGEGWSV | 8 |
| HCDR3 | 99-120 | ARTGKYYDFWSGYPPGEEYFQD | 9 |

10E8 $V_L$

| $V_L$ | SEQ ID NO: 2 positions (linear) | A.A. Sequence | LCDR SEQ ID NO |
|---|---|---|---|
| LCDR1 | 26-31 | SLRSHY | 10 |
| LCDR2 | 49-51 | GKN | 11 |
| LCDR3 | 88-99 | SSRDKSGSRLSV | 12 |

TABLE 1-continued

IMGT CDR sequences of 10E8 and 10E8 variants.

10E8v4 S100cW or 10E8v5 S100cW $V_H$

| $V_H$ | SEQ ID NO: 35 (v4) or SEQ ID NO: 38 (v5) positions (linear) | CDR protein sequence | HCDR SEQ ID NO |
|---|---|---|---|
| HCDR1 | 26-33 | GEDFDNAW | 7 |
| HCDR2 | 51-60 | ITGPGEGWSV | 8 |
| HCDR3 | 99-120 | ARTGKYYDFWWGYPPGEEYFQD | 52 |

10E8v4 DS or 10E8v5 DS $V_H$

| $V_H$ | SEQ ID NO: 36 (v4) or SEQ ID NO: 39 (v5) positions (linear) | CDR protein sequence | HCDR SEQ ID NO |
|---|---|---|---|
| HCDR1 | 26-33 | GEDFDNAW | 7 |
| HCDR2 | 51-60 | ITGPGEGWSV | 8 |
| HCDR3 | 99-120 | ARTGKYYDFWSGCPPGEEYFQD | 53 |

10E8v4 S100cW-DS or 10E8v5 S100cW-DS $V_H$

| $V_H$ | SEQ ID NO: 37 (v4) or SEQ ID NO: 40 (v5) positions (linear) | CDR protein sequence | HCDR SEQ ID NO |
|---|---|---|---|
| HCDR1 | 26-33 | GEDFDNAW | 7 |
| HCDR2 | 51-60 | ITGPGEGWSV | 8 |
| HCDR3 | 99-120 | ARTGKYYDFWWGCPPGEEYFQD | 54 |

10E8v4 DS or 10E8v5 DS $V_L$

| $V_L$ | SEQ ID NO: 41 positions (linear) | A.A. Sequence | LCDR SEQ ID NO |
|---|---|---|---|
| LCDR1 | 26-31 | SLRCHY | 55 |
| LCDR2 | 49-51 | GKN | 11 |
| LCDR3 | 88-99 | SSRDKSGSRLSV | 12 |

10E8v4 Y32W or 10E8v5 Y32W $V_L$

| $V_L$ | SEQ ID NO: 42 positions (linear) | A.A. Sequence | LCDR SEQ ID NO |
|---|---|---|---|
| LCDR1 | 26-31 | SLRSHW | 56 |
| LCDR2 | 49-51 | GKN | 11 |
| LCDR3 | 88-99 | SSRDKSGSRLSV | 12 |

10E8v4 Y32F or 10E8v5 Y32F $V_L$

| $V_L$ | SEQ ID NO: 43 positions (linear) | A.A. Sequence | LCDR SEQ ID NO |
|---|---|---|---|
| LCDR1 | 26-31 | SLRSHF | 57 |
| LCDR2 | 49-51 | GKN | 11 |
| LCDR3 | 88-99 | SSRDKSGSRLSV | 12 |

TABLE 1-continued

IMGT CDR sequences of 10E8 and 10E8 variants.

10E8v4 DS Y32W or 10E8v5 DS Y32W V_L

| V_L | SEQ ID NO: 58 positions (linear) | A.A. Sequence | LCDR SEQ ID NO |
|---|---|---|---|
| LCDR1 | 26-31 | SLRCHW | 85 |
| LCDR2 | 49-51 | GKN | 11 |
| LCDR3 | 88-99 | SSRDKSGSRLSV | 12 |

10E8v4 DS Y32F or 10E8v5 DS Y32F V_L

| V_L | SEQ ID NO: 59 positions (linear) | A.A. Sequence | LCDR SEQ ID NO |
|---|---|---|---|
| LCDR1 | 26-31 | SLRCHF | 86 |
| LCDR2 | 49-51 | GKN | 11 |
| LCDR3 | 88-99 | SSRDKSGSRLSV | 12 |

10E8 Variant 4
H6-511-4mut V_H (SEQ ID NO: 5) + rL3-6mut V_L (SEQ ID NO: 6)

| V_H | SEQ ID NO: 5 positions | CDR protein sequence | HCDR SEQ ID NO |
|---|---|---|---|
| HCDR1 | 26-33 | GEDFDNAW | 7 |
| HCDR2 | 51-60 | ITGPGEGWSV | 8 |
| HCDR3 | 99-120 | ARTGKYYDFWSGYPPGEEYFQD | 9 |

| V_L | SEQ ID NO: 2 positions (linear) | A.A. Sequence | LCDR SEQ ID NO |
|---|---|---|---|
| LCDR1 | 26-31 | SLRSHY | 10 |
| LCDR2 | 49-51 | GKN | 11 |
| LCDR3 | 88-99 | SSRDKSGSRLSV | 12 |

10E8 Variant 4-S100cF
H6-511-4mut-S100cF V_H (SEQ ID NO: 75) + rL3-6mut V_L (SEQ ID NO: 6)

| V_H | SEQ ID NO: 75 positions | CDR protein sequence | HCDR SEQ ID NO |
|---|---|---|---|
| HCDR1 | 26-33 | GEDFDNAW | 7 |
| HCDR2 | 51-60 | ITGPGEGWSV | 8 |
| HCDR3 | 99-120 | ARTGKYYDFWEGYPPGEEYFQD | 77 |

| V_L | SEQ ID NO: 6 positions | A.A. Sequence | LCDR SEQ ID NO |
|---|---|---|---|
| LCDR1 | 26-31 | SLRSHY | 10 |
| LCDR2 | 49-51 | GKN | 11 |
| LCDR3 | 88-99 | SSRDKSGSRLSV | 12 |

10E8 Variant 4-V5R, S100cF
H6-511-4mut V_H (SEQ ID NO: 76) + rL3-6mut V_L (SEQ ID NO: 6)

| V_H | SEQ ID NO: 76 positions | CDR protein sequence | HCDR SEQ ID NO |
|---|---|---|---|
| HCDR1 | 26-33 | GEDFDNAW | 7 |
| HCDR2 | 51-60 | ITGPGEGWSV | 8 |
| HCDR3 | 99-120 | ARTGKYYDFWEGYPPGEEYFQD | 77 |

TABLE 1-continued

IMGT CDR sequences of 10E8 and 10E8 variants.

| $V_L$ | SEQ ID NO: 6 positions | A.A. Sequence | LCDR SEQ ID NO |
|---|---|---|---|
| LCDR1 | 26-31 | SLRSHY | 10 |
| LCDR2 | 49-51 | GKN | 11 |
| LCDR3 | 88-99 | SSRDKSGSRLSV | 12 |

10E8 Variant 1 (10E8v1)

As disclosed in the examples, the "10E8 variant 1," which includes the HC6-S74Y-511 $V_H$ (SEQ ID NO: 3) and rL3 $V_L$ (SEQ ID NO: 4), specifically binds gp41 and has an unexpectedly superior combination of HIV-1 neutralization breadth and potency, solubility, and auto-reactivity. The HC6-S74Y-511 $V_H$ includes the 10E8 heavy chain CDRs, as well as Q3R, V5A, L72D, S74Y, I75K, F77T, M84T, and T110I framework amino acid substitutions compared to the 10E8 $V_H$ (SEQ ID NO: 1). The rL3 $V_L$ includes the 10E8 light chain CDRs, as well as E7D, I45V, V58I, S76T, D83E, and E85D framework amino acid substitutions compared to the 10E8 $V_L$ (SEQ ID NO: 2).

Accordingly, in some embodiments, a disclosed antibody or antigen binding fragment comprises a $V_H$ including the 10E8 $V_H$ CDRs (such as SEQ ID NOs: 7, 8, and 9) and can further include arginine, alanine, aspartate, tyrosine, lysine, threonine, threonine, and isoleucine residues at kabat positions 3, 5, 72, 74, 75, 77, 84, and 110, respectively, and a $V_L$ including the 10E8 $V_L$ CDRs (such as SEQ ID NOs: 10, 11, 12) and aspartate, valine, isoleucine, threonine, glutamate, and aspartate residues at kabat positions 7, 45, 58, 76, 83, and 85, respectively.

In additional embodiments, the antibody or antigen binding fragment comprises a $V_H$ including the 10E8 $V_H$ CDRs (such as SEQ ID NOs: 7, 8, and 9), arginine, alanine, aspartate, tyrosine, lysine, threonine, threonine, and isoleucine residues at kabat positions 3, 5, 72, 74, 75, 77, 84, and 110, respectively, and an amino acid sequence at least 80% (such as at least 90%, or at least 95%) identical to SEQ ID NO: 3 (HC6-S S74Y-511), and a $V_L$ including the 10E8 $V_L$ CDRs (such as SEQ ID NOs: 10, 11, and 12), and aspartate, valine, isoleucine, threonine, glutamate, and aspartate residues at kabat positions 7, 45, 58, 76, 83, and 85, respectively, and an amino acid sequence at least 80% (such as at least 90%, or at least 95%) identical to SEQ ID NO: 4 (rL3).

In more embodiments, the antibody or antigen binding fragment comprises a $V_H$ including the amino acid sequence set forth as SEQ ID NO: 3 (HC6-S74Y-511), and a $V_L$ including the amino acid sequence set forth as SEQ ID NO: 4 (rL3).

10E8 Variant 3 (10E8v3)

As disclosed in the examples, the "10E8 variant 3," which includes the H6-511-4mut $V_H$ (SEQ ID NO: 5) and rL3 $V_L$ (SEQ ID NO: 4), specifically binds gp41 and has an unexpectedly superior combination of HIV-1 neutralization breadth and potency, solubility, and auto-reactivity. The H6-511-4mut $V_H$ includes the 10E8 heavy chain CDRs, as well as Q3R, A61E, P62S, E64K, L72D, S74T, I75K, F77T, L82cV, M84T, S87T, L89Y, R105Q, T110I framework amino acid substitutions compared to the 10E8 $V_H$ (SEQ ID NO: 1). The rL3 $V_L$ is described above.

Accordingly, in some embodiments, a disclosed antibody or antigen binding fragment comprises a $V_H$ including the 10E8 $V_H$ CDRs (such as SEQ ID NOs: 7, 8, and 9) and arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively, and a $V_L$ including the 10E8 $V_L$ CDRs (such as SEQ ID NOs: 10, 11, 12) and aspartate, valine, isoleucine, threonine, glutamate, and aspartate residues at kabat positions 7, 45, 58, 76, 83, and 85, respectively.

In additional embodiments, the antibody or antigen binding fragment comprises a $V_H$ including the 10E8 $V_H$ CDRs (such as SEQ ID NOs: 7, 8, and 9) and arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively, and an amino acid sequence at least 80% (such as at least 90%, or at least 95%) identical to SEQ ID NO: 5 (H6-511-4mut), and a $V_L$ including the 10E8 $V_L$ CDRs (such as SEQ ID NOs: 10, 11, and 12), and aspartate, valine, isoleucine, threonine, glutamate, and aspartate residues at kabat positions 7, 45, 58, 76, 83, and 85, respectively, and an amino acid sequence at least 80% (such as at least 90%, or at least 95%) identical to SEQ ID NO: 4 (rL3).

In more embodiments, the antibody or antigen binding fragment comprises a $V_H$ including the amino acid sequence set forth as SEQ ID NO: 5 (H6-511-4mut), and a $V_L$ including the amino acid sequence set forth as SEQ ID NO: 4 (rL3).

10E8 Variant 4 (10E8v4)

As disclosed in the examples, the "10E8 variant 4," which includes the H6-511-4mut $V_H$ (SEQ ID NO: 5) and rL3-6mut $V_L$ (SEQ ID NO: 6), specifically binds gp41 and has an unexpectedly superior combination of HIV-1 neutralization breadth and potency, solubility, and auto-reactivity. The H6-511-4mut $V_H$ is described above. The rL3-6mut $V_L$ includes the 10E8 light chain CDRs, as well as S1A, Y2S, E7D, T8P, G9A, G16K, R17Q, I45V, V58I, S76T, D83E, E85D framework amino acid substitutions compared to the 10E8 $V_L$ (SEQ ID NO: 2).

Accordingly, in some embodiments, a disclosed antibody or antigen binding fragment comprises a $V_H$ including the 10E8 $V_H$ CDRs (such as SEQ ID NOs: 7, 8, and 9) and arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively, and a $V_L$ including the 10E8 $V_L$ CDRs (such as SEQ ID NOs: 10, 11, 12) and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively In additional embodiments, the antibody or antigen binding fragment comprises a $V_H$ including the 10E8 $V_H$ CDRs (such as SEQ ID NOs: 7, 8, and 9) and arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively, and an amino acid sequence at least 80% (such as at least 90%, or at least 95%) identical to SEQ ID NO: 5 (H6-511-4mut), and a $V_L$ including the 10E8 $V_L$ CDRs (such as SEQ ID NOs: 10, 11, and 12), alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, and an amino acid sequence at least 80% (such as at least 90%, or at least 95%) identical to SEQ ID NO: 6 (rL3-6mut).

In more embodiments, the antibody or antigen binding fragment comprises a $V_H$ including the amino acid sequence set forth as SEQ ID NO: 5 (H6-511-4mut), and a $V_L$ including the amino acid sequence set forth as SEQ ID NO: 6 (rL3-6mut).

10E8 Variant 5 (10E8v5)

As disclosed in the examples, the "10E8 variant 5," which includes the HC6-S74Y-511 $V_H$ (SEQ ID NO: 3) and rL3-6mut $V_L$ (SEQ ID NO: 6), specifically binds gp41 and has an unexpectedly superior combination of HIV-1 neutralization breadth and potency, solubility, and auto-reactivity. The HC6-S74Y-511 $V_H$ and rL3-6mut $V_L$ are described above.

Accordingly, in some embodiments, a disclosed antibody or antigen binding fragment comprises a $V_H$ including the 10E8 $V_H$ CDRs (such as SEQ ID NOs: 7, 8, and 9) and can further include arginine, alanine, aspartate, tyrosine, lysine, threonine, threonine, and isoleucine residues at kabat positions 3, 5, 72, 74, 75, 77, 84, and 110, respectively, and a $V_L$ including the 10E8 $V_L$ CDRs (such as SEQ ID NOs: 10, 11, 12) and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively In additional embodiments, the antibody or antigen binding fragment comprises a $V_H$ including the 10E8 $V_H$ CDRs (such as SEQ ID NOs: 7, 8, and 9), arginine, alanine, aspartate, tyrosine, lysine, threonine, threonine, and isoleucine residues at kabat positions 3, 5, 72, 74, 75, 77, 84, and 110, respectively, and an amino acid sequence at least 80% (such as at least 90%, or at least 95%) identical to SEQ ID NO: 3 (HC6-S74Y-511), and a $V_L$ including the 10E8 $V_L$ CDRs (such as SEQ ID NOs: 10, 11, and 12), alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, and an amino acid sequence at least 80% (such as at least 90%, or at least 95%) identical to SEQ ID NO: 6 (rL3-6mut).

In more embodiments, the antibody or antigen binding fragment comprises a $V_H$ including the amino acid sequence set forth as SEQ ID NO: 3 (HC6-S74Y-511), and a $V_L$ including the amino acid sequence set forth as SEQ ID NO: 6 (rL3-6mut).

S100cW, S100cF, and V5R

As disclosed in the examples, incorporation of a hydrophobic amino acid substitution at VH kabat position S100c (such as a S100cW or S100cF substitution) into certain 10E8 antibodies (such as the 10E8 variant 4 antibody) produces an antibody that specifically binds gp41 and has an unexpectedly superior combination of HIV-1 neutralization breadth and potency, solubility, and auto-reactivity. Accordingly, in some embodiments, any of the antibodies described herein (such as 10E8, or 10E8 variants including variant 1, 3, 4, or 5) can further include a S100cW substitution. In some embodiments, any of the antibodies described herein (such as 10E8, or 10E8 variants including variant 1, 3, 4, or 5) can further include a S100cF substitution.

10E8 Variant 4 S100cF (10E8v4 S100cF)

In some embodiments, the antibody or antigen binding fragment comprises the $V_H$ and $V_L$ of the 10E8v4 antibody (VH: H6-511-4mut, SEQ ID NO: 5; VL: rL3-6mut, SEQ ID NO: 6) with a S100cF substitution in the $V_H$. Antibodies including such a $V_H$ and $V_L$ are denoted as "10E8v4 S100cF," and corresponding $V_H$ and $V_L$ amino acid sequences are provided herein as SEQ ID NOs: 75 and 6 respectively. The 10E8v4 S100cF antibody specifically binds gp41 and neutralizes HIV-1, and also has an unexpectedly superior combination of HIV-1 neutralization breadth and potency, solubility, and auto-reactivity.

In some embodiments, the antibody or antigen binding fragment comprises a $V_H$ including the 10E8 $V_H$ CDRs with S100cF substitution (such as SEQ ID NOs: 7, 8, and 77) a $V_L$ including the 10E8 $V_L$ CDRs (such as SEQ ID NOs: 10, 11, 12), wherein the antibody specifically binds to gp41 and neutralizes HIV-1.

In some embodiments, the antibody or antigen binding fragment comprises a $V_H$ including the 10E8 $V_H$ CDRs with S100cF substitution (such as SEQ ID NOs: 7, 8, and 77) and arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively, and a $V_L$ including the 10E8 $V_L$ CDRs (such as SEQ ID NOs: 10, 11, 12) and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, wherein the monoclonal antibody specifically binds to gp41 and neutralizes HIV-1.

In additional embodiments, the antibody or antigen binding fragment comprises a $V_H$ including the 10E8 $V_H$ CDRs with S100cF substitution (such as SEQ ID NOs: 7, 8, and 77), arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively, and an amino acid sequence at least 80% (such as at least 90%, or at least 95%) identical to SEQ ID NO: 75 (H6-511-4mut-S100cF), and a $V_L$ including the 10E8 $V_L$ CDRs (such as SEQ ID NOs: 10, 11, and 12), alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, and an amino acid sequence at least 80% (such as at least 90%, or at least 95%) identical to SEQ ID NO: 6 (rL3-6mut), wherein the monoclonal antibody specifically binds to gp41 and neutralizes HIV-1.

In more embodiments, the antibody or antigen binding fragment comprises a $V_H$ including the amino acid sequence set forth as SEQ ID NO: 75 (H6-511-4mut-S100cW), and a $V_L$ including the amino acid sequence set forth as SEQ ID NO: 6 (rL3-6mut).

10E8 Variant 4 V5R S100cF (10E8v4 V5R S100cF)

In some embodiments, the antibody or antigen binding fragment comprises the $V_H$ and $V_L$ of the 10E8v4 antibody (VH: H6-511-4mut, SEQ ID NO: 5; VL: rL3-6mut, SEQ ID NO: 6) with V5R and S100cF substitutions in the $V_H$. Antibodies including such a $V_H$ and $V_L$ are denoted as "10E8v4 V5R S100cF," and corresponding $V_H$ and $V_L$ amino acid sequences are provided herein as SEQ ID NOs:

76 and 6 respectively. The 10E8v4 V5R S100cF antibody specifically binds gp41 and neutralizes HIV-1, and also has an unexpectedly superior combination of HIV-1 neutralization breadth and potency, solubility, and auto-reactivity.

In some embodiments, the antibody or antigen binding fragment comprises a $V_H$ including the 10E8 $V_H$ CDRs with S100cF substitution (such as SEQ ID NOs: 7, 8, and 77) and arginine, arginine glutamate, serine, lysine, aspartate, threonine, lysine, threonine, valine, threonine, threonine, tyrosine, glutamine, and isoleucine residues at kabat positions 3, 5, 61, 62, 64, 72, 74, 75, 77, 82C, 84, 87, 89, 105, and 110, respectively, and a $V_L$ including the 10E8 $V_L$ CDRs (such as SEQ ID NOs: 10, 11, 12) and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, wherein the monoclonal antibody specifically binds to gp41 and neutralizes HIV-1.

In additional embodiments, the antibody or antigen binding fragment comprises a $V_H$ including the 10E8 $V_H$ CDRs with S100cF substitution (such as SEQ ID NOs: 7, 8, and 77), arginine, arginine, glutamate, serine, lysine, aspartate, threonine, lysine, threonine, valine, threonine, threonine, tyrosine, glutamine, and isoleucine residues at kabat positions 3, 5, 61, 62, 64, 72, 74, 75, 77, 82C, 84, 87, 89, 105, and 110, respectively, and an amino acid sequence at least 80% (such as at least 90%, or at least 95%) identical to SEQ ID NO: 76 (H6-511-4mut-V5R S100cF), and a $V_L$ including the 10E8 $V_L$ CDRs (such as SEQ ID NOs: 10, 11, and 12), alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, and an amino acid sequence at least 80% (such as at least 90%, or at least 95%) identical to SEQ ID NO: 6 (rL3-6mut), wherein the monoclonal antibody specifically binds to gp41 and neutralizes HIV-1.

In more embodiments, the antibody or antigen binding fragment comprises a $V_H$ including the amino acid sequence set forth as SEQ ID NO: 76 (H6-511-4mut-V5R S100cW), and a $V_L$ including the amino acid sequence set forth as SEQ ID NO: 6 (rL3-6mut).

Additional Modification of 10E8 Variant 4 V5R S100cF

In some embodiments, the antibody or antigen binding fragment comprises the $V_H$ and $V_L$ of the 10E8v4 V5R S100cF antibody further comprising one or more amino acid substitutions that improve the HIV-1 neutralization breadth and potency, solubility, and/or auto-reactivity of the modified antibody compared to 10E8v4 V5R S100cF. The modified 10E8v4 V5R S100cF antibodies specifically bind gp41 and neutralize HIV-1, and also have an unexpectedly superior combination of HIV-1 neutralization breadth and potency, solubility, and auto-reactivity.

In some embodiments, the antibody or antigen binding fragment comprises a $V_H$ including the amino acid sequence set forth as SEQ ID NO: 76 (H6-511-4mut-V5R S100cW) that further comprises one of a E1R, E1W, G15R, S25W, D28W, D30W, D30R, N31W, N31R, P52bR, D72R, or E81R substitution (kabat numbering) relative to SEQ ID NO: 76, and a $V_L$ including the amino acid sequence set forth as SEQ ID NO: 6 (rL3-6mut), wherein the antibody specifically binds to gp41 and neutralizes HIV-1.

In some embodiments, the antibody or antigen binding fragment comprises a $V_H$ including the amino acid sequence set forth as SEQ ID NO: 76 (H6-511-4mut-V5R S100cW), and a $V_L$ including the amino acid sequence set forth as SEQ ID NO: 6 (rL3-6mut) that further comprises one of a D7W, A14R, Q17R, T18R, T20R, D26R, K51R, N53R, S65R, G68R, G77R, or G100R substitution (kabat numbering) relative to SEQ ID NO: 6, wherein the antibody specifically binds to gp41 and neutralizes HIV-1. In a preferred embodiment, the antibody or antigen binding fragment comprises a $V_H$ including the amino acid sequence set forth as SEQ ID NO: 76 (H6-511-4mut-V5R S100cW), and a $V_L$ including the amino acid sequence set forth as SEQ ID NO: 6 (rL3-6mut) that further comprises a G68R substitution (kabat numbering) relative to SEQ ID NO: 6, wherein the antibody specifically binds to gp41 and neutralizes HIV-1.

In some embodiments, the antibody or antigen binding fragment comprises a $V_H$ comprising the amino acid sequence set forth as SEQ ID NO: 76 (H6-511-4mut-V5R S100cW), and a $V_L$ comprising the amino acid sequence set forth as SEQ ID NO: 6 (rL3-6mut), wherein the $V_H$ and $V_L$ further comprise one of the following pairs of substitution relative to SEQ ID NOs: 76 and 6, respectively: E1R and D7W; E1R and D26R; E1R and G68R; D28W and D7W; D28W and D26R; D28W and G68R; D28W and Q17R; D28W and T18R; D28W and T20R; D28W and K51R; D28W and G77R; P52bR and D7W; P52bR and D26R; P52bR and G68R; P52bR and Q17R; P52bR and T18R; P52bR and T20R; P52bR and K51R; P52bR and G77R; D72R and D7W; D72R and D26R; or D72R and G68R; and wherein the antibody specifically binds to gp41 and neutralizes HIV-1.

In some embodiments, the antibody or antigen binding fragment comprises a $V_H$ comprising the amino acid sequence set forth as SEQ ID NO: 76 (H6-511-4mut-V5R S100cW), and a $V_L$ comprising the amino acid sequence set forth as SEQ ID NO: 6 (rL3-6mut), wherein the $V_H$ further comprises D72R, E1R D28W, and P52bR substitutions and wherein the antibody specifically binds to gp41 and neutralizes HIV-1. In some embodiments, the antibody or antigen binding fragment comprises a $V_H$ comprising the amino acid sequence set forth as SEQ ID NO: 76 (H6-511-4mut-V5R S100cW), and a $V_L$ comprising the amino acid sequence set forth as SEQ ID NO: 6 (rL3-6mut), wherein the $V_L$ further comprises D7W, D26R, and G68R substitutions and wherein the antibody specifically binds to gp41 and neutralizes HIV-1. In some embodiments, the antibody or antigen binding fragment comprises a $V_H$ comprising the amino acid sequence set forth as SEQ ID NO: 76 (H6-511-4mut-V5R S100cW), and a $V_L$ comprising the amino acid sequence set forth as SEQ ID NO: 6 (rL3-6mut), wherein the $V_H$ further comprises D72R, E1R D28W, and P52bR substitutions, and the $V_L$ further comprises D7W, D26R, and G68R substitutions, and wherein the antibody specifically binds to gp41 and neutralizes HIV-1.

In some embodiments, the antibody or antigen binding fragment comprises a $V_H$ comprising the amino acid sequence set forth as SEQ ID NO: 76 (H6-511-4mut-V5R S100cW), and a $V_L$ comprising the amino acid sequence set forth as SEQ ID NO: 6 (rL3-6mut), wherein the $V_H$ and/or $V_L$ further comprise the amino acid substitutions of any one of the combinations of substitutions listed in Table 10 and wherein the antibody specifically binds to gp41 and neutralizes HIV-1. In some embodiments, the antibody or antigen binding fragment comprises a $V_H$ comprising the amino acid sequence set forth as SEQ ID NO: 76 (H6-511-4mut-V5R S100cW), and a $V_L$ comprising the amino acid sequence set forth as SEQ ID NO: 6 (rL3-6mut), wherein the $V_H$ and/or $V_L$ further comprise the amino acid substitutions of listed in Table 10 for any one of the 10E8-1053, 10E8-1054, 10E8-1055, 10E8-1056, 10E8-1057, 10E8-1058, 10E8-1059, 10E8-1060, 10E8-1061, 10E8-1062, 10E8-1063, 10E8-1064, 10E8-1065, 10E8-1066, 10E8-1067, 10E8-1068, 10E8-1069, 10E8-1070, 10E8-1071, 10E8-1072, 10E8-1073, 10E8-1074, 10E8-1075, 10E8-1076, 10E8-1077, 10E8-1078, 10E8-1079, 10E8-1080, 10E8-1081, 10E8-1082, 10E8-1083, 10E8-1084, 10E8-1085, 10E8-1086, 10E8-1087, 10E8-1088, 10E8-1089, 10E8-1090, 10E8-1091, 10E8-1092, 10E8-1093, 10E8-1094, or 10E8-1095 antibodies, and wherein the antibody specifically binds to gp41 and neutralizes HIV-1.

In some embodiments, the antibody or antigen binding fragment comprises a $V_H$ comprising the amino acid sequence set forth as SEQ ID NO: 76 (H6-511-4mut-V5R S100cW), and a $V_L$ comprising the amino acid sequence set forth as SEQ ID NO: 6 (rL3-6mut) (corresponding to the 10E8-1073 antibody listed in Table 10), wherein the $V_H$ further comprises a D28Y substitution and wherein the antibody specifically binds to gp41 and neutralizes HIV-1. In some embodiments, the antibody or antigen binding fragment comprises a $V_H$ comprising the amino acid sequence set forth as SEQ ID NO: 76 (H6-511-4mut-V5R S100cW), and a $V_L$ comprising the amino acid sequence set forth as SEQ ID NO: 6 (rL3-6mut), wherein the $V_H$ further comprises a P52bR substitution, and the $V_L$ further comprises D7W and G68R substitutions (corresponding to the 10E8-1081 antibody listed in Table 10), and wherein the antibody specifically binds to gp41 and neutralizes HIV-1.

10E8 Variant 4 S100cW

In some embodiments, a disclosed antibody or antigen binding fragment comprises a $V_H$ including the 10E8 $V_H$ CDRs with S100cW substitution (such as SEQ ID NOs: 7, 8, and 52) and arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively, and a $V_L$ including the 10E8 $V_L$ CDRs (such as SEQ ID NOs: 10, 11, 12) and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively In additional embodiments, the antibody or antigen binding fragment comprises a $V_H$ including the 10E8 $V_H$ CDRs with S100cW substitution (such as SEQ ID NOs: 7, 8, and 52), arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively, and an amino acid sequence at least 80% (such as at least 90%, or at least 95%) identical to SEQ ID NO: 35 (H6-511-4mut-S100cW), and a $V_L$ including the 10E8 $V_L$ CDRs (such as SEQ ID NOs: 10, 11, and 12), alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, and an amino acid sequence at least 80% (such as at least 90%, or at least 95%) identical to SEQ ID NO: 6 (rL3-6mut).

In more embodiments, the antibody or antigen binding fragment comprises a $V_H$ including the amino acid sequence set forth as SEQ ID NO: 35 (H6-511-4mut-S100cW), and a $V_L$ including the amino acid sequence set forth as SEQ ID NO: 6 (rL3-6mut).

10E8 Variant 5 S100cW

In some embodiments, a disclosed antibody or antigen binding fragment comprises a $V_H$ including the 10E8 $V_H$ CDRs with S100cW substitution (such as SEQ ID NOs: 7, 8, and 52) and can further include arginine, alanine, aspartate, tyrosine, lysine, threonine, threonine, and isoleucine residues at kabat positions 3, 5, 72, 74, 75, 77, 84, and 110, respectively, and a $V_L$ including the 10E8 $V_L$ CDRs (such as SEQ ID NOs: 10, 11, 12) and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively In additional embodiments, the antibody or antigen binding fragment comprises a $V_H$ including the 10E8 $V_H$ CDRs with S100cW substitution (such as SEQ ID NOs: 7, 8, and 52), arginine, alanine, aspartate, tyrosine, lysine, threonine, threonine, and isoleucine residues at kabat positions 3, 5, 72, 74, 75, 77, 84, and 110, respectively, and an amino acid sequence at least 80% (such as at least 90%, or at least 95%) identical to SEQ ID NO: 38 (HC6-S74Y-511-S100cW), and a $V_L$ including the 10E8 $V_L$ CDRs (such as SEQ ID NOs: 10, 11, and 12), alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, and an amino acid sequence at least 80% (such as at least 90%, or at least 95%) identical to SEQ ID NO: 6 (rL3-6mut).

In more embodiments, the antibody or antigen binding fragment comprises a $V_H$ including the amino acid sequence set forth as SEQ ID NO: 38 (HC6-S74Y-511-S100cW), and a $V_L$ including the amino acid sequence set forth as SEQ ID NO: 6 (rL3-6mut).

DS

As disclosed in the examples, incorporation of the "DS" modification, a non-native disulfide bond between the LCDR1 kabat position 30 and the HCDR3 kabat position 100e, into certain 10E8 antibodies (such as the 10E8 variant 4 antibody) produces an antibody that specifically binds gp41 and has an unexpectedly superior combination of HIV-1 neutralization breadth and potency, solubility, and auto-reactivity. Accordingly, any of the antibodies described herein (such as 10E8, or 10E8 variants including variant 1, 3, 4, or 5) can further include a DS substitution.

10E8 Variant 4 DS

In some embodiments, a disclosed antibody or antigen binding fragment comprises a $V_H$ including the 10E8 $V_H$ CDRs with DS substitution (such as SEQ ID NOs: 7, 8, and 53) and arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively, and a $V_L$ including the 10E8 $V_L$ CDRs with DS substitution (such as SEQ ID NOs: 55, 11, 12) and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively In additional embodiments, the antibody or antigen binding fragment comprises a $V_H$ including the 10E8 $V_H$ CDRs with DS substitution (such as SEQ ID NOs: 7, 8, and 53), arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively, and an amino acid sequence at least 80% (such as at least 90%, or at least 95%) identical to SEQ ID NO: 36 (H6-511-4mut-DS), and a $V_L$ including the 10E8 $V_L$ CDRs with DS substitution (such as SEQ ID NOs: 55, 11, and 12), alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, and an amino acid sequence at least 80% (such as at least 90%, or at least 95%) identical to SEQ ID NO: 41 (rL3-6mut-DS).

In more embodiments, the antibody or antigen binding fragment comprises a $V_H$ including the amino acid sequence set forth as SEQ ID NO: 36 (H6-511-4mut-DS), and a $V_L$ including the amino acid sequence set forth as SEQ ID NO: 41 (rL3-6mut-DS).

10E8 Variant 5 DS

In some embodiments, a disclosed antibody or antigen binding fragment comprises a $V_H$ including the 10E8 $V_H$ CDRs with DS substitution (such as SEQ ID NOs: 7, 8, and 53) and can further include arginine, alanine, aspartate, tyrosine, lysine, threonine, threonine, and isoleucine residues at kabat positions 3, 5, 72, 74, 75, 77, 84, and 110, respectively, and a $V_L$ including the 10E8 $V_L$ CDRs with DS substitution (such as SEQ ID NOs: 55, 11, 12) and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively In additional embodiments, the antibody or antigen binding fragment comprises a $V_H$ including the 10E8 $V_H$ CDRs with DS substitution (such as SEQ ID NOs: 7, 8, and 53), arginine, alanine, aspartate, tyrosine, lysine, threonine, threonine, and isoleucine residues at kabat positions 3, 5, 72, 74, 75, 77, 84, and 110, respectively, and an amino acid sequence at least 80% (such as at least 90%, or at least 95%) identical to SEQ ID NO: 39 (HC6-S74Y-511-DS), and a $V_L$ including the 10E8 $V_L$ CDRs with DS substitution (such as SEQ ID NOs: 55, 11, and 12), alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, and an amino acid sequence at least 80% (such as at least 90%, or at least 95%) identical to SEQ ID NO: 41 (rL3-6mut-DS).

In more embodiments, the antibody or antigen binding fragment comprises a $V_H$ including the amino acid sequence set forth as SEQ ID NO: 39 (HC6-S74Y-511-DS), and a $V_L$ including the amino acid sequence set forth as SEQ ID NO: 41 (rL3-6mut-DS).

S100cW-DS

As disclosed in the examples, incorporation the S100cW and DS modifications, a non-native disulfide bond between the LCDR1 kabat position 30 and the HCDR3 kabat position 100e, and a S100cW substitution, into certain 10E8 antibodies (such as the 10E8 variant 4 antibody) produces an antibody that specifically binds gp41 and has an unexpectedly superior combination of HIV-1 neutralization breadth and potency, solubility, and auto-reactivity. Accordingly, any of the antibodies described herein (such as 10E8, or 10E8 variants including variant 1, 3, 4, or 5) can further include S100cW and DS substitutions.

10E8 Variant 4 S100cW-DS

In some embodiments, a disclosed antibody or antigen binding fragment comprises a $V_H$ including the 10E8 $V_H$ CDRs with s100cW and DS substitutions (such as SEQ ID NOs: 7, 8, and 54) and arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively, and a $V_L$ including the 10E8 $V_L$ CDRs with DS substitution (such as SEQ ID NOs: 55, 11, 12) and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively In additional embodiments, the antibody or antigen binding fragment comprises a $V_H$ including the 10E8 $V_H$ CDRs with S-100cW and DS substitutions (such as SEQ ID NOs: 7, 8, and 54), arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively, and an amino acid sequence at least 80% (such as at least 90%, or at least 95%) identical to SEQ ID NO: 37 (H6-511-4mut-S100cW-DS), and a $V_L$ including the 10E8 $V_L$ CDRs with DS substitution (such as SEQ ID NOs: 55, 11, and 12), alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, and an amino acid sequence at least 80% (such as at least 90%, or at least 95%) identical to SEQ ID NO: 41 (rL3-6mut-DS).

In more embodiments, the antibody or antigen binding fragment comprises a $V_H$ including the amino acid sequence set forth as SEQ ID NO: 37 (H6-511-4mut-S100cW-DS), and a $V_L$ including the amino acid sequence set forth as SEQ ID NO: 41 (rL3-6mut-DS).

10E8 Variant 5 S100cW-DS

In some embodiments, a disclosed antibody or antigen binding fragment comprises a $V_H$ including the 10E8 $V_H$ CDRs with S100cW and DS substitutions (such as SEQ ID NOs: 7, 8, and 54) and can further include arginine, alanine, aspartate, tyrosine, lysine, threonine, threonine, and isoleucine residues at kabat positions 3, 5, 72, 74, 75, 77, 84, and 110, respectively, and a $V_L$ including the 10E8 $V_L$ CDRs with DS substitution (such as SEQ ID NOs: 55, 11, 12) and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively In additional embodiments, the antibody or antigen binding fragment comprises a $V_H$ including the 10E8 $V_H$ CDRs with S100cW and DS substitutions (such as SEQ ID NOs: 7, 8, and 54), arginine, alanine, aspartate, tyrosine, lysine, threonine, threonine, and isoleucine residues at kabat positions 3, 5, 72, 74, 75, 77, 84, and 110, respectively, and an amino acid sequence at least 80% (such as at least 90%, or at least 95%) identical to SEQ ID NO: 40 (HC6-S74Y-511-S100cW-DS), and a $V_L$ including the 10E8 $V_L$ CDRs with DS substitution (such as SEQ ID NOs: 55, 11, and 12), alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, and an amino acid sequence at least 80% (such as at least 90%, or at least 95%) identical to SEQ ID NO: 41 (rL3-6mut-DS).

In more embodiments, the antibody or antigen binding fragment comprises a $V_H$ including the amino acid sequence set forth as SEQ ID NO: 40 (HC6-S74Y-511-S100cW-DS), and a $V_L$ including the amino acid sequence set forth as SEQ ID NO: 41 (rL3-6mut-DS).

Substitution at $V_L$ Kabat Position 32

As disclosed in the examples, incorporation of an amino acid substitution at kabat position 32 of the $V_L$ of certain 10E8 antibodies (such as the 10E8 variant 4 antibody) produces an antibody that specifically binds gp41 and has an unexpectedly superior combination of HIV-1 neutralization breadth and potency, solubility, and auto-reactivity. Accordingly, any of the antibodies described herein (such as 10E8, or 10E8 variants including variants 1, 3, 4, or 5; or 10E8 or 10E8 variants including variants 1, 3, 4, or 5 with a S100cW substitution; or 10E8 or 10E8 variants including variants 1, 3, 4, or 5 with a DS substitution; or 10E8 or 10E8 variants including variants 1, 3, 4, or 5 with S100cW-DS substitutions) can further include an amino acid substitution at kabat position 32 of the $V_L$. In some embodiments, the substation can be a Y32F substitution. In additional embodiments, the substitution can be a Y32W substitution.

In some embodiments, the $V_L$ of any of the 10E8 variants disclosed in the "10E8 variant 4" section above can further include an amino acid substitution (such as a Y32F or Y32W substitution) at kabat position 32. In some embodiments, the $V_L$ of any of the 10E8 variants disclosed in the "10E8 variant 5" section above can further include an amino acid substitution (such as a Y32F or Y32W substitution) at kabat position 32. In some embodiments, the $V_L$ of any of the 10E8 variants disclosed in the "S100cW and S100cF" section above can further include an amino acid substitution (such as a Y32F or Y32W substitution) at kabat position 32. In some embodiments, the $V_L$ of any of the 10E8 variants disclosed in the "DS" section above can further include an amino acid substitution (such as a Y32F or Y32W substitution) at kabat position 32. In some embodiments, the $V_L$ of any of the 10E8 variants disclosed in the "S100cW-DS" section above can further include an amino acid substitution (such as a Y32F or Y32W substitution) at kabat position 32.

In some embodiments, the antibody or antigen binding fragment includes a $V_H$ and a $V_L$ including SEQ ID NO: 3 (HC6-S74Y-511) and SEQ ID NO: 42 (rL3-6mut-Y32W), respectively. In some embodiments, an antibody or antigen binding fragment is provided that includes a $V_H$ and a $V_L$ including SEQ ID NO: 3 (HC6-S74Y-511) and SEQ ID NO: 43 (rL3-6mut-Y32F), respectively.

In some embodiments, the antibody or antigen binding fragment includes a $V_H$ and a $V_L$ including SEQ ID NO: 5 (H6-511-4mut) and SEQ ID NO: 42 (rL3-6mut-Y32W), respectively. In some embodiments, an antibody or antigen binding fragment is provided that includes a $V_H$ and a $V_L$ including SEQ ID NO: 5 (H6-511-4mut) and SEQ ID NO: 43 (rL3-6mut-Y32F), respectively.

In some embodiments, the antibody or antigen binding fragment includes a $V_H$ and a $V_L$ including SEQ ID NO: 35 (H6-511-4mut-S100cW) and SEQ ID NO: 42 (rL3-6mut-Y32W), respectively. In some embodiments, an antibody or antigen binding fragment is provided that includes a $V_H$ and a $V_L$ including SEQ ID NO: 35 (H6-511-4mut-S100cW) and SEQ ID NO: 43 (rL3-6mut-Y32F), respectively.

In some embodiments, the antibody or antigen binding fragment includes a $V_H$ and a $V_L$ including SEQ ID NO: 38 (HC6-S74Y-511-S100cW) and SEQ ID NO: 42 (rL3-6mut-Y32W), respectively. In some embodiments, an antibody or antigen binding fragment is provided that includes a $V_H$ and a $V_L$ including SEQ ID NO: 38 (HC6-S74Y-511-S100cW) and SEQ ID NO: 43 (rL3-6mut-Y32F), respectively.

In some embodiments, the antibody or antigen binding fragment includes a $V_H$ and a $V_L$ including SEQ ID NO: 36 (H6-511-4mut-DS) and SEQ ID NO: 58 (rL3-6mut-DS-Y32W), respectively. In some embodiments, an antibody or antigen binding fragment is provided that includes a $V_H$ and a $V_L$ including SEQ ID NO: 36 (H6-511-4mut-DS) and SEQ ID NO: 59 (rL3-6mut-DS-Y32F), respectively.

In some embodiments, the antibody or antigen binding fragment includes a $V_H$ and a $V_L$ including SEQ ID NO: 39 (HC6-S74Y-511-DS) and SEQ ID NO: 58 (rL3-6mut-DS-Y32W), respectively. In some embodiments, an antibody or antigen binding fragment is provided that includes a $V_H$ and a $V_L$ including SEQ ID NO: 39 (HC6-S74Y-511-DS) and SEQ ID NO: 59 (rL3-6mut-DS-Y32F), respectively.

In some embodiments, the antibody or antigen binding fragment includes a $V_H$ and a $V_L$ including SEQ ID NO: 37 (H6-511-4mut-S100cW-DS) and SEQ ID NO: 58 (rL3-6mut-DS-Y32W), respectively. In some embodiments, an antibody or antigen binding fragment is provided that includes a $V_H$ and a $V_L$ including SEQ ID NO: 37 (H6-511-4mut-S100cW-DS) and SEQ ID NO: 59 (rL3-6mut-DS-Y32F), respectively.

In some embodiments, the antibody or antigen binding fragment includes a VH and a VL including SEQ ID NO: 40 (HC6-S74Y-511-S100cW-DS) and SEQ ID NO: 58 (rL3-6mut-DS-Y32W), respectively. In some embodiments, an antibody or antigen binding fragment is provided that includes a VH and a VL including SEQ ID NO: 40 (HC6-S74Y-511-S100cW-DS) and SEQ ID NO: 59 (rL3-6mut-DS-Y32F), respectively.

Individual Heavy and Light Chain Variable Regions

Any of the following heavy chain variable regions can be "mixed and matched" with any of the 10E8 light chain (or variant thereof) variable regions disclosed herein to generate an antibody that specifically binds to gp41 and neutralizes HIV-1. Further, any of the following light chain variable regions can be "mixed and matched" with any of the 10E8 heavy chain (or variant thereof) variable regions disclosed herein to generate an antibody that specifically binds to gp41 and neutralizes HIV-1.

HC6-S74Y-511 $V_H$

In some embodiments, the antibody or antigen binding fragment comprises a $V_H$ including the 10E8 $V_H$ CDRs (such as SEQ ID NOs: 7, 8, and 9) and arginine, alanine, aspartate, tyrosine, lysine, threonine, threonine, and isoleucine residues at kabat positions 3, 5, 72, 74, 75, 77, 84, and 110, respectively. In additional embodiments, the antibody or antigen binding fragment comprises a $V_H$ including the 10E8 $V_H$ CDRs (such as SEQ ID NOs: 7, 8, and 9), and arginine, alanine, aspartate, tyrosine, lysine, threonine, threonine, and isoleucine residues at kabat positions 3, 5, 72, 74, 75, 77, 84, and 110, respectively, and an amino acid sequence at least 80% (such as at least 90%, or at least 95%) identical to SEQ ID NO: 3 (HC6-S74Y-511). In more embodiments, the antibody or antigen binding fragment comprises a $V_H$ including the amino acid sequence set forth as SEQ ID NO: 3 (HC6-S74Y-511).

H6-511-4mut $V_H$

In some embodiments, the antibody or antigen binding fragment comprises a $V_H$ including the 10E8 $V_H$ CDRs (such as SEQ ID NOs: 7, 8, and 9) and arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively. In additional embodiments, the antibody or antigen binding fragment comprises a $V_H$ including the 10E8 $V_H$ CDRs (such as SEQ ID NOs: 7, 8, and 9), and arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively, and an amino acid sequence at least 80% (such as at least 90%, or at least 95%) identical to SEQ ID NO: 5 (H6-511-4mut). In more embodiments, the antibody or antigen binding fragment comprises a $V_H$ including the amino acid sequence set forth as SEQ ID NO: 5 (H6-511-4mut).

HC6-S74Y-511-S100cW $V_H$

In some embodiments, the antibody or antigen binding fragment comprises a $V_H$ including the 10E8 $V_H$ CDRs with S100cW substitution (such as SEQ ID NOs: 7, 8, and 62)

and arginine, alanine, aspartate, tyrosine, lysine, threonine, threonine, and isoleucine residues at kabat positions 3, 5, 72, 74, 75, 77, 84, and 110, respectively. In additional embodiments, the antibody or antigen binding fragment comprises a $V_H$ including the 10E8 $V_H$ CDRs with S100cW substitution (such as SEQ ID NOs: 7, 8, and 62), and arginine, alanine, aspartate, tyrosine, lysine, threonine, threonine, and isoleucine residues at kabat positions 3, 5, 72, 74, 75, 77, 84, and 110, respectively, and an amino acid sequence at least 80% (such as at least 90%, or at least 95%) identical to SEQ ID NO: 38 (HC6-S74Y-511-S100cW). In more embodiments, the antibody or antigen binding fragment comprises a $V_H$ including the amino acid sequence set forth as SEQ ID NO: 38 (HC6-S74Y-511-S100cW).

H6-511-4mut-S100cW $V_H$

In some embodiments, the antibody or antigen binding fragment comprises a $V_H$ including the 10E8 $V_H$ CDRs with S100cW substitution (such as SEQ ID NOs: 7, 8, and 62) and arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively. In additional embodiments, the antibody or antigen binding fragment comprises a $V_H$ including the 10E8 $V_H$ CDRs with S100cW substitution (such as SEQ ID NOs: 7, 8, and 62), and arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82C, 84, 87, 89, 105, and 110, respectively, and an amino acid sequence at least 80% (such as at least 90%, or at least 95%) identical to SEQ ID NO: 35 (H6-511-4mut-S100cW). In more embodiments, the antibody or antigen binding fragment comprises a $V_H$ including the amino acid sequence set forth as SEQ ID NO: 35 (H6-511-4mut-S100cW).

rL3 $V_L$

In some embodiments, the antibody or antigen binding fragment comprises a $V_L$ including the 10E8 $V_L$ CDRs (such as SEQ ID NOs: 10, 11, 12) and can further include aspartate, valine, isoleucine, threonine, glutamate, and aspartate residues at kabat positions 7, 45, 58, 76, 83, and 85, respectively. In additional embodiments, the antibody or antigen binding fragment comprises a $V_L$ including the 10E8 $V_L$ CDRs (such as SEQ ID NOs: 10, 11, and 12), and aspartate, valine, isoleucine, threonine, glutamate, and aspartate residues at kabat positions 7, 45, 58, 76, 83, and 85, respectively, and an amino acid sequence at least 80% (such as at least 90%, or at least 95%) identical to SEQ ID NO: 4 (rL3). In more embodiments, the antibody or antigen binding fragment comprises a $V_L$ including the amino acid sequence set forth as SEQ ID NO: 4 (rL3).

rL3-6mut $V_L$

In some embodiments, the antibody or antigen binding fragment comprises a $V_L$ including the 10E8 $V_L$ CDRs (such as SEQ ID NOs: 10, 11, 12) and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively. In additional embodiments, the antibody or antigen binding fragment comprises a $V_L$ including the 10E8 $V_L$ CDRs (such as SEQ ID NOs: 10, 11, and 12), and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, and an amino acid sequence at least 80% (such as at least 90%, or at least 95%) identical to SEQ ID NO: 6 (rL3-6mut). In more embodiments, the antibody or antigen binding fragment comprises a $V_L$ including the amino acid sequence set forth as SEQ ID NO: 6 (rL3-6mut).

rL3-6mut $V_L$ with Y32W Substitution

In some embodiments, the antibody or antigen binding fragment comprises a $V_L$ including the 10E8 $V_L$ CDRs with Y32W substitution (such as SEQ ID NOs: 10, 11, 66) and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively. In additional embodiments, the antibody or antigen binding fragment comprises a $V_L$ including the 10E8 $V_L$ CDRs with Y32W substitution (such as SEQ ID NOs: 10, 11, and 66), and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, and an amino acid sequence at least 80% (such as at least 90%, or at least 95%) identical to SEQ ID NO: 42 (rL3-6mut-Y32W). In more embodiments, the antibody or antigen binding fragment comprises a $V_L$ including the amino acid sequence set forth as SEQ ID NO: 42 (rL3-6mut-Y32W).

rL3-6mut $V_L$ with Y32F Substitution

In some embodiments, the antibody or antigen binding fragment comprises a $V_L$ including the 10E8 $V_L$ CDRs with Y32F substitution (such as SEQ ID NOs: 10, 11, 67) and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively. In additional embodiments, the antibody or antigen binding fragment comprises a $V_L$ including the 10E8 $V_L$ CDRs with Y32F substitution (such as SEQ ID NOs: 10, 11, and 67), and alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively, and an amino acid sequence at least 80% (such as at least 90%, or at least 95%) identical to SEQ ID NO: 43 (rL3-6mut-Y32F). In more embodiments, the antibody or antigen binding fragment comprises a $V_L$ including the amino acid sequence set forth as SEQ ID NO: 43 (rL3-6mut-Y32F).

I. Additional Description of the Disclosed Antibodies and Antigen Binding Fragments In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In certain embodiments of the variant $V_H$ and $V_L$ sequences provided herein, each CDR either is unaltered, or contains no more than one, two or three amino acid substitutions Amino acid substitutions (such as conservative amino acid substitutions) can be made in the $V_H$ and the $V_L$ regions, for example to increase production yield or solubility. In some embodiments, the $V_H$ of the antibody or antigen binding fragment comprises up to 10 (such as up to 1, up to 2, up to 3, up to 4, up to 5, up to 6, up to 7, up to 8, or up to 9) amino acid substitutions (such as conservative amino acid substitutions) compared a disclosed 10E8 variant $V_H$, and/or the $V_L$ of the antibody or antigen binding fragment comprises up to 10 (such as up to 1, up to 2, up to 3, up to 4, up to 5, up to 6, up to 7, up to 8, or up to 9) amino acid substitutions (such as conservative amino acid substitutions) compared a disclosed 10E8 variant VL.

The disclosed modified 10E8 antibodies specifically bind to the MPER of gp41 at an epitope designated as the 10E8 epitope, which is included on the peptide sequence provided as NEQELLELDKWASLWNWFDITNWLWYIR (SEQ ID NO: 34). The 10E8 epitope has been elucidated by solving the structure of the 10E8 antibody in complex with a gp41 peptide (see Huang et al, *Nature,* 491: 406-412, 2012, incorporated by reference herein in its entirety). As described in Huang et al. (*Nature,* 491: 406-412, 2012) and PCT Pub. U.S. Pub. 2014/0348785A1, amino acids at $V_H$ kabat positions 28, 31, 33, 50, 52, 52B, 52C, 53, 56, 58, and 97-100J, and $V_L$ kabat positions 91 and 95B, of the 10E8 antibody contribute to the buried surface area of the antibody interface with gp41. Accordingly, in some embodiments, any of the modified 10E8 antibodies or antigen binding fragments disclosed herein comprises the corresponding amino acids of the parent 10E8 antibody at $V_H$ kabat positions 28, 31, 33, 50, 52, 52B, 52C, 53, 56, 58, and 97-100J, and $V_L$ kabat positions 91 and 95B, of the 10E8. These residues are D, N, W, R, T, P, G, E, S, D, K, Y, Y, D, F, W, S, G, Y, P, P, G, E, and E, respectively. In some embodiments, the $V_H$ of any of the modified 10E8 antibodies or antigen binding fragments provided herein comprises an arginine residue at kabat position 50 and an aspartate residue at kabat position 58.

In some embodiments, any of the disclosed modified 10E8 antibodies or antigen binding fragments that specifically bind to gp41 and neutralize HIV-1 can further comprise one or more of the gain of function amino acid substitutions listed in any one of Tables 3, 4, 9, or 10.

In some embodiments, the antibody or antigen binding fragment can also be distinguished by neutralization breadth. For example, in some embodiments, the antibody or antigen binding fragment can neutralize at least 80% (such as at least 75%, at least 80%, at least 85%, at least 90%, at least 95%, at least 96%, at least 97%, at least 98%, or at least 99%) of the HIV-1 isolates listed in FIG. 16A with an $IC_{50}$ of less than 50 μg/ml. The person of ordinary skill in the art is familiar with methods of measuring the neutralization breadth and potency of an HIV-1 Env specific monoclonal antibody, for example such methods include the single-round HIV-1 Env-pseudoviruses infection of TZM-b1 cells. Exemplary pseudovirus neutralization assays and panels of HIV-1 pseudovirus are described for example, in Li et al., *J Virol* 79, 10108-10125, 2005, Seaman et al, J. Virol., 84:1439-1452, 2010; Sarzotti-Kelsoe et al., *J. Immunol. Methods,* 409:131-46, 2014; and WO2011/038290, each of which is incorporated by reference herein.

In some embodiments, the antibody or antigen binding fragment can also be distinguished by its solubility in aqueous solution. For example, in some embodiments, the antibody or antigen binding fragment (for example, including 10E8v4 S100cF or 10E8v4 V5R S100cF variable regions) can dissolve to a concentration of at least 1.0 mg/ml (such as at least 1.0 mg/ml, at least 2.0 mg/ml, at least 3.0 mg/ml, at least 4.0 mg/ml, at least 5.0 mg/ml, at least 6.0 mg/ml, at least 7.0 mg/ml, at least 8.0 mg/ml, at least 9.0 mg/ml, or at least 10.0 mg/ml) in phosphate buffered saline (pH 7.4) at room temperature (e.g., 20-22 degrees Celsius) and remains dissolved for at least 12 hours (such as at least 24 hours, at least 48 hours, at least one week, at least two weeks, or more time). In some embodiments, the antibody or antigen binding fragment (for example, including 10E8v4 S100cF or 10E8v4 V5R S100cF variable regions) can dissolve to a concentration of at least 10 mg/ml (such as at least 15 mg/ml, at least 20 mg/ml, at least 25 mg/ml, at least 30 mg/ml, at least 35 mg/ml, at least 40 mg/ml, at least 45 mg/ml, or at least 50 mg/ml) in phosphate buffered saline (pH 7.4) at room temperature (e.g., 20-22 degrees Celsius) and remains dissolved for at least 12 hours (such as at least 24 hours, at least 48 hours, at least one week, at least two weeks, or more time). In some embodiments, the antibody or antigen binding fragment (for example, including 10E8v4 S100cF or 10E8v4 V5R S100cF variable regions) can dissolve to a concentration of at least 10 mg/ml (such as at least 15 mg/ml, at least 20 mg/ml, at least 25 mg/ml, at least 30 mg/ml, at least 35 mg/ml, at least 40 mg/ml, at least 45 mg/ml, or at least 50 mg/ml) in phosphate buffered saline (pH 7.4) at room temperature (e.g., 20-22 degrees Celsius) and remains dissolved for at least 12 hours (such as at least 24 hours, at least 48 hours, at least one week, at least two weeks, or more time). In some embodiments, the antibody or antigen binding fragment (for example, including 10E8v4 S100cF or 10E8v4 V5R S100cF variable regions) can dissolve to a concentration of at least 20 mg/ml in phosphate buffered saline (pH 7.4) at room temperature (e.g., 20-22 degrees Celsius) and remains dissolved for at least 12 hours (such as at least 24 hours, at least 48 hours, at least one week, at least two weeks, or more time). In some embodiments, the antibody or antigen binding fragment (for example, including 10E8v4 S100cF or 10E8v4 V5R S100cF variable regions) can dissolve to a concentration of at least 40 mg/ml in phosphate buffered saline (pH 7.4) at room temperature (e.g., 20-22 degrees Celsius) and remains dissolved for at least 12 hours (such as at least 24 hours, at least 48 hours, at least one week, at least two weeks, or more time). In some embodiments, the antibody or antigen binding fragment (for example, including 10E8v4 S100cF or 10E8v4 V5R S100cF variable regions) can dissolve to a concentration of at least 30 mg/ml in phosphate buffered saline (pH 7.4) at room temperature (e.g., 20-22 degrees Celsius) and remains dissolved for at least 12 hours (such as at least 24 hours, at least 48 hours, at least one week, at least two weeks, or more time). In one embodiment, the phosphate buffered saline includes NaCl (137 mM), KCl (2.7 mM), $Na_2HPO_4$ (10 mM), $KH_2PO_4$ (1.8 mM) at pH 7.4. In some embodiments, the phosphate buffered saline further includes $CaCl_2$ (1 mM) and $MgCl_2$ (0.5 mM). The person of skill in the art is familiar with methods of determining if a protein remains in solution over time. For example, the concentration of the protein dissolved in an aqueous solution can be tested over time using standard methods. In some embodiments, the antibody or antigen binding fragment can also be distinguished by its auto-reactivity, that is, its binding to self antigens. For example, in some embodiments, a disclosed antibody or antigen binding fragment comprises an autoreactivity that is comparable to that of the 10E8 antibody. For example the antibody or antigen binding fragment can have not more than 10% greater autoreactivity compared to the 10E8 antibody as measured using a standard assay, such as HEp-2 staining assay or cardiolipin binding assay.

The antibody or antigen binding fragment can be a human antibody or fragment thereof. Chimeric antibodies are also provided. The antibody or antigen binding fragment comprises any suitable framework region, such as (but not limited to) a human framework region. Human framework regions, and mutations that can be made in a human antibody framework regions, are known in the art (see, for example, in U.S. Pat. No. 5,585,089, which is incorporated herein by reference). Alternatively, a heterologous framework region, such as, but not limited to a mouse or monkey framework region, can be included in the heavy or light chain of the antibodies. (See, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993.)

The antibody can be of any isotype. The antibody can be, for example, an IgM or an IgG antibody, such as $IgG_1$, $IgG_2$, $IgG_3$, or $IgG_4$. The class of an antibody that specifically binds gp41 can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. A nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds gp41, that was originally IgG may be class switched to an IgM. Class switching can be used to convert one IgG subclass to another, such as from $IgG_1$ to $IgG_2$, $IgG_3$, or $IgG_4$.

In some examples, the disclosed antibodies are oligomers of antibodies, such as dimers, trimers, tetramers, pentamers, hexamers, septamers, octomers and so on.

(a) Binding Affinity

In several embodiments, the antibody or antigen binding fragment can specifically bind gp41 with an affinity (e.g., measured by $K_D$) of no more than $1.0 \times 10^{-8}$ M, no more than $5.0 \times 10^{-8}$ M, no more than $1.0 \times 10^{-9}$ M, no more than $5.0 \times 10^{-9}$ M, no more than $1.0 \times 10^{-10}$ M, no more than $5.0 \times 10^{-10}$ M, or no more than $1.0 \times 10^{-11}$ M. $K_D$ can be measured, for example, by a radiolabeled antigen binding assay (RIA) performed with the Fab version of an antibody of interest and its antigen using known methods. In one assay, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 μM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

In another assay, $K_D$ can be measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE®, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 l/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 l/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

(b) Multispecific Antibodies

In some embodiments, the antibody or antigen binding fragment is included on a multispecific antibody, such as a bi-specific antibody or a tri-specific antibody. Such multispecific antibodies can be produced by known methods, such as crosslinking two or more antibodies, antigen binding fragments (such as scFvs) of the same type or of different types. Exemplary methods of making multispecific antibodies include those described in PCT Pub. No. WO2013/163427, which is incorporated by reference herein in its entirety. Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

In some embodiments, the antibody or antigen binding fragment is included on a bispecific antibody that that specifically binds to gp41 and further specifically binds to CD3. Examples of CD3 binding domains that can be included on the bispecific antibody or antigen binding fragment are known and include those disclosed in PCT Pub. No. WO2013/163427, which is incorporated by reference herein in its entirety.

Various types of multi-specific antibodies are known. Bispecific single chain antibodies can be encoded by a single nucleic acid molecule. Examples of bispecific single chain antibodies, as well as methods of constructing such antibodies are known in the art (see, e.g., U.S. Pat. Nos. 8,076,459, 8,017,748, 8,007,796, 7,919,089, 7,820,166, 7,635,472, 7,575,923, 7,435,549, 7,332,168, 7,323,440, 7,235,641, 7,229,760, 7,112,324, 6,723,538, incorporated by reference herein). Additional examples of bispecific single chain antibodies can be found in PCT application No. WO 99/54440; Mack, *J. Immunol.*, 158:3965-3970, 1997; Mack, *PNAS,* 92:7021-7025, 1995; Kufer, *Cancer Immunol. Immunother.*, 45:193-197, 1997; Loffler, *Blood,* 95:2098-2103, 2000; and Bruhl, *J. Immunol.*, 166:2420-2426, 2001.

Production of bispecific Fab-scFv ("bibody") molecules are described, for example, in Schoonjans et al. (J. Immunol. 165:7050-57, 2000) and Willems et al. (J Chromatogr B Analyt Technol Biomed Life Sci. 786:161-76, 2003). For bibodies, a scFv molecule can be fused to one of the VL-CL (L) or VH-CH1 chains, e.g., to produce a bibody one scFv is fused to the C-term of a Fab chain.

(c) Fragments

Antigen binding fragments are encompassed by the present disclosure, such as Fab, F(ab')$_2$, and Fv which include a heavy chain and $V_L$ and specifically bind gp41. In several embodiments, the antigen binding fragment includes the heavy and light chain variable regions from the 10E8v4 S100cF or 10E8v4 V5R S100cF antibody.

These antibody fragments retain the ability to selectively bind with the antigen and are "antigen-binding" fragments. Non-limiting examples of such fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the $V_L$ and $V_L$ expressed as two chains; and (5) Single chain antibody (such as scFv), defined as a genetically engineered molecule containing the $V_H$ and the $V_L$ linked by a suitable polypeptide linker as a genetically fused single chain molecule (see, e.g., Ahmad et al., Clin. Dev. Immunol., 2012, doi:10.1155/2012/980250; Marbry, IDrugs, 13:543-549, 2010). The intramolecular orientation of the $V_H$-domain and the $V_L$-domain in a scFv, is not decisive for the provided antibodies (e.g., for the provided multispecific antibodies). Thus, scFvs with both possible arrangements ($V_H$-domain-linker domain-$V_L$-domain; $V_L$-domain-linker domain-$V_H$-domain) may be used.

(6) A dimer of a single chain antibody (scFV$_2$), defined as a dimer of a scFV. This has also been termed a "miniantibody."

Methods of making these fragments are known in the art (see for example, Harlow and Lane, *Antibodies: A Laboratory Manual*, 2$^{nd}$, Cold Spring Harbor Laboratory, New York, 2013).

In some embodiments, the antigen binding fragment can be an Fv antibody, which is typically about 25 kDa and contain a complete antigen-binding site with three CDRs per each heavy chain and each light chain. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker Thus, in one example, the Fv can be a disulfide stabilized Fv (dsFv), wherein the $V_H$ and the $V_L$ are chemically linked by disulfide bonds. In an additional example, the Fv fragments include $V_H$ and $V_L$ chains connected by a peptide linker. These single-chain antigen binding proteins (scFv) can be prepared by constructing a nucleic acid molecule encoding the $V_H$ and $V_L$ domains connected by an oligonucleotide. The nucleic acid molecule is inserted into an expression vector, which is subsequently introduced into a host cell such as a mammalian cell. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., Science 242:423, 1988; U.S. Pat. No. 4,946,778; Pack et al., *Bio/Technology* 11:1271, 1993; Ahmad et al., Clin. Dev. Immunol., 2012, doi:10.1155/2012/980250; Marbry, *IDrugs,* 13:543-549, 2010). Dimers of a single chain antibody (scFV$_2$), are also contemplated.

Antigen binding fragments can be prepared by proteolytic hydrolysis of the antibody or by expression in a host cell (such as an *E. coli* cell) of DNA encoding the fragment. Antigen binding fragments can also be obtained by pepsin or papain digestion of whole antibodies by conventional methods. For example, antigen binding fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Antigen binding single $V_H$ domains, called domain antibodies (dAb), have also been identified from a library of murine $V_H$ genes amplified from genomic DNA of immunized mice (Ward et al. *Nature* 341:544-546, 1989). Human single immunoglobulin variable domain polypeptides capable of binding antigen with high affinity have also been described (see, for example, PCT Publication Nos. WO 2005/035572 and WO 2003/002609). The CDRs disclosed herein can also be included in a dAb.

In some embodiments, one or more of the heavy and/or light chain complementarity determining regions (CDRs) from a disclosed antibody (such as the HC6-S74Y-511/rL3-6mut or H6-511-4mut/rL3-6mut antibody) is expressed on the surface of another protein, such as a scaffold protein. The expression of domains of antibodies on the surface of a scaffolding protein are known in the art (see e.g., Liu et al., *J. Virology* 85(17): 8467-8476, 2011). Such expression creates a chimeric protein that retains the binding for gp41. In some specific embodiments, one or more of the heavy chain CDRs is grafted onto a scaffold protein, such as one or more of heavy chain CDR1, CDR2, and/or CDR3. One or more CDRs can also be included in a diabody or another type of single chain antibody molecule.

(d) Variants

In certain embodiments, amino acid sequence variants of the antibodies provided herein are contemplated. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the CDRs and the framework regions. Amino acid substitutions may be introduced into an antibody of interest and the products screened for a desired activity, e.g., retained/improved antigen binding, decreased immunogenicity, or improved ADCC or CDC.

The variants typically retain amino acid residues necessary for correct folding and stabilizing between the $V_H$ and the $V_L$ regions, and will retain the charge characteristics of the residues in order to preserve the low pI and low toxicity of the molecules Amino acid substitutions (such as conservative amino acid substitutions) can be made in the $V_H$ and the $V_L$ regions, for example to increase production yield or solubility.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In certain embodiments of the variant $V_H$ and $V_L$ sequences provided above, each CDR either is unaltered, or contains no more than one, two or three amino acid substitutions.

To increase binding affinity of the antibody, the $V_L$ and $V_H$ segments can be randomly mutated, such as within HCDR3 region or the LCDR3 region, in a process analogous to the in vivo somatic mutation process responsible for affinity maturation of antibodies during a natural immune response. Thus in vitro affinity maturation can be accomplished by amplifying $V_H$ and $V_L$ regions using PCR primers complementary to the HCDR3 or LCDR3, respectively. In this process, the primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be tested to determine the binding affinity for gp41. Methods of in vitro affinity maturation are known (see, e.g., Chowdhury, *Methods Mol. Biol.* 207:179-196 (2008)), and Hoogenboom et al. in *Methods in Molecular Biology* 178:1-37 (O'Brien et al., ed., Human Press, Totowa, N.J., (2001).)

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

In certain embodiments, an antibody or antigen binding fragment is altered to increase or decrease the extent to which the antibody or antigen binding fragment is glycosylated. Addition or deletion of glycosylation sites may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the $CH_2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region; however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec 13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In several embodiments, the constant region of the antibody includes one or more amino acid substitutions to optimize in vivo half-life of the antibody. The serum half-life of IgG Abs is regulated by the neonatal Fc receptor (FcRn). Thus, in several embodiments, the antibody includes an amino acid substitution that increases binding to the FcRn. Several such substitutions are known to the person of ordinary skill in the art, such as substitutions at IgG constant regions T250Q and M428L (see, e.g., Hinton et al., *J Immunol.*, 176:346-356, 2006); M428L and N434S (the "LS" mutation, see, e.g., Zalevsky, et al., *Nature Biotechnology*, 28:157-159, 2010); N434A (see, e.g., Petkova et al., *Int. Immunol.*, 18:1759-1769, 2006); T307A, E380A, and N434A (see, e.g., Petkova et al., *Int. Immunol.*, 18:1759-1769, 2006); and M252Y, S254T, and T256E (see, e.g., Dall'Acqua et al., *J. Biol. Chem.*, 281:23514-23524, 2006). The disclosed antibodies and antigen binding fragments can be linked to a Fc polypeptide including any of the substitutions listed above, for example, the Fc polypeptide comprises the M428L and N434S substitutions.

In some embodiments, the constant region of the antibody includes one of more amino acid substitutions to optimize antibody-dependent cell-mediated cytotoxicity (ADCC). ADCC is mediated primarily through a set of closely related Fcγ receptors. In some embodiments, the antibody includes one or more amino acid substitutions that increase binding to FcγRIIIa. Several such substitutions are known to the person of ordinary skill in the art, such as substitutions at IgG constant regions S239D and I332E (see, e.g., Lazar et al., *Proc. Natl., Acad. Sci. U.S.A.*, 103:4005-4010, 2006); and S239D, A330L, and I332E (see, e.g., Lazar et al., *Proc. Natl., Acad. Sci. U.S.A.*, 103:4005-4010, 2006).

Combinations of the above substitutions are also included, to generate an IgG constant region with increased binding to FcRn and FcγRIIIa. The combinations increase antibody half-life and ADCC. For example, such combination include antibodies with the following amino acid substitution in the Fc region: (1) S239D/I332E and T250Q/M428L; (2) S239D/I332E and M428L/N434S; (3) S239D/I332E and N434A; (4) S239D/I332E and T307A/E380A/N434A; (5) S239D/I332E and M252Y/S254T/T256E; (6) S239D/A330L/I332E and 250Q/M428L; (7) S239D/A330L/I332E and M428L/N434S; (8) S239D/A330L/I332E and N434A; (9) S239D/A330L/I332E and T307A/E380A/N434A; or (10) S239D/A330L/I332E and M252Y/S254T/T256E. In some examples, the antibodies, or an antigen binding fragment thereof is modified such that it is directly cytotoxic to infected cells, or uses natural defenses such as complement, antibody dependent cellular cytotoxicity (ADCC), or phagocytosis by macrophages.

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

The antibody or antigen binding fragment can be derivatized or linked to another molecule (such as another peptide or protein). In general, the antibody or antigen binding fragment is derivatized such that the binding to gp41 is not affected adversely by the derivatization or labeling. For example, the antibody or antigen binding fragment can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the antibody or antibody portion with another molecule (such as a streptavidin core region or a polyhistidine tag).

B. Conjugates

The antibodies and antigen binding fragments that specifically bind to an epitope on gp41 can be conjugated to an agent, such as an effector molecule or detectable marker, using any number of means known to those of skill in the art. Both covalent and noncovalent attachment means may be used. One of skill in the art will appreciate that various effector molecules and detectable markers can be used, including (but not limited to) toxins and radioactive agents such as $^{125}I$, $^{32}P$, $^{14}C$, $^{3}H$ and $^{35}S$ and other labels, target moieties and ligands, etc. The choice of a particular effector molecule or detectable marker depends on the particular target molecule or cell, and the desired biological effect.

The choice of a particular effector molecule or detectable marker depends on the particular target molecule or cell, and the desired biological effect. Thus, for example, the effector molecule can be a cytotoxin that is used to bring about the death of a particular target cell (such as an HIV-1 infected cell). In other embodiments, the effector molecule can be a cytokine, such as IL-15; conjugates including the cytokine can be used, e.g., to stimulate immune cells locally.

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on a polypeptide to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In view of the large number of methods that have been reported for attaching a variety of radiodiagnostic compounds, radiotherapeutic compounds, labels (such as enzymes or fluorescent molecules), toxins, and other agents to antibodies one skilled in the art will be able to determine a suitable method for attaching a given agent to an antibody or antigen binding fragment or other polypeptide. For example, the antibody or antigen binding fragment can be conjugated with effector molecules such as small molecular weight drugs such as Monomethyl Auristatin E (MMAE), Monomethyl Auristatin F (MMAF), maytansine, maytansine derivatives, including the derivative of maytansine known as DM1 (also known as mertansine), or other agents to make an antibody drug conjugate (ADC). In several embodiments, conjugates of an antibody or antigen binding fragment and one or more small molecule toxins, such as a calicheamicin, maytansinoids, dolastatins, auristatins, a trichothecene, and CC1065, and the derivatives of these toxins that have toxin activity, are provided.

The antibody or antigen binding fragment can be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

The antibody or antigen binding fragment can be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

The antibody or antigen binding fragment can also be conjugated with a radiolabeled amino acid. The radiolabel may be used for both diagnostic and therapeutic purposes. For instance, the radiolabel may be used to detect gp41 and gp41 expressing cells by x-ray, emission spectra, or other diagnostic techniques. Examples of labels for polypeptides include, but are not limited to, the following radioisotopes or radionucleotides $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The average number of effector molecule or detectable marker moieties per antibody or antigen binding fragment in a conjugate can range, for example, from 1 to 20 moieties per antibody or antigen binding fragment. In certain embodiments, the average number of effector molecule or detectable marker moieties per antibody or antigen binding fragment in a conjugate range from about 1 to about 2, from about 1 to about 3, about 1 to about 8; from about 2 to about 6; from about 3 to about 5; or from about 3 to about 4. The loading (for example, effector molecule/antibody ratio) of an conjugate may be controlled in different ways, for example, by: (i) limiting the molar excess of effector molecule-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number or position of linker-effector molecule attachments.

C. Polynucleotides and Expression

Nucleic acids molecules (for example, cDNA molecules) encoding the amino acid sequences of antibodies, antigen binding fragments, and conjugates that specifically bind gp41 are provided. Nucleic acids encoding these molecules can readily be produced by one of skill in the art, using the amino acid sequences provided herein (such as the CDR sequences and $V_H$ and $V_L$ sequences), sequences available in the art (such as framework or constant region sequences), and the genetic code. In several embodiments, a nucleic acid molecule can encode the $V_H$, the $V_L$, or both the $V_H$ and $V_L$ (for example in a bicistronic expression vector) of a disclosed antibody or antigen binding fragment. In several embodiments, the nucleic acid molecules can be expressed in a host cell (such as a mammalian cell) to produce a disclosed antibody or antigen binding fragment.

One of skill in the art can readily use the genetic code to construct a variety of functionally equivalent nucleic acids, such as nucleic acids which differ in sequence but which encode the same antibody sequence, or encode a conjugate or fusion protein including the $V_L$ and/or $V_H$ nucleic acid sequence.

In a non-limiting example, an isolated nucleic acid molecule encodes the $V_H$ of a disclosed antibody or antigen binding fragment and includes the nucleic acid sequence set forth as any one of SEQ ID NOs: 20, 21, 44, 45, 78, or 79. In a non-limiting example, an isolated nucleic acid molecule encodes the $V_L$ of a disclosed antibody or antigen binding fragment and includes the nucleic acid sequence set forth as any one of SEQ ID NOs: 24, 46 or 47. In a non-limiting example, an isolated nucleic acid molecule encodes the $V_H$ and $V_L$ of a disclosed antibody or antigen binding fragment and includes the nucleic acid sequences set forth as any one of SEQ ID NOs: 44 and 46, respectively; SEQ ID NOs: 44 and 47, respectively, SEQ ID NOs: 45 and 46, respectively, SEQ ID NOs: 45 and 47, respectively (10E8v4), SEQ ID NOs: 78 and 47, respectively (10E8v4 S100cF), or SEQ ID NOs: 79 and 47, respectively (10E8v4 V5R, S100cF).

Nucleic acid sequences encoding the antibodies, antigen binding fragments, and conjugates that specifically bind gp41 can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, $4^{th}$ ed., Cold Spring Harbor, N.Y., 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The nucleic acid molecules can be expressed in a recombinantly engineered cell such as bacteria, plant, yeast, insect and mammalian cells. The antibodies, antigen binding fragments, and conjugates can be expressed as individual $V_H$ and/or $V_L$ chain (linked to an effector molecule or detectable marker as needed), or can be expressed as a fusion protein. Methods of expressing and purifying antibodies and antigen binding fragments are known and further described herein (see, e.g., Al-Rubeai (ed), *Antibody Expression and Production*, Springer Press, 2011). An immunoadhesin can also be expressed. Thus, in some examples, nucleic acids encoding a $V_H$ and $V_L$, and immunoadhesin are provided. The nucleic acid sequences can optionally encode a leader sequence.

To create a scFv the $V_H$- and $V_L$-encoding DNA fragments can be operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ domains joined by the flexible linker (see, e.g., Bird et al., *Science* 242:423-426, 1988; Huston et al., *Proc. Natl. Acad. Sci. USA* 85:5879-5883, 1988; McCafferty et al., *Nature* 348:552-554, 1990; Kontermann and Dubel (Ed), Antibody Engineering, Vols. 1-2, $2^{nd}$ Ed., Springer Press, 2010; Harlow and Lane, *Antibodies: A Laboratory Manual*, $2^{nd}$, Cold Spring Harbor Laboratory, New York, 2013). Optionally, a cleavage site can be included in a linker, such as a furin cleavage site.

The nucleic acid encoding a $V_H$ and/or the $V_L$ optionally can encode an Fc region (immunoadhesin). The Fc region can be an IgA, IgM or IgG Fc region. The Fc region can be an optimized Fc region, as described in U.S. Published Patent Application No. 20100/093979, incorporated herein by reference. In one example, the immunoadhesin is an $IgG_1$ Fc.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to gp41 and another antigen, such as, but not limited to CD3. The encoded $V_H$ and $V_L$ optionally comprises a furin cleavage site between the $V_H$ and $V_L$ domains.

Those of skill in the art are knowledgeable in the numerous expression systems available for expression of proteins including *E. coli*, other bacterial hosts, yeast, and various higher eukaryotic cells such as the COS, CHO, HeLa and myeloma cell lines.

One or more DNA sequences encoding the antibodies, antigen binding fragments, or conjugates can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

The expression of nucleic acids encoding the antibodies and antigen binding fragments described herein can be achieved by operably linking the DNA or cDNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes comprises appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For $E.$ $coli$, this comprises a promoter such as the T7, trp, lac, or lambda promoters, a ribosome binding site, and preferably a transcription termination signal. For eukaryotic cells, the control sequences comprises a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for $E.$ $coli$ and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or antigen biding fragment, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

Also provided is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the antibodies, antigen binding fragments, and conjugates can be purified according to standard procedures in the art, including ammonium sulfate precipitation, affinity columns, column chromatography, and the like (see, generally, Simpson ed., Basic methods in Protein Purification and Analysis: A laboratory Manual, Cold Harbor Press, 2008). The antibodies, antigen binding fragment, and conjugates need not be 100% pure. Once purified, partially or to homogeneity as desired, if to be used therapeutically, the polypeptides should be substantially free of endotoxin.

Methods for expression of the antibodies, antigen binding fragments, and conjugates, and/or refolding to an appropriate active form, from mammalian cells, and bacteria such as $E.$ $coli$ have been described and are well-known and are applicable to the antibodies disclosed herein. See, e.g., Harlow and Lane, $Antibodies:$ $A$ $Laboratory$ $Manual$, $2^{nd}$, Cold Spring Harbor Laboratory, New York, 2013, Simpson ed., Basic methods in Protein Purification and Analysis: A laboratory Manual, Cold Harbor Press, 2008, and Ward et al., $Nature$ 341:544, 1989.

In addition to recombinant methods, the antibodies, antigen binding fragments, and/or conjugates can also be constructed in whole or in part using standard peptide synthesis. Solid phase synthesis of the polypeptides can be accomplished by attaching the C-terminal amino acid of the sequence to an insoluble support followed by sequential addition of the remaining amino acids in the sequence. Techniques for solid phase synthesis are described by Barany & Merrifield, $The$ $Peptides:$ $Analysis,$ $Synthesis,$ $Biology$. Vol. 2: $Special$ $Methods$ $in$ $Peptide$ $Synthesis,$ $Part$ $A$. pp. 3-284; Merrifield et al., $J.$ $Am.$ $Chem.$ $Soc.$ 85:2149-2156, 1963, and Stewart et al., $Solid$ $Phase$ $Peptide$ $Synthesis$, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

D. Methods and Compositions

1. Therapeutic Methods

Methods are disclosed herein for the prevention or treatment of an HIV-1 infection. Prevention comprises inhibition of infection with HIV-1. The methods include contacting a cell with a therapeutically effective amount of a disclosed antibody, antigen binding fragment, or conjugate that specifically binds gp41, or a nucleic acid encoding such an antibody, antigen binding fragment, or conjugate. The method can also include administering to a subject a therapeutically effective amount of a disclosed antibody, antigen binding fragment, or conjugate that specifically binds gp41, or a nucleic acid encoding such an antibody, antigen binding fragment, or conjugate, to a subject. In some examples, the antibody, antigen binding fragment, conjugate, or nucleic acid molecule can be used pre-exposure (for example, to prevent or inhibit HIV-1 infection). In some examples, the antibody, antigen binding fragment, conjugate, or nucleic acid molecule can be used in post-exposure prophylaxis. In some examples, the antibody, antigen binding fragment, conjugate, or nucleic acid molecule, can be used to eliminate or reduce the viral reservoir of HIV-1 in a subject. For example a therapeutically effective amount of an antibody, antigen binding fragment, conjugate, or nucleic acid molecule can be administered to a subject with HIV-1, such as a subject being treated with anti-viral therapy. In some examples the antibody, antigen binding fragment, conjugate, or nucleic acid molecule is modified such that it is directly cytotoxic to infected cells (e.g., by conjugation to a toxin), or uses natural defenses such as complement, antibody dependent cellular cytotoxicity (ADCC), or phagocytosis by macrophages.

HIV-1 infection does not need to be completely eliminated or prevented for the method to be effective. For example, a method can decrease HIV-1 infection by a desired amount, for example by at least 10%, at least 20%, at least 50%, at least 60%, at least 70%, at least 80%, at least 90%, at least 95%, at least 98%, or even at least 100% (elimination of detectable HIV-1 infected cells), as compared to HIV-1 infection in the absence of the treatment. In some embodiments, the cell is also contacted with a therapeutically effective amount of an additional agent, such as anti-viral agent. The cell can be in vivo or in vitro. The methods comprises administration of one on more additional agents known in the art. In additional embodiments, HIV-1 replication can be reduced or inhibited by similar methods. HIV-1 replication does not need to be completely eliminated for the method to be effective. For example, a method can decrease HIV-1 replication by a desired amount, for example by at least 10%, at least 20%, at least 50%, at least 60%, at least 70%, at least 80%, at least 90%, at least 95%, at least 98%, or even at least 100% (elimination of detectable HIV-1), as compared to HIV-1 replication in the absence of the treatment.

Methods to assay for neutralization activity include, but are not limited to, a single-cycle infection assay as described in Martin et al. (2003) *Nature Biotechnology* 21:71-76. In this assay, the level of viral activity is measured via a selectable marker whose activity is reflective of the amount of viable virus in the sample, and the $IC_{50}$ is determined. In other assays, acute infection can be monitored in the PM1 cell line or in primary cells (normal PBMC). In this assay, the level of viral activity can be monitored by determining the p24 concentrations using ELISA. See, for example, Martin et al. (2003) *Nature Biotechnology* 21:71-76.

In one embodiment, administration of a disclosed antibody, antigen binding fragment, conjugate, or nucleic acid molecule, results in a reduction in the establishment of HIV-1 infection and/or reducing subsequent HIV-1 disease progression in a subject. A reduction in the establishment of HIV-1 infection and/or a reduction in subsequent HIV-1 disease progression encompass any statistically significant reduction in HIV-1 activity. In some embodiments, methods are disclosed for treating a subject with an HIV-1 infection. These methods include administering to the subject a therapeutically effective amount of a disclosed antibody, antigen binding fragment, conjugate, or nucleic acid molecule, thereby preventing or treating the HIV-1 infection.

Studies have shown that the rate of HIV-1 transmission from mother to infant is reduced significantly when zidovudine is administered to HIV-infected women during pregnancy and delivery and to the offspring after birth (Connor et al., 1994 *Pediatr Infect Dis J* 14: 536-541). Several studies of mother-to-infant transmission of HIV-1 have demonstrated a correlation between the maternal virus load at delivery and risk of HIV-1 transmission to the child. The present disclosure provides antibodies, antigen binding fragments, conjugates, and nucleic acid molecule that are of use in decreasing HIV-transmission from mother to infant. Thus, in some examples, a therapeutically effective amount of a gp41-specific antibody or antigen binding fragment thereof or nucleic acid encoding such antibodies or antibody antigen binding fragments, is administered in order to prevent transmission of HIV-1, or decrease the risk of transmission of HIV-1, from a mother to an infant. In some examples, a therapeutically effective amount of the antibody, or an antigen binding fragment or nucleic acid encoding such antibody or antigen binding fragment, is administered to mother and/or to the child at childbirth. In other examples, a therapeutically effective amount of the antibody, antigen binding fragment, or nucleic acid encoding the antibody or antigen binding fragment is administered to the mother and/or infant prior to breast feeding in order to prevent viral transmission to the infant or decrease the risk of viral transmission to the infant. In some embodiments, both a therapeutically effective amount of the antibody, antigen binding fragment, or nucleic acid encoding the antibody or antigen binding fragment and a therapeutically effective amount of another agent, such as zidovudine, is administered to the mother and/or infant.

For any application, the antibody, antigen binding fragment, conjugate, or nucleic acid molecule can be combined with anti-retroviral therapy. Antiretroviral drugs are broadly classified by the phase of the retrovirus life-cycle that the drug inhibits. The disclosed antibodies can be administered in conjunction with nucleoside analog reverse-transcriptase inhibitors (such as zidovudine, didanosine, zalcitabine, stavudine, lamivudine, abacavir, emtricitabine, entecavir, and apricitabine), nucleotide reverse transcriptase inhibitors (such as tenofovir and adefovir), non-nucleoside reverse transcriptase inhibitors (such as efavirenz, nevirapine, delavirdine, etravirine, and rilpivirine), protease inhibitors (such as saquinavir, ritonavir, indinavir, nelfinavir, amprenavir, lopinavir, fosamprenavir, atazanavir, tipranavir, and darunavir), entry or fusion inhibitors (such as maraviroc and enfuvirtide), maturation inhibitors, (such as bevirimat and vivecon), or a broad spectrum inhibitors, such as natural antivirals. In some examples, a disclosed antibody or active fragment thereof or nucleic acids encoding such is administered in conjunction with IL-15, or conjugated to IL-15.

Studies have shown that cocktails of HIV-1 neutralizing antibodies that target different epitopes of HIV-1 Env can treat macaques chronically infected with SHIV (Shingai et al., Nature, 503, 277-280, 2013; and Barouch et al., Nature, 503, 224-228, 2013). Accordingly, in some examples, a subject is further administered one or more additional antibodies that bind HIV-1 Env (e.g., that bind to gp120 and/or gp41), and that can neutralize HIV-1 infection. The additional antibodies can be administrated before, during, or after administration of the novel antibodies disclosed herein (e.g., 10E8v4, 10E8v5, 10E8v4 S100cF, or 10E8v4 V5R S100cF). In some embodiments, the additional antibody can be an antibody that specifically binds to an epitope on HIV-1 Env such as the CD4 binding site (e.g., b12, 3BNC117, VRC01, VRC07, VRC07-523 antibody), the V1/V2 domain (e.g., PG9 antibody, CAP256-VRC26), or the V3 loop (e.g., 10-1074, PGT 121, or PGT128 antibody), or those that bind both gp120 and gp41 subunits (e.g., 35O22, PGT151, or 8ANC195). In these combinatorial antibody treatment methods, the antibodies can all be in the IgG format, or another formal. Antibodies that specifically bind to these regions and neutralizing HIV-1 infection are known to the person of ordinary skill in the art. Non-limiting examples can be found, for example, in PCT Pub. No. WO 2011/038290, WO/2013/086533, WO/2013/090644, WO/2012/158948, which are each incorporated herein by reference in their entirety.

In some examples, a subject is administered the DNA encoding the antibody or antigen binding fragments thereof, to provide in vivo antibody production, for example using the cellular machinery of the subject. Immunization by nucleic acid constructs is well known in the art and taught, for example, in U.S. Pat. Nos. 5,643,578, and 5,593,972 and 5,817,637. U.S. Pat. No. 5,880,103 describes several methods of delivery of nucleic acids encoding to an organism. One approach to administration of nucleic acids is direct administration with plasmid DNA, such as with a mammalian expression plasmid. The nucleotide sequence encoding the disclosed antibody, or antigen binding fragments thereof, can be placed under the control of a promoter to increase expression. The methods include liposomal delivery of the nucleic acids. Such methods can be applied to the production of an antibody, or antigen binding fragments thereof, by one of ordinary skill in the art. In some embodiments, a disclosed antibody or antigen binding fragment is expressed in a subject using the pVRC8400 vector (described in Barouch et al., J. Virol, 79, 8828-8834, 2005, which is incorporated by reference herein).

The nucleic acid molecules encoding the disclosed antibodies (such as 10E8v4 S100cW-DS) or antigen binding fragments can be included in a viral vector, for example for expression of the antibody or antigen binding fragment in a host cell, or a subject (such as a subject with or at risk of HIV-1 infection). A number of viral vectors have been constructed, that can be used to express the disclosed antibodies or antigen binding fragments, such as a retroviral vector, an adenoviral vector, or an adeno-associated virus (AAV) vector. In several examples, the viral vector can be replication-competent. For example, the viral vector can have a mutation in the viral genome that does not inhibit viral replication in host cells. The viral vector also can be conditionally replication-competent. In other examples, the viral vector is replication-deficient in host cells.

In several embodiments, a subject (such as a human subject with or at risk of HIV-1 infection) can be administered a therapeutically effective amount of an adeno-associated virus (AAV) viral vector that comprises one or more nucleic acid molecules encoding a disclosed antibody or antigen binding fragment (such as 10E8v4 S100cF antibody). The AAV viral vector is designed for expression of the nucleic acid molecules encoding a disclosed antibody or antigen binding fragment, and administration of the therapeutically effective amount of the AAV viral vector to the subject leads to expression of a therapeutically effective amount of the antibody or antigen binding fragment in the subject. Non-limiting examples of AAV viral vectors that can be used to express a disclosed antibody or antigen binding fragment in a subject include those provided in Johnson et al ("Vector-mediated gene transfer engenders long-lived neutralizing activity and protection against SIV infection in monkeys," Nat. Med., 15(8):901-906, 2009) and Gardner et al. ("AAV-expressed eCD4-Ig provides durable protection from multiple SHIV challenges," Nature, 519 (7541): 87-91, 2015), each of which is incorporated by reference herein in its entirety.

In one embodiment, a nucleic acid encoding a disclosed antibody, or antigen binding fragments thereof, is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

In another embodiment, an mRNA-based administration protocol can be used to deliver a nucleic acid encoding a disclosed antibody directly into cells. In some embodiments, nucleic acid-based therapeutics based on mRNA may provide a potent alternative to the previously mentioned approaches. mRNA therapeutics preclude safety concerns about DNA integration into the host genome and can be directly translated in the host cell cytoplasm. Moreover, the simple cell-free, in vitro synthesis of RNA avoids the manufacturing complications associated with viral vectors or cellular production and purification of complex biomolecules. Two exemplary forms of RNA-based delivery of therapeutics that can be used to deliver a nucleic acid encoding a disclosed antibody include conventional non-amplifying mRNA therapeutic delivery (see, e.g., Petsch et al., "Protective efficacy of in vitro synthesized, specific mRNA vaccines against influenza A virus infection," Nature biotechnology, 30(12):1210-6, 2012) and self-amplifying mRNA therapeutic delivery (see, e.g., Geall et al., "Nonviral delivery of self-amplifying RNA vaccines," PNAS, 109(36): 14604-14609, 2012; Magini et al., "Self-Amplifying mRNA Vaccines Expressing Multiple Conserved Influenza Antigens Confer Protection against Homologous and Heterosubtypic Viral Challenge," PLoS One, 11(8):e0161193, 2016; and Brito et al., "Self-amplifying mRNA vaccines," Adv Genet., 89:179-233, 2015).

2. Dosages

A therapeutically effective amount of a gp41-specific antibody, antigen binding fragment, conjugate, or nucleic acid molecule encoding such molecules, will depend upon the severity of the disease and/or infection and the general state of the patient's health. A therapeutically effective amount is that which provides either subjective relief of a symptom(s) or an objectively identifiable improvement as noted by the clinician or other qualified observer. The gp41-specific antibody, antigen binding fragment, conjugate, or nucleic acid molecule encoding such molecules, can be administered in conjunction with another therapeutic agent, either simultaneously or sequentially.

Single or multiple administrations of a composition including a disclosed gp41-specific antibody, antigen binding fragment, conjugate, or nucleic acid molecule encoding such molecules, can be administered depending on the dosage and frequency as required and tolerated by the patient. Compositions including the gp41-specific antibody, antigen binding fragment, conjugate, or nucleic acid molecule encoding such molecules, should provide a sufficient quantity of at least one of the gp41-specific antibody, antigen binding fragment, conjugate, or nucleic acid molecule encoding such molecules to effectively treat the patient. The dosage can be administered once, but may be applied periodically until either a therapeutic result is achieved or until side effects warrant discontinuation of therapy. In one example, a dose of the antibody or antigen binding fragment is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Data obtained from cell culture assays and animal studies can be used to formulate a range of dosage for use in humans. The dosage normally lies within a range of circulating concentrations that include the $ED_{50}$, with little or minimal toxicity. The dosage can vary within this range depending upon the dosage form employed and the route of administration utilized. The therapeutically effective dose can be determined from cell culture assays and animal studies.

In certain embodiments, the antibody or antigen binding fragment that specifically binds gp41, or conjugate thereof, or a nucleic acid molecule or vector encoding such a molecule, or a composition including such molecules, is administered at a dose in the range of from about 5 or 10 nmol/kg to about 300 nmol/kg, or from about 20 nmol/kg to about 200 nmol/kg, or at a dose of about 5, 10, 15, 20, 25, 30, 35, 40, 45, 50, 55, 60, 65, 70, 75, 80, 85, 90, 95, 100, 110, 120, 125, 130, 140, 150, 160, 170, 175, 180, 190, 200, 210, 220, 230, 240, 250, 260, 270, 280, 290, 300, 350, 400, 450, 500, 750, 1000, 1250, 1500, 1750 or 2000 nmol/kg, or at a dose of about 5, 10, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950 or 1000 µg/kg, or about 1, 1.25, 1.5, 2, 2.5, 3, 3.5, 4, 4.5, 5, 5.5, 6, 6.5, 7, 7.5, 8, 8.5, 9, 9.5 or 10 mg/kg, or other dose deemed appropriate by the treating physician. In some embodiments, the antibody or antigen binding fragment can be administered to a subject at a dose of from about 0.5 to about 40 mg/kg, such as about 1 to about 30, about 1 to about 20, about 1 to about 15, about 1 to about 10, about 1 to about 5, about 1 to about 3, about 0.5 to about 40 mg/kg, such as about 0.5 to about 30, about 0.5 to about 20, about 0.5 to about 15, about 0.5 to about 10, about 0.5 to about 5, about 0.5 to about 3, about 3 to about 7, about 8 to about 12, about 15 to about 25, about 18 to about 22, about 28 to about 32, about 10 to about 20, about 5 to about 15, or about 20 to about 40 mg/kg. The doses described herein can be administered according to the dosing frequency/frequency of administration described herein, including without limitation daily, 2 or 3 times per week, weekly, every 2 weeks, every 3 weeks, monthly, every other month, etc.

In some embodiments, a disclosed therapeutic agent may be administered intravenously, subcutaneously, or by another mode daily or multiple times per week for a period of time, followed by a period of no treatment, then the cycle is repeated. In some embodiments, the initial period of treatment (e.g., administration of the therapeutic agent daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks, or 12 weeks. In a related embodiment, the period of no treatment lasts for 3 days, 1 week, 2 weeks, 3 weeks, or 4 weeks. In certain embodiments, the dosing regimen of the therapeutic agent is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2, or 3 weeks off; or daily or multiple times per week for 4, 5, 6, 7, 8, 9, 10, 11, or 12 weeks followed by 1, 2, 3, or 4 weeks off.

3. Modes of Administration

The gp41-specific antibody, antigen binding fragment, conjugate, or nucleic acid molecule encoding such molecules, or a composition including such molecules, as well as additional agents, can be administered to subjects in various ways, including local and systemic administration, such as, e.g., by injection subcutaneously, intravenously, intra-arterially, intraperitoneally, intramuscularly, intradermally, or intrathecally. In an embodiment, a therapeutic agent is administered by a single subcutaneous, intravenous, intra-arterial, intraperitoneal, intramuscular, intradermal or intrathecal injection once a day. The therapeutic agent can also be administered by direct injection at or near the site of disease.

The gp41-specific antibody, antigen binding fragment, conjugate, or nucleic acid molecule encoding such molecules, or a composition including such molecules may also be administered orally in the form of microspheres, microcapsules, liposomes (uncharged or charged (e.g., cationic)), polymeric microparticles (e.g., polyamides, polylactide, polyglycolide, poly(lactide-glycolide)), microemulsions, and the like.

A further method of administration is by osmotic pump (e.g., an Alzet pump) or mini-pump (e.g., an Alzet mini-osmotic pump), which allows for controlled, continuous and/or slow-release delivery of the therapeutic agent or pharmaceutical composition over a pre-determined period. The osmotic pump or mini-pump can be implanted subcutaneously, or near a target site.

It will be apparent to one skilled in the art that the gp41-specific antibody, antigen binding fragment, conjugate, or nucleic acid molecule encoding such molecules, or a composition including such molecules can also be administered by other modes. Determination of the most effective mode of administration is within the skill of the skilled artisan. The gp41-specific antibody, antigen binding fragment, conjugate, or nucleic acid molecule encoding such molecules, or a composition including such molecules can be administered as pharmaceutical formulations suitable for, e.g., oral (including buccal and sub-lingual), rectal, nasal, topical, pulmonary, vaginal or parenteral (including intramuscular, intraarterial, intrathecal, subcutaneous and intravenous) administration, or in a form suitable for administration by inhalation or insufflation. Depending on the intended mode of administration, the pharmaceutical formulations can be in the form of solid, semi-solid or liquid dosage forms, such as tablets, suppositories, pills, capsules, powders, liquids, suspensions, emulsions, creams, ointments, lotions, and the like. The formulations can be provided in unit dosage form suitable for single administration of a precise dosage. The formulations comprise an effective amount of a therapeutic agent, and one or more pharmaceutically acceptable excipients, carriers and/or diluents, and optionally one or more other biologically active agents.

4. Compositions

Compositions are provided that include one or more of the gp41-specific antibody, antigen binding fragment, conjugate, or nucleic acid molecule encoding such molecules, that are disclosed herein in a carrier. The compositions are useful, for example, for example, for the treatment or detection of an HIV-1 infection. The compositions can be prepared in unit dosage forms for administration to a subject. The amount and timing of administration are at the discretion of the treating physician to achieve the desired purposes. The gp41-specific antibody, antigen binding fragment, conjugate, or nucleic acid molecule encoding such molecules can be formulated for systemic or local administration. In one example, the gp41-specific antibody, antigen binding fragment, conjugate, or nucleic acid molecule encoding such molecules, is formulated for parenteral administration, such as intravenous administration.

In some embodiments, the compositions comprise an antibody, antigen binding fragment, or conjugate thereof, in at least 70% (such as at least 75%, at least 80%, at least 85%, at least 90%, at least 95%, at least 96%, at least 97%, at least 98% or at least 99% purity. In certain embodiments, the compositions contain less than 10% (such as less than 5%, less than 4%, less than 3%, less than 2%, less than 1%, less than 0.5%, or even less) of macromolecular contaminants, such as other mammalian (e.g., human) proteins.

The compositions for administration comprises a solution of the gp41-specific antibody, antigen binding fragment, conjugate, or nucleic acid molecule encoding such molecules, dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical composition for intravenous administration includes about 0.01 to about 50 mg/kg of antibody or antigen binding fragment or conjugate per subject per day (or the corresponding dose of a conjugate including the antibody or antigen binding fragment). Actual methods for preparing administrable compositions will be known or apparent to those skilled in the art and are described in more detail in such publications as *Remington's Pharmaceutical Science*, 22th ed., Pharmaceutical Press, London, UK (2012). In some embodiments, the composition can be a liquid formulation including one or more antibodies, antigen binding fragments (such as an antibody or antigen binding fragment that specifically binds to gp41), in a concentration range from about 0.1 mg/ml to about 40 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

Antibodies, or an antigen binding fragment thereof or a conjugate or a nucleic acid encoding such molecules, can be provided in lyophilized form and rehydrated with sterile water before administration, although they are also provided in sterile solutions of known concentration. The antibody solution, or an antigen binding fragment or a nucleic acid encoding such antibodies or antigen binding fragments, can then be added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of Rituxan® in 1997. Antibodies, antigen binding fragments, conjugates, or a nucleic acid encoding such molecules, can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Controlled-release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

5. Methods of Detection and Diagnosis

Methods are also provided for the detection of the expression of gp41 in vitro or in vivo. In one example, expression of gp41 is detected in a biological sample, and can be used to detect HIV-1 infection as the presence of HIV-1 in a sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. The method of detection comprises contacting a cell or sample, or administering to a subject, an antibody or antigen binding fragment that specifically binds to gp41, or conjugate there of (e.g. a conjugate including a detectable marker) under conditions sufficient to form an immune complex, and detecting the immune complex (e.g., by detecting a detectable marker conjugated to the antibody or antigen binding fragment.

In several embodiments, a method is provided for detecting an HIV-1 infection in a subject. The disclosure provides a method for detecting HIV-1 in a biological sample, wherein the method comprises contacting a biological sample from a subject with a disclosed antibody or antigen binding fragment under conditions sufficient for formation of an immune complex, and detecting the immune complex, to detect the gp41 in the biological sample. In one example, the detection of gp41 in the sample indicates that the subject has an HIV-1 infection. In another example, detection of gp41 in the sample confirms a diagnosis of an HIV-1 infection in the subject.

In some embodiments, the disclosed antibodies or antigen binding fragments thereof are used to test vaccines. For example to test if a vaccine composition including gp41 assumes a conformation including the 10E8 epitope. Thus provided herein is a method for testing a vaccine, wherein the method comprises contacting a sample containing the vaccine, such as a HIV-1 Env immunogen, with a disclosed antibody or antigen binding fragment under conditions sufficient for formation of an immune complex, and detecting the immune complex, to detect the vaccine with an HIV-1 immunogen including the 10E8 epitope in the sample. In one example, the detection of the immune complex in the sample indicates that vaccine component, such as a HIV-1 Env immunogen assumes a conformation capable of binding the antibody or antigen binding fragment.

In one embodiment, the antibody or antigen binding fragment is directly labeled with a detectable marker. In another embodiment, the antibody that binds HIV-1 Env (the first antibody) is unlabeled and a second antibody or other molecule that can bind the antibody that binds the first antibody is utilized for detection. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody, antigen binding fragment or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

E. Kits

Kits are also provided. For example, kits for treating a subject with an HIV-1 infection, or for detecting gp41 in a sample or in a subject. The kits will typically include a disclosed gp41-specific antibody, antigen binding fragment, conjugate, or nucleic acid molecule encoding such molecules, or compositions including such molecules. More than one of the disclosed gp41-specific antibody, antigen binding fragment, conjugate, or nucleic acid molecule encoding such molecules, or compositions including such molecules can be included in the kit.

In one embodiment, the kit is a diagnostic kit and comprises an immunoassay. Although the details of the immunoassays may vary with the particular format employed, the method of detecting gp41 in a biological sample generally includes the steps of contacting the biological sample with an antibody which specifically reacts, under conditions sufficient to form an immune complex, to gp41. The antibody is allowed to specifically bind under immunologically reactive conditions to form an immune complex, and the presence of the immune complex (bound antibody) is detected directly or indirectly.

The kit comprises a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, or compositions. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of the antibodies, antigen binding fragments, conjugates, nucleic acid molecules, or compositions included in the kit. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

F. Additional Embodiments

Clause 1. An isolated monoclonal antibody or antigen binding fragment, comprising:

(A) a heavy chain variable region ($V_H$) comprising a heavy chain complementarity determining region (HCDR)1, a HCDR2, and a HCDR3 of the $V_H$ set forth as SEQ ID NO: 35 (10E8v4 S100cW), and a light chain variable region ($V_L$) comprising a light chain complementarity determining region (LCDR)1, a LCDR2, and a LCDR3 of the $V_L$ set forth as SEQ ID NO: 6 (rL3-6mut);

(B) a $V_H$ comprising a HCDR1, a HCDR2, and a HCDR3 of the variable region set forth as SEQ ID NO: 36 (10E8v4 DS), and a $V_L$ comprising a LCDR1, a LCDR2, and a LCDR3 of the variable region set forth as SEQ ID NO: 41 (rL3-6mut-DS); or (C) a $V_H$ comprising a HCDR1, a HCDR2, and a HCDR3 of the variable region set forth as SEQ ID NO: 37 (10E8v4 S100cW-DS), and a $V_L$ comprising a LCDR1, a LCDR2, and a LCDR3 of the variable region set forth as SEQ ID NO: 41 (rL3-6mut-DS); and wherein the monoclonal antibody or antigen binding fragment specifically binds to gp41 and neutralizes HIV-1.

Clause 2. The isolated monoclonal antibody or antigen binding fragment of clause 1, wherein the HCDR1, the HCDR2, the HCDR3, the LCDR1, the LCDR2, and the LCDR3 comprise the amino acid sequences set forth as:

SEQ ID NOs: 7, 8, 52, 10, 11, and 12 respectively (10E8v4/v5 S100cW IMGT CDRs);

SEQ ID NOs: 7, 8, 53, 55, 11, and 12 respectively (10E8v4/v5 DS IMGT CDRs); or

SEQ ID NOs: 7, 8, 54, 55, 5, and 6 respectively (10E8v4/v5 S100cW-DS IMGT CDRs).

Clause 3. The isolated monoclonal antibody or antigen binding fragment of clause 1, wherein the $V_H$ and $V_L$ comprise the amino acid sequences set forth as:

SEQ ID NOs: 35 and 6, respectively (10E8v4 S100cW);
SEQ ID NOs: 36 and 41, respectively (10E8v4 DS);
SEQ ID NOs: 37 and 41, respectively (10E8v4 S100cW-DS);
SEQ ID NOs: 38 and 6, respectively (10E8v5 S100cW);
SEQ ID NOs: 39 and 41, respectively (10E8v5 DS); or
SEQ ID NOs: 40 and 41, respectively (10E8v5 S100cW-DS).

Clause 4. An isolated monoclonal antibody or antigen binding fragment comprising:

(A) heavy and light chain variable regions comprising the amino acid sequences set forth as SEQ ID NOs: 5 and 6, respectively (10E8v4);

(B) heavy and light chain variable regions comprising the amino acid sequences set forth as SEQ ID NOs: 3 and 6, respectively (10E8v5);

wherein the monoclonal antibody or antigen binding fragment specifically binds to gp41 and neutralizes HIV-1.

Clause 5. The isolated antibody or antigen binding fragment of any of the prior clauses, wherein the LCDR1 further comprises an amino acid substitution of the serine residue at kabat position 32.

Clause 6. The isolated antibody or antigen binding fragment of clause 5, wherein the amino acid substitution is an Y32F substitution Clause 7. The isolated antibody or antigen binding fragment of clause 5, wherein the amino acid substitution is an Y32W substitution.

Clause 8. The isolated monoclonal antibody or antigen binding fragment of clause 5, wherein the HCDR1, the HCDR2, the HCDR3, the LCDR1, the LCDR2, and the LCDR3 comprise the amino acid sequences set forth as:

SEQ ID NOs: 7, 8, 9, 56, 11, and 12 respectively (10E8v4/v5 Y32W IMGT CDRs);

SEQ ID NOs: 7, 8, 52, 56, 11, and 12 respectively (10E8v4/v5 S100cW Y32W IMGT CDRs);

SEQ ID NOs: 7, 8, 53, 85, 11, and 12 respectively (10E8v4/v5 DS Y32W IMGT CDRs);

SEQ ID NOs: 7, 8, 54, 85, 5, and 6 respectively (10E8v4/v5 S100cW-DS Y32W IMGT CDRs).

SEQ ID NOs: 7, 8, 52, 57, 11, and 12 respectively (10E8v4/v5 S100cW Y32F IMGT CDRs);

SEQ ID NOs: 7, 8, 53, 86, 11, and 12 respectively (10E8v4/v5 DS Y32F IMGT CDRs); or SEQ ID NOs: 7, 8, 54, 86, 5, and 6 respectively (10E8v4/v5 S100cW-DS Y32F IMGT CDRs).

Clause 9. The isolated monoclonal antibody or antigen binding fragment of clause 5, wherein the $V_H$ and $V_L$ comprise the amino acid sequences set forth as:

SEQ ID NOs: 5 and 41, respectively (10E8v4 Y32W);
SEQ ID NOs: 35 and 6, respectively (10E8v4 S100cW);
SEQ ID NOs: 36 and 41, respectively (10E8v4 DS);
SEQ ID NOs: 37 and 41, respectively (10E8v4 S100cW-DS);
SEQ ID NOs: 3 and 41, respectively (10E8v5 Y32W);
SEQ ID NOs: 38 and 6, respectively (10E8v5 S100cW Y32W);
SEQ ID NOs: 39 and 41, respectively (10E8v5 DS Y32W); or
SEQ ID NOs: 40 and 41, respectively (10E8v5 S100cW-DS Y32W).

Clause 10. The antibody or antigen binding fragment of any of the prior clauses, further comprising one or more gain of function amino acid substitutions listed in Table 3 or Table 4.

Clause 11. The isolated antibody or antigen binding fragment of any of the prior clauses, wherein the antibody or antigen binding fragment dissolves to a concentration of at least 5 mg/ml in phosphate buffered saline, pH 7.4, at 20° C.

Clause 12. The isolated antibody or antigen binding fragment of any of the prior clauses, wherein the antibody or antigen binding fragment neutralizes at least 95% of the viral strains listed in FIG. 16A with an $IC_{50}$ of 50 µg/ml or less.

Clause 13. The antibody or antigen binding fragment of any of the prior clauses, comprising human framework regions.

Clause 14. The antibody of any of the prior clauses, comprising a human constant region.

Clause 15. The antibody of any of the prior clauses, wherein the antibody is an IgG, IgM or IgA.

Clause 16. The antibody of any of the prior clauses, comprising a recombinant constant domain comprising a modification that increases binding to the neonatal Fc receptor.

Clause 17. The antibody of clause 16, wherein the antibody is an IgG1 and the modification that increases binding to the neonatal Fc receptor comprises M428L and N434S amino acid substitutions.

Clause 18. The antigen binding fragment of any of clauses 1-13.

Clause 19. The antigen binding fragment of clause 18, wherein the antigen binding fragment is a Fv, Fab, F(ab')$_2$, scFV or a scFV$_2$ fragment.

Clause 20. A bispecific antibody comprising the isolated human monoclonal antibody or antigen binding fragment of any of the preceding clauses.

Clause 21. The bispecific antibody of clause 20, wherein the antibody specifically binds to gp41 and to CD3.

Clause 22. The antibody or antigen binding fragment of any of the prior clauses, linked to an effector molecule or a detectable marker Clause 23. The antibody or antigen binding fragment of clause 22, wherein the detectable marker is a fluorescent, enzymatic, or radioactive marker.

Clause 24. An isolated nucleic acid molecule encoding the antibody or antigen binding fragment of any of clauses 1-21.

Clause 25. An isolated nucleic acid molecule encoding the $V_H$, the $V_L$, or the $V_H$ and $V_L$, of the antibody or antigen binding fragment of any of clauses 1-21.

Clause 26. The nucleic acid molecule of any of clauses 21-24, wherein the $V_H$ of the antibody or antigen binding fragment comprises the nucleic acid sequence set forth as SEQ ID NO: 44;

the $V_H$ of the antibody or antigen binding fragment comprises the nucleic acid sequence set forth as SEQ ID NO: 45;

the $V_L$ of the antibody or antigen binding fragment comprises the nucleic acid sequence set forth as SEQ ID NO: 47;

the $V_H$ and the $V_L$ of the antibody or antigen binding fragment comprise the nucleic acid sequence set forth as SEQ ID NOs: 44 and 47, respectively; or the $V_H$ and the $V_L$ of the antibody or antigen binding fragment comprise the nucleic acid sequence set forth as SEQ ID NOs: 45 and 47, respectively Clause 27. The nucleic acid molecule of any of clauses 24-26, operably linked to a promoter.

Clause 28. An expression vector comprising the nucleic acid molecule of any of clauses 24-27.

Clause 29. The expression vector of clause 28, wherein the expression vector is a viral vector.

Clause 30. The expression vector of clause 29, wherein the viral vector is an adeno-associated viral vector.

Clause 31. A host cell comprising the nucleic acid molecule of clause 27, particularly wherein the host cell is a eukaryotic host cell such as a human host cell.

Clause 32. A pharmaceutical composition for use in treating an HIV-1 infection, comprising:

a therapeutically effective amount of the antibody, antigen binding fragment, nucleic acid molecule, or expression vector of any of clauses 1-21; and a pharmaceutically acceptable carrier.

Clause 33. A method of producing an antibody or antigen binding fragment that specifically binds to gp41, comprising:

incubating the host cell of clause 31 under in vitro conditions sufficient for expression of the nucleic acid molecule or expression vector to produce the antibody or antigen binding fragment; and purifying the antibody or antigen binding fragment.

Clause 34. A method of detecting an HIV-1 infection in a subject, comprising:

contacting a biological sample from the subject with the antibody or antigen binding fragment of any of clauses 1-23 under conditions sufficient to form an immune complex; and detecting the presence of the immune complex on the sample, wherein the presence of the immune complex on the sample indicates that the subject has the HIV-1 infection.

Clause 35. A method of inhibiting or treating an HIV-1 infection in a subject, comprising administering to the subject a therapeutically effective amount of the antibody, antigen binding fragment, nucleic acid molecule, or expression vector of any of clauses 1-30, thereby preventing or treating the HIV-1 infection.

Clause 36. The method of clause 35, wherein the subject is at risk of an HIV-1 infection.

Clause 37. The method of clause 35, wherein the subject has an HIV-infection

Clause 38. The method of clause 37, wherein the subject has AIDS.

Clause 39. The method of any of clauses 35-38, further comprising administering to the subject an additional antibody, antigen binding fragment, or nucleic acid encoding the additional antibody or antigen binding fragment, wherein the additional antibody or antigen binding fragment specifically binds to HIV-1 Env and neutralizes HIV-1 infection.

Clause 40. The method of clause 39, wherein the additional antibody is a VRC01-class antibody.

Clause 41. The method of clause 40, wherein the VRC01-class antibody is VRC01 or VRC07-523.

Clause 42. Use of the antibody, antigen binding fragment, nucleic acid molecule, expression vector, or pharmaceutical composition of any of clauses 1-30 or 32 to inhibit or treat HIV-1 infection in a subject.

III. EXAMPLES

The following examples are provided to illustrate particular features of certain embodiments, but the scope of the claims should not be limited to those features exemplified.

Example 1

Optimized 10E8 Antibodies

This example illustrates identification of modified 10E8 antibodies that have an improved combination of neutralization, solubility, and auto-reactivity properties compared to the parent 10E8 antibody.

The broadly neutralizing antibody 10E8 was isolated from the HIV-1-infected donor N152, and recognizes a helix in the membrane-proximal external region (MPER) just prior to the transmembrane-spanning region of the HIV-1 gp41 glycoprotein. 10E8 neutralizes 98% of diverse HIV-1 isolates with a 50% inhibitory concentration ($IC_{50}$) of approximately 0.32μ/ml, which is substantially more potent and broad than other antibodies that bind the MPER of gp41, such as the 2F5 and 4E10 antibodies. See Huang et al. (*Nature*, 491: 406-412, 2012) for a description of the 10E8 antibody.

Prior efforts to improve the neutralization properties of the 10E8 antibody identified the serine residue at kabat position 74 of the 10E8 $V_H$ as a potential site of mutation (see U.S. Pub. 2014/0348785A1, FIG. 44). For example, a 10E8 antibody with a S74W substitution improved 10E8 neutralization 3-5 fold (see U.S. Pub. 2014/0348785A1, FIG. 45). However, when the S74W substitution was incorporated into the HC6 $V_H$ (discussed below) and paired with 10E8 $V_L$, the resulting antibody was autoreactive by cardiolipin antibody assay (see U.S. Pub. 2014/0348785A1, FIG. 56), indicating that antibodies with this substitution may not be optimal for therapeutic use.

Many clonal variants of the 10E8 heavy and light chains were identified by next generation sequencing of donor N152 samples and assessed for function by pairing with the complementary wild-type 10E8 chain (see pages 104-107 and FIGS. 50-52 of U.S. Pub. 2014/0348785A1). Among the many identified clonal variants were the HC6 $V_H$ (referred to as gVRC-H2$_{dN152}$ and provided as SEQ ID NO: 154 in U.S. Pub. 2014/0348785A1), the H6 V$_H$ (referred to as gVRC-H6$_{dN152}$ and provided as SEQ ID NO: 158 in U.S. Pub. 2014/0348785A1), the H8 V$_H$ (referred to as gVRC-H8$_{dN152}$ and provided as SEQ ID NO: 160 in U.S. Pub. 2014/0348785A1), the L10 V$_L$ (referred to as gVRC-L10$_{dN152}$ and provided as SEQ ID NO: 173 in U.S. Pub. 2014/0348785A1) and the L19 V$_L$ (referred to as gVRC-L19$_{dN152}$ and provided as SEQ ID NO: 192 in U.S. Pub. 2014/0348785A1).

Additional modifications of the 10E8 antibody V$_H$ were made to generate the HC6-S74Y V$_H$ (provided as SEQ ID NO: 192 in U.S. Pub. 2014/0348785A1), and HC6-S74Y-511 V$_H$ (referred to as HC6_S77Y_hp_L02 and provided as SEQ ID NO: 201 in U.S. Pub. 2014/0348785A1). Modifications of the 10E8 antibody V$_L$ were made to generate the rL3 V$_L$ (referred to as "L3," or "10E8gL03" and provided as SEQ ID NO: 152 in U.S. Pub. 2014/0348785A1).

Despite the improvements to the 10E8 antibody described above, additional 10E8 variants that are highly soluble, lack auto-reactivity, and retain (or improve) the neutralization capability of wild-type 10E8 are needed.

Figure 1D:
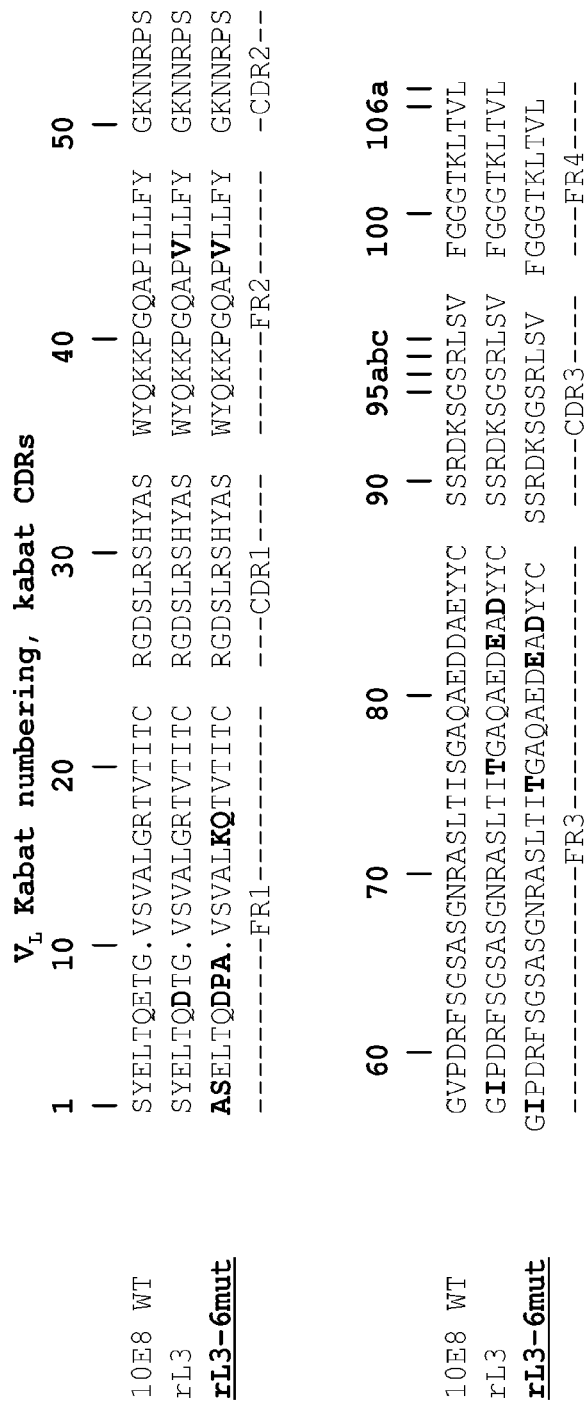

The amino acid sequences of the above antibody V$_H$ and V$_L$ domains are provided in FIGS. 1A-1E. FIGS. 1A and 1B show the CDRs of these heavy and light chain variable regions by IMGT positioning, and FIGS. 1C and 1D show the CDRs of these heavy and light chain variable regions by kabat positioning. The amino acid sequences of the heavy and light chain variable regions discussed in this example are set forth in Table 2.

TABLE 2

10E8 variant sequences

| V$_H$ | |
|---|---|
| 10E8 | SEQ ID NO: 1 |
| H6 | SEQ ID NO: 14 |
| H8 | SEQ ID NO: 16 |
| HC6-S74Y | SEQ ID NO: 13 |
| HC6-S74Y-511 | SEQ ID NO: 3 |
| H6-511 | SEQ ID NO: 15 |
| H8-511 | SEQ ID NO: 17 |
| H6-511-4mut | SEQ ID NO: 5 |
| V$_L$ | |
| 10E8 | SEQ ID NO: 1 |
| L10 | SEQ ID NO: 18 |
| L19 | SEQ ID NO: 19 |
| rL3 | SEQ ID NO: 4 |
| rL3-6mut | SEQ ID NO: 6 |

The modified 10E8 antibodies were produced substantially as previously described (see, e.g., Wu et al., Science, 333(6049):1593-1602, 2011 and Zhu et al., Front Microbiol 3(2012):315, 2012). Briefly, antibodies were expressed by co-transfection of Expi293F cells with equal amount of the paired heavy and light chain plasmids and purified using a recombinant protein-A column (GE Healthcare). Unless context indicates otherwise, all antibody assays described in the examples utilizing variant 10E8 antibodies (having one or more amino acid substitutions in the variable regions) that were in the IgG format and were produced as discussed above.

Figure 2:
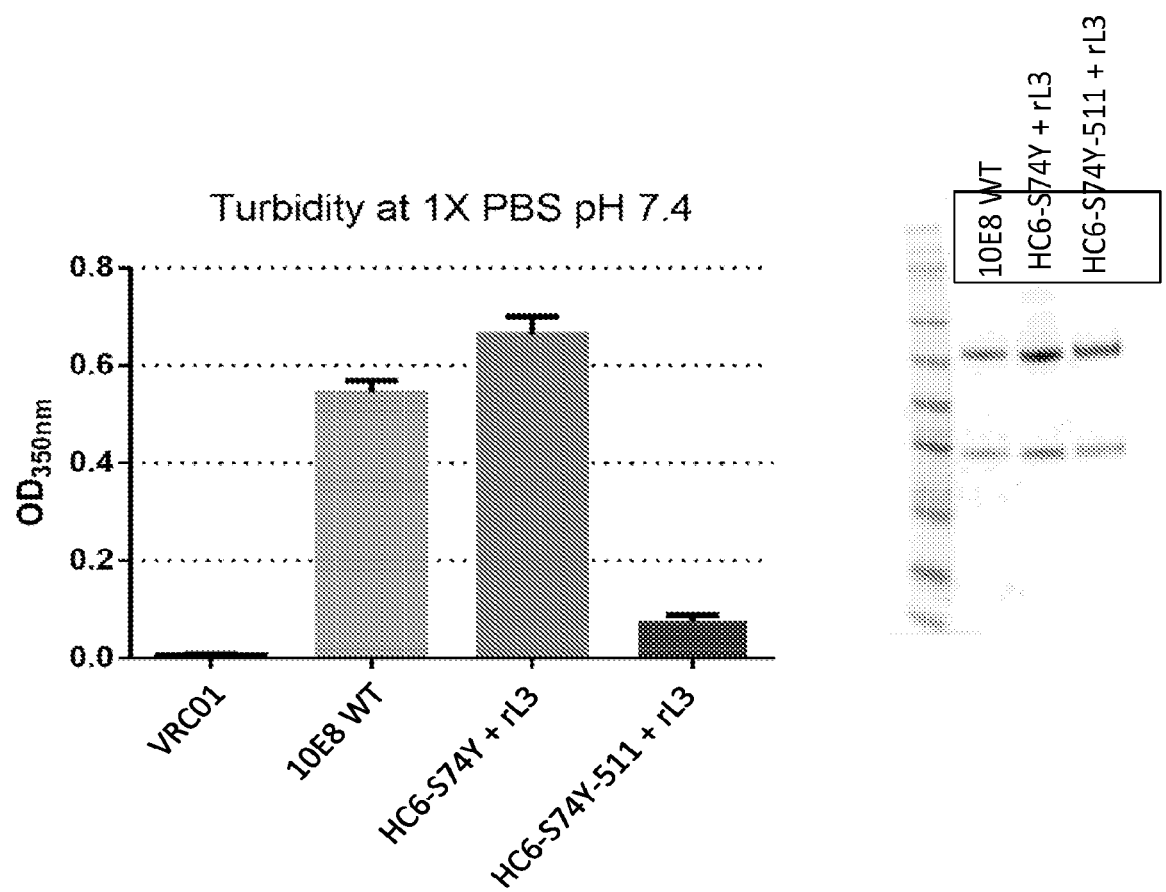
FIG. 2 is a graph and an image of a coommassie blue stained gel illustrating the turbidity (as measured at OD350) in phosphate buffered saline of the 10E8 antibody and 10E8 variants including the HC6-S74Y $V_H$ and the rL3 $V_L$, or the HC6-S74Y-511 $V_H$ and the rL3 $V_L$. The highly soluble VRC01 antibody was used as a control.

One method for assessing antibody solubility is to examine the turbidity of a solution containing the antibody by measuring the optical density OD of the solution at 350 nm. Accordingly, the turbidity of solutions containing the 10E8 antibody, an antibody including the HC6-S74Y V$_H$ and the rL3 V$_L$, an antibody including the HC6-S74Y-511 V$_H$ and the rL3 V$_L$, or the VRC01 antibody (which is highly soluble in aqueous solution) was determined by measuring the OD350 of the antibody solution. Briefly, the antibodies were expressed in mammalian cells and the resulting supernatant was passed over a Protein A column. The column was washed, and bound antibody was eluted from the column using Elution Buffer (10 mM Glycine, pH 2.7) that dripped into a collection tube continuing neutralization buffer of 1M Tris-HCl, pH 8.5. As shown in FIG. 2, eluate containing the 10E8 antibody or the HC6-S74Y/rL3 antibody exhibited substantially higher OD350 readings (indicating increased turbidity) compared to the VRC01 antibody. This finding indicated that these two antibodies are prone to aggregation and less soluble than the VRC01 antibody. However, the HC6-S74Y-511/rL3 antibody was significantly less turbid (that is, more soluble) than the 10E8 and HC6-S74Y/rL3 antibodies as determined by OD350 (FIG. 2), and was nearly as effective at neutralizing HIV-1 (FIG. 3).

Figure 4:
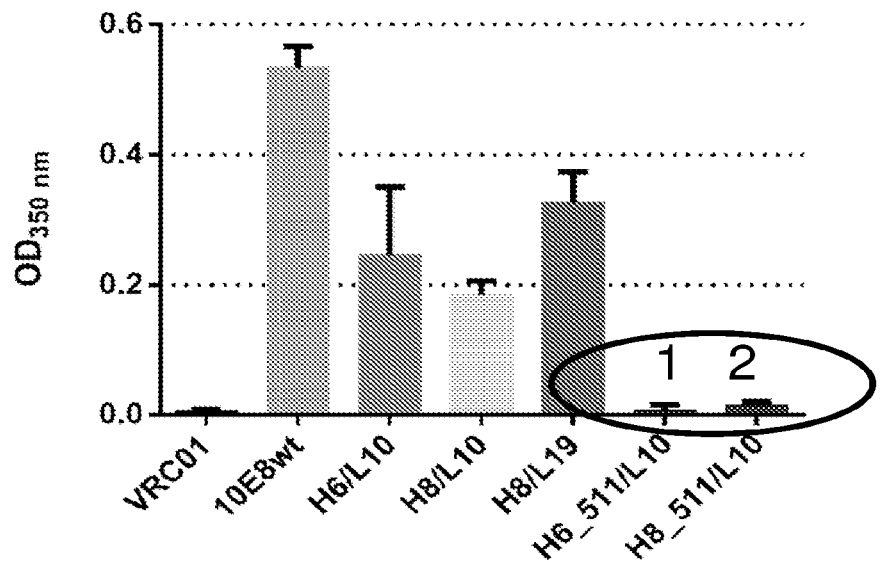
FIG. 4A is a graph illustrating the turbidity (as measured at OD350) in phosphate buffered saline of the 10E8 antibody and 10E8 variants including the H6 $V_H$ and the L10 $V_L$, the H8 $V_H$ and the L10 $V_L$, the H8 $V_H$ and the L19 $V_L$, the H6-511 $V_H$ and the L10 $V_L$, or the H8-511 $V_H$ and the L10 $V_L$. The highly soluble VRC01 antibody was used as a control.
FIG. 4B is a table illustrating neutralization of a representative panel of HIV-1 pseudoviruses by the 10E8 antibody, and 10E8 variants including the H6-511 $V_H$ and the L10 $V_L$, or the H8-511 $V_H$ and the L10 $V_L$. Neutralization was determined using the TZM-b1 cell pseudovirus neutralization assay; $IC_{50}$ values are shown.

Additional heavy and light chain combinations were tested using the turbidity assay as a screen for solubility (FIG. 4). As shown in FIG. 4, antibodies including combinations of the H8 V$_H$ and L10 V$_L$ or L19 V$_L$, or the H6 V$_H$ and L10 V$_L$ all exhibited improved solubility as determined by turbidity at OD350 compared to the unmodified 10E8 antibody.

To further improve the solubility of the H6- and H8-based antibodies, the L72, I75, and F77 residues of the V$_H$ were targeted for substitution with more hydrophilic amino acids. These residues are located within a hydrophobic patch of the 10E8 V$_H$ (identified from the structure of 10E8/MPER complex, described in Huang et al., Nature, 491: 406-412, 2012). As shown in FIG. 4A, antibodies including the H8-511 V$_H$ and the L10 V$_L$, or the H6-511 V$_H$ and the L10 V$_L$ exhibited greatly improved solubility compared to the unmodified 10E8 antibody, or modified 10E8 antibodies including the H6/L10, H8/L10, or H8/L19 variable regions as determined by turbidity at OD350. However, combinations of the H8-511 V$_H$ and L10 V$_L$, or the H6-511 V$_H$ and L10 V$_L$ were each approximately 10-fold less effective for neutralization of HIV-1 viral strains (FIG. 4B). The hydrophilic substitutions were expected to reduce the overall hydrophobicity and increase solubility of the H6 and H8 V$_H$ domains, but the dramatic reduction in neutralization potency and breadth was unexpected.

Figure 5:
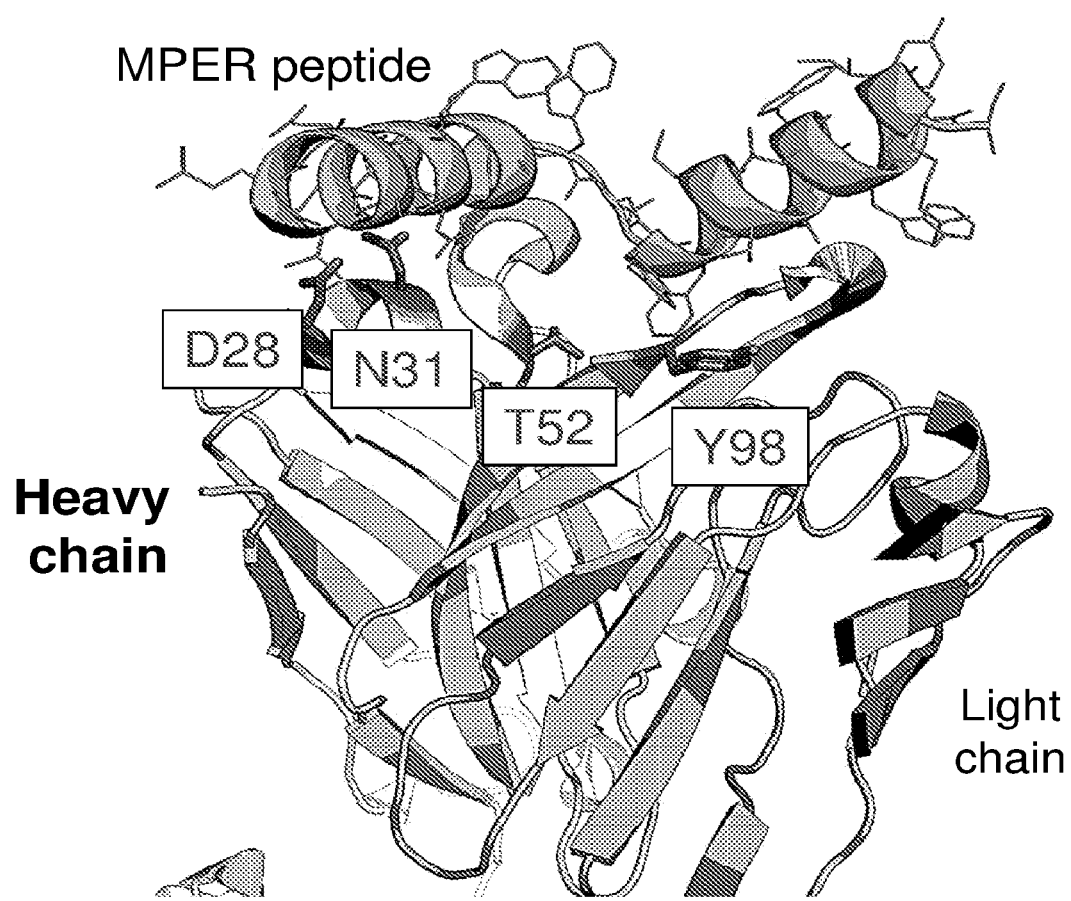
FIG. 5 is a ribbon diagram illustrating a portion of the structure of the 10E8 antibody bound to the MPER peptide. The "4mut" residues D28, N31, T52, and Y98 (kabat numbering) of the heavy chain variable domain are highlighted.
Figure 6:
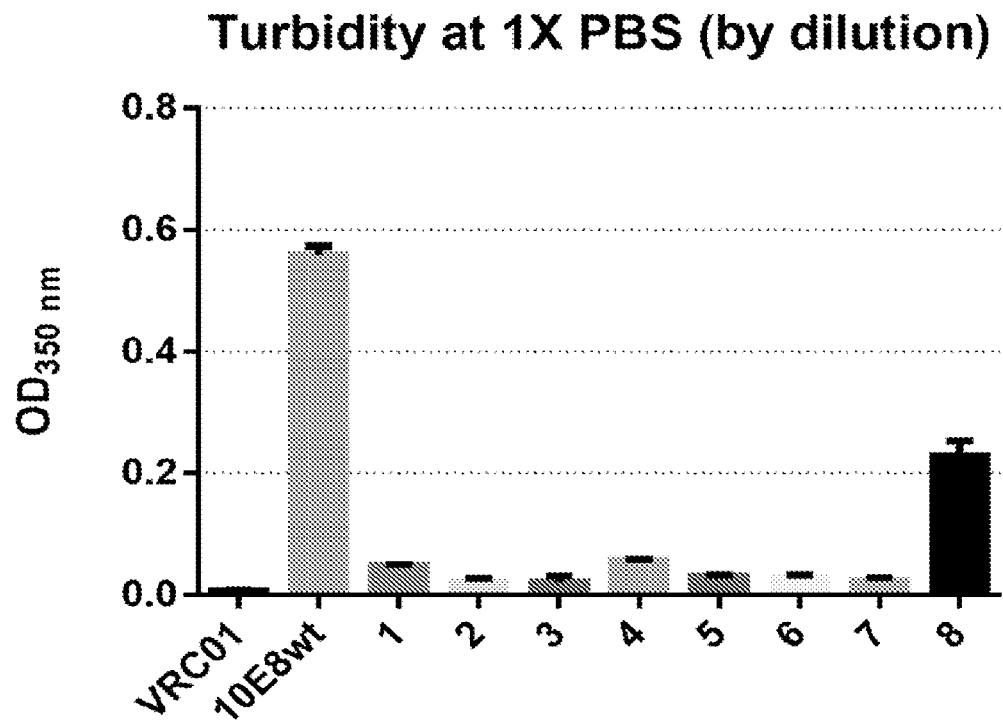
FIG. 6 is a graph illustrating the turbidity (as measured at OD350) in phosphate buffered saline of the 10E8 antibody and the indicated 10E8 variants. The highly soluble VRC01 antibody was used as a control.

Additional modifications of the H6-511 V$_H$ was engineered in an attempt to improve HIV-1 neutralization, without a corresponding reduction in antibody solubility. As shown in FIG. 5, residues at kabat positions 28, 31, 52, and 98 are located near the epitope binding region of 10E8. In the H6-511 V$_H$ kabat positions 28, 31, 52, and 98 are occupied by asparagine, aspartate, serine, and histidine residues, respectively. In contrast, in the HC6 V$_H$ (which is strongly neutralizing when paired with the rL3 V$_L$), kabat positions 28, 31, 52, and 98 are occupied by aspartate, asparagine, threonine, and tyrosine residues, respectively. Various combinations of kabat positions 28, 31, 52, and 98 from H6-511 V$_H$ were substituted with the corresponding residues from the HC6 V$_H$ to generate a series of mutant V$_H$ domains that were paired with the rL3 V$_L$ and tested for solubility and neutralization. As shown in FIG. 6, all the mutants exhibited improved solubility as determined by turbidity at OD350 compared to the unmodified 10E8 antibody. Further, one of the modified antibodies, H6-511-4mut (No. 7, which includes H98Y, N28D, D31N, S52T substitutions compared to H6-511) broadly neutralized HIV-1 viral strains (FIG. 7). Compared to wild-type 10E8 V$_H$, the H6-511-4mut $V_H$ includes Q3R, A61E, P62S, E64K, L72D, S74T, I75K, F77T, L(82C)V, M84T, S87T, Y98H, R105Q, and T110I substitutions.

Figure 8:
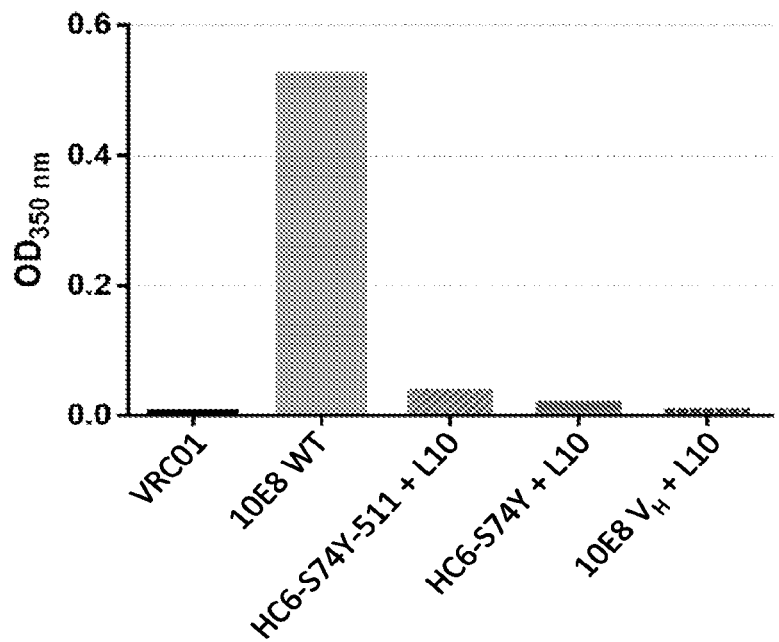
FIG. 8 is a graph illustrating the turbidity (as measured at OD350) in phosphate buffered saline of the 10E8 antibody and the 10E8 variants including the HC6-S74Y-511 $V_H$ and the L10 $V_L$, the HC6-S74Y $V_H$ and the L10 $V_L$, or the 10E8 $V_H$ and the L10 $V_L$. The highly soluble VRC01 antibody was used as a control.

As shown in FIG. 8, the modified 10E8 antibodies including the L10 $V_L$ were identified as highly soluble (compare unmodified 10E8 to 10E8H/L10). However, modified 10E8 antibodies including the L10 $V_L$ lack the broadly neutralizing properties of the parent 10E8 antibody (FIG. 4B). In contrast, the modified 10E8 antibodies including the rL3 $V_L$ paired with the 10E8 $V_H$ are broad and potent neutralizers of HIV-1 infection, but are not as soluble as antibodies including the L10 $V_L$.

Figure 1F:
Figure 9:
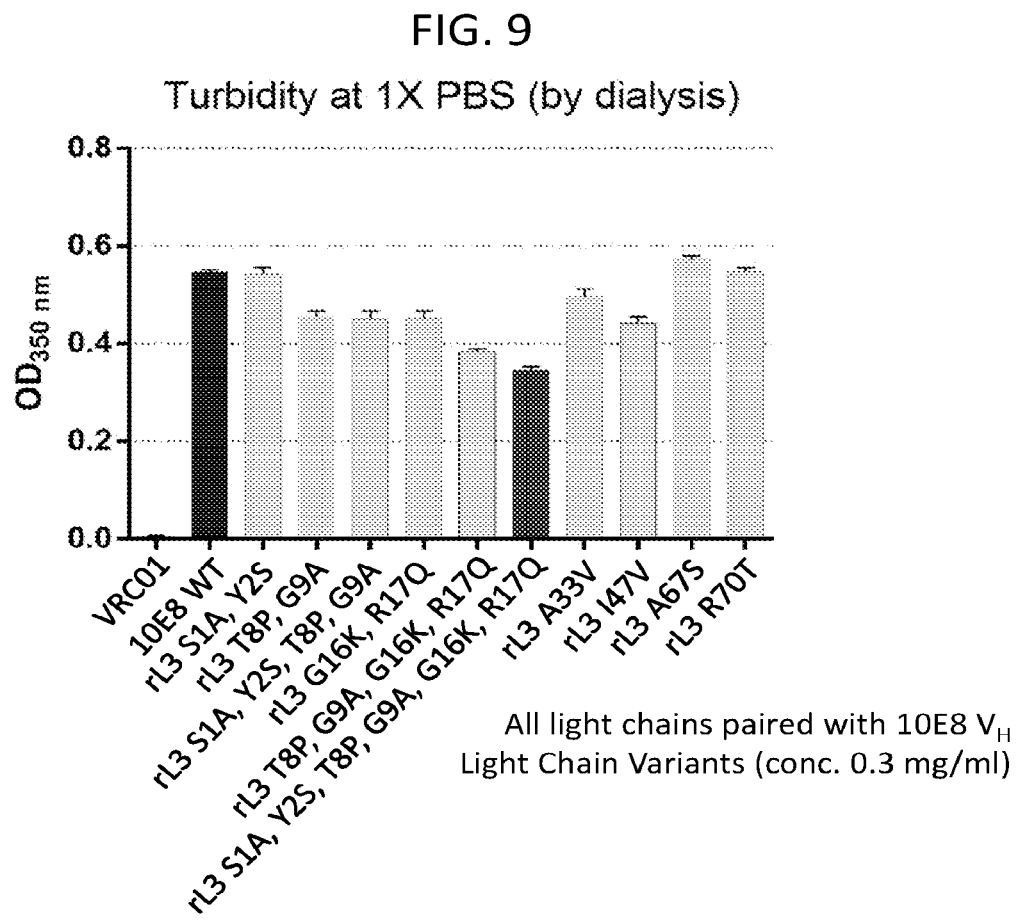
FIG. 9 is a graph illustrating the turbidity (as measured at OD350) in phosphate buffered saline of the 10E8 antibody and 10E8 variants including the 10E8 $V_H$ paired with the indicated $V_L$ domains. The rL3 $V_L$ with S1A, Y2S, T8P, G9A, G16K, R17Q substitutions ("rL3-6mut") paired with the 10E8 $V_H$ had the least turbidity of the 10E8 variants. The highly soluble VRC01 antibody was used as a control.

Accordingly, screening assays were performed to determine if a modified $V_L$ could be generated with the HIV-1 neutralizing properties of the rL3 $V_L$, and the solubility of the L10 $V_L$. The L10 $V_L$ and the rL3 $V_L$ differ in sequence at 12 positions (see FIG. 1). Antibodies with substitutions at each of these positions were screened for solubility and neutralization properties. As shown in FIG. 9, an antibody solution containing a modified 10E8 antibody including the 10E8 $V_H$ paired with rL3 $V_L$ with S1A, Y2S, T8P, G9A, G16K, and R17Q substitutions was substantially less turbid than corresponding 10E8 WT or other rL3 variants. The rL3 $V_L$ variant with S1A, Y2S, T8P, G9A, G16K, and R17Q substitutions was termed "rL3-6mut" and includes S1A, Y2S, E7D, T8P, G9A, G16K, R17Q, I45V, V58I, S76T, D83E, and E85D substitutions compared to the native 10E8 $V_L$.

Figure 10:
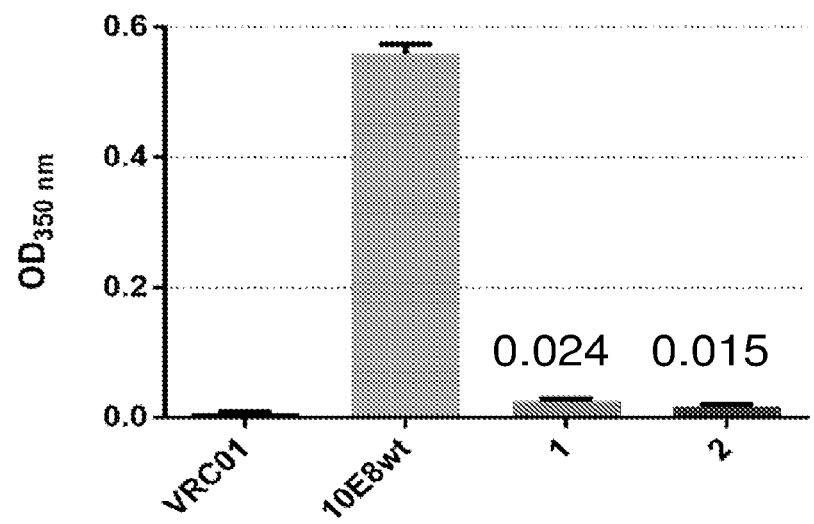
FIG. 10 is a graph illustrating the turbidity (as measured at OD350) in phosphate buffered saline of the 10E8 antibody and the 10E8 variants including the H6-511-4mut $V_H$ and the rL3 $V_L$, or the H6-511-4mut $V_H$ and the rL3-6mut $V_L$. The highly soluble VRC01 antibody was used as a control.

An antibody including the H6-511-4mut $V_H$ paired with the rL3-6mut $V_L$ was substantially more soluble (as measured using the turbidity assay) than 10E8 wt antibody or the H6-511-4mut/rL3 antibody (FIG. 10). Further, each of the H6-511-4mut $V_H$/rL3-6mut, and H6-511-4mut/rL3 antibodies neutralized HIV-1 with IC50 and IC80 values less than that of 10E8 wt (FIG. 11).

Figure 12:
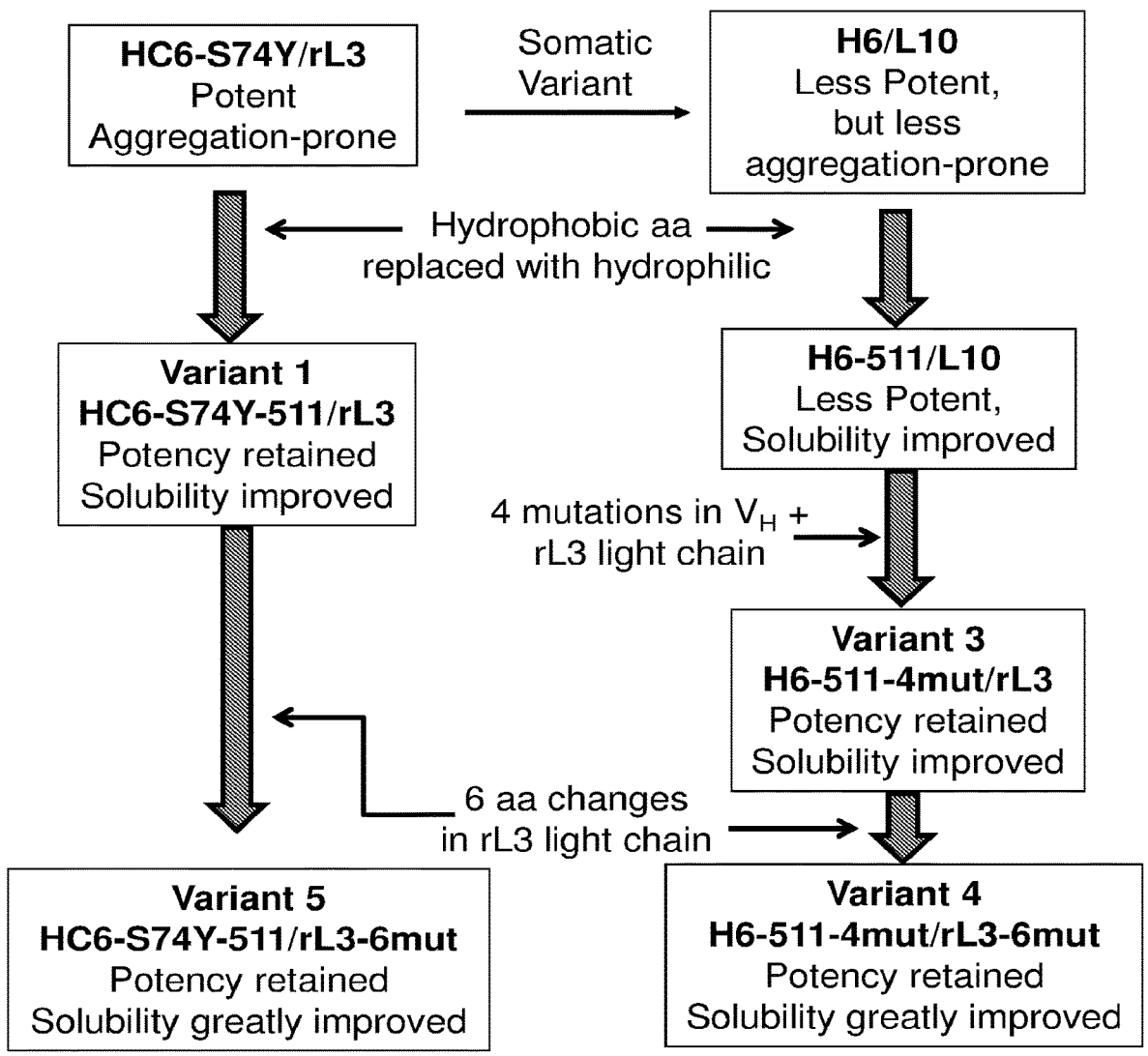
FIG. 12 is a flowchart illustrating the development of modified 10E8 antibodies.

FIG. 12 provides a summary of the development process for the HC6-S74Y-511/rL3 (Variant 1), H6-511-4mut/rL3-6mut (Variant 4), and HC6-S74Y-511/rL3-6mut (Variant 5) antibodies. The nomenclature, sequence, and substitutions compared to wild-type 10E8 for these variant antibodies is summarized in Table 3.

Additional assays were performed to further analyze the solubility, autoreactivity, and neutralization of the HC6-S74Y-511/rL3, H6-511-4mut/rL3-6mut, and HC6-S74Y-511/rL3-6mut antibodies (FIGS. 13-16).

Figure 13A:
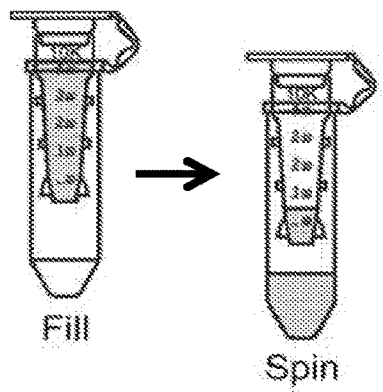
FIGS. 13A-13C illustrate the results of kinetic concentration assays of the 10E8 antibody or the 10E8 variants including the HC6-S74Y-511 $V_H$ and the rL3 $V_L$, the HC6-S74Y-511 $V_H$ and the rL3, or the H6-511-4mut and the rL3-6mut $V_L$. Three milliliters of the indicated antibodies (OD 0.35) were concentrated using a centrifugal concentrator (FIG. 13A) and the volume (FIG. 13B) and protein concentration (FIG. 13C, OD280) of resulting concentrate was measured.
Figure 13B:
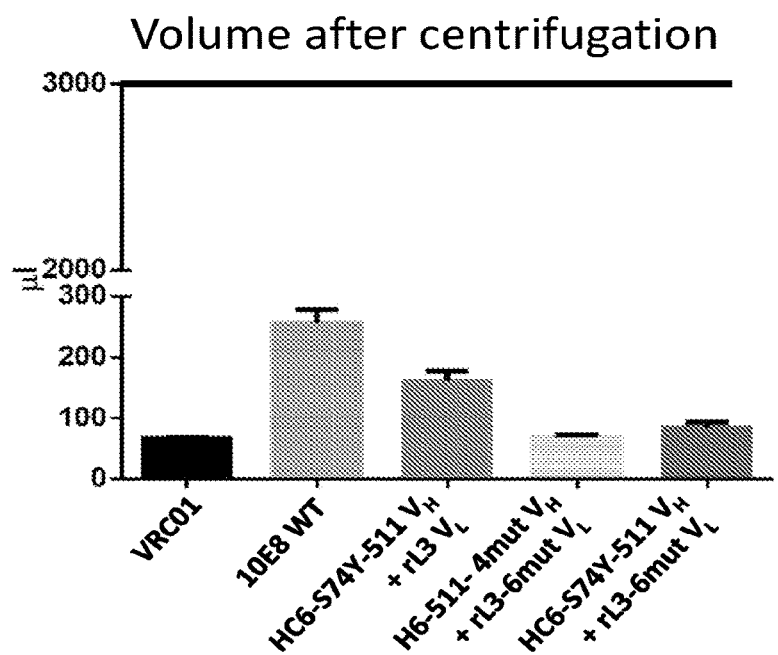
Figure 13C:
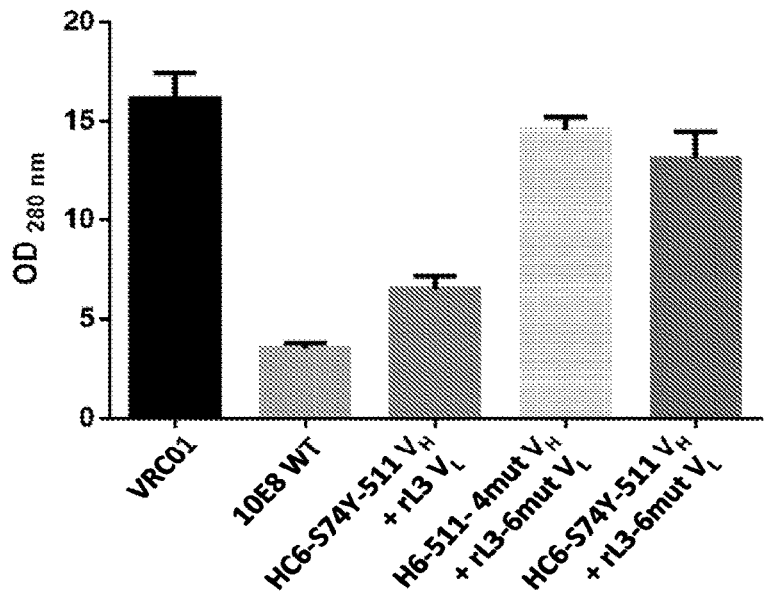

Kinetic concentration. A kinetic concentration assay was performed to assess solubility of the HC6-S74Y-511/rL3, H6-511-4mut/rL3-6mut, and HC6-S74Y-511/rL3-6mut antibodies. Three milliliters (conc. 0.35 OD) of each variant in phosphate buffered saline, pH 7.4 was loaded into a centrifugal concentrator with a molecule weight cut-off of 30,000 daltons, and centrifuged at 4000 g for 20 minutes (FIG. 13A). After centrifugation, the volume of each of the modified antibodies was less than that of wild-type 10E8, with the volume of the H6-511-4mut/rL3-6mut and HC6-S74Y-511/rL3-6mut antibodies substantially less than that of the 10E8 antibody (FIG. 13B). A significant increase in the protein concentrations of the H6-511-4mut/rL3-6mut and HC6-S74Y-511/rL3-6mut antibody solutions was also observed (FIG. 13C).

Dynamic Light Scattering. The HC6-S74Y-511/rL3, H6-511-4mut/rL3-6mut, and HC6-S74Y-511/rL3-6mut antibodies were assessed by dynamic light scattering. Dynamic light scattering is useful technique for determine the heterogeneity of the size of polymers dissolved in a solution. A monodisperse solution is one containing dissolved polymers (proteins) that are of equal size. A polydisperse solution contains polymers of varying size. In the case of a protein solution containing a protein that aggregates, the dynamic light scattering assay will identify a polydisperse solution. As shown in FIG. 14, antibody solution containing wild-type 10E8 is polydisperse, whereas antibody solutions containing the HC6-S74Y-511/rL3, H6-511-4mut/rL3-6mut, or HC6-S74Y-511/rL3-6mut antibody were monodisperse. This finding shows that these variant antibodies do not aggregate in solution.

Figure 15:
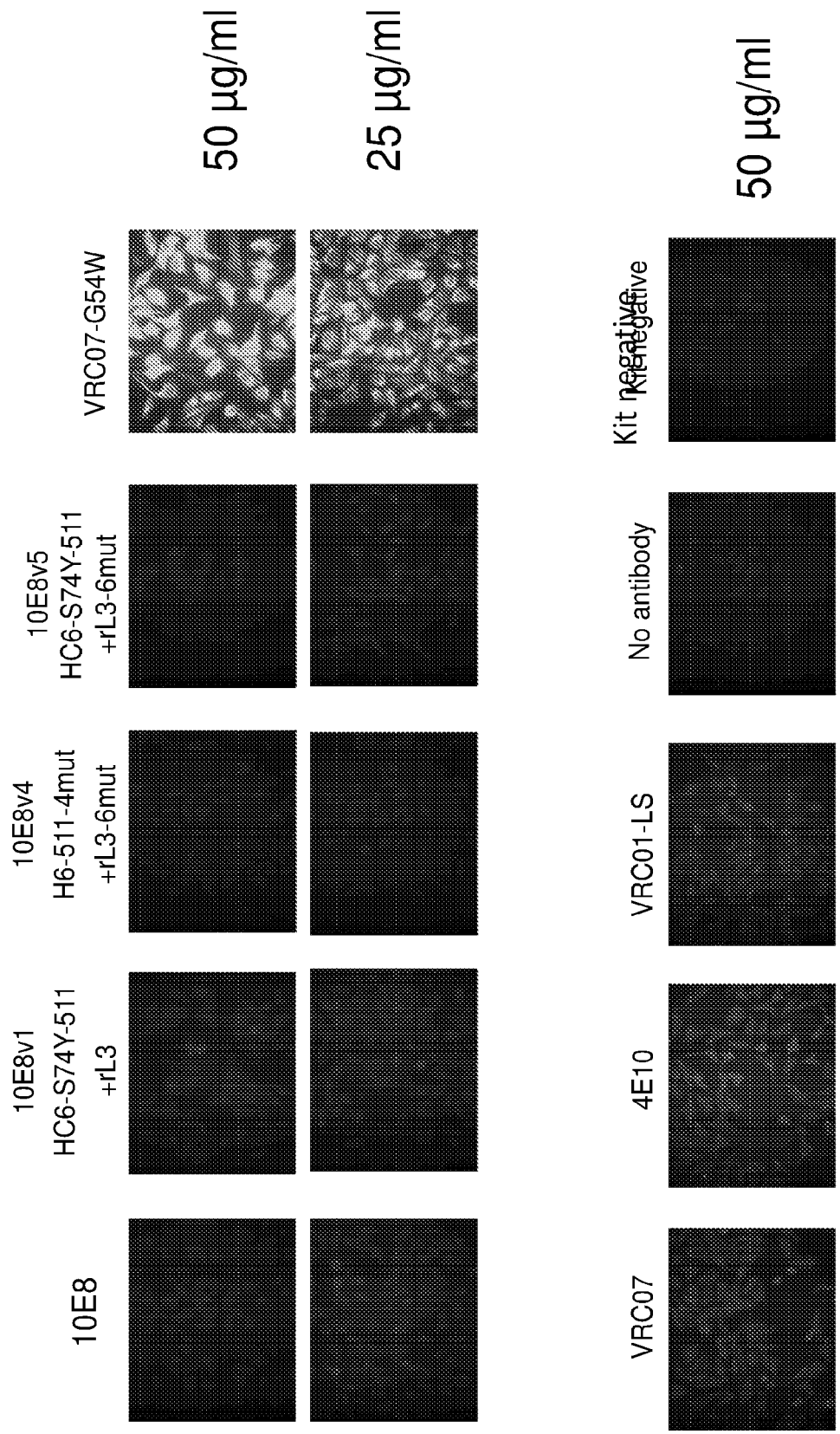
FIG. 15 is a set of immunofluorescence images illustrating that the 10E8 antibody and the 10E8 variants including the HC6-S74Y-511 $V_H$ and the rL3 $V_L$, the HC6-S74Y-511 $V_H$ and the rL3-6mut $V_L$, or the H6-511-4mut and the rL3-6mut $V_L$ are not autoreactive. Reactivity to HIV-1 negative human epithelial (HEp-2) cells was determined by indirect immunofluorescence.

Autoreactivity. A property common to the previously characterized MPER mAbs 2F5 and 4E10 is that they cross-react with self-antigens, and consequently are known to bind to self antigens present on HIV-1 naive HEp-2 cells (Haynes et al., *Science* 308, 1906-1908, 2005; Huang et al., *Nature,* 491: 406-412, 2012). Accordingly, the auto-reactivity of the HC6-S74Y-511/rL3, H6-511-4mut/rL3-6mut, and HC6-S74Y-511/rL3-6mut antibodies was tested by HEp-2 cell straining. Reactivity to HIV-1 negative human epithelial (HEp-2) cells was determined by indirect immunofluorescence on slides using Evans Blue as a counterstain and FITC-conjugated goat anti-human IgG (Zeus Scientific) substantially as previously described (Haynes et al., Science, 308(5730):1906-1908, 2005). As shown in FIG. 15, the HC6-S74Y-511/rL3, H6-511-4mut/rL3-6mut, and HC6-S74Y-511/rL3-6mut antibodies showed little to no staining of the HEp-2 cells compared to the know autoreactive antibody VRC07-G54W. Less staining intensity was observed for the H6-511-4mut/rL3-6mut and HC6-S74Y-511/rL3-6mut antibodies than the HC6-S74Y-511/rL3 antibody.

Neutralization. To further assess the neutralizing breadth and potency of the HC6-S74Y-511/rL3, H6-511-4mut/rL3-6mut, and HC6-S74Y-511/rL3-6mut antibodies, these antibodies were tested on a large panel of 200 HIV-1 pseudoviruses using a previously described pseudovirus

TABLE 3

10E8 variants

| Antibody | Name | SEQ ID NO | Mutations compared to 10E8 $V_H$ or $V_L$ |
|---|---|---|---|
| Variant 1 | $V_H$ HC6-S74Y-511 | 3 | Q3R, V5A, L72D, S74Y, I75K, F77T, M84T, T110I |
|  | $V_L$ rL3 | 4 | E7D, I45V, V58I, S76T, D83E, E85D |
| Variant 4 | $V_H$ H6-511-4mut | 5 | Q3R, A61E, P62S, E64K, L72D, S74T, I75K, F77T, L82cV, M84T, S87T, L89Y, R105Q, T110I |
|  | $V_L$ rL3-6mut | 6 | S1A, Y2S, E7D, T8P, G9A, G16K, R17Q, I45V, V58I, S76T, D83E, E85D |
| Variant 5 | $V_H$ HC6-S74Y-511 | 3 | Q3R, V5A, L72D, S74Y, I75K, F77T, M84T, T110I |
|  | $V_L$ rL3-6mut | 6 | S1A, Y2S, E7D, T8P, G9A, G16K, R17Q, I45V, V58I, S76T, D83E, E85D | neutralization assay (see Wu et al., Science, 329(5993):856-861, 2010, incorporated by reference herein in its entirety). Briefly, monoclonal antibody was serially diluted five-fold with Dulbecco's modified Eagle medium 10% FCS (Gibco), and 10 µl was incubated with 40 µl of pseudovirus in a 96-well plate at 37° C. for 30 min. TZM-b1 cells were then added and plates were incubated for 48 h. Assays were then developed with a luciferase assay system (Promega), and the relative light units (RLU) were read on a luminometer (Perkin Elmer). HIV-1 Env pseudoviruses were generated by co-transfection of 293T cells with pSG3 delta Env backbone and a second plasmid that expressed HIV-1 Env at a ratio of 2:1. 72 h after transfection, supernatants containing pseudoviruses were harvested and frozen at −80° C. until further use. Neutralization curves were fit by nonlinear regression using a five-parameter hill slope equation as described. The $IC_{50}$ and $IC_{80}$ values were reported as the antibody concentrations required to inhibit infection by 50% or 80%, respectively.

Figures 16F, 17:
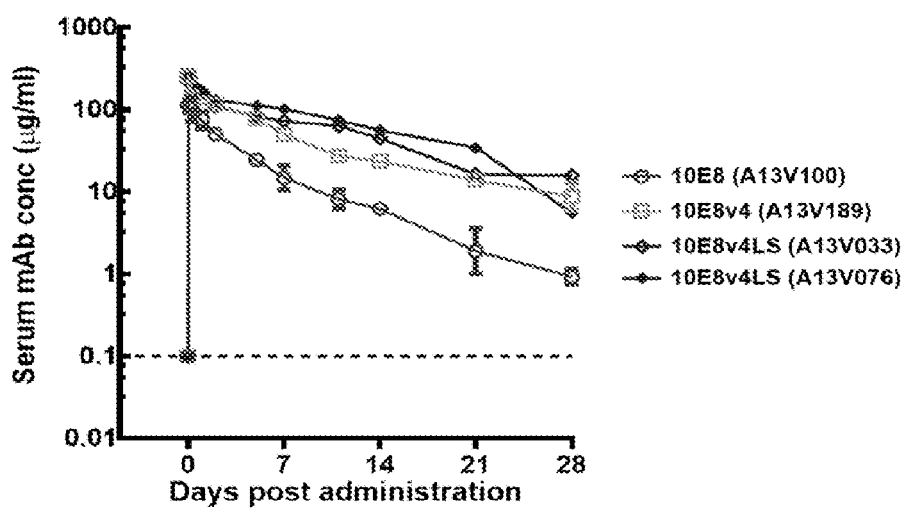

Each of the 10E8, HC6-S74Y-511/rL3, H6-511-4mut/rL3-6mut, and HC6-S74Y-511/rL3-6mut antibodies neutralized 98% of the viruses in the large panel with a median $IC_{50}$ of approximately 0.4 µg/ml (FIGS. 16A-16C) and a median $IC_{80}$ of approximately 2.0 µg/ml, respectively (FIGS. 16D-16F).

Serum half-life. The serum half-life of the 10E8v4 antibody was assessed in macaques. Antibodies including the heavy and light chain variable regions of the 10E8 or 10E8v4 antibodies were generated with IgG1 constant region or IgG1 with "LS" mutation constant region, and injected IV into macaques to assess serum half-life. As shown in FIG. 17, the 10E8v4 antibody (with or without LS substitution in the constant region) has a substantially increased half-life compared to the parent 10E8 antibody.

In summary, the potency, breadth, and autoreactivity of the HC6-S74Y-511/rL3, H6-511-4mut/rL3-6mut, and HC6-S74Y-511/rL3-6mut antibodies are similar to that of unmodified 10E8 antibody, but the modified 10E8 antibodies are far more soluble in aqueous solution, particularly the H6-511-4mut/rL3-6mut and HC6-S74Y-511/rL3-6mut antibodies.

Example 2

Optimized 10E8 Antibodies

This example illustrates a series of modified 10E8 antibodies developed using a surface-matrix approach where individual surface mutants were assessed for neutralization potency and manufacturability. To improve antibody 10E8, a human antibody capable of neutralizing 98% of HIV-1 isolates, 280 surface mutants were created that incorporated hydrophobic changes (Phe/Trp), hydrophilic protrusions (Arg), large steric protrusions (N-linked glycan), and side-chain removal (poly-glycine). For potency, these mutants were assessed by neutralization.

A hydrophobic substitution at heavy chain-residue 100c was observed to increase neutralization. A 10E8 variant including a S100 cW substitution (10E8v4-100 cW) yielded the broadest and most potent HIV-1-neutralizing antibody yet described. Further, a poly-glycine substitution including modification of light chain-residue 32 was observed to enhance homogeneity in size exclusion chromatography, an effect also achieved by introducing a disulfide bond in this region.

1. Surface-Matrix Approach

Macromolecular function is often critically dependent on surface interactions. While alanine scanning or Arg scanning have been used to understand function, such scanning has not been used to directly improve function. Specific protein surface alterations were chosen that might enhance function.

280 surface mutants of 10E8 that incorporated hydrophobic changes (Phe/Trp—to enhance binding to hydrophobic patches), hydrophilic protrusions (Arg—to aid in solubility or to interact with membrane), large steric protrusions (N-linked glycan—to aid in solubility or to aid in steric inhibition of entry), and side-chain removal (poly-glycine—to aid in solubility or to remove steric restrictions on recognition) were generated. These 10E8 mutants were screened for HIV-1 neutralization using a 9-isolate HIV-1 panel as described above, and all except Phe/Trp changes were assessed for turbidity as described above.

TABLE 4

| Surface Scan of 10E8 antibody | | | | |
|---|---|---|---|---|
| | 10E8 Arg Scan | | | |
| Fold improvement | $IC_{50}$ | | Turbidity | |
| | Heavy chain | Light chain | Heavy chain | Light chain |
| >2-fold (gain of function) | V5R | S76R | | |
| >1-fold, but < 2-fold (gain of function) | Q3R, S56R, T68R, Y100eR, L108R, S113R | E3R, T20R | S56R, E64R, T68R, S70R, S74R, I75R, N76R, F77R, E81R, N82aR, L89R, F100aR, S100cR, Y100eR, P100fR, L108R, S113R | T5R, E7R, A14R, T20R, D26R, G41R, Q42R, I45R, N52R, N53R, P59R, D60R, S63R, S65R, A66R, S67R, S76R, Q79R, A80R, E81R, E85R, S94R, L95cR, G100R, T105R, L107R |

TABLE 4-continued

Surface Scan of 10E8 antibody

10E8 Glycan Scan

| Fold improvement | IC$_{50}$ | | Turbidity | |
| --- | --- | --- | --- | --- |
| | Heavy chain | Light chain | Heavy chain | Light chain |
| >2-fold (gain of function) | L170, L178, V207 | S115 | S21, S25, D28, S70, T75, R105, S115, S128, G134, S153, S161, L170, T191, N204 | T8, V13, T22, S76, Q79, S94, L95c, |
| >1-fold, but < 2-fold (gain of function) | G54, S161 | | G54, F100a, L178, V207 | N52, S67, K111, S115, N129, A151, A158, K187, K205 |

10E8 Glycine Scan

| Fold improvement | IC$_{50}$ & IC$_{80}$ | | Turbidity | |
| --- | --- | --- | --- | --- |
| | Heavy chain | Light chain | Heavy chain | Light chain |
| >2-fold (gain of function) | | | | (T74G, S76G and Q79G), (K103G and T105G), (T105G, L107G, S108G, Q109G, P110G and K111G) |
| >1-fold, but < 2-fold (gain of function) | (F27F, D28G, D30G, N31G and A32G), (P52bG and E53G) | | (N31G, A32G and W33G), E53G, (N82aG, N82bG, R83G, M84G and E85G), R94G, (K97g, Y98G, Y99G, D100G and F100aG), (D100G, F100aG, W100bG, S100cG, Y100eG and P100fG) | (Q79G, A80G, E81G and D83G), (E83G and E85G), (K93G, S92G, S95aG, R95bG and L95cG), (L95cG and V97G) |

10E8 Phe/Trp Scan

| Fold improvement | IC$_{50}$ | | Turbidity | |
| --- | --- | --- | --- | --- |
| | Heavy chain | Light chain | Heavy chain | Light chain |
| >2-fold (gain of function) | P41F, R94F, S100cF | | | |
| >1-fold, but < 2-fold (gain of function) | V5F, K13F, P52bF, L89F, F100aW | T5F, E7F, T8F, N52F | | |

In the above table, "Turbidity improvement >x-fold" indicates that the actual turbidity of the variants at PBS, pH7.4 is decreased by x-fold compared to that of 10E8 antibody. For the Glycan scan, indicated residues (Ri) were substituted with Asn and the residue two position c-terminal to the indicated residue (Ri+2) was substituted with Ser or Thr to add glycan at position Ri.

A summary of mutations of interest and corresponding change in neutralization profile is provided in the following table.

TABLE 5

Summary of certain 10E8 amino acid substitutions that increase HIV-1 neutralization and/or decrease turbidity.

| Variant | Neutralization potency fold improvement (IC$_{50}$/IC$_{80}$) |
| --- | --- |
| HC_V5R | 2.8/0.6 |
| HC_S23R | 2.8/0.6 |
| LC_S67R | 1.9/2.3 |
| HC_S100cF | 2.8/3.3 |
| HC_R94F | 3.6/2.1 |
| HC_K13F | 1.6/2.1 |
| LC_T5F | 1.8/1.4 |
| LC_E7F | 3.1/2.7 |

TABLE 5-continued

Summary of certain 10E8 amino acid substitutions that increase HIV-1 neutralization and/or decrease turbidity.

| Variant | Neutralization potency fold improvement (IC$_{50}$/IC$_{80}$) |
| --- | --- |
| HC_Glyc_L178 | 3.4/2.7 |
| HC_Glyc_L170 | 4.1/3.3 |
| HC_Glyc_V207 | 3.4/1.7 |
| HC_Glyc_S161 | 1.5/0.8 |
| HC_Glyc_R105 | 1.2/0.96 |
| HC_Glyc_S134 | 1.02/0.74 |
| HC_Glyc_S153 | 1.1/0.7 |

2. Substitution at Light Chain Kabat Position 32

Figure 18B:
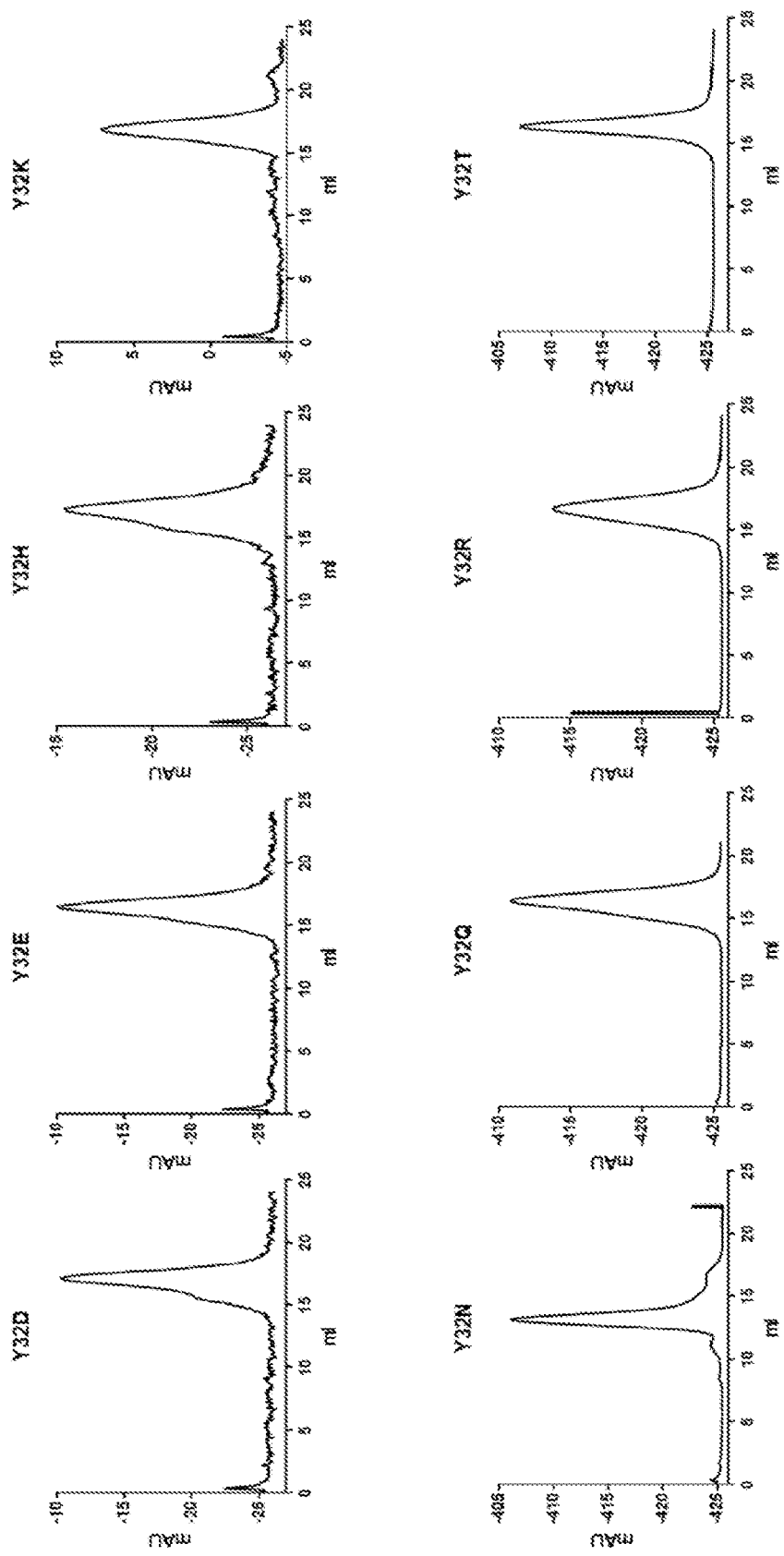
Figure 18C:
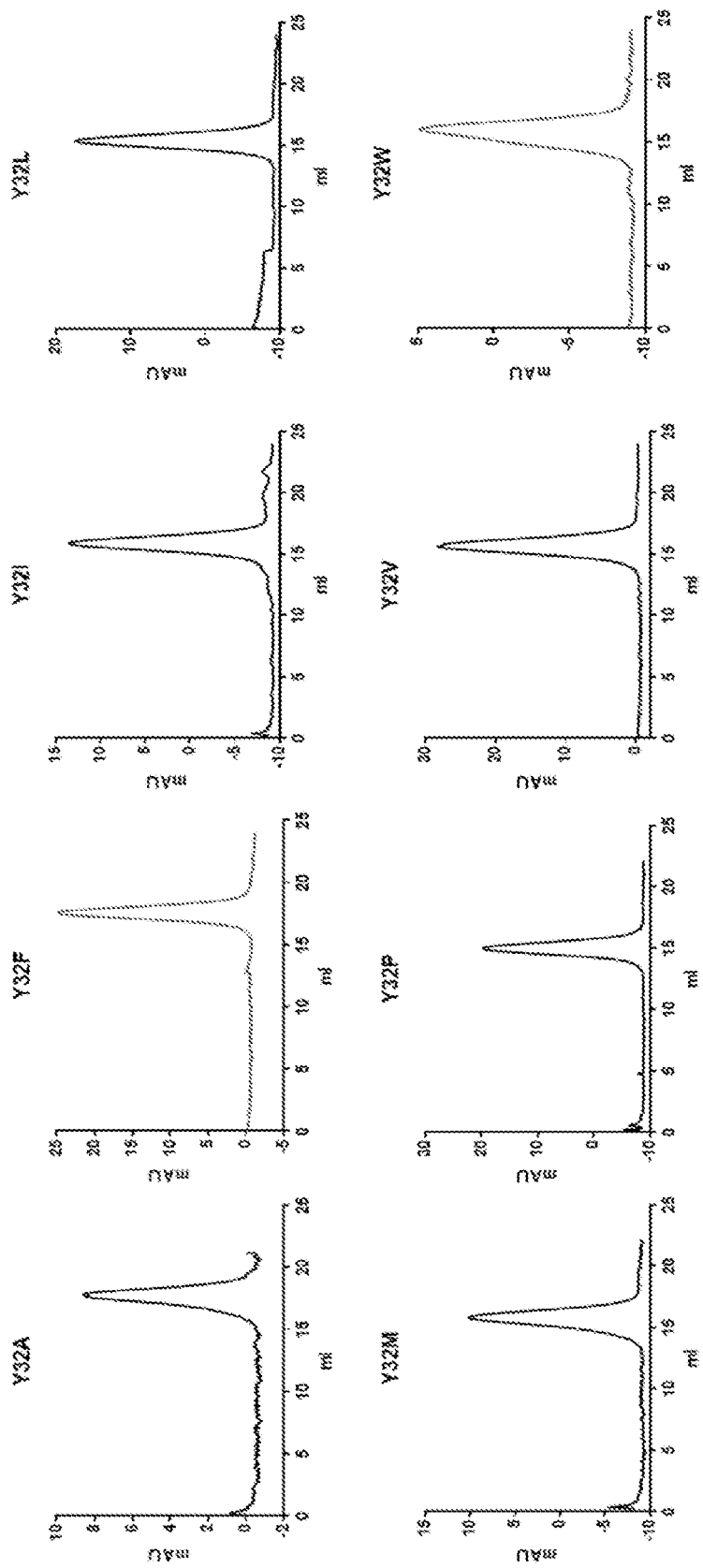

When 10E8, 10E8 variant 4 and 10E8 variant 5 are purified using gel chromatography, an unusual "double peak" is observed (see FIG. 18A). Although this double peak does not appear to affect neutralization breadth or potency, or antibody solubility, additional modifications of 10E8 antibody sequence were pursued to determine if the double peak could be removed. Based on the structure of 10E8 bound to MPER peptide, many amino acid substitutions were assayed, including kabat position 32 of the V$_L$. Surprisingly, substitution of the tyrosine residue at kabat position 32 of the $V_L$ with nearly any other amino acid removed the "double peak" (FIGS. 18B and 18C). The resulting 10E8 variants were assayed for HIV-1 neutralization using the 9-isolate HIV-1 panel, specifically chosen to represent diversity. As indicated in the tables below, a 10E8 variant 4 antibody further including a Y32W substitution has improved HIV-1 neutralization properties compared to 10E8 variant 4, and a variant with a Y32F substitution was nearly as potent as 10E8 variant 4.

10E8v4 and analyzed for HIV-1 neutralization (FIG. 19). Testing 10E8v4-100cW on a panel of 208 HIV-1 isolates indicated it to be the most potent and broadest antibody yet identified.

ANA Hep-2 staining analysis and anti-cardiolipin ELISA were performed to test the auto-reactivity of several 10E8 variants. The Hep-2 staining assays were performed as described above. The anti-cardiolipin ELISA was performed

TABLE 6

Neutralization profile of 10E8 variants

| | | Antibody | | | | | | | | | |
|---|---|---|---|---|---|---|---|---|---|---|---|
| clade | Virus | 10E8v4 $V_L$ Y32D | 10E8v4 $V_L$ Y32E | 10E8v4 $V_L$ Y32H | 10E8v4 $V_L$ Y32K | 10E8v4 $V_L$ Y32N | 10E8v4 $V_L$ Y32Q | 10E8v4 $V_L$ Y32R | 10E8v4 $V_L$ Y32T | 10E8v4 | 10E8 wt |
| A | KER2008.12.SG3 | >50 | >50 | >50 | >50 | >50 | >50 | >50 | >50 | >50 | >50 |
| ACD | 6095.V1.C10.SG3 | 1.550 | 0.215 | 0.032 | 0.359 | 2.920 | 0.281 | 0.152 | 0.145 | 0.001 | 0.001 |
| AE | TH966.8.SG3 | >50 | 19.000 | 0.788 | 10.200 | >50 | 11.500 | 4.080 | 3.760 | 0.021 | 0.023 |
| B | 6101.10.SG3 | >50 | >50 | 7.400 | >50 | >50 | >50 | >50 | >50 | 0.007 | 0.001 |
| B | PVO.04.SG3 | >50 | >50 | >50 | >50 | >50 | >50 | >50 | >50 | 1.130 | 0.997 |
| B | YU2.DG.SG3 | >50 | >50 | 8.760 | >50 | >50 | >50 | >50 | 43.500 | 0.386 | 0.280 |
| C | CNE31.SG3 | >50 | >50 | 29.900 | >50 | >50 | >50 | >50 | >50 | 1.160 | 0.995 |
| C | ZM106.9.SG3 | >50 | >50 | >50 | >50 | >50 | >50 | >50 | >50 | >50 | >50 |
| C | ZM215.8.SG3 | >50 | >50 | 1.390 | 33.000 | >50 | >50 | 7.520 | 9.250 | 0.013 | 0.018 |
| | Median IC50 | 1.550 | 9.608 | 4.395 | 10.200 | 2.920 | 5.891 | 4.080 | 6.505 | 0.021 | 0.023 |
| | Geometric Mean | 1.550 | 2.021 | 2.020 | 4.944 | 2.920 | 1.798 | 1.671 | 3.849 | 0.048 | 0.033 |

| | | Antibody | | | | | | | | | |
|---|---|---|---|---|---|---|---|---|---|---|---|
| clade | Virus | 10E8v4 $V_L$ Y32A | 10E8v4 $V_L$ Y32F | 10E8v4 $V_L$ Y32I | 10E8v4 $V_L$ Y32L | 10E8v4 $V_L$ Y32M | 10E8v4 $V_L$ Y32P | 10E8v4 $V_L$ Y32V | 10E8v4 $V_L$ Y32W | 10E8v4 | 10E8 wt |
| A | KER2008.12.SG3 | >50 | >50 | >50 | >50 | >50 | >50 | >50 | >50 | >50 | >50 |
| ACD | 6095.V1.C10.SG3 | 0.409 | 0.017 | 1.300 | 0.593 | 1.030 | 3.200 | 0.558 | 0.005 | 0.014 | 0.012 |
| AE | TH966.8.SG3 | 3.530 | 0.031 | 21.400 | 4.260 | 29.800 | >50 | 4.960 | 0.029 | 0.036 | 0.032 |
| B | 6101.10.SG3 | >50 | 0.080 | >50 | 38.600 | >50 | >50 | >50 | 0.055 | 0.042 | 0.014 |
| B | PVO.04.SG3 | >50 | 2.250 | >50 | >50 | >50 | >50 | >50 | 1.400 | 2.390 | 2.090 |
| B | YU2.DG.SG3 | >50 | 2.000 | >50 | >50 | >50 | >50 | >50 | 1.070 | 1.600 | 1.050 |
| C | CNE31.SG3 | >50 | 3.200 | >50 | >50 | >50 | >50 | >50 | 0.719 | 1.160 | 1.190 |
| C | ZM106.9.SG3 | >50 | >50 | >50 | >50 | >50 | >50 | >50 | >50 | >50 | >50 |
| C | ZM215.8.SG3 | 11.700 | 0.102 | >50 | 8.750 | >50 | >50 | 28.200 | 0.089 | 0.070 | 0.085 |
| | Median IC50 | 3.53 | 0.102 | 11.35 | 6.505 | 15.415 | 3.2 | 4.96 | 0.089 | 0.07 | 0.085 |
| | Geometric Mean | 2.56583 | 0.25052 | 5.27447 | 5.40462 | 5.54022 | 3.2 | 4.27355 | 0.13372 | 0.18184 | 0.1425 |

Figure 18D:
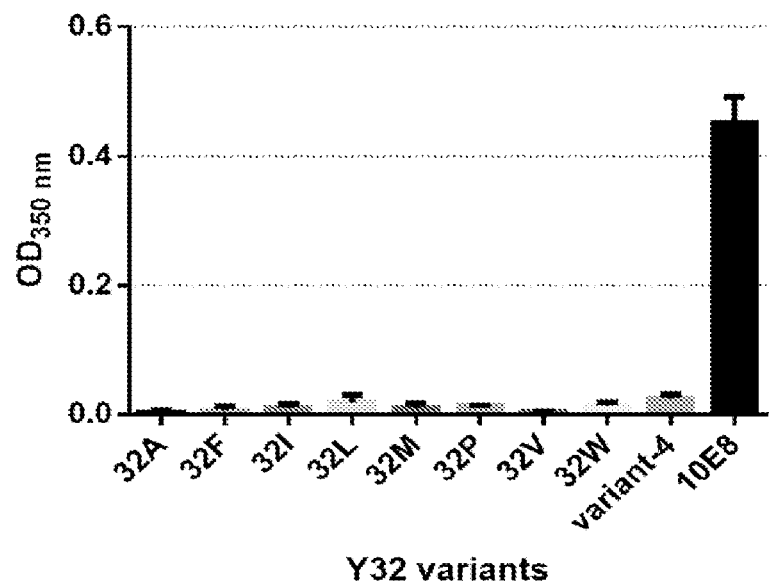

Several of the 10E8 variant 4 antibodies that further include a substitution at $V_L$ kabat position 32 were also assayed for turbidity (FIG. 18D). 10E8 variant 4 with Y32A, Y32F, Y32I, Y32L, Y32M, Y32P, Y32V, or Y32W substitution each had a turbidity profile similar to that of 10E8 variant 4.

2. 10E8v4-100cW

The surface-matrix mutagenesis assay discussed above identified a hydrophobic change at kabat position 100c of the heavy chain to improve HIV-1 neutralization potency (the S100cF substitution). Analysis of the antibody surface suggested potential membrane interaction, and that a Trp substitution at kabat position 100c might also be of interest. Accordingly, a S100cW substitution was introduced into as described in Asokan et al. J. Virol., doi: 10.1128/JVI. 02097-15, 2015). The results of these assays are summarized in the following table.

TABLE 7

Autoreactivity of 10E8 variants

| Antibody | ANA HEp2 staining assay | Anti-cardiolipin ELISA |
|---|---|---|
| 10E8 wt | Non-reactive | Non-reactive |
| 10E8v4 | Non-reactive | Non-reactive |
| 10E8v4 w/ LS heavy chain | Non-reactive | Non-reactive |
| 10E8v4 s100cW | Non-reactive | Non-reactive |

TABLE 7-continued

Autoreactivity of 10E8 variants

| Antibody | ANA HEp2 staining assay | Anti-cardiolipin ELISA |
|---|---|---|
| 10E8v4 Y32W | Non-reactive | Non-reactive |
| 10E8v4 Y32F | Non-reactive | Non-reactive |
| 10E8v4 S100cW/Y32F | Non-reactive | Non-reactive |
| 10E8v4 S100cW/Y32W | Reactive (1+) | Non-reactive |
| 10E8v4 S100cF | Non-reactive | Non-reactive |
| 10E8v4 S100cF/Y32F | Non-reactive | Non-reactive |
| 10E8v4 S100cF/Y32W | Non-reactive | Non-reactive |
| 10E8v4 S100cY | Non-reactive | Non-reactive |
| 10E8v4 S100cY/Y32F | Non-reactive | Non-reactive |
| 10E8v4 S100cY/Y32W | Non-reactive | Non-reactive |

3. 10E8v4-100cW-DS

An atypical purification profile for 10E8v4 100cW was observed by size exclusion chromatography. Accordingly, the purification profile of several additional 10E8 variants was assayed by size exclusion chromatography. The variants included:

1. 10E8v4 S100cF
2. 10E8v4 S100cF with an A, D, E, F, H, I, K, L, M, N, P, Q, R, T, V, or W substitution at $V_L$ kabat position 32
3. 10E8v4 S100cW
4. 10E8v4 S100cW with an A, D, E, F, H, I, K, L, M, N, P, Q, R, T, V, or W substitution at $V_L$ kabat position 32
5. 10E8v4 with a D, E, I, K, M, N, P, Q, T, or V substitution at $V_H$ kabat position 100c
6. 10E8v4-DS ($V_H$ Y100eC and $V_L$ S30C substitutions)
7. 10E8v4 S100cW-DS
8. 10E8v4-HCDR3 (HCDR3 deletion)

Figure 20:
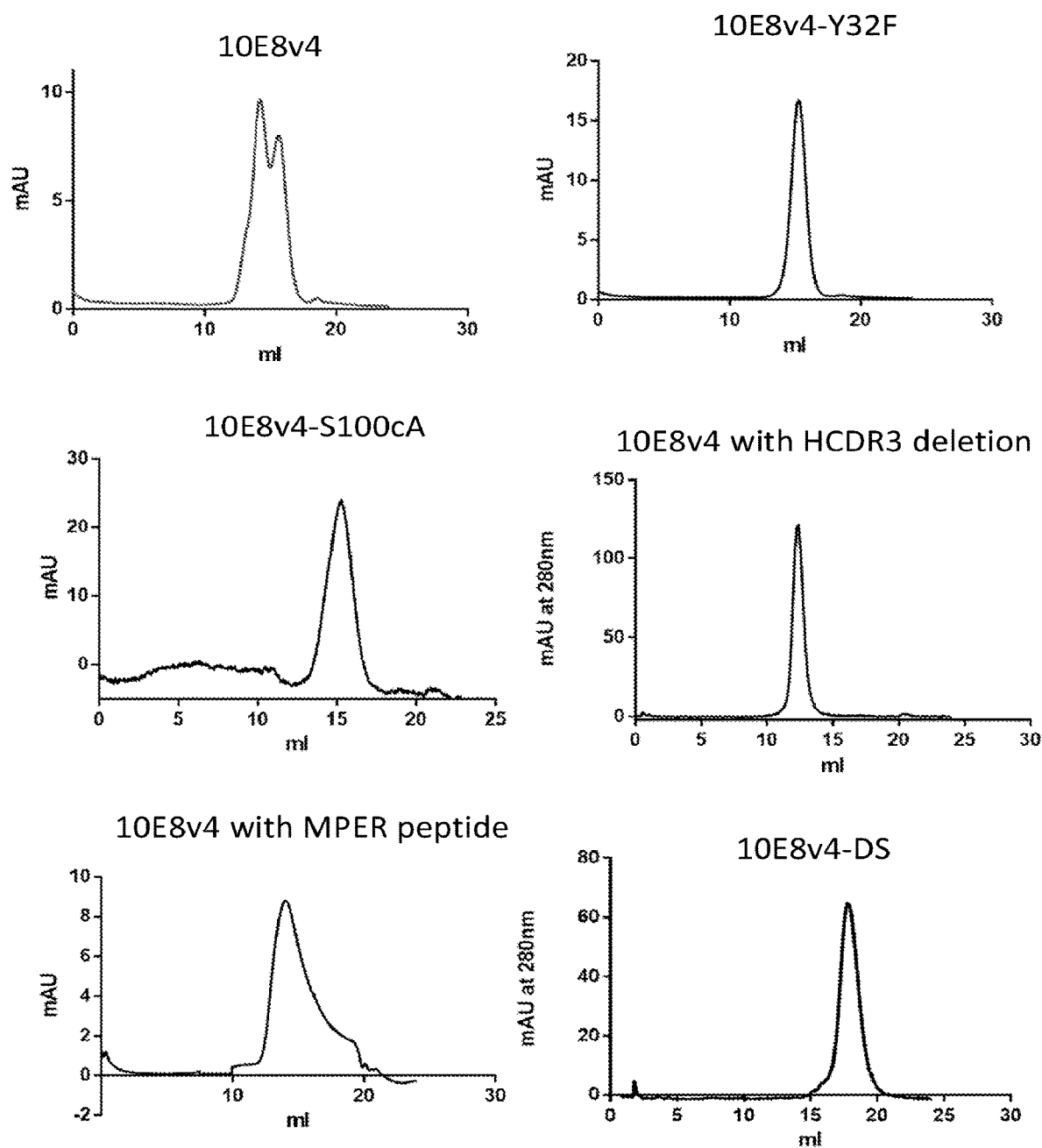
FIG. 20 is a set of graphs and ribbon diagrams illustrating that alteration of the 10E8v4 HCDR3 can refine the size exclusion chromatography profile to a single peak.
Figure 21:
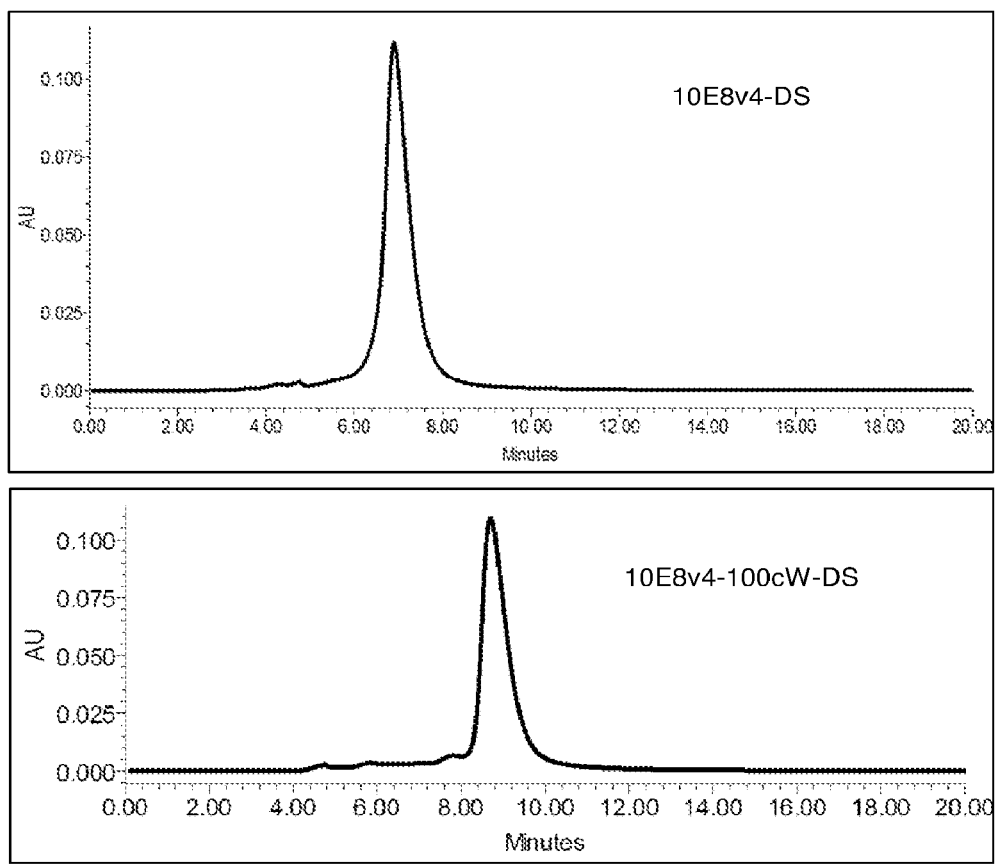
FIG. 21 is a set of graphs showing size exclusion chromatography results for the 10E8v4-DS and 10E8v4-100cW-DS antibodies.

Of these modified 10E8 antibodies, 10E8v4 S100cP and 10E8v4 HCDR3 showed a typical antibody profile based on size exclusion chromatography, and 10E8v4 S100cF/Y32N, 10E8v4 S100cW/Y32N, 10E8v4-DS, and 10E8v4 S100cW-DS showed a nearly typical antibody profile based on size exclusion chromatography. The remaining antibodies eluted from the size exclusion column in multiple peaks. A summary of the size exclusion chromatography profiles for the 10E8v4, 10E8v4/Y32F, 10E8v4 S100cA, 10E8v4 with HCDR3 deletion, 10E8v4-DS, and 10E8v4 S100cW-DS antibodies is provided in FIGS. 20 and 21. A brief summary of the size exclusion chromatography assays is provided below:

System: Acquity Waters UPLC H-class;
Column: Acquity UPLC Protein BEH200 SEC, Particle Size: 200 Å, Pore Size: 1.7 µm,
Column Dimension: 4.6 mm×150 mm
UV Absorbance: 280 nm
Mobile Phase: 2×PBS
Flow Rate: 0.4 mL/min (isocratic)
Run Time: 20 minutes
Sample Volume Injected: 50 µL
Sample Concentration: 1 mg/mL
Sample Mass: 50 µg
The Sample was ran in duplicate.
Control 1: VRC01 D-13-0030A, 1 mg/mL; Volume injected: 50 µL
Control 2: Gel Filtration Standard, 9 mg/mL; Volume injected: 30 µL The ability of the following variants to bind to the MPER peptide was assessed: 10E8v4 S100cF/LC-Y32N, 10E8v4 S100cW/LC-Y32N, 10E8v4 S100cP, 10E8v4-DS, and 10E8v4 HCDR3 (10E8v4 w/HCDR3 deletion). The binding of all was severely impaired, except for 10E8v4_DS, which bound 2-fold more tightly than 10E8v4. 10E8v4-100cW-DS binding to MPER peptide was also assessed and found to be similar to that of 10E8v4-DS.

Several of these 10E8 variants were assayed for HIV-1 neutralization using the 9-isolate HIV-1 panel, specifically chosen to represent diversity, with the results shown in the table below.

TABLE 8

HIV-1 neutralization of 10E8 variants.

| | | $IC_{50}$ | | | | $IC_{80}$ | | | |
|---|---|---|---|---|---|---|---|---|---|
| clade | Virus | 10E8v4 | 10E8v4 DS | 10E8v4 100cW | 10E8v4 100cW DS | 10E8v4 | 10E8v4 DS | 10E8v4 100cW | 10E8v4 100cW DS |
| A | KER2008.12.SG3 | >50 | >50 | >50 | >50 | >50 | >50 | >50 | >50 |
| ACD | 6095.V1.C10.SG3 | 0.004 | 0.002 | 0.000 | 0.002 | 0.021 | 0.017 | 0.001 | 0.013 |
| AE | TH966.8.SG3 | 0.026 | 0.092 | 0.003 | 0.019 | 0.169 | 0.345 | 0.013 | 0.092 |
| B | 6101.10.SG3 | 0.011 | 2.410 | 0.002 | 1.220 | 0.090 | 22.200 | 0.010 | 10.100 |
| B | PVO.04.SG3 | 0.894 | 2.530 | 0.085 | 0.331 | 8.000 | 10.100 | 0.459 | 3.670 |
| B | YU2.DG.SG3 | 0.668 | 0.275 | 0.031 | 0.213 | 5.320 | 2.440 | 0.260 | 2.200 |
| C | CNE31.SG3 | 1.740 | 2.280 | 0.107 | 0.806 | 4.850 | 6.480 | 0.295 | 2.930 |
| C | ZM106.9.SG3 | >50 | >50 | >50 | >50 | >50 | >50 | >50 | >50 |
| C | ZM215.8.SG3 | 0.042 | 0.208 | 0.004 | 0.037 | 0.326 | 0.798 | 0.025 | 0.245 |
| | Median IC50 or IC80 | 0.042 | 0.275 | 0.004 | 0.213 | 0.326 | 2.440 | 0.025 | 2.200 |
| | Geometric Mean | 0.091 | 0.283 | 0.008 | 0.100 | 0.578 | 1.494 | 0.038 | 0.684 |

Example 3

Detecting HIV-1 in a Sample or a Subject using a gp41-Specific Antibody

This example describes the use of HIV-1 monoclonal neutralizing antibodies specific to gp41 for the detection of HIV-1 in a sample or a subject. This example further describes the use of these antibodies to confirm the diagnosis of HIV-1 infection in a subject.

A biological sample, such as a blood sample, is obtained from the patient diagnosed with, undergoing screening for, or suspected of having an HIV-1 infection. A blood sample taken from a patient who is not infected is used as a control, although a standard result can also be used as a control. An ELISA is performed to detect the presence of gp41 in the blood sample. Proteins present in the blood samples (the patient sample and control sample) are immobilized on a solid support, such as a 96-well plate, according to methods well known in the art (see, for example, Robinson et al., Lancet 362:1612-1616, 2003, incorporated herein by reference). Following immobilization, HIV-1 monoclonal neutralizing antibodies specific to gp41 that are directly labeled with a fluorescent marker are applied to the protein-immobilized plate. The plate is washed in an appropriate buffer, such as PBS, to remove any unbound antibody and to minimize non-specific binding of antibody. Fluorescence can be detected using a fluorometric plate reader according to standard methods. An increase in fluorescence intensity of the patient sample, relative to the control sample, indicates the gp41 antibody specifically bound proteins from the blood sample, thus detecting the presence of gp41 protein in the sample. Detection of gp41 protein in the patient sample indicates the patient has an HIV-1 infection, or confirms diagnosis of HIV-1 infection in the subject.

Example 4

Treatment of HIV-1 Using a Monoclonal Antibody Specific for Gp41

This example describes a particular method that can be used to treat HIV-1 infection in a human subject by administration of one or more gp41-specific human neutralizing antibodies. Although particular methods, dosages, and modes of administrations are provided, one skilled in the art will appreciate that variations can be made without substantially affecting the treatment.

Based upon the teaching disclosed herein, HIV-1 infection can be treated by administering a therapeutically effective amount of one or more of the neutralizing antibodies described herein, thereby reducing or eliminating HIV-1 infection.

Screening subjects: In particular examples, the subject is first screened to determine if they have an HIV-1 infection. Examples of methods that can be used to screen for HIV-1 infection include a combination of measuring a subject's CD4+ T cell count and the level of HIV-1 virus in serum blood levels. Additional methods using the gp41-specific antibodies described herein can also be used to screen for HIV-1 infection.

In some examples, HIV-1 testing consists of initial screening with an enzyme-linked immunosorbent assay (ELISA) to detect antibodies to HIV-1. Specimens with a nonreactive result from the initial ELISA are considered HIV-1-negative unless new exposure to an infected partner or partner of unknown HIV-1 status has occurred. Specimens with a reactive ELISA result are retested in duplicate. If the result of either duplicate test is reactive, the specimen is reported as repeatedly reactive and undergoes confirmatory testing with a more specific supplemental test (e.g., Western blot or an immunofluorescence assay (IFA)). Specimens that are repeatedly reactive by ELISA and positive by IFA or reactive by Western blot are considered HIV-positive and indicative of HIV-1 infection. Specimens that are repeatedly ELISA-reactive occasionally provide an indeterminate Western blot result, which may be either an incomplete antibody response to HIV-1 in an infected person, or nonspecific reactions in an uninfected person. IFA can be used to confirm infection in these ambiguous cases. In some instances, a second specimen will be collected more than a month later and retested for subjects with indeterminate Western blot results. In additional examples, nucleic acid testing (e.g., viral RNA or proviral DNA amplification method) can also help diagnosis in certain situations.

The detection of HIV-1 in a subject's blood is indicative that the subject is infected with HIV-1 and is a candidate for receiving the therapeutic compositions disclosed herein. Moreover, detection of a CD4+ T cell count below 350 per microliter, such as 200 cells per microliter, is also indicative that the subject is likely to have an HIV-1 infection.

Pre-screening is not required prior to administration of the therapeutic compositions disclosed herein Pre-treatment of subjects: In particular examples, the subject is treated prior to administration of a therapeutic agent that includes one or more antiretroviral therapies known to those of skill in the art. However, such pre-treatment is not always required, and can be determined by a skilled clinician.

Administration of therapeutic compositions: Following subject selection, a therapeutically effective dose of a gp41-specific neutralizing antibody described herein (such as the H6-511-4mut/rL3-6mut antibody) is administered to the subject (such as an adult human or a newborn infant either at risk for contracting HIV-1 or known to be infected with HIV-1). Additional agents, such as anti-viral agents, can also be administered to the subject simultaneously or prior to or following administration of the disclosed agents. Administration can be achieved by any method known in the art, such as oral administration, inhalation, intravenous, intramuscular, intraperitoneal, or subcutaneous.

The amount of the composition administered to prevent, reduce, inhibit, and/or treat HIV-1 or a condition associated with it depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., HIV-1) in a subject without causing a substantial cytotoxic effect in the subject. An effective amount can be readily determined by one skilled in the art, for example using routine trials establishing dose response curves. As such, these compositions may be formulated with an inert diluent or with a pharmaceutically acceptable carrier.

In one specific example, antibodies are administered at 5 mg per kg every two weeks or 10 mg per kg every two weeks depending upon the particular stage of HIV-1. In an example, the antibodies are administered continuously. In another example, antibodies or antibody fragments are administered at 50 µg per kg given twice a week for 2 to 3 weeks.

Administration of the therapeutic compositions can be taken long term (for example over a period of months or years).

Assessment: Following the administration of one or more therapies, subjects with HIV-1 can be monitored for reductions in HIV-1 levels, increases in a subject's CD4+ T cell count, or reductions in one or more clinical symptoms associated with HIV-1. In particular examples, subjects are analyzed one or more times, starting 7 days following treatment. Subjects can be monitored using any method known in the art. For example, biological samples from the subject, including blood, can be obtained and alterations in HIV-1 or CD4+ T cell levels evaluated.

Additional treatments: In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least 20%, at least 30%, at least 40%, at least 50%, or at least 70% in HIV-1 infection, HIV-1 replication or combination thereof. A partial response may also be an increase in CD4+ T cell count such as at least 350 T cells per microliter.

Example 5

Optimized 10E8 Antibodies

This example describes arginine and tryptophan scanning mutagenesis assays to identity variants of the 10E8 V5R S100cF antibody (which include a VH and VL set forth as SEQ ID NOs: 76 and 6) with improved HIV-1 neutralization.

Heavy chain variable region residues E1, V5, S7, G8, G10, L11, K13, G15, G16, S17, S21, S23, S25, D28, D30, N31, P41, G42, K43, E46, P52b, G52c, E53, G54, W55, S56, E61, S62, K64, G65, T68, S70, D72, T74, K75, N76, E81, N82a, N82b, T84, E85, Y89, K97, Y99, F100a, W100b, Y100e, P100f, P100g, Q101, D102, Q105, L108, and S113 (kabat numbering) of the 10E8v4 V5R S100cF antibody were individually mutated to arginine or tryptophan. Additionally, light chain variable region residues S2, E3, T5, D7, P8, A9, S12, A14, L15, K16, Q17, T18, T20, D26, S30, P40, G41, Q42, V45, K51, N52, S56, G57, P59, D60, S63, S65, A66, S67, G68, N69, T76, G77, Q79, A80, E81, D85, K93, S94, G100, K103, and L107 (kabat numbering) of the 10E8v4 V5R S100cF antibody were individually mutated to arginine or tryptophan. Thus, a total of 172 10E8v4 V5R S100cF mutants were generated. Each of the resulting 10E8v4 V5R S100cF mutants was expressed (as an IgG) and tested using the pseudovirus neutralization assay described above. Of these, the following variants were identified to improve HIV-1 neutralization (by geometric mean) at least 2-fold compared to the parent 10E8v4 V5R S100cF antibody:

TABLE 9

10E8 variants.

| Fold improvement | Geometric mean IC$_{50}$ | | Geometric mean IC$_{80}$ | |
|---|---|---|---|---|
| | $V_H$ substitution | $V_L$ substitution | $V_H$ substitution | $V_L$ substitution |
| >4-fold, but < 5-fold | | | | G68R |
| >3-fold, but < 4-fold | E1R, D28W, P52bR, D72R | D7W, D26R | | |
| >2-fold, but < 3-fold | G15R, D30R, N31R, E81R, E1W, S25W, D30W, N31W | A14R, T18R | | Q17R, T18R, T20R, K51R, N53R, S65R, G77R, G100R |

Figure 22:
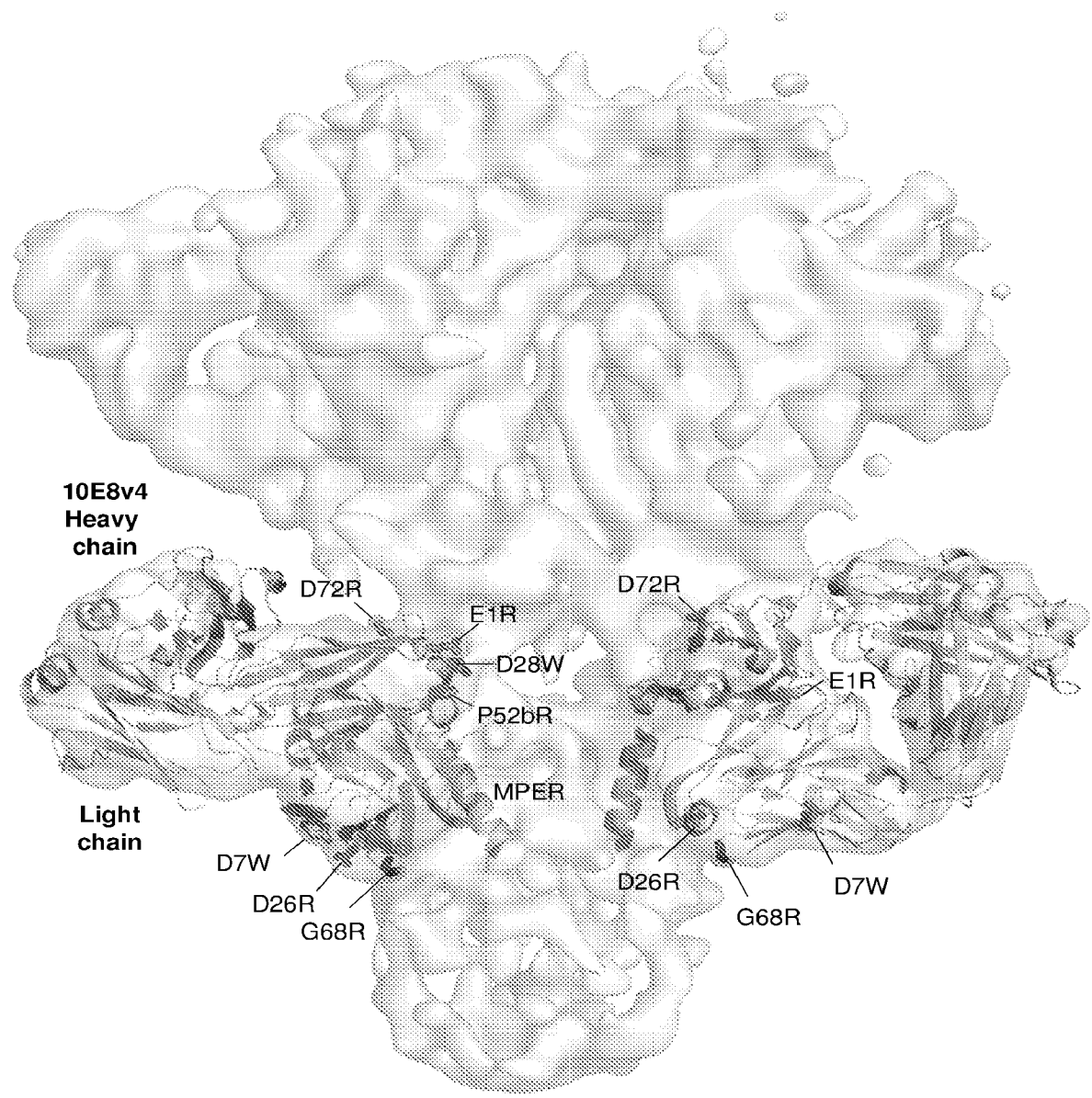
FIG. 22 is an illustration of the positioning within the Cryo-EM HIV-1 Env structure fitted with the 10E8v4 antibody of certain amino acid substitutions to 10E8v4 that improve HIV-1 neutralization. One group of mutations was in a membrane-proximal region of 10E8v4 when 10E8v4 is bound to HIV-1 Env (D7W, D26R, and G68R substitutions to the $V_L$), and another group was in a region of 10E8v4 that is not proximal to the cell membrane (D72R, E1R D28W, and P52bR substitutions to the $V_H$).

The 10E8v4 V5R S100cF variants that led to at least a 3 fold improvement in HIV-1 neutralization were positioned within the Cryo-EM HIV-1 Env structure fitted with the 10E8v4 antibody (see FIG. 22). This analysis revealed that some of the identified mutations clustered together on the 10E8 antibody. One group of mutations was in a membrane-proximal region of 10E8 when 10E8 is bound to HIV-1 Env (D7W, D26R, and G68R substitutions to the $V_L$), and another group was in a region of 10E8 that is not proximal to the cell membrane (D72R, E1R D28W, and P52bR substitutions to the $V_H$). These groups of substitutions can be introduced into the sequence of the 10E8v4 V5R S100cF antibody to generate additional 10E8 variants as follows:

10E8v4 V5R S100cF with D72R, E1R D28W, and P52bR substitutions to the $V_H$;

10E8v4 V5R S100cF with D7W, D26R, and G68R substitutions to the $V_L$;

10E8v4 V5R S100cF with D72R, E1R D28W, and P52bR substitutions to the $V_H$ and D7W, D26R, and G68R substitutions to the $V_L$;

10E8v4 V5R S100cF variants that include combinations of the mutations identified in the individual mutation screens were then generated and assayed for HIV-1 neutralization. Of the combination of interest identified (see the following table), several were expressed and tested using the pseudovirus neutralization assay described above. Of these, several variants were identified to improve HIV-1 neutralization compared to the parent 10E8v4 V5R S100cF antibody (see FIGS. 23A-23F).

TABLE 10

10E8 variants.

| Name of combination | Substitutions in VH compared to 10E8v4 V5R S100cF VH (SEQ ID NO: 76) | Substitutions in VL compared to 10E8v4 VL (SEQ ID NO: 6) |
|---|---|---|
| 10E8-1053 | E1R | D7W |
| 10E8-1054 | E1R | D26R |
| 10E8-1055 | E1R | G68R |
| 10E8-1056 | D28W | D7W |
| 10E8-1057 | D28W | D26R |
| 10E8-1058 | D28W | G68R |
| | D28W | Q17R |
| | D28W | T18R |
| | D28W | T20R |
| | D28W | K51R |
| | D28W | G77R |
| 10E8-1059 | P52bR | D7W |
| 10E8-1060 | P52bR | D26R |
| 10E8-1061 | P52bR | G68R |
| | P52bR | Q17R |
| | P52bR | T18R |
| | P52bR | T20R |
| | P52bR | K51R |
| | P52bR | G77R |
| 10E8-1062 | D72R | D7W |
| 10E8-1063 | D72R | D26R |
| 10E8-1064 | D72R | G68R |
| 10E8-1065 | D28F | D7W |
| 10E8-1066 | D28F | D26R |
| 10E8-1067 | D28F | G68R |
| 10E8-1068 | D28F | D7W + D26R |
| 10E8-1069 | D28F | D7W + G68R |
| 10E8-1070 | D28F | D26R + G68R |
| 10E8-1071 | D28F | D7W + D26R + G68R |
| 10E8-1072 | D28F | No change |
| 10E8-1073 | D28Y | No change |
| 10E8-1074 | D30F | |
| 10E8-1075 | D30Y | |
| 10E8-1076 | N31F | |
| 10E8-1077 | N31Y | |
| 10E8-1078 | E1F | |
| 10E8-1079 | E1Y | |
| 10E8-1080 | P52bR | D7W + D26R |
| 10E8-1081 | P52bR | D7W + G68R |
| 10E8-1082 | P52bR | D26R + G68R |
| 10E8-1083 | P52bR | D7W + D26R + G68R |
| 10E8-1084 | P52bR | No change |
| 10E8-1085 | P52bR | |
| 10E8-1086 | D28F | Q17R |
| 10E8-1087 | D28F | T18R |
| 10E8-1088 | D28F | T20R |
| 10E8-1089 | D28F | K51R |
| 10E8-1090 | D28F | G77R |
| 10E8-1091 | P52bR | Q17R |

TABLE 10-continued

10E8 variants.

| Name of combination | Substitutions in VH compared to 10E8v4 V5R S100cF VH (SEQ ID NO: 76) | Substitutions in VL compared to10E8v4 VL (SEQ ID NO: 6) |
|---|---|---|
| 10E8-1092 | P52bR | T18R |
| 10E8-1093 | P52bR | T20R |
| 10E8-1094 | P52bR | K51R |
| 10E8-1095 | P52bR | G77R |
| 10E8-1022 (10E8v4 V5R S100cF) | No change | No change |

Several variants listed had an improved neutralization profile compared to the patent 10E8v4V5R S100cF antibody, including 10E8-1081, which was about two fold more potent compared to 10e8v4 V5R 100cF (10E8-1022), and 10E8-1073, which neutralized all the viruses in the panel with an IC50 value of less than 25 µg/ml.

Example 6

Antibody Characterization

Assays were performed with the 10E8v4, 10E8v4 S100cW, 10E8v4 S100cF, and 10E8v4 V5R S100cF antibodies to determine the appropriateness of each of these antibodies for clinical production. The 10E8 variants were produced by transient expression in CHO cells, purified using standard techniques, and subjected to a panel of assays concerning the physical characteristics of the purified antibody. The expressed antibodies included the 10E8v4, 10E8v4 S100cW, 10E8v4 S100cF, and 10E8v4 V5R S100cF $V_H$ and VL regions in the context of an IgG1 that includes the "LS" substitution in the constant region to increase half-life in serum. Results of these assays are listed in Table 11. The assays included:
1. Size Exclusion Chromatography (SEC) to determine the level of aggregation and multimerization of the purified 10E8 variants. Each of the 10E8 variants was primarily in one peak coming off the size exclusion column.
2. Size Exclusion Chromatography (SEC) following 5 freeze thaw cycles to determine if freeze stress would induce antibody aggregation. The freeze thaw cycles did not significantly alter the elution profile of the 10E8 variants from the size exclusion column.
3. The appearance of the antibody solution was evaluated following initial purification. All antibody solutions were clear, colorless, and had no visible particulate.
4. Antibody Concentration (UV-VIS): The concentration of the antibody in solution following initial purification determined by absorbance (A) at 280 nm (characteristic of proteins) and light scattering (OD) due to sub-visible/visible particles in the solution at 350 nm. Low OD350 nm (<0.05 OD) values indicated minimal large particles in the starting material.
5. Thermal Transition measured by Differential Scanning calorimetry (DSC): These measurements determined that the structural transition temperatures of the 10E8 variants fell within a normal range.
6. Circular Dichroism (CD): CD assays were performed to determine if the secondary structure of the 10E8 variants falls within a normal range. As shown in the table, the CD assays identified CD signal minimums at about 218 nm and 230 nm. Overall the CD results indicate that the 10E8 variants have somewhat typical secondary structure for an antibody. Similar CD measurements were obtained for each variant.
7. Dynamic Light Scattering (DLS): DLS was used to evaluate heterogeneity of population size for the variant antibodies in solution. The DLS assays showed that the 10E8 variants each exhibited almost no heterogeneity of population size, indicating that the 10E8 variants were monodisperse in solution. The identified hydrodynamic radius for each variant fell within a normal range.
8. DLS thermal ramping (DLS-Melt) was used to evaluate the colloidal and structural thermal transition points for the 10E8 variants. The onset of aggregation ($T_{onset}$) was within the normal range for each of the 10E8 variants.
9. Isothermal Chemical Denaturation was used to evaluate the intrinsic stability of the 10E8 variants as a function of pH. Each of the 10E8 variants had a pH sensitivity in the normal range.

TABLE 11

Physical properties of 10E8 variants.

| Assay | Attribute | VRC01 | 10E8v4-100cF | 10E8v4-100cW | 10E8v4 V5R 100cF | 10E8v4 |
|---|---|---|---|---|---|---|
| SEC | Peak (isomer) % | Monomer > 95% Aggregate < 5% | Peak 1: 4.36% Peak 2: 25.77% Peak 3: 69.87% | Peak 1: 11.97% Peak 2: 23.14% Peak 3: 64.88% | Peak 1: 7.2% Peak 2: 25.6% Peak 3: 67.2% | Peak 1 = 72.7% Peak 2 = 20.3% Peak 3 = 7.0% |
| SEC (Freeze-Thaw 5x) | Freeze Stress | No significant change | No Significant Change | No significant Change | No significant Change | |
| Appearance | Appearance | Clear, colorless; no visible particles | Clear, colorless; no visible particles | Clear, colorless; no visible particles | Clear, colorless; no visible particles | Clear, colorless; no visible particles |
| UV-VIS (A280, OD350) | Conc. & optical density | OD350 < 0.05 | A280: 0.065 OD350: −0.006 | A280: 0.65 OD350: −0.013 | A280: 0.74 OD350: 0.0009 | A280: 0.77 OD350: 0.02 |
| DSC | Thermal Transition Temperature | $T_m 1 \geq 65°$ C. | $T_m 1$: 73.4° C. | $T_m 1$: 72.8° C. | $T_m 1$: 72.9° C. | $T_m 1$: 75.2° C. |
| CD | Secondary Structure | Primary Minimum at ~218 nm | Min. ~218 nm and ~230 nm | Min. ~218 nm and ~230 nm | min. ~218 nm and ~230 nm | Min. ~218 nm and 230 nm, |

TABLE 11-continued

Physical properties of 10E8 variants.

| Assay | Attribute | VRC01 | 10E8v4-100cF | 10E8v4-100cW | 10E8v4 V5R 100cF | 10E8v4 |
|---|---|---|---|---|---|---|
| DLS | Pop. Size and heterogeneity | >95% material is primary population (~5-6 nm) % Pd ≤ 20 | 100% material is primary population (~5-6 nm) | 100% material is primary population (~5-6 nm) | 99% material is primary population (~5-6 nm) | 100% material is primary population (~5-6 nm) |
| DLS Melt | Colloidal/ Structural Thermal Transition | $T_{onset} \geq 60°$ C. | $T_{onset} = 70.2$ | $T_{onset} = 70.0$ | $T_{onset} = 69.3$ | $T_{onset} = 71.5°$ C. |
| Isothermal Chemical Denaturation | $C_{1/2} \geq 5.5$ at one or more conditions tested | $C_{1/2} \geq 5.5$ (pH ≥ 5.5 and 0-200 mM NaCl) | $C_{1/2} \geq 5.5$ (pH ≥ 5.5 and 0-200 mM NaCl) | $C_{1/2} \geq 5.5$ (pH ≥ 5.5 and 0-200 mM NaCl) | $C_{1/2} \geq 5.5$ (pH ≥ 5.5 and 0-200 mM NaCl) | |

In view of the above, the 10E8v4, 10E8v4 S100cW, 10E8v4 S100cF, and 10E8v4 V5R S100cF antibodies were found to have substantially similar physical characteristics that fell within a normal range for antibodies that have successfully been produced using large-scale production techniques.

However, additional analysis of antibody solubility and the ability to concentrate the antibody variants revealed that 10E8v4 S100cF and 10E8v4 V5R S100cF antibodies were superior in some ways to 10E8v4 S100cW. In particular, difficulties with concentrating 10E8v4 S100cW were observed, with substantial precipitation of antibody from solution when trying to reach concentrations of 20 mg/ml. The other three antibodies (10E8v4, 10E8v4 S100cF, and 10E8v4 V5R S100cF) did not have difficulties reaching 20 mg/ml.

For example, the standard antibody expression and purification protocol used to generate the 10E8v4 variants included transient expression of heavy and light chains in Expi293F cells, purification of secreted antibody from the cell media using a Protein A purification column, elution of the antibody from the column with elution buffer (pH 2.8), buffer exchange into PBS (pH 7.4) by dialysis, and concentration of the antibody solution. For the 10E8v4, 10E8v4 S100cF, and 10E8v4 V5R S100cF antibodies, yield fell within a normal range of about 70-80% purified concentrated antibody relative to the amount of corresponding antibody eluted from the column. However, yield of 10E8v4 S100cW antibody was only about 60% purified concentrated antibody relative to the amount of 10E8v4 S100cW antibody eluted from the column. The loss of 10E8v4 S100cW antibody was primarily due to precipitation from solution during the concentration step. In contrast, there was minimal loss of antibody from solution during the concentration step for the 10E8v4 S100cF and 10E8v4 V5R S100cF antibodies.

Additionally, when the concentration step was conducted using Amicon Stirred Cell Ultrafiltration (nitrogen pressure) in 10 mM Citrate-Phosphate, 150 mM NaCl pH 6.0 (10E8v4 S100cW) or 10 mM Citrate-Phosphate, 150 mM NaCl pH 6.5 (10E8v4 S100cF and 10E8 V5R S100cF)), approximately 5-10% protein loss was observed for 10E8v4 V5R 100cF and 10E8v4-100cF during the concentration step, but an approximate 40% protein loss was observed for the 10E8v4-100cW variant. The final antibody concentration resulting from these concentration steps also differed substantially between the tested variants. A final concentration of 23-25 mg/mL was achieved for the 10E8v4 S100cF and 10E8v4S100cW antibodies. In contrast, a final concentration of about 40 mg/mL was achieved for the 10E8v4 V5R S100cF antibody.

Figure 24:
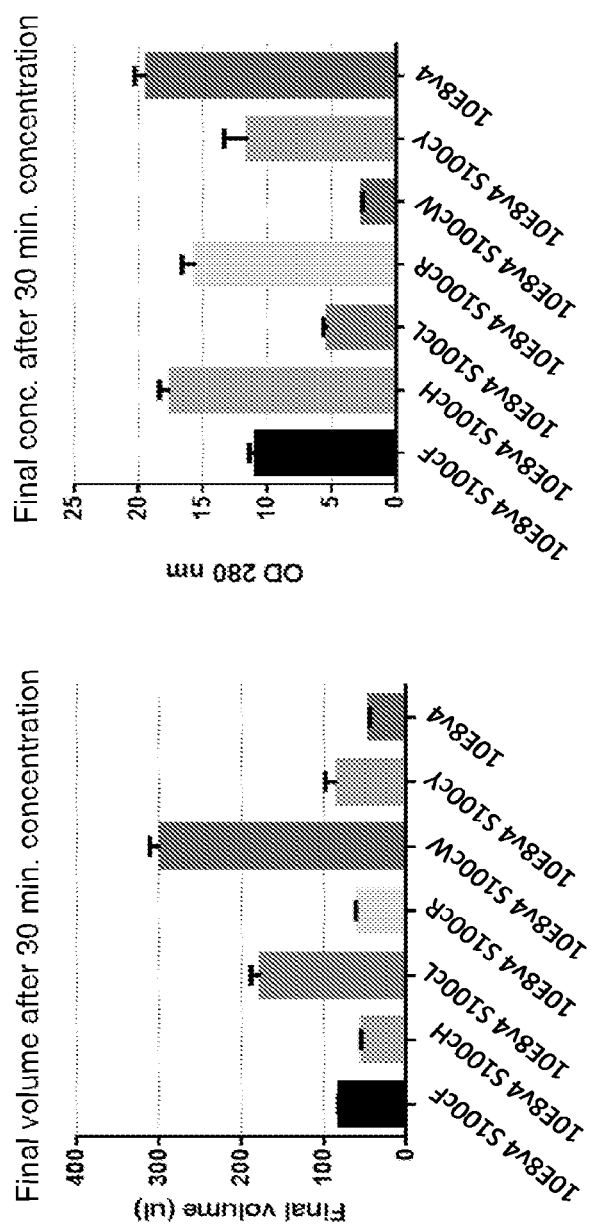
FIG. 24 is a set of graphs showing results from solubility assays of 10E8v4 variants including S100cF, S100cH, S100cL, S100cR, S100cW, or S100cY substitutions performed by measuring the volume and protein concentration of solutions of these antibodies following concentration using a standard centrifugal concentrator.

To further investigate the effect of the residue present at kabat position 100c of the 10E8 antibody on solubility, 10E8v4 antibodies with S100cF, S100cH, S100cL, S100cR, S100cW, or S100cY substitutions were expressed and purified as discussed above, and assayed for the solubility based on the ability to concentrate (FIG. 24). The antibodies were eluted from the purification column using elution buffer (pH 7.4), dialyzed into PBS (pH 7.4), and 3 ml (0.35 OD) of each variant was concentrated for 30 minutes at 4000 rpm using a 30,000 MWCO concentrator (Amicon Ultra-15 filter MWCO 30,000), in triplicate. As shown in FIG. 24, the 10E8v4 S100cW variant was the most difficult to concentrate, and had the greatest final volume of solution following concentration (and the lowest antibody concentration) as assessed by OD280 measurement.

Example 7

Optimized 10E8 Antibodies

This example describes mutagenesis of kabat position S100c of the 10E8v4 antibody to several different amino acids to evaluate the relative effect of this residue HIV-1 neutralization by the 10E8v4 antibody. 10E8v4 antibodies with S100cF, S100cH, S100cL, S100cR, S100cW, or S100cY substitutions were expressed and purified as discussed in Example 5, and assayed for the HIV-1 neutralization using a pseudovirus assay. As shown in Table 12, 10E8v4 variants with the s100cF and S100cW substitutions showed the greatest improvement in mean neutralization potency over 10E8v4 (~20- and 40-fold lower mean IC50 values relative to 10E8v4). In combination with the findings discussed above, these results show that 10E8v4 variant antibodies that include a S100cF substitution possess an optimal combination of HIV-1 neutralization, solubility, and auto-reactivity properties, relative to the many 10E8 variants tested.

TABLE 12

| | | HIV-1 neutralization by 10E8v4 variants | | | | | | |
|---|---|---|---|---|---|---|---|---|
| Clade | Virus | 10E8v4 100cF YDK | 10E8v4 100cH YDK | 10E8v4 100cL YDK | 10E8v4 100cR YDK | 10E8v4 100cW YDK | 10E8v4 100cY YDK | 10E8v4 YDK |
| | | IC50 µg/ml | | | | | | |
| A | KER2008.12.SG3 | >50 | >50 | >50 | >50 | >50 | >50 | >50 |
| ACD | 6095.V1.C10.SG3 | 0.001 | 0.011 | 0.001 | 0.011 | 0.001 | 0.001 | 0.004 |
| AE | TH966.8.SG3 | 0.002 | 0.091 | 0.011 | 0.168 | 0.001 | 0.011 | 0.056 |
| B | 6101.10.SG3 | 0.001 | 0.103 | 0.007 | 0.176 | 0.001 | 0.009 | 0.052 |
| B | PVO.04.SG3 | 0.147 | 3.400 | 0.507 | 6.450 | 0.088 | 0.412 | 3.070 |
| B | YU2.DG.SG3 | 0.073 | 2.590 | 0.333 | 3.870 | 0.042 | 0.376 | 1.490 |
| C | CNE31.SG3 | 0.097 | 2.240 | 0.354 | 2.540 | 0.041 | 0.368 | 1.320 |
| C | ZM106.9.SG3 | >50 | >50 | >50 | >50 | >50 | >50 | >50 |
| C | ZM215.8.SG3 | 0.003 | 0.141 | 0.015 | 0.363 | 0.001 | 0.028 | 0.122 |
| | Median IC50 | 0.003 | 0.141 | 0.015 | 0.363 | 0.001 | 0.028 | 0.122 |
| | Geometric Mean | 0.009 | 0.312 | 0.033 | 0.497 | 0.004 | 0.037 | 0.189 |
| | Fold Improvement over 10E8v4 | 21.7 | 0.6 | 5.7 | 0.4 | 42.8 | 5.1 | 1 |
| | | IC80 µg/ml | | | | | | |
| A | KER2008.12.SG3 | >50 | >50 | >50 | >50 | >50 | >50 | >50 |
| ACD | 6095.V1.C10.SG3 | 0.001 | 0.046 | 0.002 | 0.048 | 0.001 | 0.006 | 0.015 |
| AE | TH966.8.SG3 | 0.017 | 0.488 | 0.079 | 0.648 | 0.007 | 0.075 | 0.291 |
| B | 6101.10.SG3 | 0.008 | 0.643 | 0.049 | 0.891 | 0.006 | 0.063 | 0.263 |
| B | PVO.04.SG3 | 0.696 | 14.000 | 2.210 | 25.000 | 0.388 | 3.440 | 11.900 |
| B | YU2.DG.SG3 | 0.482 | 10.900 | 1.750 | 12.000 | 0.331 | 2.250 | 6.330 |
| C | CNE31.SG3 | 0.306 | 6.790 | 1.010 | 8.420 | 0.149 | 1.390 | 4.040 |
| C | ZM106.9.SG3 | >50 | >50 | >50 | >50 | >50 | >50 | >50 |
| C | ZM215.8.SG3 | 0.020 | 0.966 | 0.095 | 1.340 | 0.012 | 0.129 | 0.502 |
| | Median IC80 | 0.020 | 0.966 | 0.095 | 1.340 | 0.012 | 0.129 | 0.502 |
| | Geometric Mean | 0.040 | 1.464 | 0.162 | 1.913 | 0.025 | 0.235 | 0.780 |
| | Fold Improvement over 10E8v4 | 19.4 | 0.5 | 4.8 | 0.4 | 31.4 | 3.3 | 1.0 |

It will be apparent that the precise details of the methods or compositions described may be varied or modified without departing from the spirit of the described embodiments. We claim all such modifications and variations that fall within the scope and spirit of the claims below.

It is claimed:

1. An isolated antibody, comprising:
a heavy chain variable region ($V_H$) comprising a heavy chain complementarity determining region (HCDR)1, a HCDR2, and a HCDR3 of the $V_H$ set forth as SEQ ID NO: 75, and a light chain variable region ($V_L$) comprising a light chain complementarity determining region (LCDR)1, a LCDR2, and a LCDR3 of the $V_L$ set forth as SEQ ID NO: 6, wherein the HCDR1, the HCDR2, the HCDR3, the LCDR1, the LCDR2, and the LCDR3 comprise the amino acid sequences set forth as: SEQ ID NOs: 7, 8, 77, 10, 11, and 12, respectively (10E8v4 S100cF CDRs); and
wherein the antibody specifically binds to gp41 and neutralizes HIV-1.

2. The isolated antibody of claim 1, wherein the $V_H$ comprises arginine, glutamate, serine, lysine, aspartate, threonine, lysine, threonine, valine, threonine, threonine, tyrosine, glutamine, and isoleucine residues at kabat positions 3, 61, 62, 64, 72, 74, 75, 77, 82c, 84, 87, 89, 105, and 110, respectively; and the $V_L$ comprises alanine, serine, aspartate, proline, alanine, lysine, glutamine, valine, isoleucine, threonine, glutamate, and aspartate residues at kabat positions 1, 2, 7, 8, 9, 16, 17, 45, 58, 76, 83, and 85, respectively.

3. The isolated antibody of any of claim 1, comprising an arginine residue at kabat position 5.

4. An isolated antibody, comprising:

a $V_H$ comprising a HCDR1, a HCDR2, and a HCDR3 of the $V_H$ set forth as SEQ ID NO: 75, and a light chain variable region ($V_L$) comprising a LCDR1, a LCDR2, and a LCDR3 of the $V_L$ set forth as SEQ ID NO: 6, wherein the HCDR1, the HCDR2, the HCDR3, the LCDR1, the LCDR2, and the LCDR3 comprise the amino acid sequences set forth as: SEQ ID NOs: 7, 8, 77, 10, 11, and 12, respectively (10E8v4 S100cF CDRs);

wherein the $V_H$ and the $V_L$ framework regions (FRs) further comprise amino acid sequences at least 90% identical to the $V_H$ and $V_L$ FRs of SEQ ID NOs: 75 and 6, respectively (10E8v4 S100cF); and wherein the antibody specifically binds to gp41 and neutralizes HIV-1.

5. An isolated antibody, comprising:

a $V_H$ comprising a HCDR1, a HCDR2, and a HCDR3 of the $V_H$ set forth as SEQ ID NO: 75, and a light chain variable region ($V_L$) comprising a LCDR1, a LCDR2, and a LCDR3 of the $V_L$ set forth as SEQ ID NO: 6, wherein the HCDR1, the HCDR2, the HCDR3, the LCDR1, the LCDR2, and the LCDR3 comprise the amino acid sequences set forth as: SEQ ID NOs: 7, 8, 77, 10, 11, and 12, respectively (10E8v4 S100cF CDRs);

wherein the $V_H$ and the $V_L$ framework regions (FRs) further comprise amino acid sequences at least 90% identical to the $V_H$ and $V_L$ FRs of SEQ ID NOs: 76 and 6, respectively (10E8v4 V5R S100cF) and wherein the antibody specifically binds to gp41 and neutralizes HIV-1.

6. The isolated antibody of claim 1, wherein the $V_H$ and $V_L$ comprise the amino acid sequences set forth as SEQ ID NOs: 75 and 6, respectively (10E8v4 S100cF).

7. The isolated antibody of claim 1, wherein the $V_H$ and $V_L$ comprise the amino acid sequences set forth as SEQ ID NOs: 76 and 6, respectively (10E8v4 V5R S100cF).

8. The isolated antibody of claim 1, wherein the antibody dissolves to a concentration of at least 5 mg/ml in phosphate buffered saline, pH 7.4, at 20° C.

9. The isolated antibody of claim 1, comprising human framework regions.

10. The isolated antibody of claim 1, comprising a human constant region.

11. The isolated antibody of claim 1, wherein the antibody is an IgG, IgM or IgA.

12. The isolated antibody of claim 1, comprising a recombinant constant region comprising a modification that increases binding to the neonatal Fc receptor.

13. The isolated antibody of claim 12, wherein the antibody is an IgG1 and the modification that increases binding to the neonatal Fc receptor comprises M428L and N434S amino acid substitutions.

14. An antigen binding fragment of the antibody of claim 1.

15. The antigen binding fragment of claim 14, wherein the antigen binding fragment is a Fv, Fab, F(ab')$_2$, scFV or a scFV$_2$ fragment.

16. The antibody of claim 1, or an antigen binding fragment thereof, linked to an effector molecule or a detectable marker.

17. A method of detecting an HIV-1 infection in a subject, comprising:

contacting a biological sample from the subject with the antibody of claim 1 or an antigen binding fragment thereof under conditions sufficient to form an immune complex; and detecting the presence of the immune complex on the sample, wherein the presence of the immune complex on the sample indicates that the subject has the HIV-1 infection.

18. A method of inhibiting or treating an HIV-1 infection in a subject, comprising administering to the subject a therapeutically effective amount of the antibody of claim 1, or an antigen binding fragment thereof, thereby inhibiting or treating the HIV-1 infection.

19. The method of claim 18, wherein the subject is at risk of an HIV-1 infection, has an HIV-1 infection, or has AIDS.

20. The method of claim 18, further comprising administering to the subject an additional antibody that specifically binds to HIV-1 Env and neutralizes HIV-1 infection.

21. The method of claim 20, wherein the additional antibody is a VRC01-class antibody.

22. The method of claim 21, wherein the VRC01-class antibody is VRC01 or VRC07-523.

* * * * *